United States Patent
Matsuda et al.

(10) Patent No.: US 9,081,277 B2
(45) Date of Patent: Jul. 14, 2015

(54) ACTINIC-RAY- OR RADIATION-SENSITIVE RESIN COMPOSITION, ACTINIC-RAY- OR RADIATION-SENSITIVE FILM THEREFROM AND METHOD OF FORMING PATTERN USING THE COMPOSITION

(75) Inventors: Tomoki Matsuda, Shizuoka (JP); Akinori Shibuya, Shizuoka (JP); Yoko Tokugawa, Shizuoka (JP); Shuhei Yamaguchi, Shizuoka (JP); Mitsuhiro Fujita, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 114 days.

(21) Appl. No.: 13/520,106

(22) PCT Filed: Dec. 22, 2011

(86) PCT No.: PCT/JP2011/080559
§ 371 (c)(1),
(2), (4) Date: Jun. 29, 2012

(87) PCT Pub. No.: WO2012/086850
PCT Pub. Date: Jun. 28, 2012

(65) Prior Publication Data
US 2012/0273924 A1    Nov. 1, 2012

(30) Foreign Application Priority Data
Dec. 24, 2010   (JP) .................. 2010-288726
Aug. 30, 2011   (JP) .................. 2011-187711

(51) Int. Cl.
G03F 7/004     (2006.01)
C07C 381/12    (2006.01)
G03F 7/039     (2006.01)
G03F 7/20      (2006.01)
G03F 7/11      (2006.01)

(52) U.S. Cl.
CPC ............ *G03F 7/0045* (2013.01); *C07C 381/12* (2013.01); *G03F 7/0046* (2013.01); *G03F 7/0397* (2013.01); *G03F 7/11* (2013.01); *G03F 7/2041* (2013.01)

(58) Field of Classification Search
CPC ..... G03F 7/004; G03F 7/0045; G03F 7/2041; C07C 381/12
USPC .............................. 430/270.1, 913
IPC ...... G03F 7/004, 7/0045, 7/2041; C07C 381/12
See application file for complete search history.

(56) References Cited

U.S. PATENT DOCUMENTS

| 6,924,323 B2 * | 8/2005 | Ishihara et al. ................. 522/25 |
| 7,824,839 B2 * | 11/2010 | Ober et al. ................. 430/270.1 |
| 8,012,665 B2 * | 9/2011 | Kodama et al. ............ 430/270.1 |
| 2009/0104563 A1 | 4/2009 | Ishiduka et al. |
| 2010/0255418 A1 | 10/2010 | Yamaguchi et al. |
| 2011/0300484 A1 * | 12/2011 | Yamato et al. ............. 430/281.1 |
| 2013/0004741 A1 * | 1/2013 | Matsuda et al. ........... 428/195.1 |
| 2013/0084525 A1 * | 4/2013 | Aqad et al. ................. 430/270.1 |

FOREIGN PATENT DOCUMENTS

| JP | 2003-149800 A | 5/2003 |
| JP | 2003-307839 A | 10/2003 |
| JP | 2006290798 A * | 10/2006 |
| JP | 3841406 B2 | 11/2006 |
| JP | 2007-230913 A | 9/2007 |
| JP | 2008/129433 A1 | 6/2008 |
| JP | 2009-053665 A | 3/2009 |
| JP | 2009-122623 A | 6/2009 |
| WO | 02/079691 A1 | 10/2002 |
| WO | WO 2010143560 A1 * | 12/2010 |

OTHER PUBLICATIONS

Machine translation of JP 2009-053665 (no date).*
Machine translation of JP 2006-290798 (no date).*
European Search Report dated Jun. 26, 2014 issued in application No. 11849906.0-1564.

* cited by examiner

*Primary Examiner* — Amanda C Walke
(74) *Attorney, Agent, or Firm* — Sughrue Mion, PLLC

(57) ABSTRACT

Provided are an actinic-ray- or radiation-sensitive resin composition that excels in the sensitivity, roughness characteristics and exposure latitude, and a method of forming a pattern using the same. The composition includes (A) a resin that when acted on by an acid, is decomposed to thereby increase its solubility in an alkali developer, and (B) a compound that when exposed to actinic rays or radiation, is decomposed to thereby generate an acid, the compound being any of compounds of general formula (1-1) below.

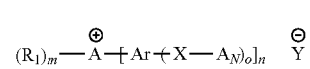

(1-1)

15 Claims, No Drawings

ACTINIC-RAY- OR RADIATION-SENSITIVE RESIN COMPOSITION, ACTINIC-RAY- OR RADIATION-SENSITIVE FILM THEREFROM AND METHOD OF FORMING PATTERN USING THE COMPOSITION

CROSS-REFERENCE TO RELATED APPLICATIONS

This application is based upon and claims the benefit of priority from prior Japanese Patent Applications No. 2010-288726, filed Dec. 24, 2010; and No. 2011-187711, filed Aug. 30, 2011, the entire contents of all of which are incorporated herein by reference.

TECHNICAL FIELD

The present invention relates to an actinic-ray- or radiation-sensitive resin composition, an actinic-ray- or radiation-sensitive film formed from the composition and a method of forming a pattern using the composition. More particularly, the present invention relates to a composition for use in, for example, a semiconductor production process for an IC or the like, a circuit board production process for a liquid crystal, a thermal head or the like and other photofabrication lithography processes, and relates to a film formed from the composition and a method of forming a pattern using the composition. In particular, the present invention is concerned with a composition that is suitable for exposure using a liquid-immersion projection exposure apparatus in which a far ultraviolet light of wavelength 300 nm or shorter is employed as a light source, and is concerned with a film formed from the composition and a method of forming a pattern using the composition.

BACKGROUND ART

Heretofore, in a semiconductor production process, etc. it is common practice to use resist compositions. An example of such compositions is a chemically amplified resist composition.

The chemically amplified resist composition typically comprises a resin that when acted on by an acid, is decomposed to thereby increase its solubility in an alkali developer, and a compound that when exposed to actinic rays or radiation, is decomposed to thereby generate an acid. With respect to this resin and compound, various developments have been effected in order to cope with, for example, the miniaturization of semiconductors (see, for example, patent references 1 to 4).

However, with respect to this composition, there is room for further improvements. In particular, in recent years, it is required to simultaneously attain excellent sensitivity and excellent roughness characteristics and exposure latitude (EL) at higher dimension.

PRIOR ART LITERATURE

Patent Reference

[Patent reference 1] Jpn. Pat. Appln. KOKAI Publication No. (hereinafter referred to as JP-A-) 2007-230913,
[Patent reference 2] JP-A-2009-122623,
[Patent reference 3] JP-A-2003-307839, and
[Patent reference 4] Japanese Patent No. 3841406.

DISCLOSURE OF INVENTION

It is an object of the present invention to provide an actinic-ray- or radiation-sensitive resin composition that excels in the sensitivity, roughness characteristics and exposure latitude. It is further objects of the present invention to provide an actinic-ray- or radiation-sensitive film formed from the composition and a method of forming a pattern using the composition.

The present invention is, for example, as defined below.

[1] An actinic-ray- or radiation-sensitive resin composition comprising:

(A) a resin that when acted on by an acid, is decomposed to thereby increase its solubility in an alkali developer, and (B) a compound that when exposed to actinic rays or radiation, is decomposed to thereby generate an acid, the compound being any of compounds of general formula (1-1) below,

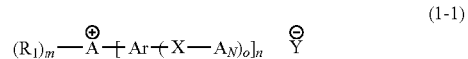
(1-1)

in which

A represents a sulfur atom or an iodine atom, $R_1$, each independently when m=2, represents an alkyl group, an alkenyl group, a cycloaliphatic group, an aromatic hydrocarbon group or a heterocyclic hydrocarbon group, provided that when m=2, two $R_1$s may be bonded to each other to thereby form a ring, Ar, each independently when n≥2, represents an aromatic ring group, X, each independently when o≥2 and/or n≥2, represents a connecting group having a carbon atom to which Ar is bonded, $A_N$, each independently when o≥2 and/or n≥2, represents a basic moiety containing a nitrogen atom, n is an integer of 1 to 3 and m is an integer satisfying the relationship m+n=3 when A is a sulfur atom, n is an integer of 1 or 2 and m is an integer satisfying the relationship m+n=2 when A is an iodine atom, o is an integer of 1 to 10, and $Y^-$ represents an anion.

[2] The composition according to item [1] above, further comprising (C) a compound that when exposed to actinic rays or radiation, is decomposed to thereby generate an acid, the compound being other than the compounds of general formula (1-1) above.

[3] The composition according to item [1] or [2] above, wherein X, or at least one of Xs, is expressed by general formula (1-2) below,

(1-2)

in which each of $R_2$ and $R_3$ independently represents a hydrogen atom, an alkyl group, an alkenyl group, a cycloaliphatic group, an aromatic hydrocarbon group or a heterocyclic hydrocarbon group, provided that $R_2$ and $R_3$ may be bonded to each other to thereby form a ring, and provided that at least one of $R_2$ and $R_3$ may be bonded to E to thereby form a ring, and E represents a connecting group or a single bond.

[4] The composition according to item [1] or [2] above, wherein X, or at least one of Xs, is expressed by general formula (1-3) below,

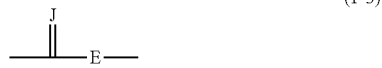

(1-3)

in which
J represents an oxygen atom or a sulfur atom, and
E represents a connecting group or a single bond.

[5] The composition according to item [3] or [4] above, wherein E is an alkylene bond.

[6] The composition according to item [3] or [4] above, wherein E contains at least one bond selected from the group consisting of an ester bond and an ether bond.

[7] The composition according to any of items [1] to [6] above, wherein A is a sulfur atom.

[8] The composition according to any of items [1] to [7] above, wherein $R_1$, or each of $R_1$s independently, is an aromatic hydrocarbon group.

[9] The composition according to any of items [1] to [8] above, wherein $Y^-$ is an organic acid anion.

[10] The composition according to any of items [1] to [9] above, wherein $Y^-$ is a sulfonate anion, an imidate anion or a methide anion.

[11] An actinic-ray- or radiation-sensitive film formed from the composition according to any of items [1] to [10] above.

[12] A method of forming a pattern, comprising:
forming the composition according to any of items [1] to [10] above into a film,
exposing the film to light, and
developing the exposed film.

[13] The method according to item [12] above, wherein the exposure is performed through an immersion liquid.

[14] A process for manufacturing a semiconductor device, comprising the pattern forming method of item [12] or [13] above.

[15] A semiconductor device manufactured by the process of item [14] above.

[16] A compound that when exposed to actinic rays or radiation, is decomposed to thereby generate acids, which compound is expressed by general formula (1-1) defined in item [1] above.

The present invention has made it feasible to provide an actinic-ray- or radiation-sensitive resin composition that excels in the sensitivity, roughness characteristics and exposure latitude and also to provide an actinic-ray- or radiation-sensitive film formed from the composition and a method of forming a pattern using the composition.

BEST MODE FOR CARRYING OUT THE INVENTION

Embodiments of the present invention will be described in detail below.

Herein, the groups and atomic groups for which no statement is made as to substitution or nonsubstitution are to be interpreted as including those containing no substituents and also those containing substituents. For example, the "alkyl groups" for which no statement is made as to substitution or nonsubstitution are to be interpreted as including not only the alkyl groups containing no substituents (unsubstituted alkyl groups) but also the alkyl groups containing substituents (substituted alkyl groups).

Further, the term "actinic rays" or "radiation" means, for example, brightline spectra from a mercury lamp, far ultraviolet represented by an excimer laser, extreme ultraviolet (EUV), X-rays and electron beams (EB). Herein, the term "light" means actinic rays or radiation. The term "exposure to light" unless otherwise specified means not only irradiation with light, such as light from a mercury lamp, far ultraviolet, X-rays or EUV light, but also lithography using particle beams, such as electron beams and ion beams.

The composition of the present invention comprises (A) a resin that when acted on by an acid, is decomposed to thereby increase its solubility in an alkali developer (hereinafter also referred to as an acid-decomposable resin) and (B) a compound that when exposed to actinic rays or radiation, is decomposed to thereby generate an acid, the compound being any of compounds of general formula (1-1) below. As will be described in detail hereinafter, excellent sensitivity, roughness characteristics and exposure latitude can be attained by employing this formulation.

These components will be sequentially described below.

(A) Acid-decomposable Resin

In the acid-decomposable resin (hereinafter also referred to as "resin (A)"), a group that is decomposed by the action of an acid to thereby produce an alkali-soluble group (hereinafter also referred to as "acid-decomposable group") is introduced in the principal chain or side chain, or both the principal chain and the side chain, of the resin. The resin (A) is preferably insoluble or hardly soluble in an alkali developer.

The acid-decomposable group preferably has a structure in which an alkali-soluble group is protected by a group removable by degradation upon the action of acid.

As the alkali-soluble group, there can be mentioned a phenolic hydroxyl group, a carboxyl group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali-soluble groups, there can be mentioned a carboxyl group, a fluoroalcohol group (preferably hexafluoroisopropanol) and a sulfonate group.

The acid-decomposable group is preferably a group as obtained by substituting the hydrogen atom of any of these alkali-soluble groups with an acid eliminable group.

As the acid eliminable group, there can be mentioned, for example, $-C(R_{36})(R_{37})(R_{38})$, $-C(R_{36})(R_{37})(OR_{39})$, $-C(R_{01})(R_{02})(OR_{39})$ or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded to each other to thereby form a ring structure.

Each of $R_{01}$ to $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

The repeating unit with an acid-decomposable group is preferably any of those of the following general formula (AI).

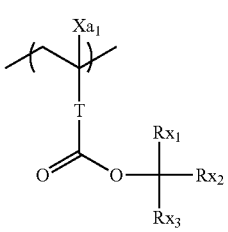

(AI)

In general formula (AI),

Xa₁ represents a hydrogen atom, an optionally substituted methyl group, or a group represented by —CH₂—R₉. R₉ represents a hydroxyl group or a monovalent organic group. R₉ preferably represents an alkyl or an acyl group having 5 or less carbon atoms, more preferably an alkyl group having 3 or less carbon atoms, and further more preferably a methyl group. Xa₁ preferably represents a hydrogen atom, a methyl group, a trifluoromethyl group or a hydroxymethyl group.

T represents a single bond or a bivalent connecting group.

Each of Rx₁ to Rx₃ independently represents a linear or branched alkyl group or a mono- or polycyclic cycloalkyl group.

At least two of Rx₁ to Rx₃ may be bonded to each other to thereby form a monocyclic or polycyclic cycloalkyl group.

As the bivalent connecting group represented by T, there can be mentioned, for example, an alkylene group, a group of the formula —(COO-Rt)- or a group of the formula —(O-Rt)-. In the formulae, Rt represents an alkylene group or a cycloalkylene group.

T is preferably a single bond or a group of the formula —(COO-Rt)-. Rt is preferably an alkylene group having 1 to 5 carbon atoms, more preferably a —CH₂— group or —(CH₂)₃— group.

The alkyl group represented by each of Rx₁ to Rx₃ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of Rx₁ to Rx₃ is preferably a monocyclic cycloalkyl group, such as a cyclopentyl group or a cyclohexyl group, or a polycyclic cycloalkyl group, such as a norbornyl group, a tetracyclodecanyl group, a tetracyclododecanyl group or an adamantyl group.

The cycloalkyl group formed by at least two of Rx₁ to Rx₃ is preferably a monocyclic cycloalkyl group, such as a cyclopentyl group or a cyclohexyl group, or a polycyclic cycloalkyl group, such as a norbornyl group, a tetracyclodecanyl group, a tetracyclododecanyl group or an adamantyl group. Monocyclic cycloalkyl groups having 5 or 6 carbon atoms are especially preferred.

In an especially preferred mode, Rx₁ is a methyl group or an ethyl group, and Rx₂ and Rx₃ are bonded to each other to thereby form any of the above-mentioned cycloalkyl groups.

One or more substituents may further be introduced in each of the groups above. As the substituents, there can be mentioned, for example, an alkyl group (preferably having 1 to 4 carbon atoms), a halogen atom, a hydroxy group, an alkoxy group (preferably having 1 to 4 carbon atoms), a carboxyl group, an alkoxycarbonyl group (preferably having 2 to 6 carbon atoms). Preferably, each of the substituents has 8 or less carbon atoms.

The content of the repeating unit containing a acid-decomposable group based on all the repeating units of the resin is preferably in the range of 20 to 70 mol %, and more preferably 30 to 50 mol %.

Preferred examples of the repeating unit containing a acid-decomposable group will be shown below, which however in no way limit the scope of the present invention.

In the specific examples, Rx and Xa1 each represents a hydrogen atom, CH₃, CF₃, or CH₂OH. Each of Rxa and Rxb represents an alkyl group having 1 to 4 carbon atoms. Z or each of Zs independently represents a substituent containing a polar group. P represents 0 or positive integer.

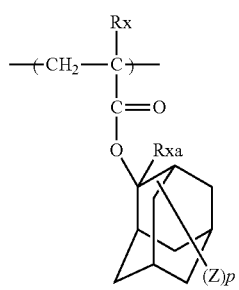

1

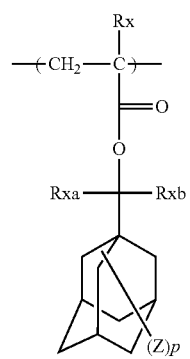

2

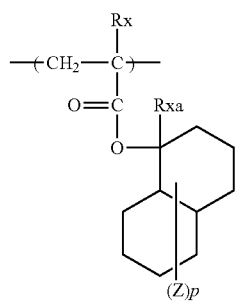

3

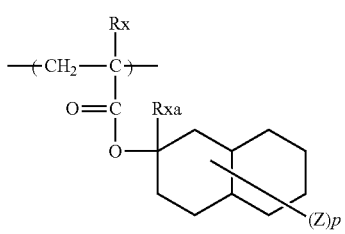

4

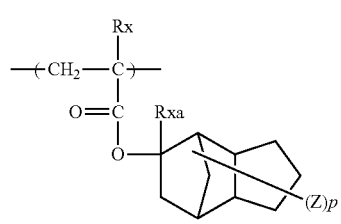

5

6
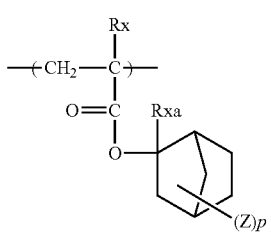
7
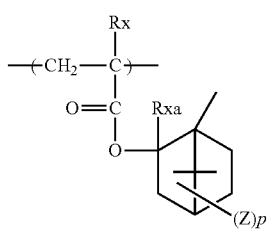
8
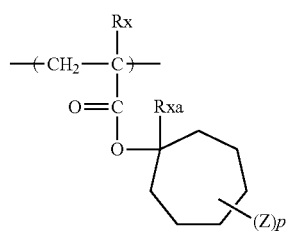
9
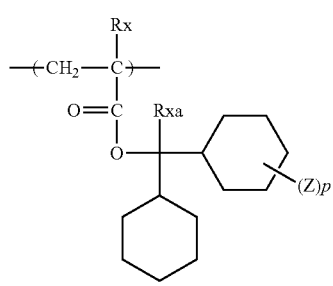
10
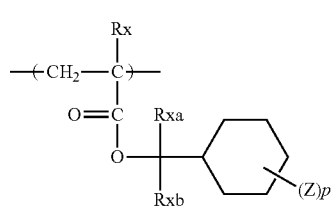
11
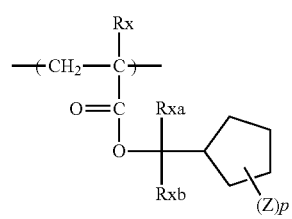
12
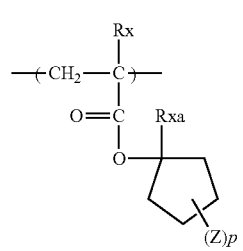
13
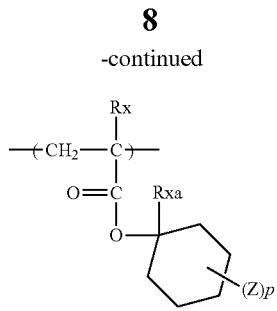
14
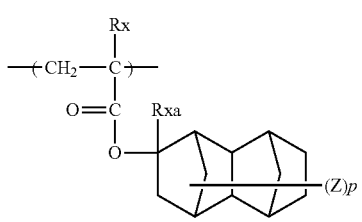
15
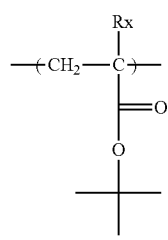
16
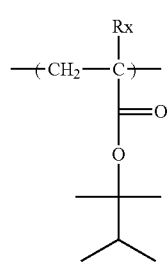
17
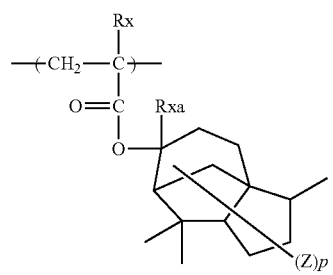
18
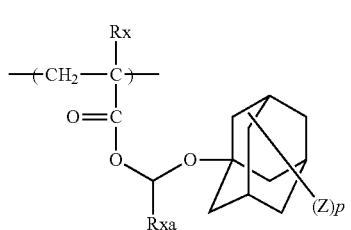

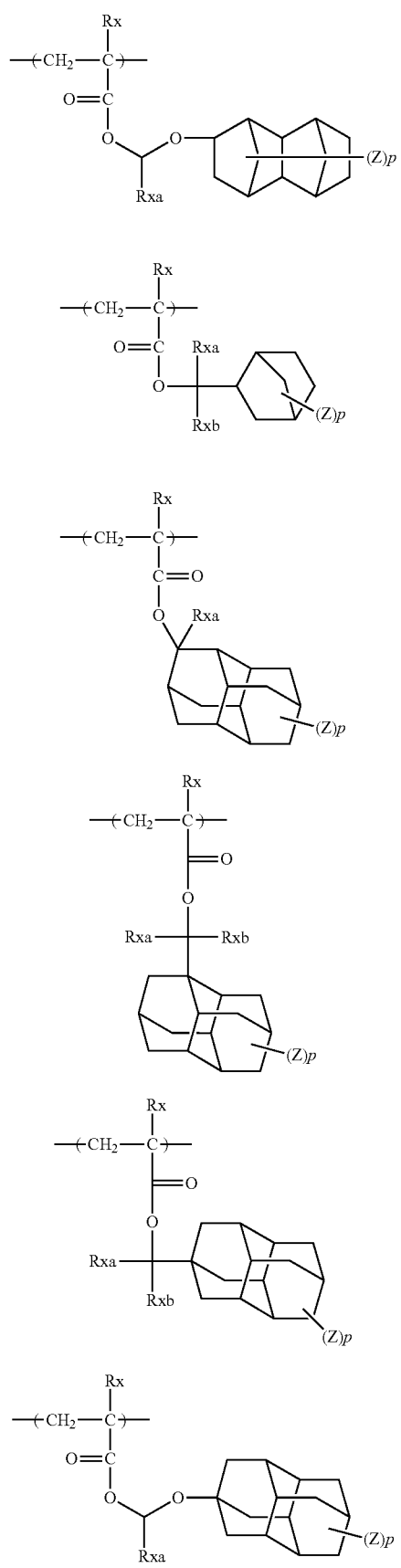
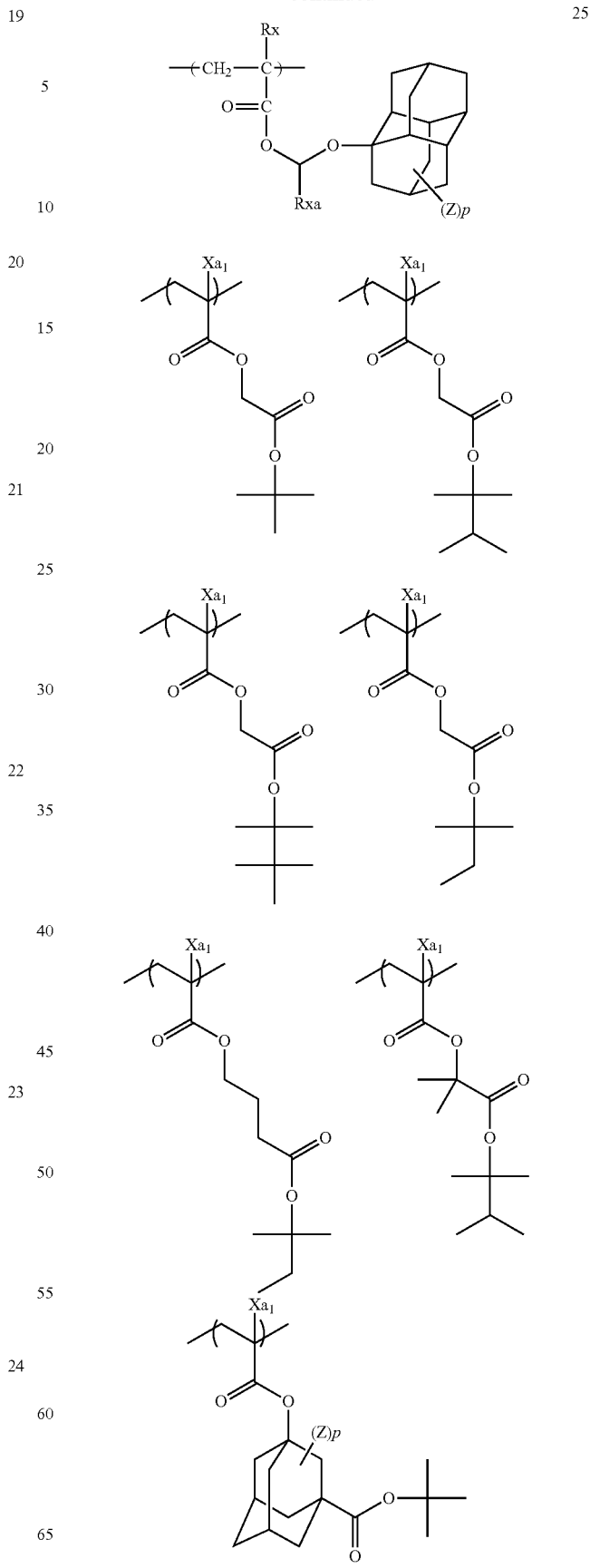

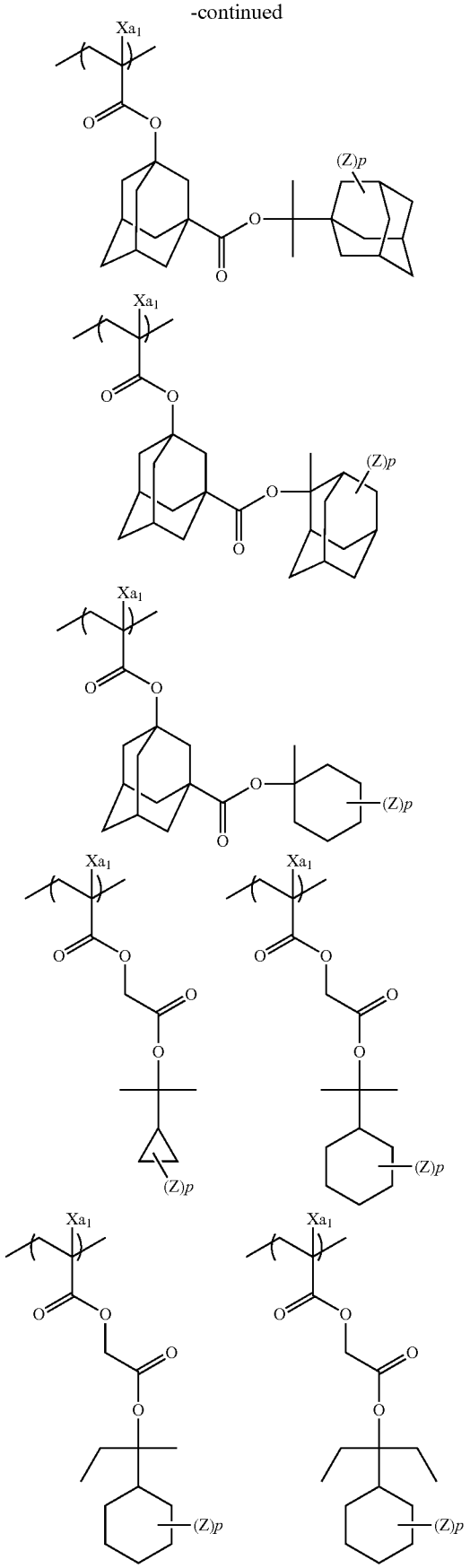
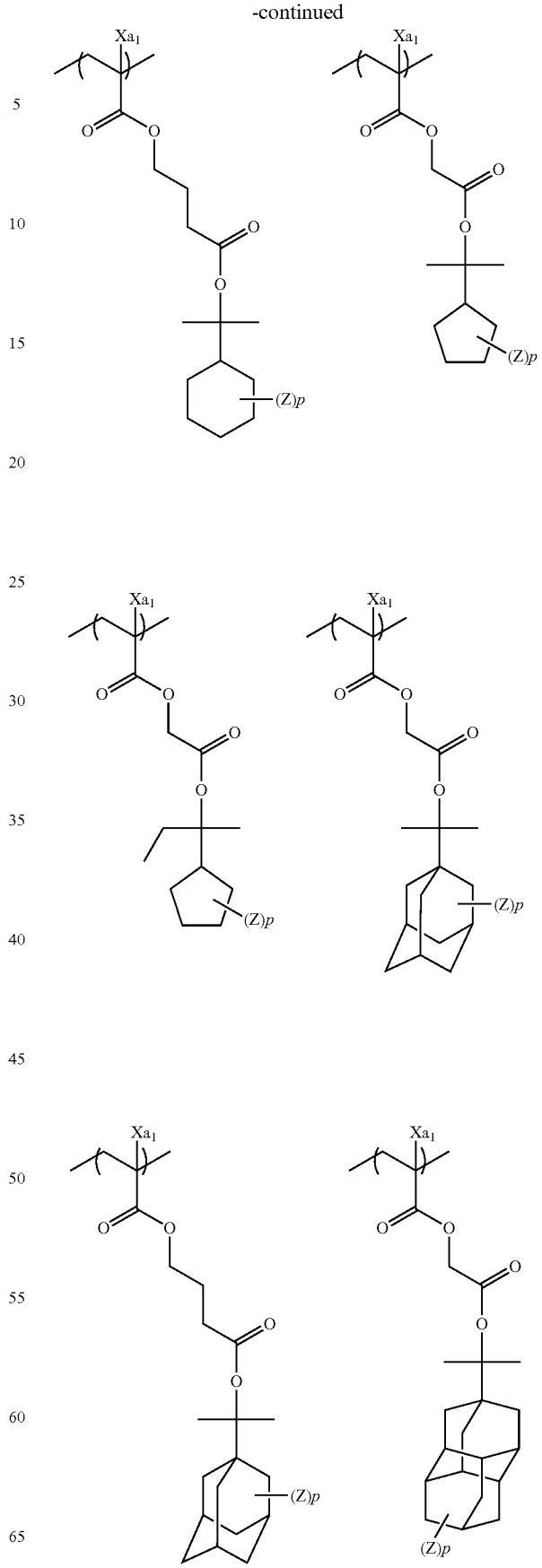

-continued
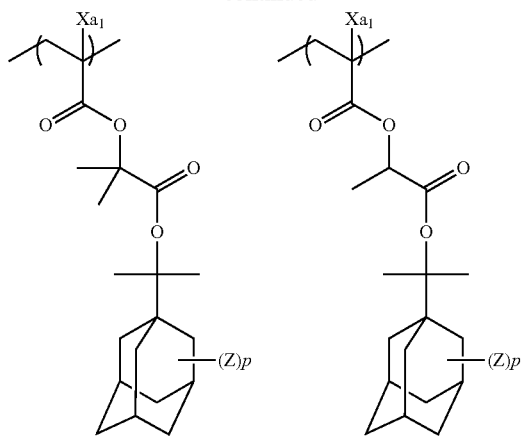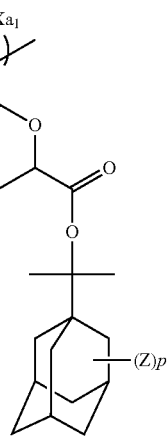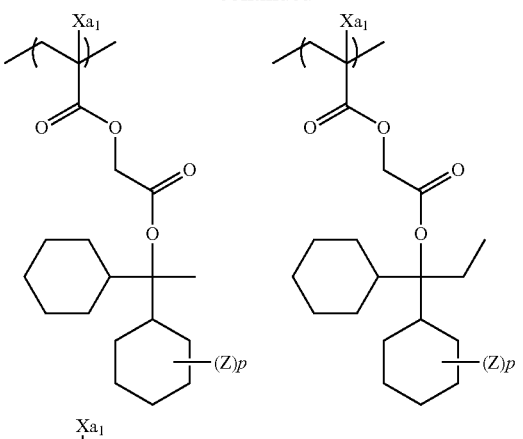
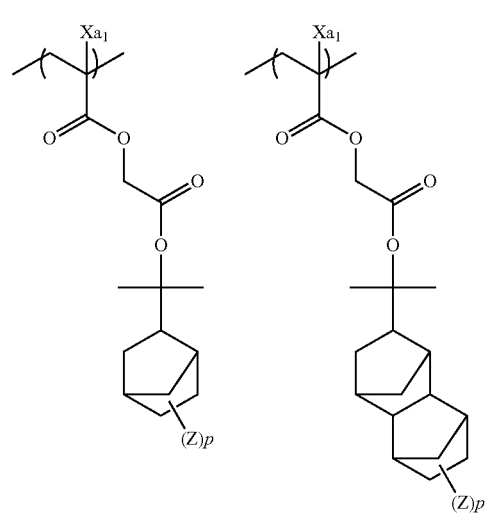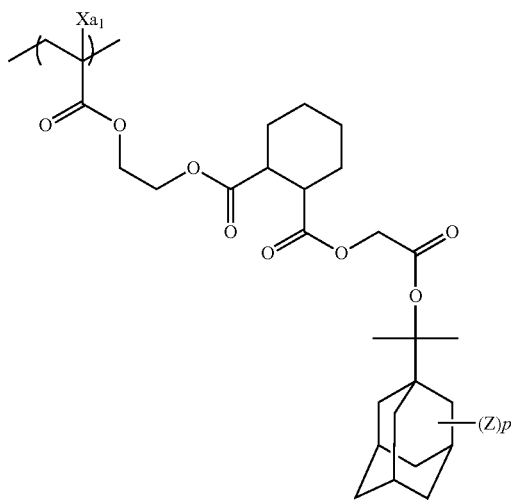
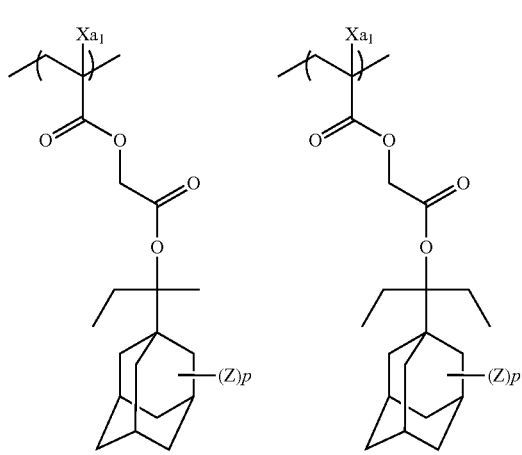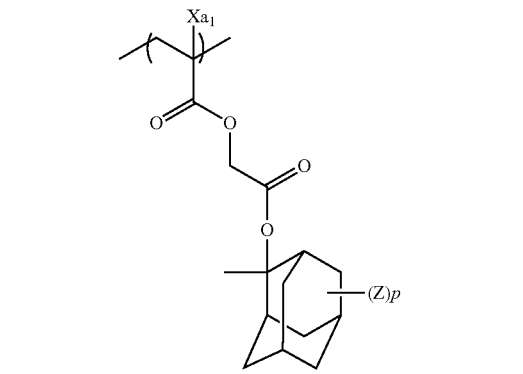
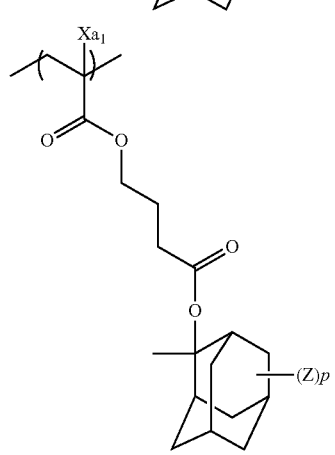

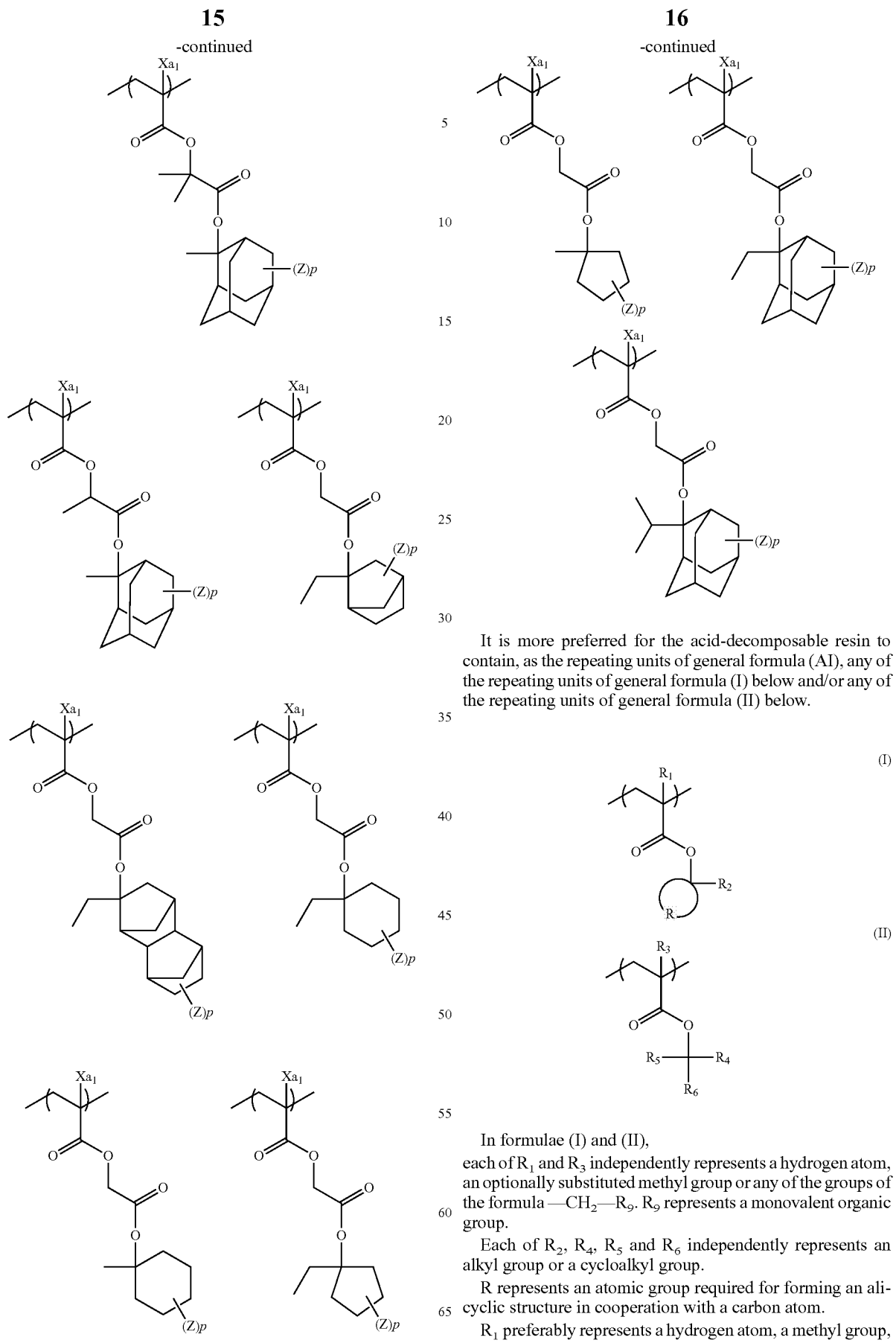

It is more preferred for the acid-decomposable resin to contain, as the repeating units of general formula (AI), any of the repeating units of general formula (I) below and/or any of the repeating units of general formula (II) below.

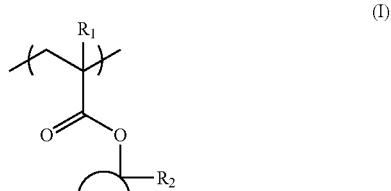

(I)

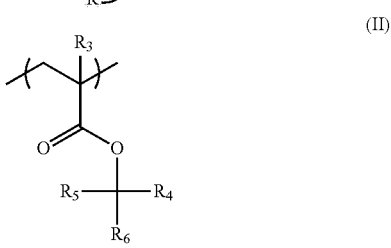

(II)

In formulae (I) and (II), each of $R_1$ and $R_3$ independently represents a hydrogen atom, an optionally substituted methyl group or any of the groups of the formula —$CH_2$—$R_9$. $R_9$ represents a monovalent organic group.

Each of $R_2$, $R_4$, $R_5$ and $R_6$ independently represents an alkyl group or a cycloalkyl group.

R represents an atomic group required for forming an alicyclic structure in cooperation with a carbon atom.

$R_1$ preferably represents a hydrogen atom, a methyl group, a trifluoromethyl group or a hydroxymethyl group.

The alkyl group represented by $R_2$ may be linear or branched, and one or more substituents may be introduced therein.

The cycloalkyl group represented by R2 may be monocyclic or polycyclic, and a substituent may be introduced therein.

$R_2$ preferably represents an alkyl group, more preferably an alkyl group having 1 to 10 carbon atoms, further more preferably 1 to 5 carbon atoms. As examples thereof, there can be mentioned a methyl group and an ethyl group.

R represents an atomic group required for forming an alicyclic structure in cooperation with a Carbon atom. The alicyclic structure formed by R is preferably an alicyclic structure of a single ring, and preferably has 3 to 7 carbon atoms, more preferably 5 or 6 carbon atoms.

$R_3$ preferably represents a hydrogen atom or a methyl group, more preferably a methyl group.

Each of the alkyl groups represented by $R_4$, $R_5$ and $R_6$ may be linear or branched, and one or more substituents may be introduced therein. The alkyl groups are preferably those each having 1 to 4 carbon atoms, such as a methyl group, an ethyl group, an n-propyl group, an isopropyl group, an n-butyl group, an isobutyl group and a t-butyl group.

Each of the cycloalkyl groups represented by $R_4$, $R_5$ and $R_6$ may be monocyclic or polycyclic, and a substituent may be introduced therein. The cycloalkyl groups are preferably a monocyclic cycloalkyl group, such as a cyclopentyl group or a cyclohexyl group, and a polycyclic cycloalkyl group, such as a norbornyl group, a tetracyclodecanyl group, a tetracyclododecanyl group or an adamantyl group.

The repeating units of general formula (II) are preferably those of general formula (II-1) below.

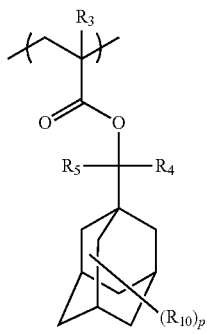

(II-1)

In general formula (II-1), $R_3$ to $R_5$ have the same meaning as in general formula (II).

$R_{10}$ represents a substituent containing a polar group. When a plurality of $R_{10}$s exist, they may be identical to or different from each other. As the substituent containing a polar group, there can be mentioned, for example, a linear or branched alkyl group, or cycloalkyl group, in which a hydroxyl group, a cyano group, an amino group, an alkylamido group or a sulfonamido group is introduced. An alkyl group in which a hydroxyl group is introduced is preferred. An isopropyl group is especially preferred as the branched alkyl group.

In the formula, p is an integer of 0 to 15, preferably in the range of 0 to 2, and more preferably 0 or 1.

When the resin (A) contains a plurality of acid-decomposable repeating units, the following combinations are preferred. In the following formulae, R each independently represents a hydrogen atom or a methyl group.

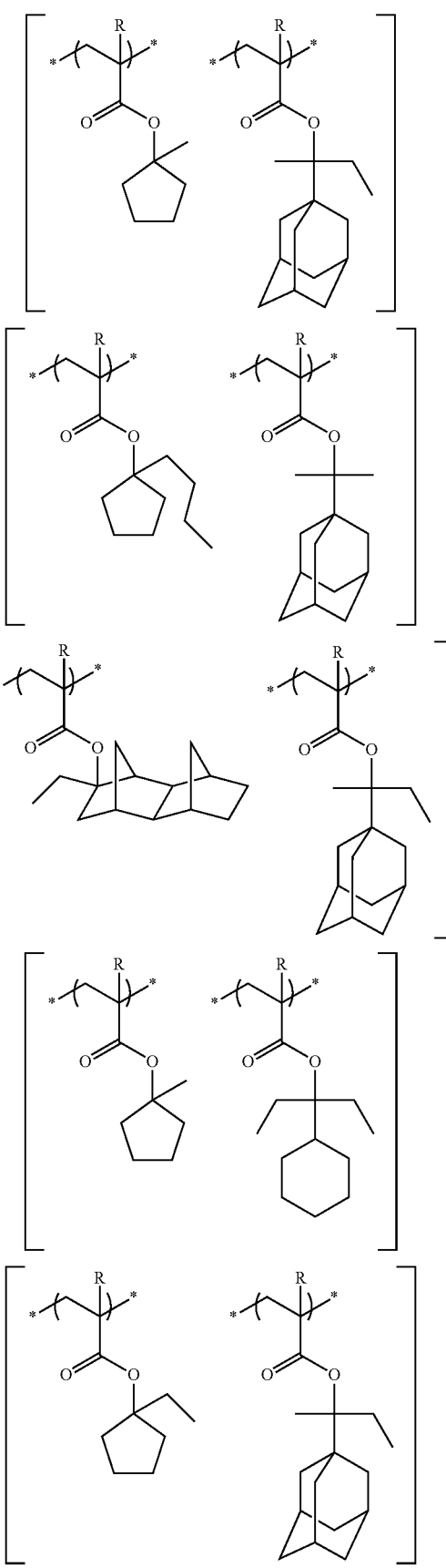

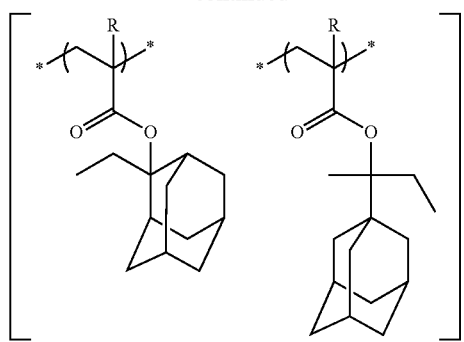
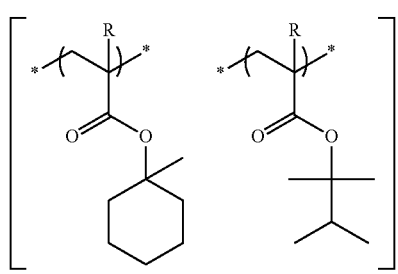
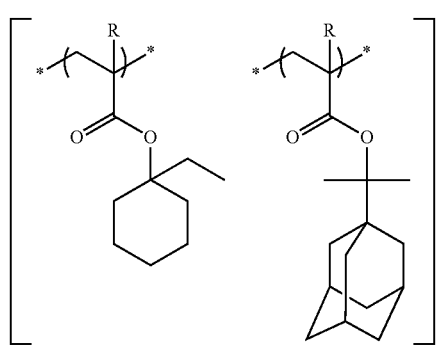
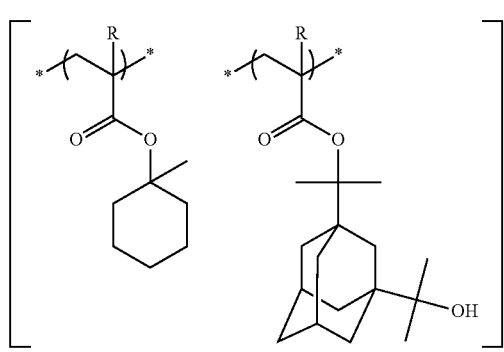
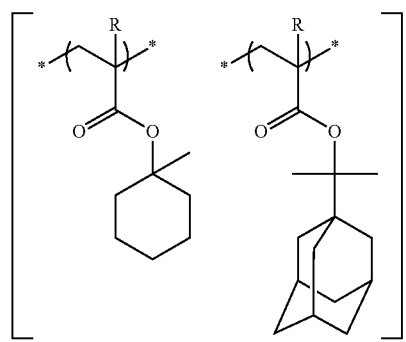
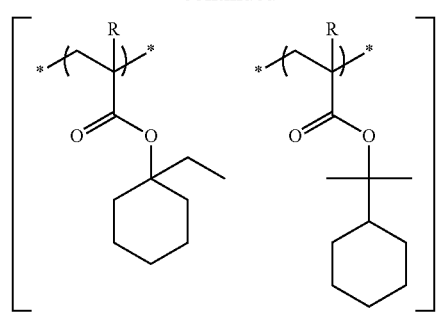
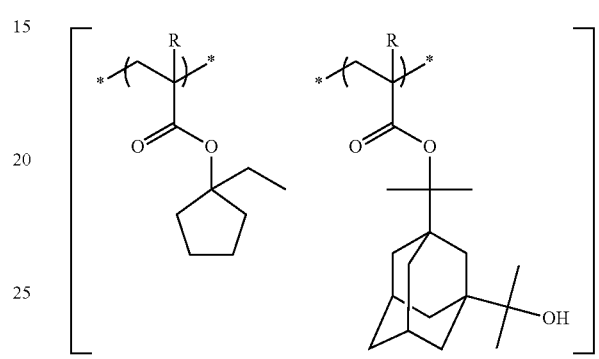
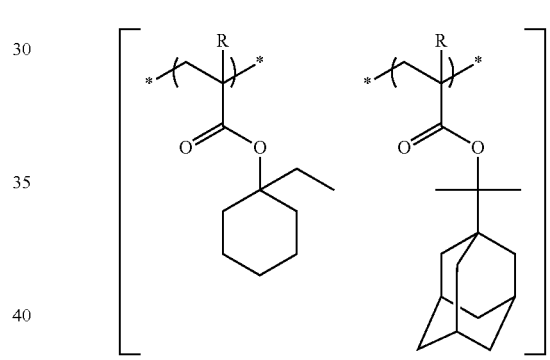
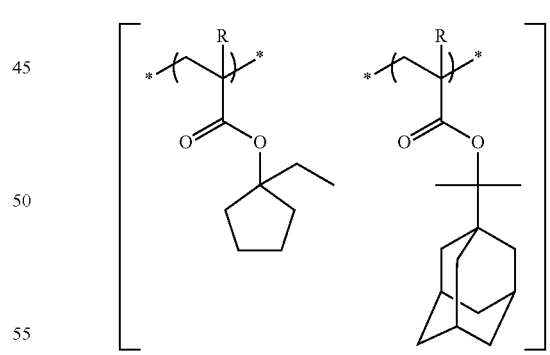
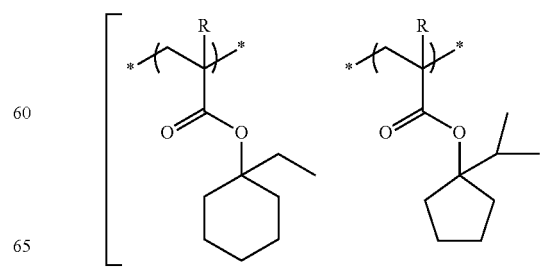

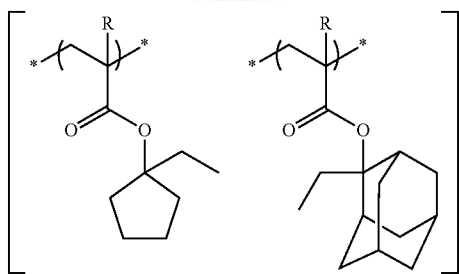

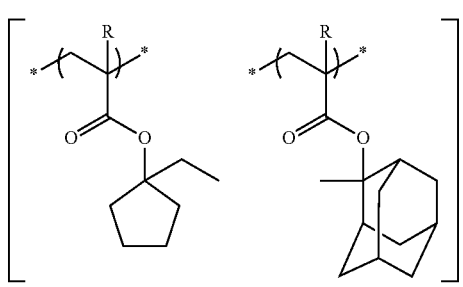

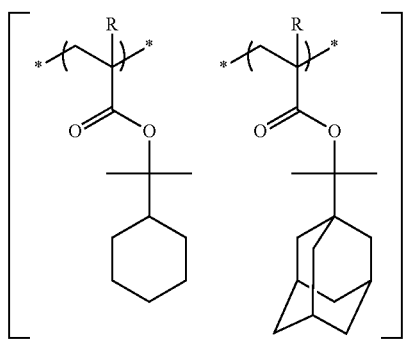

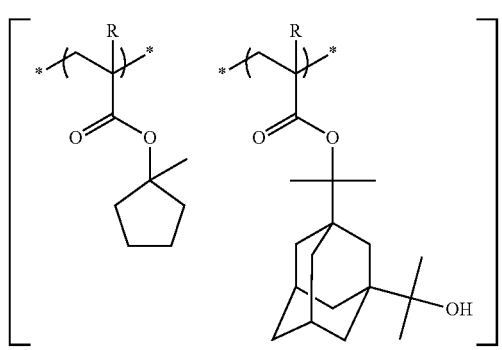

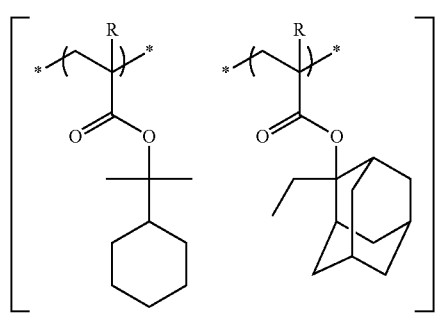

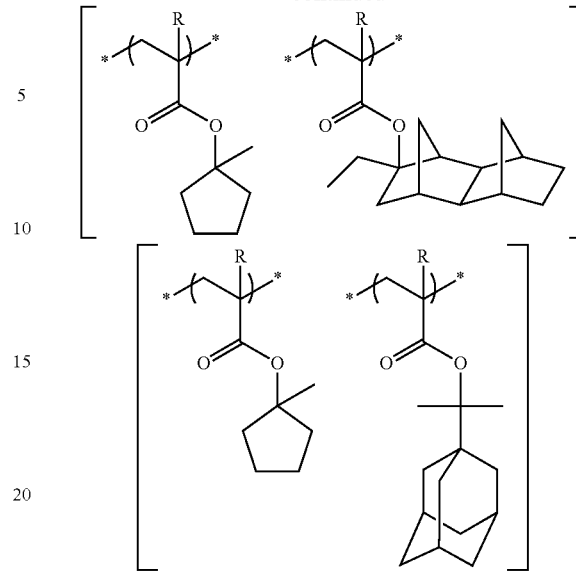

The resin (A) preferably contains a repeating unit having a lactone structure represented by general formula (III) below.

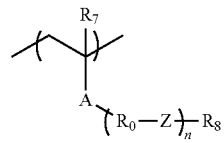

In formula (III),

A represents an ester bond (—COO—) or an amido bond (—CONH—).

Ro, each independently in the presence of two or more groups, represents an alkylene group, a cycloalkylene group or a combination thereof.

Z, each independently in the presence of two or more groups, represents an ether bond, an ester bond, an amido bond, a urethane bond
(a group represented by

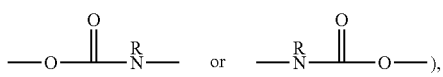

or a urea bond
(a group represented by

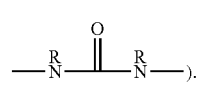

Each of Rs independently represents a hydrogen atom, an alkyl group, cycloalkyl group or an aryl group.

$R_8$ represents a monovalent organic group with a lactone structure.

n represents the number of repetitions of the structure of the formula —$R_0$—Z— and is an integer of 1 to 5.

$R_7$ represents a hydrogen atom, a halogen atom or an alkyl group.

Each of the alkylene group and cycloalkylene group represented by $R_0$ may have a substituent.

Z preferably represents an ether bond or an ester bond, most preferably an ester bond.

The alkyl group represented by $R_7$ is preferably an alkyl group having 1 to 4 carbon atoms, more preferably a methyl group or an ethyl group and most preferably a methyl group. The alkyl group represented by $R_7$ may be substituted. As substituents, there can be mentioned, for example, a halogen atom such as a fluorine atom, a chlorine atom or a bromine atom, a mercapto group, a hydroxyl group, an alkoxy group such as a methoxy group, an ethoxy group, an isopropoxy group, a t-butoxy group or a benzyloxy group, an acyl group such as an acetyl group or a propionyl group, an acetoxy group and the like. $R_7$ is preferably a hydrogen atom, a methyl group, a trifluoromethyl group or a hydroxymethyl group.

The alkylene group represented by $R_0$ is preferably a chain alkylene group having 1 to 10 carbon atoms, more preferably 1 to 5 carbon atoms, for example, a methylene group, an ethylene group, a propylene group or the like. The cycloalkylene group is preferably a cycloalkylene group having 3 to 20 carbon atoms. As such, there can be mentioned, for example, cyclohexylene, cyclopentylene, norbornylene, adamantylene or the like. The chain alkylene groups are preferred from the viewpoint of the exertion of the effect of the present invention. A methylene group is most preferred.

The monovalent organic group with a lactone structure represented by $R_8$ is not limited as long as the lactone structure is contained. As particular examples thereof, there can be mentioned the lactone structures of general formulae (LC1-1) to (LC1-17) to be described hereinafter. Of these, the structures of general formula (LC1-4) are most preferred. In general formulae (LC1-1) to (LC1-17), $n_2$ is more preferably 2 or less.

$R_8$ preferably represents a monovalent organic group with an unsubstituted lactone structure or a monovalent organic group with a lactone structure substituted with a methyl group, a cyano group or an alkoxycarbonyl group. More preferably, $R_8$ represents a monovalent organic group with a lactone structure substituted with a cyano group (cyanolactone).

Specific examples of the repeating units having a group with a lactone structure represented by general formula (III) will be shown below, which however in no way limit the scope of the present invention.

In the specific examples, R represents a hydrogen atom, an optionally substituted alkyl group or a halogen atom. R is preferably a hydrogen atom, a methyl group, a hydroxymethyl group or an acetoxymethyl group.

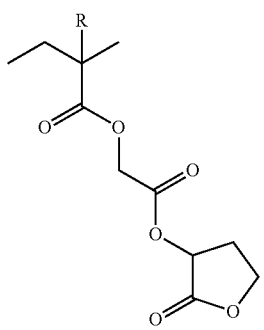

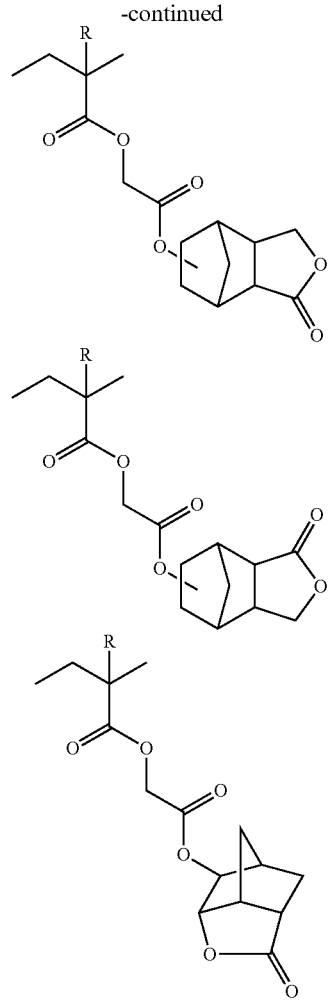

The repeating units having a lactone structure are preferably those of general formula (III-1) below.

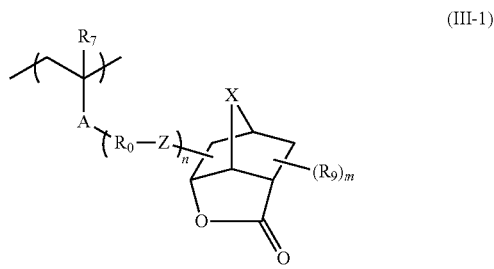

(III-1)

In general formula (III-1), $R_7$, A, $R_0$, Z and n are as defined in general formula (III) above.

$R_9$, when m≥2 each of Rb's independently, represents an alkyl group, a cycloalkyl group, an alkoxycarbonyl group, a cyano group, a hydroxyl group or an alkoxy group. When m≥2, two or more $R_9$'s may be bonded to each other to thereby form a ring.

X represents an alkylene group, an oxygen atom or a sulfur atom.

In the formula, m is the number of substituents, being an integer of 0 to 5; and preferably 0 or 1.

The alkyl group represented by $R_9$ is preferably an alkyl group having 1 to 4 carbon atoms, more preferably a methyl group or an ethyl group, and most preferably a methyl group. As the cycloalkyl group, there can be mentioned, for example, a cyclopropyl group, a cyclobutyl group, a cyclopentyl group or a cyclohexyl group. As the alkoxycarbonyl group, there can be mentioned, for example, a methoxycarbonyl group, an ethoxycarbonyl group, an n-butoxycarbonyl group or a t-butoxycarbonyl group. As the alkoxy group, there can be mentioned, for example, a methoxy group, an ethoxy group, a propoxy group, isopropoxy group or a butoxy group. These groups may have one or more substituents. As such substituents, there can be mentioned, for example, a hydroxyl group; an alkoxy group such as a methoxy group or an ethoxy group; a cyano group; and a halogen atom such as a fluorine atom. More preferably, $R_9$ is a methyl group, a cyano group or an alkoxycarbonyl group, further more preferably a cyano group.

As the alkylene group represented by X, there can be mentioned, for example, a methylene group or an ethylene group. X is preferably an oxygen atom or a methylene group, more preferably a methylene group.

When $m \geq 1$, it is preferred for the substitution with at least one $R_9$ to take place at the α- or β-position of the carbonyl group of the lactone. The substitution with $R_9$ at the α-position of the carbonyl group of the lactone is especially preferred.

Specific examples of the repeating units having a group with a lactone structure represented by formula (III-1) will be shown below, which however in no way limit the scope of the present invention. In the specific examples, R represents a hydrogen atom, an optionally substituted alkyl group or a halogen atom. R is preferably a hydrogen atom, a methyl group, a hydroxymethyl group or an acetoxymethyl group.

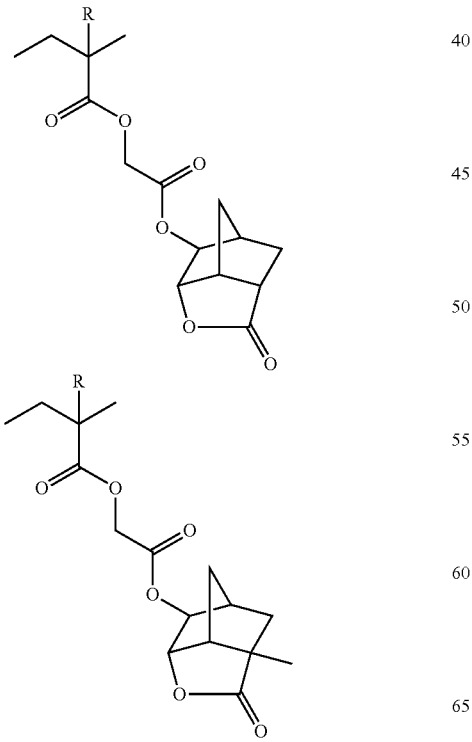

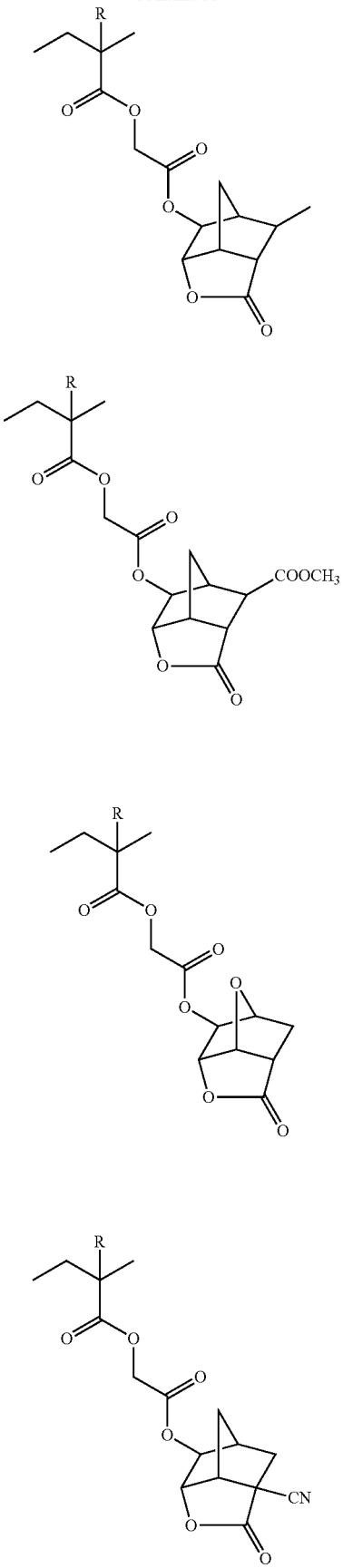

27
-continued
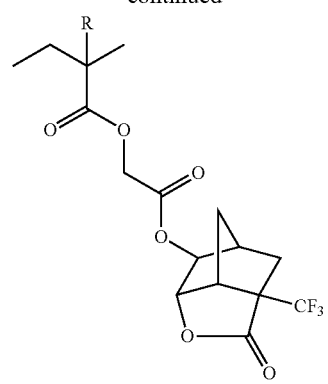
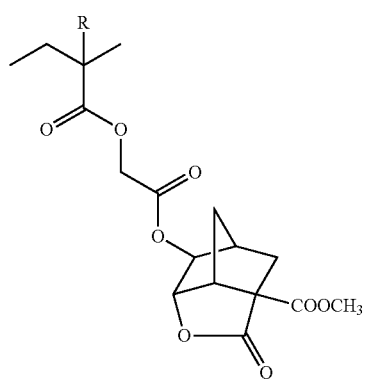
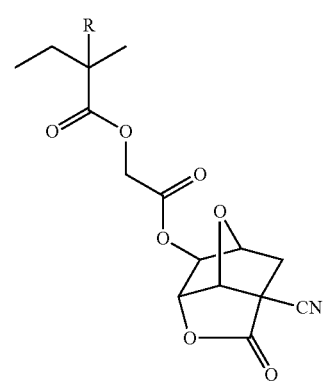
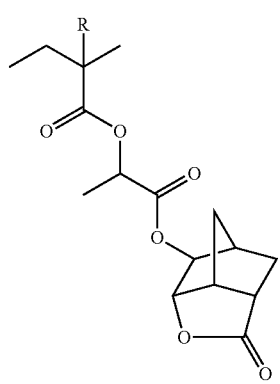
28
-continued
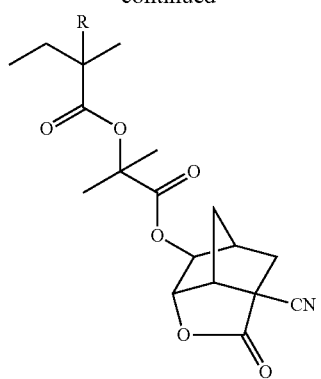
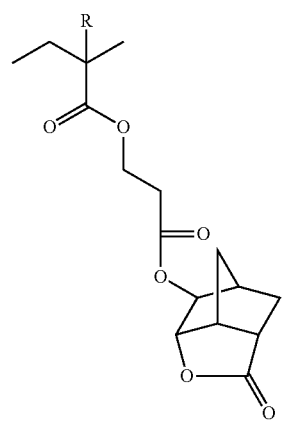
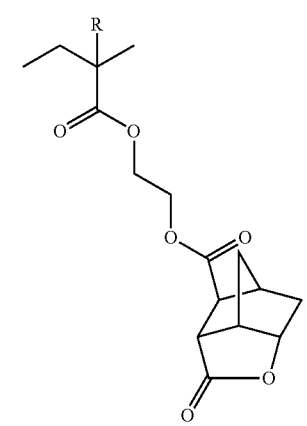
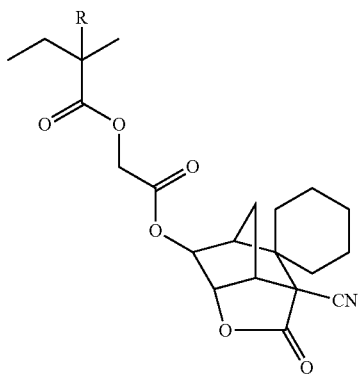

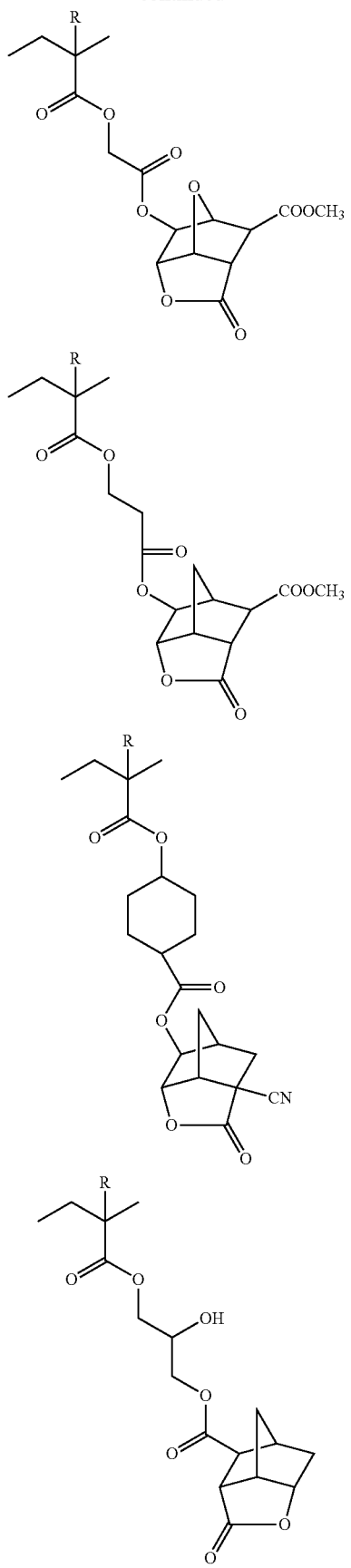
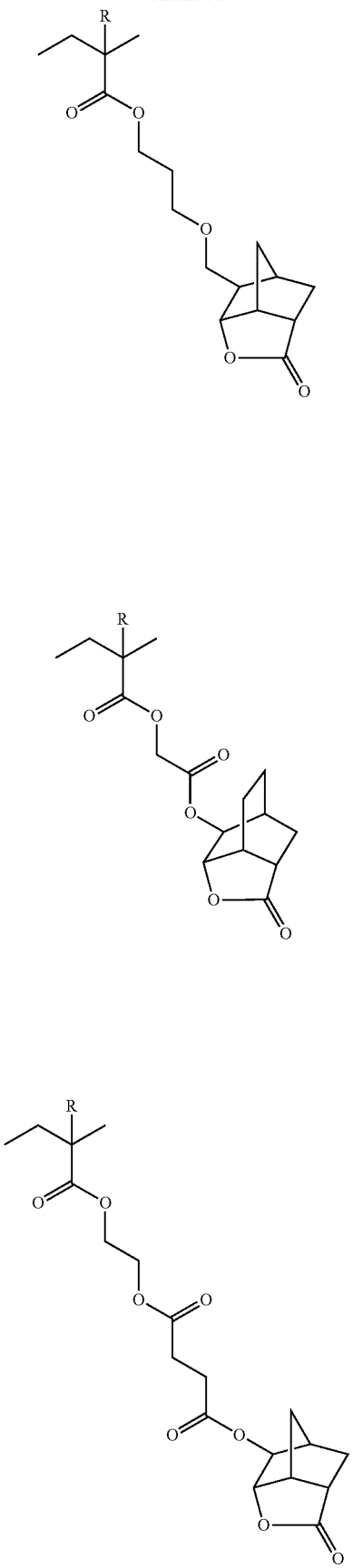

-continued

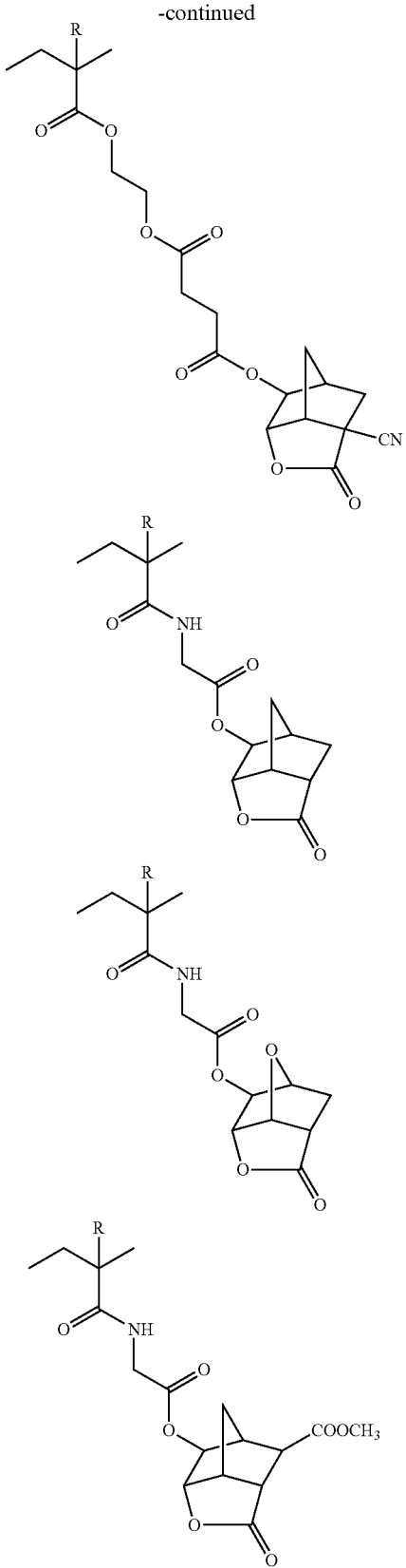

preferably 20 to 60 mol % and further more preferably 30 to 50 mol %, based on all the repeating units of the resin (A).

The resin (A) may contain a repeating unit containing a lactone group besides the units of general formula (III).

Any lactone groups can be employed as long as a lactone structure is possessed therein. However, lactone structures of a 5 to 7-membered ring are preferred, and in particular, those resulting from condensation of lactone structures of a 5 to 7-membered ring with other cyclic structures effected in a fashion to form a bicyclo structure or spiro structure are preferred. The possession of repeating units having a lactone structure represented by any of the following general formulae (LC1-1) to (LC1-17) is more preferred. The lactone structures may be directly bonded to the principal chain of the resin. Preferred lactone structures are those of formulae (LC1-1), (LC1-4), (LC1-5), (LC1-6), (LC1-13), (LC1-14) and (LC1-17). The use of these specified lactone structures would ensure improvement in the LWR and development defect.

LC1-1

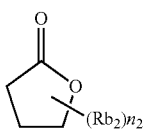

LC1-2

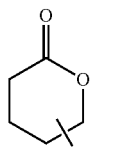

LC1-3

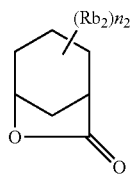

LC1-4

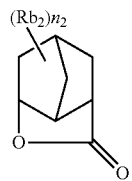

LC1-5

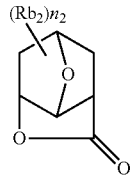

LC1-6

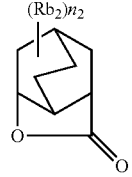

The content of any of the repeating units of general formula (III), the total content when two or more types thereof are contained, is preferably in the range of 15 to 60 mol %, more LC1-7 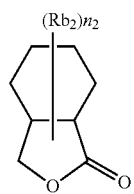

LC1-8 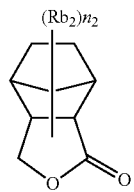

LC1-9 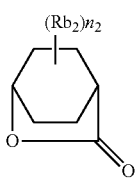

LC1-10 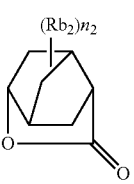

LC1-11 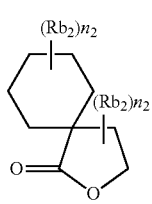

LC1-12 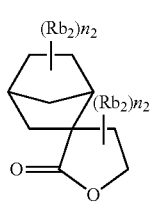

LC1-13 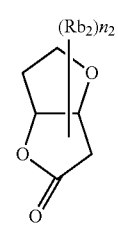

LC1-14 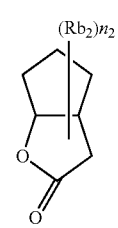

LC1-15 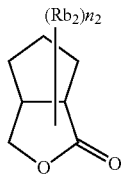

LC1-16 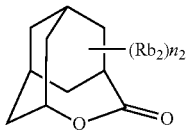

LC1-17 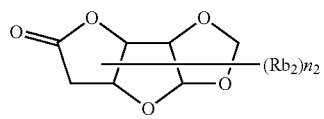

The presence of a substituent ($Rb_2$) on the portion of the lactone structure is optional. As a preferred substituent ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, $n_2$ is an integer of 0 to 4. When $n_2$ is 2 or greater, the plurality of present substituents ($Rb_2$) may be identical to or different from each other. Further, the plurality of present substituents ($Rb_2$) may be bonded to each other to thereby form a ring.

As the repeating units containing a lactone structure besides the units of general formula (III), a repeating unit represented by general formula (AII') below can be exemplified.

(AII')

In general formula (AII'), $Rb_0$ represents a hydrogen atom, a halogen atom or an alkyl group having 1 to 4 carbon atoms. As preferred substituents that may be introduced in the alkyl group represented by $Rb_0$, there can be mentioned a hydroxyl group and a halogen atom. As the halogen atom, there can be mentioned a fluorine atom, a chlorine atom, a bromine atom or an iodine atom. Preferably, $Rb_0$ represents a hydrogen atom, a methyl group, a hydroxymethyl group, or a trifluoromethyl group, and more preferably a hydrogen atom or a methyl group.

V represents any of the groups of the general formulae (LC1-1) to (LC1-17).

Specific examples of repeating unit containing a lactone structure besides the units of general formula (III) will be shown below, which in no way limit the scope of the present invention.

In the formulae, Rx represents H, $CH_3$, $CH_2OH$, or $CF_3$.

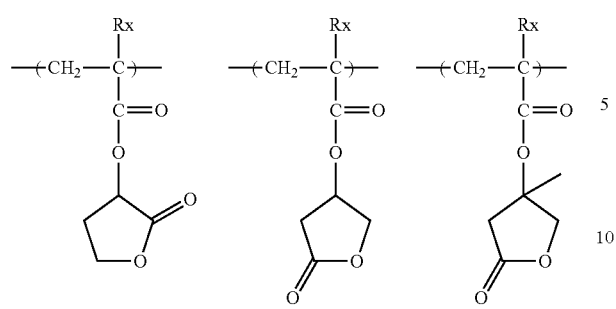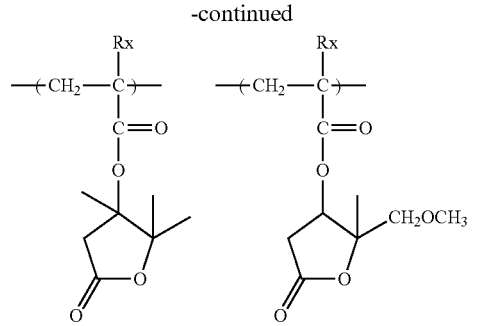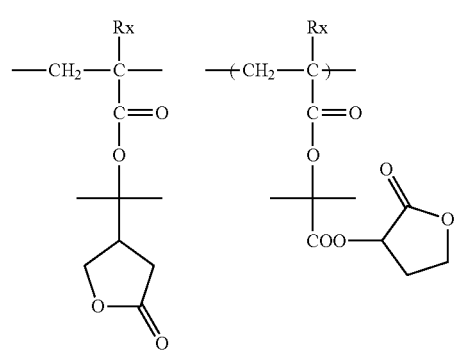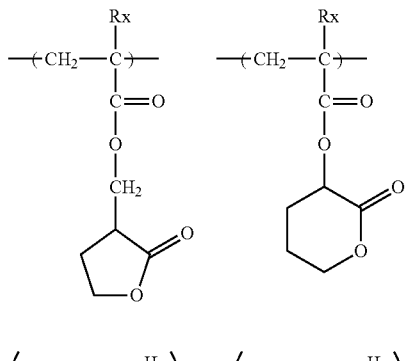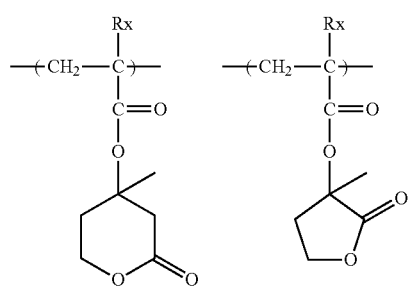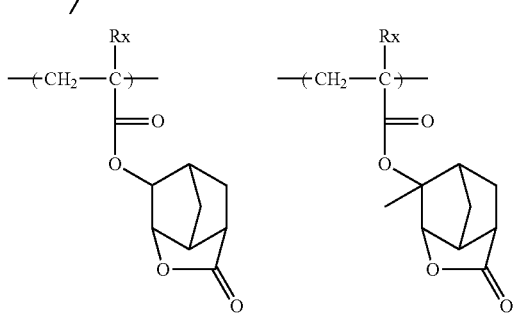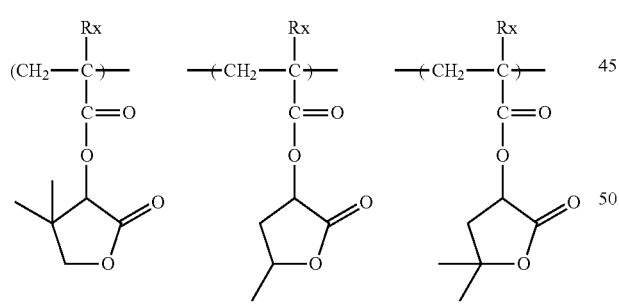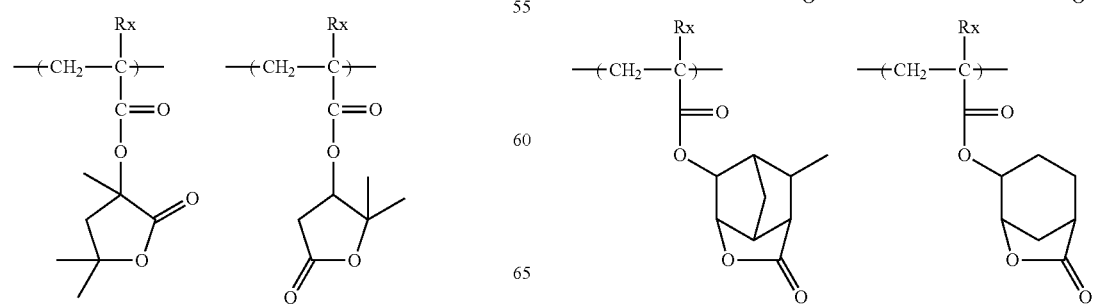

37
-continued
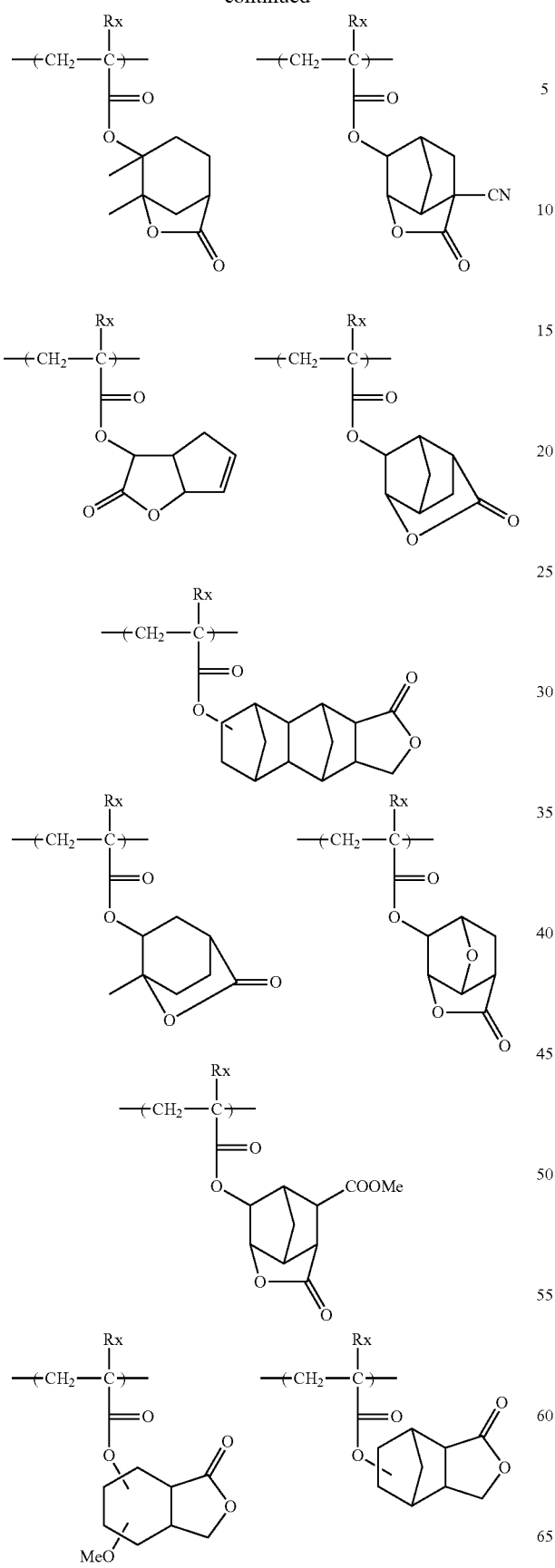
38
-continued
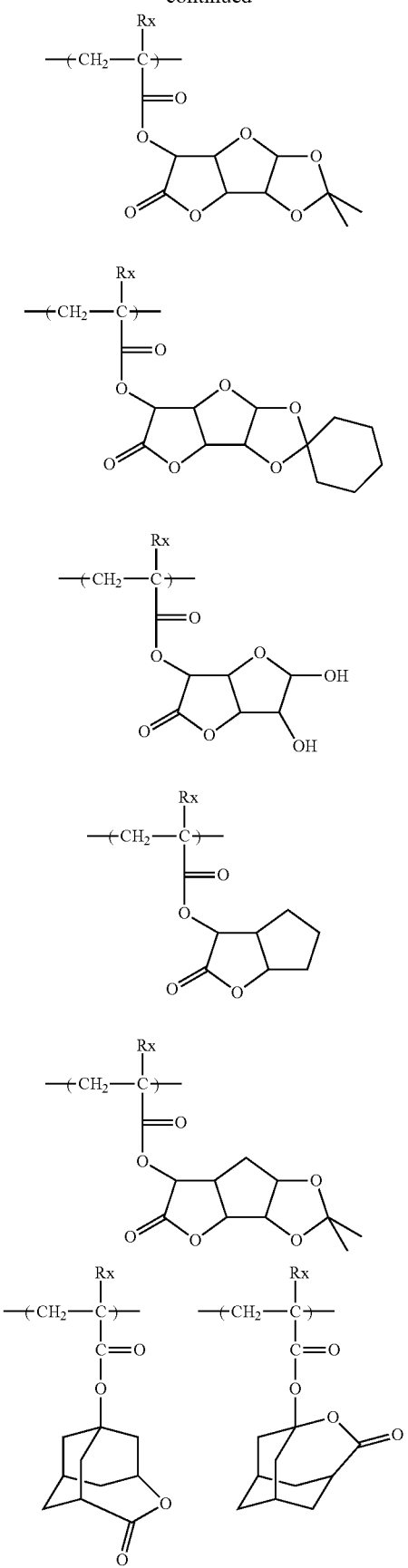

-continued
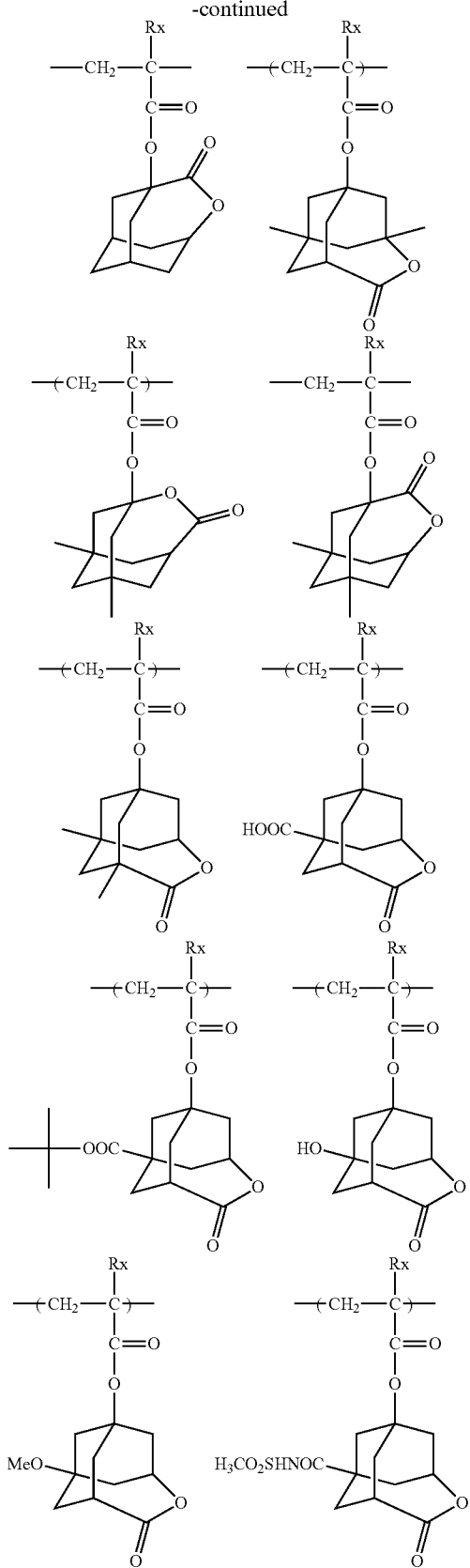
As especially preferred repeating units each containing a lactone group other than the units of general formula (III), there can be mentioned the following repeating units. Favorable pattern profile and iso/dense bias can be realized by selecting most appropriate lactone groups.
In the formulae, Rx represents H, $CH_3$, $CH_2OH$, or $CF_3$.
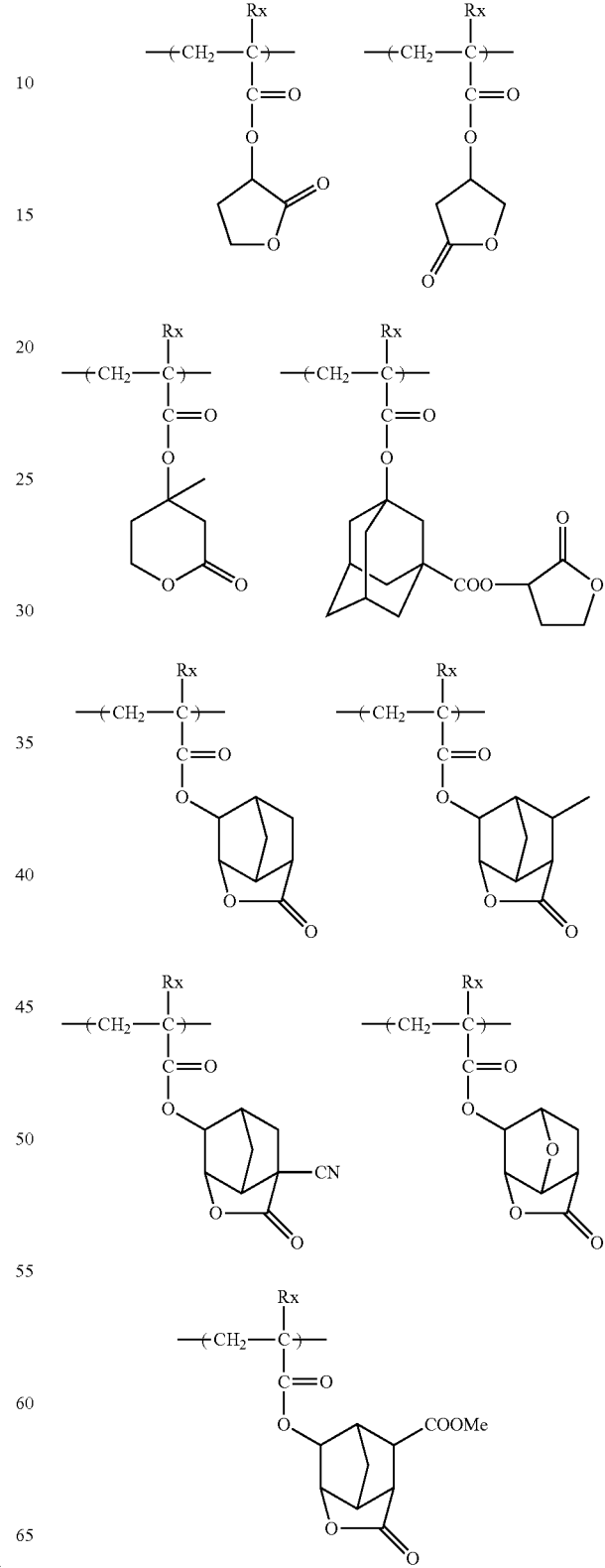

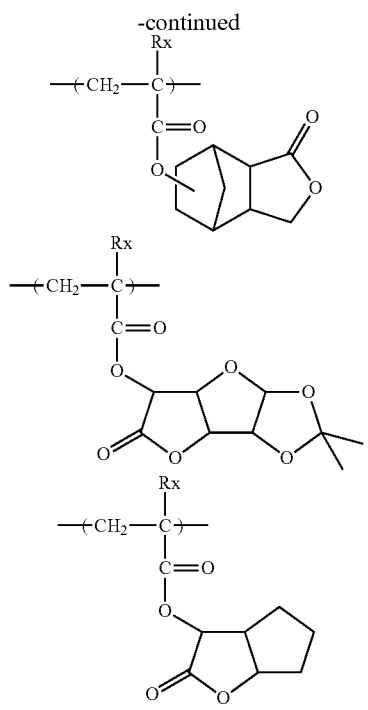

The repeating unit having a lactone group is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity thereof is preferably 90% ee or higher, more preferably 95% ee or higher.

The content of repeating unit containing a lactone group other than the repeating units of general formula (III), the total content when two or more types thereof are contained, is preferably in the range of 15 to 60 mol %, more preferably 20 to 50 mol % and further more preferably 30 to 50 mol %, based on all the repeating units of the resin.

In order to enhance the effect of the present invention, two or more types of lactone repeating units selected from among those of general formula (III) can be used in combination. When such a combinational use is conducted, it is preferred to select two or more from among the lactone repeating units of general formula (III) in which n is 1 and use them in combination.

The resin (A) may further contain a repeating unit containing a hydroxy group or a cyano group other than repeating units represented by general formulae (AI) and (III). The containment of this repeating unit would realize enhancements of adhesion to substrate and developer affinity. The repeating unit containing a hydroxy group or a cyano group is preferably a repeating unit having an alicyclic hydrocarbon structure substituted with a hydroxy group or a cyano group. Further, the repeating unit containing a hydroxy group or a cyano group is preferably free from the acid-decomposable group. In the alicyclic hydrocarbon structure substituted with a hydroxy group or a cyano group, the alicyclic hydrocarbon structure preferably consists of an adamantyl group, a diamantyl group or a norbornane group. As preferred alicyclic hydrocarbon structures substituted with a hydroxy group or a cyano group, the partial structures represented by the following general formulae (VIIa) to (VIId) can be exemplified.

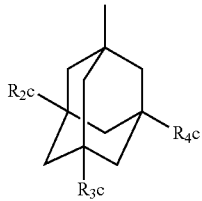

(VIIa)

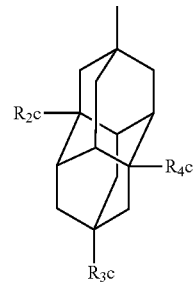

(VIIb)

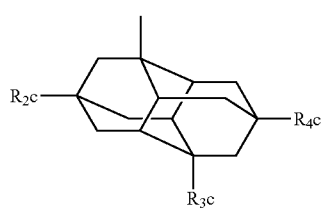

(VIIc)

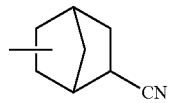

(VIId)

In the general formulae (VIIa) to (VIIc), each of $R_2c$ to $R_4c$ independently represents a hydrogen atom, a hydroxy group or a cyano group, with the proviso that at least one of the $R_2c$ to $R_4c$ represents a hydroxy group or a cyano group. Preferably, one or two of the $R_2c$ to $R_4c$ are hydroxy groups and the remainder is a hydrogen atom. In the general formula (VIIa), more preferably, two of the $R_2c$ to $R_4c$ are hydroxy groups and the remainder is a hydrogen atom.

As the repeating units having any of the partial structures represented by the general formulae (VIIa) to (VIId), those of the following general formulae (AIIa) to (AIId) can be exemplified.

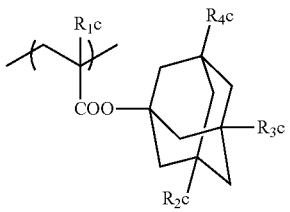

(AIIa)

-continued

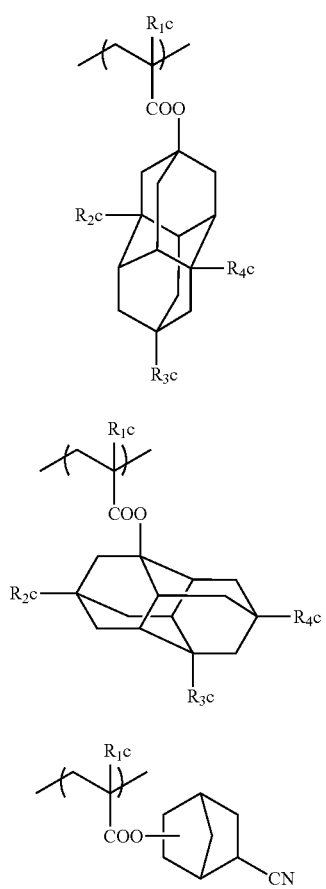

In general formulae (AIIa) to (AIId), $R_1c$ represents a hydrogen atom, a methyl group, a trifluoromethyl group or a hydroxymethyl group.

$R_2c$ to $R_4c$ have the same meaning as those of the general formulae (VIIa) to (VIIc).

The content of the repeating unit containing a hydroxyl group or a cyano group based on all the repeating units of the resin (A) is preferably in the range of 5 to 40 mol %, more preferably 5 to 30 mol % and further more preferably 10 to 25 mol %.

Specific examples of the repeating units containing a hydroxyl group or a cyano group will be shown below, which however in no way limit the scope of the present invention.

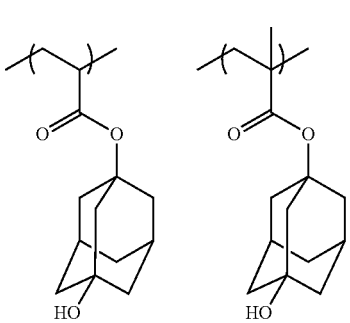

-continued

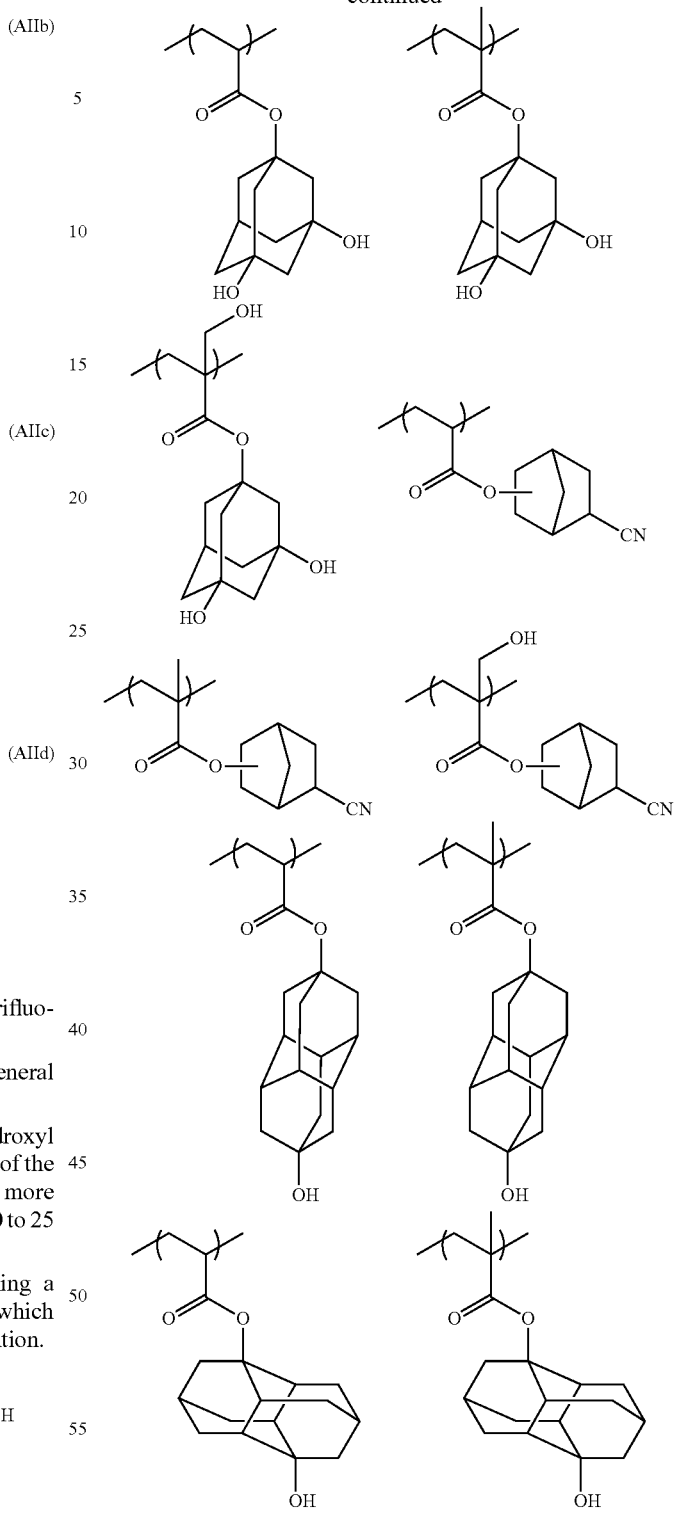

The resin (A) may contain a repeating unit containing an alkali-soluble group. As the alkali-soluble group, there can be mentioned a phenolic hydroxyl group, a carboxyl group, a sulfonamido group, a sulfonylimido group, a bisulfonylimido group or an aliphatic alcohol substituted at its α-position with an electron withdrawing group (for example, a hexafluoroisopropanol group). It is more preferred to contain a repeating unit containing a carboxyl group. The incorporation of the repeating unit containing an alkali-soluble group increases the resolution in contact hole usage. The repeating unit containing an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a mono- or polycyclohydrocarbon structure. The repeating unit of acrylic acid or methacrylic acid is especially preferred.

The content of the repeating unit containing an alkali-soluble group based on all the repeating units of the resin is preferably in the range of 0 to 20 mol %, more preferably 3 to 15 mol % and further more preferably 5 to 10 mol %.

Specific examples of the repeating units containing an alkali-soluble group will be shown below, which however in no way limit the scope of the present invention.

In the specific examples, Rx represents H, $CH_3$, $CH_2OH$, or $CF_3$.

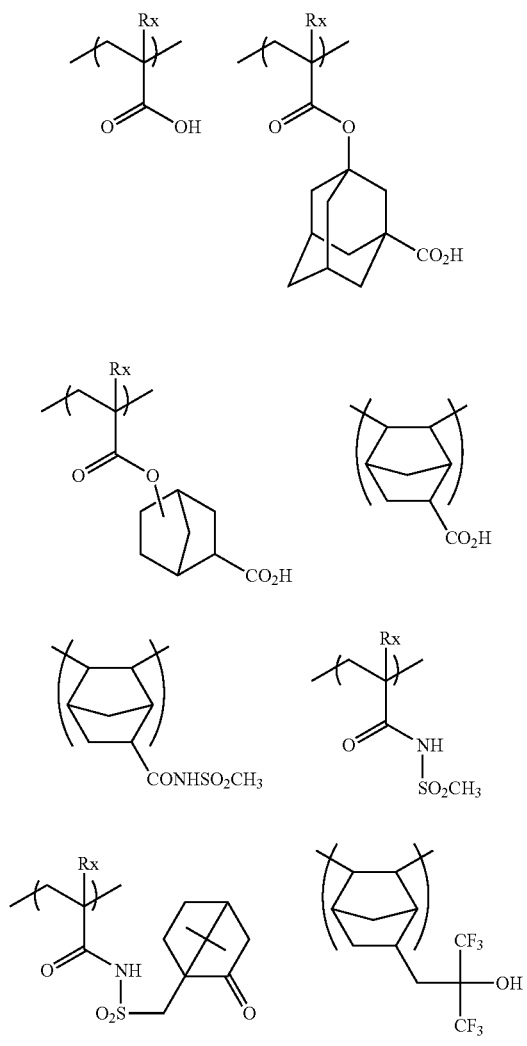

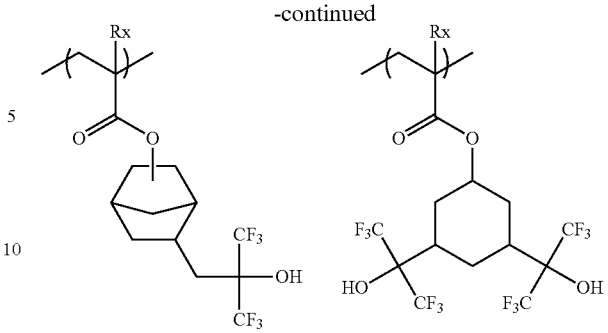

The resin (A) may further contain a repeating unit having an alicyclic hydrocarbon structure containing no polar group, which repeating unit exhibits no acid decomposability. As the repeating unit, there can be mentioned, for example, any of those of general formula (IV) below.

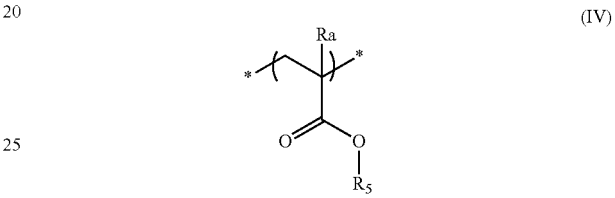

(IV)

In general formula (IV), $R_5$ represents a hydrocarbon group having at least one cyclic structure in which neither a hydroxyl group nor a cyano group is contained.

Ra represents a hydrogen atom, an alkyl group or a group of the formula —$CH_2$—O—$Ra_2$ in which $Ra_2$ represents a hydrogen atom, an alkyl group or an acyl group. Ra is preferably a hydrogen atom, a methyl group, a hydroxymethyl group or a trifluoromethyl group, further preferably a hydrogen atom or a methyl group.

The cyclic structures contained in $R_5$ include a monocyclic hydrocarbon group and a polycyclic hydrocarbon group. As the monocyclic hydrocarbon group, a cycloalkyl group having 3 to 12 carbon atoms and a cycloalkenyl group having 3 to 12 carbon atoms can be exemplified. Preferably, the monocyclic hydrocarbon group is a monocyclic hydrocarbon group having 3 to 7 carbon atoms. As such, a cyclopentyl group and a cyclohexyl group can be exemplified.

The polycyclic hydrocarbon groups include ring-assembly hydrocarbon groups and crosslinked-ring hydrocarbon groups.

As the ring-assembly hydrocarbon groups, for example, a bicyclohexyl group and a perhydronaphthalenyl group can be exemplified.

As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0$^{2,6}$]decane and tricyclo[4.3.1.1$^{2,5}$] undecane rings; and tetracyclic hydrocarbon rings, such as tetracyclo[4.4.0.1$^{2,5}$.1$^{7,10}$]dodecane and perhydro-1,4-methano-5,8-methanonaphthalene rings.

Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenalene rings.

As preferred crosslinked-ring hydrocarbon rings, there can be mentioned a norbornyl group, an adamantyl group, a bicyclooctanyl group, a tricyclo[5.2.1.0$^{2,6}$]decanyl group and the like. As more preferred crosslinked-ring hydrocarbon rings, there can be mentioned a norbornyl group and an adamantyl group.

These alicyclic hydrocarbon groups may have one or more substituents. As preferred substituents, a halogen atom, an alkyl group, a hydroxyl group protected by a protective group, and an amino group protected by a protective group can be exemplified. The halogen atom is preferably a bromine, chlorine or fluorine atom. The alkyl group is preferably a methyl, ethyl, butyl or t-butyl group. The alkyl group may further have one or more substituents. As the optional substituent, a halogen atom, an alkyl group, a hydroxyl group protected by a protective group, and an amino group protected by a protective group can be exemplified.

As the protective group, an alkyl group, a cycloalkyl group, an aralkyl group, a substituted methyl group, a substituted ethyl group, an alkoxycarbonyl group and an aralkyloxycarbonyl group can be exemplified. Preferred alkyl groups include alkyl groups having 1 to 4 carbon atoms. Preferred substituted methyl groups include methoxymethyl, methoxythiomethyl, benzyloxymethyl, t-butoxymethyl and 2-methoxyethoxymethyl groups. Preferred substituted ethyl groups include 1-ethoxyethyl and 1-methyl-1-methoxyethyl groups. Preferred acyl groups include aliphatic acyl groups having 1 to 6 carbon atoms, such as formyl, acetyl, propionyl, butyryl, isobutyryl, valeryl and pivaloyl groups. Preferred alkoxycarbonyl groups include alkoxycarbonyl groups having 1 to 4 carbon atoms and the like.

The content of the repeating unit having an alicyclic hydrocarbon structure containing no polar group, which repeating unit exhibits no acid decomposability, based on all the repeating units of the resin (A) is preferably in the range of 0 to 40 mol %, more preferably 0 to 20 mol %.

Specific examples of the repeating unit having an alicyclic hydrocarbon structure containing no polar group, which repeating unit exhibits no acid decomposability will be shown below, which however in no way limit the scope of the present invention. In the formulae, Ra represents H, $CH_3$, $CH_2OH$ or $CF_3$.

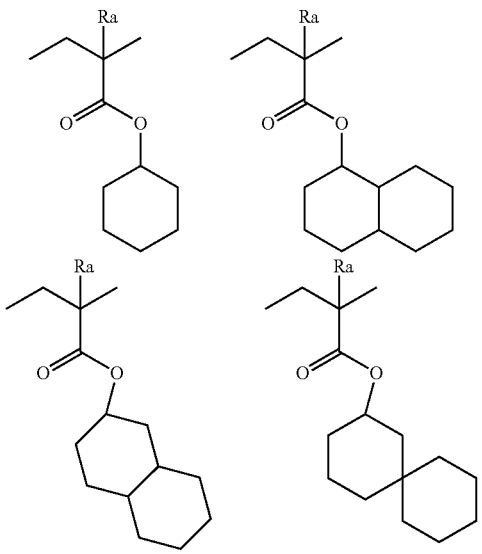

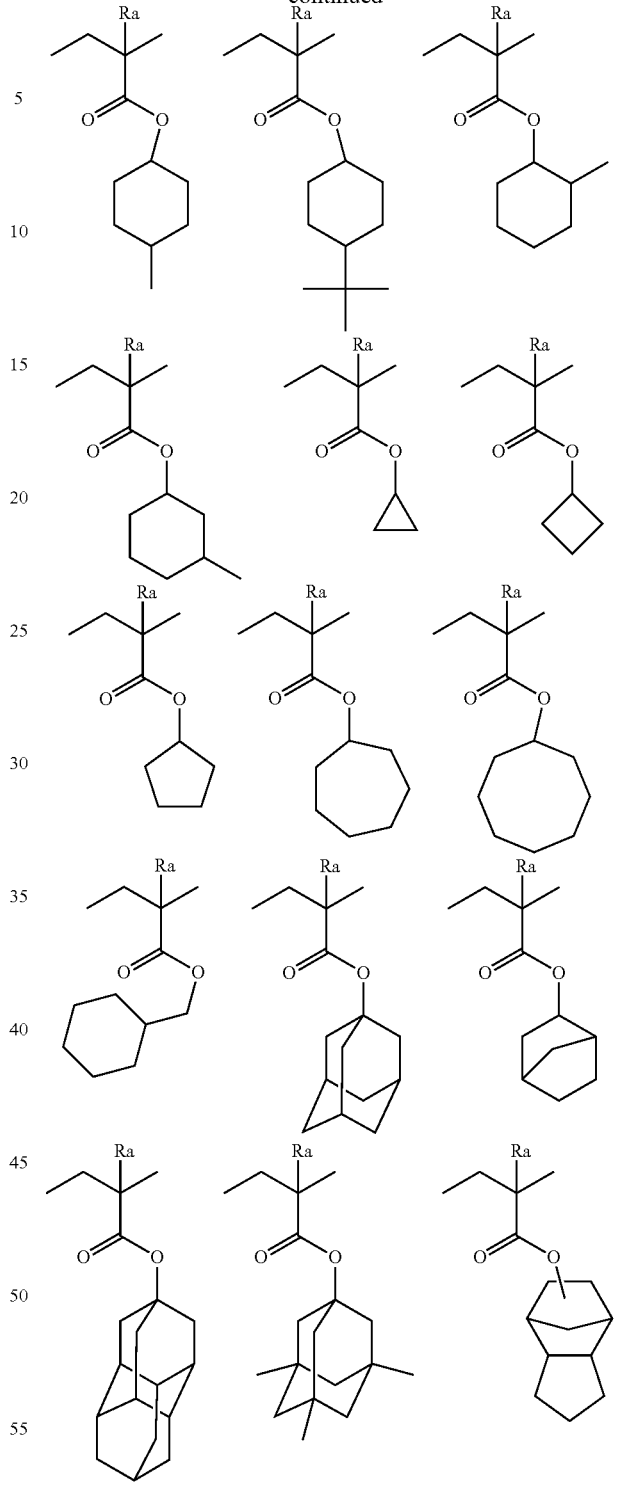

Various repeating structural units other than those mentioned hereinbefore can be introduced in the resin (A) in order to regulate the dry etching resistance, standard developer adaptability, adherence to substrates, pattern profile, resolving power, heat resistance, sensitivity, and the like.

As such other repeating structural units, those corresponding to the following monomers can be exemplified, which however are nonlimiting.

Such other repeating structural units would permit fine regulation of the properties required to have by the resin for use in the composition of the present invention, especially, (1) solubility in applied solvents, (2) film forming easiness (glass transition temperature), (3) alkali developability, (4) film thinning (selection of hydrophilicity/hydrophobicity and alkali soluble group), (5) adhesion of unexposed areas to substrate, and (6) dry etching resistance, etc.

As the above-mentioned monomers, compounds having an unsaturated bond capable of addition polymerization, selected from among acrylic esters, methacrylic esters, acrylamides, methacrylamides, allyl compounds, vinyl ethers, vinyl esters and the like can be exemplified.

The monomers are not limited to the above, and unsaturated compounds capable of addition polymerization that are copolymerizable with the monomers corresponding to the above various repeating structural units can be used in the copolymerization.

The molar ratios of individual repeating structural units contained in the resin (A) are appropriately determined from the viewpoint of regulation of not only the resist dry etching resistance but also the standard developer adaptability, substrate adhesion, pattern profile, resolving power, heat resistance, sensitivity, and the like.

When the composition of the present invention is used in ArF exposure, it is preferred for the resin (A) to contain no aromatic group from the viewpoint of transparency to ArF light. It is especially preferred for the acid-decomposable resin to contain an alicyclic hydrocarbon structure of a single ring or multiple rings.

Further, it is preferred for the resin (A) to contain neither a fluorine atom nor a silicon atom from the viewpoint of compatibility with a hydrophobic resin to be described hereinafter.

Preferred resin (A) is that whose repeating units consisting of (meth)acrylate repeating units. In that instance, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units.

Further, a copolymer containing 20 to 50 mol % of (meth) acrylate repeating unit having an acid-decomposable group; 20 to 50 mol % of (meth)acrylate repeating unit having a lactone structure; 5 to 30 mol % of (meth)acrylate repeating unit containing a hydroxy group or a cyano group; and 0 to 20 mol % of other (meth)acrylate repeating units is more preferred.

In the event of exposing the composition of the present invention to KrF excimer laser beams, electron beams, X-rays or high-energy light rays of wavelength 50 nm or less (EUV, etc.), it is preferred for the resin (A) to further have hydroxystyrene repeating units. More preferably, the resin has hydroxystyrene repeating units, hydroxystyrene repeating units protected by an acid-decomposable group and acid-decomposable repeating units of a (meth)acrylic acid tertiary alkyl ester, etc.

As preferred hydroxystyrene repeating units having an acid-decomposable group, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl(meth)acrylate and a dialkyl(1-adamantyl)methyl (meth)acrylate are more preferred.

The resin (A) of the present invention can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or the solvent capable of dissolving the composition of the present invention, such as propylene glycol monomethyl ether acetate, propylene glycol monomethyl ether or cyclohexanone, to be described hereinafter. It is preferred to perform the polymerization with the use of the same solvent as employed in the actinic-ray- or radiation-sensitive resin composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10 to 150° C., preferably 30 to 120° C. and more preferably 60 to 100° C.

Further, the operation of dissolving a synthesized resin in a solvent to thereby obtain a solution and heating the solution at about 30 to 90° C. for about 30 minutes to 4 hours as described in, for example, JP-A-2009-037108 may be added in order to inhibit any aggregation, etc. of the resin after the preparation of the composition.

The weight average molecular weight of the resin (A) in terms of polystyrene molecular weight as measured by GPC is preferably in the range of 1000 to 200,000, more preferably 2000 to 20,000, still more preferably 3000 to 15,000 and further preferably 5000 to 13,000. The regulation of the weight average molecular weight to 1000 to 200,000 would prevent deteriorations of heat resistance and dry etching resistance and also prevent deterioration of developability and increase of viscosity leading to poor film forming property.

Use is made of the resin whose dispersity (molecular weight distribution) is usually in the range of 1 to 3, preferably 1 to 2.6, more preferably 1 to 2 and most preferably 1.4 to 2.0. The lower the molecular weight distribution, the more excellent the resolving power and resist profile and the smoother the side wall of the resist pattern to thereby attain an excellence in roughness.

The resin (A) of the present invention may either be used individually or in combination.

In the present invention, the content ratio of the resin (A) based on the total solid content of the whole composition is preferably in the range of 30 to 99 mass %, and more preferably 60 to 95 mass %.

(B) Compounds of General Formula (1-1)

As mentioned above, the composition of the present invention comprises any of the compounds of general formula (1-1) below (hereinafter also referred to as component (B)). These compounds are decomposed when exposed to actinic rays or radiation to thereby generate acids. Namely, these compounds work as acid generators.

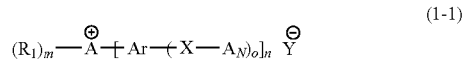

(1-1)

In the formula,

A represents a sulfur atom or an iodine atom.

$R_1$, each independently when m=2, represents an alkyl group, an alkenyl group, a cycloaliphatic group, an aromatic hydrocarbon group or a heterocyclic hydrocarbon group, provided that when m=2, two $R_1$s may be bonded to each other to thereby form a ring.

Ar, each independently when n≥2, represents an aromatic ring group.

X, each independently when o≥2 and/or n≥2, represents a connecting group having a carbon atom to which Ar is bonded.

$A_N$, each independently when o≥2 and/or n≥2, represents a basic moiety containing a nitrogen atom.

When A is a sulfur atom, n is an integer of 1 to 3 and m is an integer satisfying the relationship m+n=3.

When A is an iodine atom, n is an integer of 1 or 2 and m is an integer satisfying the relationship m+n=2.

o is an integer of 1 to 10.

$Y^-$ represents an anion.

The compounds of general formula (1-1) above exhibit high photodecomposability, so that when the compounds are used as acid generators, high sensitivity can be realized.

$R_1$, each independently when m=2, represents an alkyl group, an alkenyl group, a cycloaliphatic group, an aromatic hydrocarbon group or a heterocyclic hydrocarbon group. When m=2, two $R_1$s may be bonded to each other to thereby form a ring. A substituent may further be introduced in each of the groups and ring.

The alkyl group represented by $R_1$ may be in the form of a linear or branched chain. This alkyl group preferably has 1 to 50 carbon atoms, more preferably 1 to 30 carbon atoms and further more preferably 1 to 20 carbon atoms. As such an alkyl group, there can be mentioned, for example, a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group or a 2-ethylhexyl group.

The alkenyl group represented by $R_1$ may be in the form of a linear or branched chain. This alkenyl group preferably has 2 to 50 carbon atoms, more preferably 2 to 30 carbon atoms and further more preferably 3 to 20 carbon atoms. As such an alkenyl group, there can be mentioned, for example, a vinyl group, an allyl group or a styryl group.

The cycloaliphatic group represented by $R_1$ is, for example, a cycloalkyl group. The cycloalkyl group may be monocyclic or polycyclic. This cycloaliphatic group is preferably a monocycloalkyl group having 3 to 8 carbon atoms, such as a cyclopropyl group, a cyclopentyl group or a cyclohexyl group.

The aromatic hydrocarbon group represented by $R_1$ is preferably one having 6 to 14 carbon atoms. As such a group, there can be mentioned, for example, an aryl group, such as a phenyl group or a naphthyl group. It is preferred for the aromatic hydrocarbon group represented by $R_1$ to be a phenyl group.

The heterocyclic hydrocarbon group represented by $R_1$ may have and may not have aromaticity. It is preferred for the heterocyclic hydrocarbon group to have aromaticity.

The heterocycle contained in the heterocyclic hydrocarbon group may be monocyclic or polycyclic. As the heterocycle, there can be mentioned, for example, an imidazole ring, a pyridine ring, a pyrazine ring, a pyrimidine ring, a pyridazine ring, a 2H-pyrrole ring, a 3H-indole ring, a 1H-indazole ring, a purine ring, an isoquinoline ring, a 4H-quinolizine ring, a quinoline ring, a phthalazine ring, a naphthyridine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isooxazole ring or a benzothiazole ring.

The ring formed by two $R_1$s is preferably a 4- to 7-membered ring, more preferably a 5- or 6-membered ring and most preferably a 5-membered ring.

Preferably, $R_1$ is an aromatic hydrocarbon group, or two $R_1$s are bonded to each other to thereby form a ring.

When substituents are further introduced in the groups represented by $R_1$ and the rings formed by the mutual bonding of two $R_1$s, the substituents are, for example, as follows. Namely, as the substituents, there can be mentioned, for example, a halogen atom (—F, —Br, —Cl or —I), a hydroxyl group, an alkoxy group, an aryloxy group, a mercapto group, an alkylthio group, an arylthio group, an amino group, an acyloxy group, a carbamoyloxy group, an alkylsulfoxy group, an arylsulfoxy group, an acylthio group, an acylamino group, a ureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, a carboxyl group, a carbamoyl group, an alkylsulfinyl group, an arylsulfinyl group, an alkylsulfonyl group, an arylsulfonyl group, a sulfo group (—SO$_3$H) or its conjugated base group (referred to as a sulfonato group), an alkoxysulfonyl group, an aryloxysulfonyl group, a sulfinamoyl group, a phosphono group (—PO$_3$H$_2$) or its conjugated base group (referred to as a phosphonato group), a phosphonooxy group (—OPO$_3$H$_2$) or its conjugated base group (referred to as a phosphonatooxy group), a cyano group, a nitro group, an aryl group, an alkenyl group, an alkynyl group, a heterocyclic group, a silyl group and an alkyl group.

Among these substituents, a halogen atom, an alkyl group, a cycloalkyl group and an alkoxy group are especially preferred. The alkyl group is, for example, the same as mentioned above in connection with $R_1$.

Ar, each independently when n≥2, represents an aromatic ring group. This aromatic ring group may contain a heterocycle as the aromatic ring. This aromatic ring may be monocyclic or polycyclic.

This aromatic ring group preferably has 6 to 14 carbon atoms. As such a group, there can be mentioned, for example, an aryl group, such as a phenyl group, a naphthyl group or an anthryl group. When the aromatic ring group contains a heterocycle, as the heterocycle, there can be mentioned, for example, a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring or a thiazole ring.

The aromatic ring group represented by Ar is preferably a phenyl group or a naphthyl group, most preferably a phenyl group.

A substituent other than the groups of formula: —(X-$A_N$) to be described hereinafter may further be introduced in the aromatic ring group represented by Ar. As the substituent, use can be made of, for example, any of those set forth above in connection with $R_1$.

The aromatic ring group represented by Ar is substituted with any of the groups of formula: —(X-$A_N$).

X, each independently when o≥2 and/or n≥2, represents a connecting group having a carbon atom to which Ar is bonded. $A_N$, each independently when o≥2 and/or n≥2, represents a basic moiety containing a nitrogen atom.

Namely, in the compounds of general formula (1-1), the basic moiety represented by $A_N$ is bonded, through the carbon atom directly bonded to the aromatic ring group represented by Ar, to the aromatic ring group. The inventors have found that excellent roughness characteristics and exposure latitude can be attained by employing this configuration as compared with those realized when the basic moiety is bonded, through the oxygen atom or sulfur atom directly bonded to the aromatic ring group, to the aromatic ring group.

While the relevant mechanism is not necessarily apparent, the inventors presume the following. Namely, when the basic moiety is bonded, through the oxygen atom or sulfur atom directly bonded to the aromatic ring group, to the aromatic ring group, the sensitivity of photoacid generator is lowered as the oxygen atom and sulfur atom exhibit high electron donating properties to the aromatic ring. It can be presumed that the roughness characteristics and exposure latitude are deteriorated in accordance with the lowering of the sensitivity.

The connecting group represented by X is not particularly limited as long as the portion of bonding to Ar is a carbon atom. This connecting group comprises, for example, an alkylene group, a cycloalkylene group, an arylene group, —COO—, —CO— or a combination of these. This connecting group may comprise a combination of any of these groups with at least one member selected from the group consisting of —O—, —S—, —OCO—, —S(=O)—, —S(=O)$_2$—, —OS(=O)$_2$— and —NR—. In the —NR—, R represents a hydrogen atom, an alkyl group, a cycloalkyl group or an aryl group.

The alkylene group optionally contained in the connecting group represented by X may be in the form of a linear or branched chain. The alkylene group preferably has 1 to 20 carbon atoms, more preferably 1 to 10 carbon atoms. As such an alkylene group, there can be mentioned, for example, a methylene group, an ethylene group, a propylene group or a butylene group.

The cycloalkylene group optionally contained in the connecting group represented by X may be monocyclic or polycyclic. The cycloalkylene group preferably has 3 to 20 carbon atoms, more preferably 3 to 10 carbon atoms. As such a cycloalkylene group, there can be mentioned, for example, a 1,4-cyclohexylene group.

The arylene group optionally contained in the connecting group represented by X preferably has 6 to 20 carbon atoms, more preferably 6 to 10 carbon atoms. As such an arylene group, there can be mentioned, for example, a phenylene group or a naphthylene group.

X, or at least one of Xs, is preferably expressed by general formula (1-2) or (1-3) below.

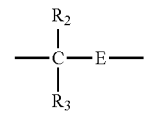

(1-2)

In the formula, each of $R_2$ and $R_3$ independently represents a hydrogen atom, an alkyl group, an alkenyl group, a cycloaliphatic group, an aromatic hydrocarbon group or a heterocyclic hydrocarbon group, provided that $R_2$ and $R_3$ may be bonded to each other to thereby form a ring, and provided that at least one of $R_2$ and $R_3$ may be bonded to E to thereby form a ring.

E represents a connecting group or a single bond.

(1-3)

In the formula,

J represents an oxygen atom or a sulfur atom. J is preferably an oxygen atom.

E represents a connecting group or a single bond.

The groups represented by $R_2$ and $R_3$ and substituents that may further be introduced in the groups are, for example, the same as mentioned above in connection with $R_1$. Each of the ring formed by the bonding of $R_2$ and $R_3$ and the ring formed by the bonding of at least one of $R_2$ and $R_3$ to E is preferably a 4- to 7-membered ring, more preferably a 5- or 6-membered ring. Preferably, each of $R_2$ and $R_3$ independently is a hydrogen atom or an alkyl group.

The connecting group represented by E comprises, for example, an alkylene group, a cycloalkylene group, an arylene group, —COO—, —CO—, —O—, —S—, —OCO—, —S(=O)—, —S(=O)$_2$—, —OS(=O)$_2$—, —NR— or a combination of these.

It is preferred for the connecting group represented by E to be at least one member selected from the group consisting of an alkylene bond, an ester bond, an ether bond, a thioether bond, a urethane bond (a group represented by

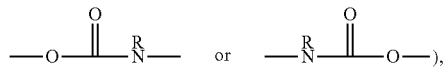

a urea bond
(a group represented by

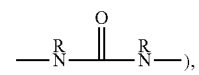

an amide bond and a sulfonamido bond. In the formulae, R represents, for example, a hydrogen atom, an alkyl group, a cycloalkyl group or an aryl group. The connecting group represented by E is more preferably an alkylene bond, an ester bond or an ether bond.

As mentioned above, $A_N$ represents a basic moiety containing a nitrogen atom. Herein, the "basic moiety" refers to the portion of the cation moiety of general formula (1-1) whose conjugate acid exhibits a pKa value of −3 or higher. This pKa value is preferably in the range of −3 to 15, more preferably 0 to 15. The pKa value refers to a value calculated by ACD/ChemSketch (ACD/Labs 8.00 Release Product Version: 8.08).

The basic moiety represented by $A_N$ comprises, for example, an amino group [a group resulting from the removal of one hydrogen atom from ammonia or an amine (a primary amine, a secondary amine, etc.); same hereinafter] or a nitrogen-containing heterocyclic group. In the structure thereof, it is preferred for all the atoms adjacent to nitrogen atom contained in the structure to be carbon or hydrogen atoms from the viewpoint of basicity increase. Also, from the viewpoint of basicity increase, it is preferred that no electron withdrawing functional group (a carbonyl group, a sulfonyl group, a cyano group, a halogen atom, etc.) be directly bonded to the nitrogen atom.

The basic moiety represented by $A_N$ may comprise two or more basic groups, such as amino groups and nitrogen-containing heterocyclic groups.

When the basic moiety represented by $A_N$ comprises an amino group, it is preferred for the amino group to be any of the groups of the formula —NR$_2$. In the formula, R represents, for example, a hydrogen atom, an alkyl group, a cycloalkyl group, an aryl group, an alkoxy group, a cyano group, an ester group, a lactone group or a group containing any of these.

The alkyl group, cycloalkyl group and aryl group represented by R are, for example, the same as set forth above in connection with the alkyl group, cycloalkyl group as a cycloaliphatic group and aromatic hydrocarbon group each represented by R$_1$. Substituents that can further be introduced in the groups represented by R are also the same as set forth above in connection with R$_1$.

When the basic moiety represented by $A_N$ comprises a nitrogen-containing heterocyclic group, the nitrogen-containing heterocyclic group may have and may not have aromaticity. The nitrogen-containing heterocyclic group may be monocyclic or polycyclic. The nitrogen-containing heterocyclic group is preferably a group containing a piperidine ring, a morpholine ring, a pyrrolidine ring, a pyridine ring, an imidazole ring, a pyrazine ring, a pyrrole ring or a pyrimidine ring.

In one aspect of the present invention, it is preferred to introduce a steric hindrance around the nitrogen atom contained in the basic moiety represented by $A_N$. The nucleophilicity of the nitrogen atom can be lowered by introducing a steric hindrance around the nitrogen atom. If so, the nucleophilic reaction between the compounds of general formula (1-1) and other components of the actinic-ray- or radiation-sensitive resin composition is suppressed so that an improvement of the stability of pattern line width over time can be expected.

From this viewpoint, it is preferred that at least one of a cycloaliphatic group, an aromatic hydrocarbon group, a heterocyclic hydrocarbon group and a chain aliphatic group whose portion adjacent to the nitrogen atom is a tertiary or quaternary carbon atom be directly bonded to the nitrogen atom contained in the basic moiety.

As nonlimiting examples of cycloaliphatic groups, there can be mentioned mono- or polycycloalkyl groups, such as a cyclohexyl group, a cyclopentyl group, a norbornyl group and an adamantyl group, and groups with a lactone structure (in particular, those of general formulae (LC1-1) to (LC1-17) set forth by way of example in connection with the resin (A) and the like).

As the aromatic hydrocarbon group, there can be mentioned, for example, a phenyl group, a naphthyl group or the like.

As the heterocyclic hydrocarbon group, there can be mentioned, for example, any of those set forth above in connection with R$_1$.

As the chain aliphatic group whose portion adjacent to the nitrogen atom is a tertiary carbon atom, there can be mentioned, for example, an isopropyl group, a sec-butyl group or the like. Further, there can be mentioned, for example, any of groups as obtained by substituting a branched aliphatic group, such as an isopropyl group, with an alkoxy group, for example, the following groups.

As the chain aliphatic group whose portion adjacent to the nitrogen atom is a quaternary carbon atom, there can be mentioned, for example, a tert-butyl group or the like.

In general formula (1-1), o is an integer of 1 to 10, preferably 1 to 4 and more preferably 1 or 2.

It is preferred for Y$^-$ to be a nonnucleophilic anion. Herein, the nonnucleophilic anion refers to an anion whose capability of inducing a nucleophilic reaction is markedly low, which anion is capable of suppressing any decomposition over time by an intramolecular nucleophilic reaction. The nonnucleophilic anion enhances the stability over time of the composition of the present invention.

As the nonnucleophilic anion represented by Y$^-$, there can be mentioned, for example, a sulfonate anion, a carboxylate anion, a sulfonylimide anion, a bis(alkylsulfonyl)imide anion, a tris(alkylsulfonyl)methyl anion or the like.

As the sulfonate anion, there can be mentioned, for example, an aliphatic sulfonate anion, an aromatic sulfonate anion, a camphor sulfonate anion or the like.

As the carboxylate anion, there can be mentioned, for example, an aliphatic carboxylate anion, an aromatic carboxylate anion, an aralkyl carboxylate anion or the like.

The aliphatic moiety of the aliphatic sulfonate anion may be an alkyl group or a cycloalkyl group, being preferably an alkyl group having 1 to 30 carbon atoms or a cycloalkyl group having 3 to 30 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a bornyl group or the like.

As a preferred aromatic group of the aromatic sulfonate anion, there can be mentioned an aryl group having 6 to 14 carbon atoms, for example, a phenyl group, a tolyl group, a naphthyl group or the like.

Substituents may be introduced in the alkyl group, cycloalkyl group and aryl group of the aliphatic sulfonate anion and aromatic sulfonate anion. As the substituents introduced in the alkyl group, cycloalkyl group and aryl group of the aliphatic sulfonate anion and aromatic sulfonate anion, there can be mentioned, for example, a nitro group, a halogen atom (fluorine atom, chlorine atom, bromine atom or iodine atom), a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) and the like. With respect to the aryl group or ring structure of each of these groups, as its substituent, there can further be mentioned an alkyl group (preferably having 1 to 15 carbon atoms).

As the aliphatic moiety of the aliphatic carboxylate anion, there can be mentioned any of the same alkyl groups and cycloalkyl groups as mentioned above with respect to the aliphatic sulfonate anion.

As the aromatic group of the aromatic carboxylate anion, there can be mentioned any of the same aryl groups as mentioned above with respect to the aromatic sulfonate anion.

As a preferred aralkyl group of the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

Substituents may be introduced in the alkyl group, cycloalkyl group, aryl group and aralkyl group of the aliphatic carboxylate anion, aromatic carboxylate anion and aralkyl carboxylate anion. As the substituents introduced in the alkyl group, cycloalkyl group, aryl group and aralkyl group of the aliphatic carboxylate anion, aromatic carboxylate anion and aralkyl carboxylate anion, there can be mentioned, for example, the same halogen atoms, alkyl groups, cycloalkyl groups, alkoxy groups, alkylthio groups, etc., as mentioned above with respect to the aromatic sulfonate anion.

As the sulfonylimide anion, there can be mentioned, for example, a saccharin anion.

The alkyl group of the bis(alkylsulfonyl)imide anion and tris(alkylsulfonyl)methyl anion is preferably an alkyl group having 1 to 5 carbon atoms. As such, there can be mentioned, for example, a methyl group, an ethyl group, a propyl group, an isopropyl group, an n-butyl group, an isobutyl group, a sec-butyl group, a pentyl group, a neopentyl group or the like. As substituents introduced in these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. An alkyl group substituted with a fluorine atom is preferred. In a preferred form, two alkyl groups of the bis(alkylsulfonyl)imide anion may be bonded to each other to thereby form a ring structure. In that instance, the formed ring structure is preferably a 5- to 7-membered ring.

As the other nonnucleophilic anions, there can be mentioned, for example, phosphorus fluoride, boron fluoride, antimony fluoride and the like.

The nonnucleophilic anion represented by Y$^-$ is preferably selected from among an aliphatic sulfonate anion substituted at its α-position of sulfonic acid with a fluorine atom, an aromatic sulfonate anion substituted with a fluorine atom or a group having a fluorine atom, a bis(alkylsulfonyl)imide anion whose alkyl group is substituted with a fluorine atom and a tris(alkylsulfonyl)methide anion whose alkyl group is substituted with a fluorine atom. More preferably, the nonnucleophilic anion is a perfluorinated aliphatic sulfonate anion having 4 to 8 carbon atoms or a benzenesulfonate anion having a fluorine atom. Further more preferably, the nonnucleophilic anion is a nonafluorobutanesulfonate anion, a perfluorooctanesulfonate anion, a pentafluorobenzenesulfonate anion or a 3,5-bis(trifluoromethyl)benzenesulfonate anion.

The non-nucleophilic anion represented by Z$^-$ is preferably expressed by, for example, general formula (LD1) below:

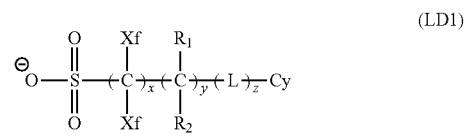

In the formula, each of Xf's independently represents a fluorine atom or an alkyl group substituted with at least one fluorine atom.

Each of $R_1$ and $R_2$ independently represents a group selected from the group consisting of a hydrogen atom, a fluorine atom, an alkyl group and an alkyl group substituted with at least one fluorine atom.

L, or each of L's independently, represents a single bond or a bivalent connecting group.

Cy represents a group with a cyclic structure.

In the formula, x is an integer of 1 to 20, y is an integer of 0 to 10, and z is an integer of 0 to 10.

Xf represents a fluorine atom or an alkyl group substituted with at least one fluorine atom. This alkyl group preferably has 1 to 10 carbon atoms, more preferably 1 to 4 carbon atoms. The alkyl group substituted with at least one fluorine atom is preferably a perfluoroalkyl group.

Xf is preferably a fluorine atom or a perfluoroalkyl group having 1 to 4 carbon atoms. In particular, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$.

Each of $R_1$ and $R_2$ independently represents a group selected from the group consisting of a hydrogen atom, a fluorine atom, an alkyl group and an alkyl group substituted with at least one fluorine atom. Each of the alkyl group and the alkyl group of the alkyl group substituted with at least one fluorine atom preferably has 1 to 4 carbon atoms. More preferably, each of $R_1$ and $R_2$ is a perfluoroalkyl group having 1 to 4 carbon atoms. In particular, there can be mentioned, for example, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, $CF_3$ is preferred.

L represents a single bond or a bivalent connecting group. As the bivalent connecting group, there can be mentioned, for example, —COO—, —OCO—, —CONH—, —CO—, —O—, —S—, —SO—, —SO$_2$—, an alkylene group, a cycloalkylene group or an alkenylene group. Of these, —CONH—, —CO— and —SO$_2$— are preferred. —CONH— and —SO$_2$— are more preferred.

Cy represents a group with a cyclic structure. As the group with a cyclic structure, there can be mentioned, for example, an alicyclic group, an aryl group or a group with a heterocyclic structure.

The alicyclic group may be monocyclic or polycyclic. As the alicyclic group that is monocyclic, there can be mentioned, for example, a monocycloalkyl group, such as a cyclopentyl group, a cyclohexyl group or a cyclooctyl group. As the alicyclic group that is polycyclic, there can be mentioned, for example, a polycycloalkyl group, such as a norbornyl group, a tricyclodecanyl group, a tetracyclodecanyl group, a tetracyclododecanyl group or an adamantyl group. Of the mentioned groups, alicyclic groups with a bulky structure having at least 7 carbon atoms, such as a norbornyl group, a tricyclodecanyl group, a tetracyclodecanyl group, a tetracyclododecanyl group and an adamantyl group, are preferred from the viewpoint of inhibition of any in-film diffusion in the PEB (post-exposure bake) operation and enhancement of MEEF (Mask Error Enhancement Factor).

The aryl group may be monocyclic or polycyclic. As the aryl group, there can be mentioned, for example, a phenyl group, a naphthyl group, a phenanthryl group or an anthryl group. Of these, a naphthyl group exhibiting a relatively low light absorbance at 193 nm is preferred.

The group with a heterocyclic structure may be monocyclic or polycyclic. The polycyclic structure is superior in the inhibition of any acid diffusion. It is optional for the group with a heterocyclic structure to have aromaticity. As the heterocycle having aromaticity, there can be mentioned, for example, a furan ring, a thiophene ring, a benzofuran ring, a benzothiophene ring, a dibenzofuran ring, a dibenzothiophene ring or a pyridine ring. As the heterocycle having no aromaticity, there can be mentioned, for example, a tetrahydropyran ring, a lactone ring or a decahydroisoquinoline ring. It is especially preferred for the heterocycle of the group with a heterocyclic structure to be a furan ring, a thiophene ring, a pyridine ring or a decahydroisoquinoline ring. As examples of the lactone rings, there can be mentioned the lactone structures set forth above by way of example in connection with the resin (A).

A substituent may be introduced in the above group with a cyclic structure. As the substituent, there can be mentioned, for example, an alkyl group, a cycloalkyl group, an aryl group, a hydroxyl group, an alkoxy group, an ester group, an amido group, a urethane group, a ureido group, a thioether group, a sulfonamido group or a sulfonic ester group. The alkyl group may be in the form of a linear or branched chain. It is preferred for the alkyl group to have 1 to 12 carbon atoms. The cycloalkyl group may be monocyclic or polycyclic. It is preferred for the cycloalkyl group to have 3 to 12 carbon atoms. The aryl group preferably has 6 to 14 carbon atoms.

In the formula, x is preferably 1 to 8, more preferably 1 to 4 and most preferably 1; y is preferably 0 to 4, more preferably 0; and z is preferably 0 to 8, more preferably 0 to 4.

Also, the nonnucleophilic anion represented by $Y^-$ is preferably expressed by, for example, general formula (LD2) below.

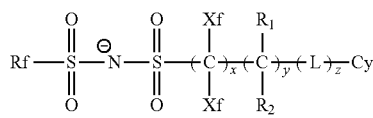

(LD2)

In general formula (LD2), Xf, $R_1$, $R_2$, L, Cy, x, y and z are as defined above in connection with general formula (LD1). Rf is a group containing a fluorine atom.

As the group containing a fluorine atom represented by Rf, there can be mentioned, for example, an alkyl group containing at least one fluorine atom, a cycloalkyl group containing at least one fluorine atom or an aryl group containing at least one fluorine atom.

These alkyl group, cycloalkyl group and aryl group may be those substituted with a fluorine atom, or those substituted with another substituent containing a fluorine atom. When Rf is a cycloalkyl group containing at least one fluorine atom or an aryl group containing at least one fluorine atom, the other substituent containing a fluorine atom can be, for example, an alkyl group substituted with at least one fluorine atom.

Further, these alkyl group, cycloalkyl group and aryl group may further be substituted with a substituent containing no fluorine atom. As this substituent, there can be mentioned, for example, any of those mentioned above with respect to Cy wherein no fluorine atom is contained.

As the alkyl group containing at least one fluorine atom represented by Rf, there can be mentioned, for example, any of those mentioned hereinbefore as the alkyl group substituted with at least one fluorine atom, represented by Xf. As the cycloalkyl group containing at least one fluorine atom represented by Rf, there can be mentioned, for example, a perfluorocyclopentyl group or a perfluorocyclohexyl group. As the aryl group containing at least one fluorine atom represented by Rf, there can be mentioned, for example, a perfluorophenyl group.

Specific examples of the cation moieties of the compounds of general formula (1-1) are shown below.

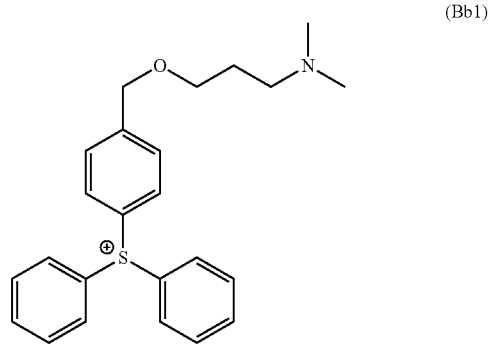

(Bb1)

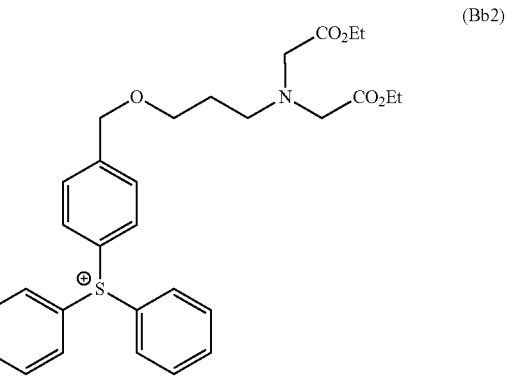

(Bb2)

(Bb3)
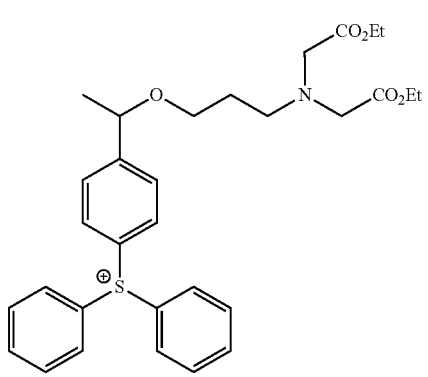
(Bb7)
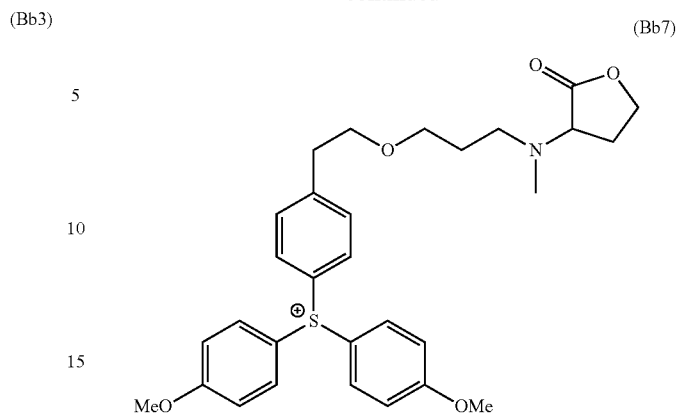
(Bb4)
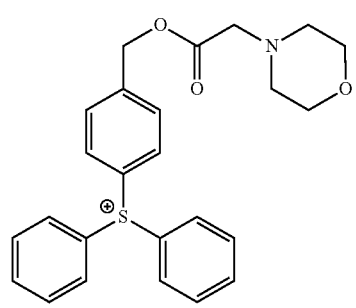
(Bb8)
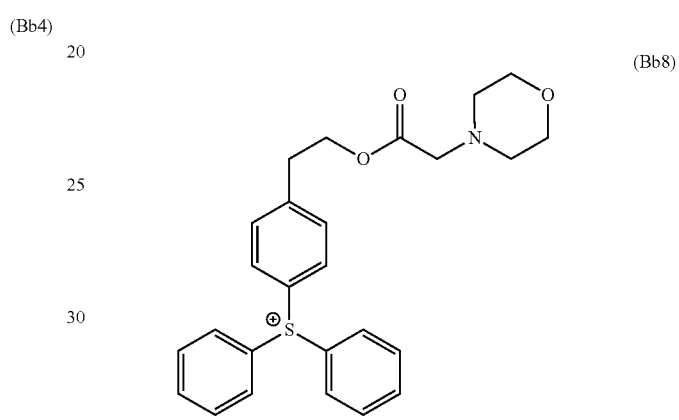
(Bb5)
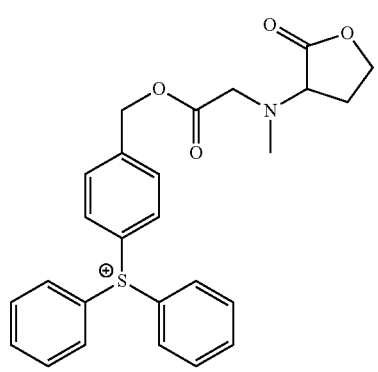
(Bb9)
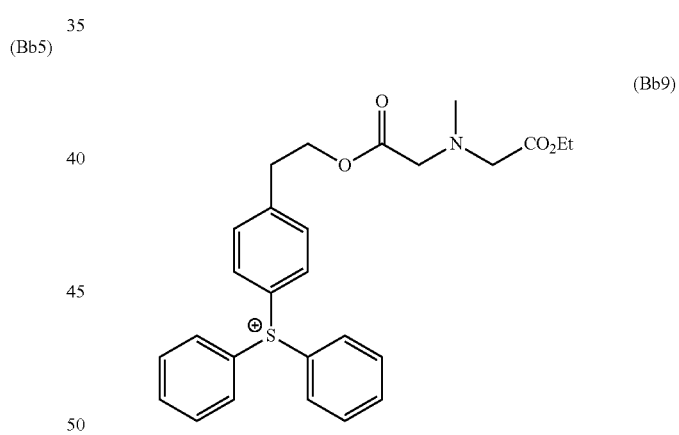
(Bb6)
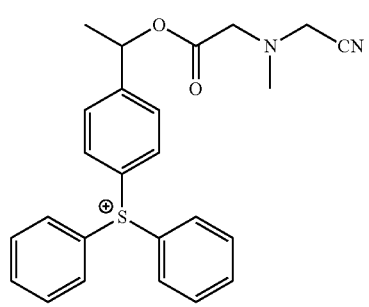
(Bb10)
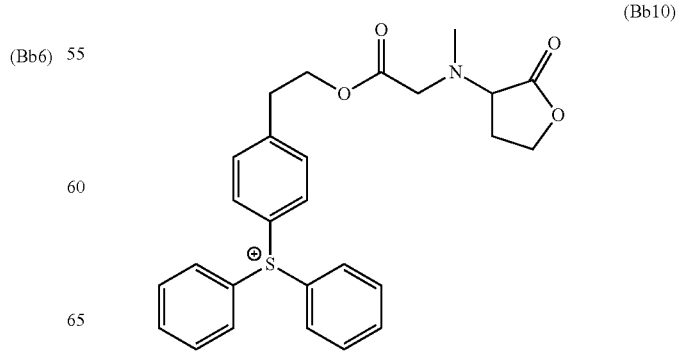

-continued
(Bb11) (Bb15) (Bb12) (Bb13) (Bb14) (Bb16) (Bb17) (Bb18)
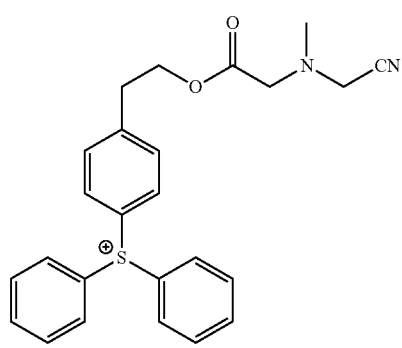
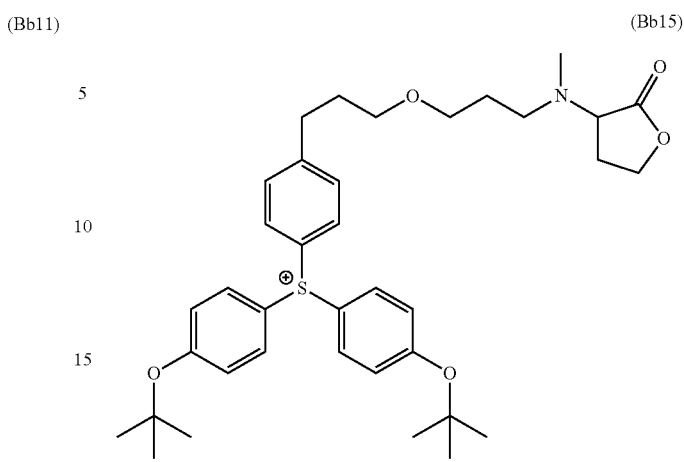

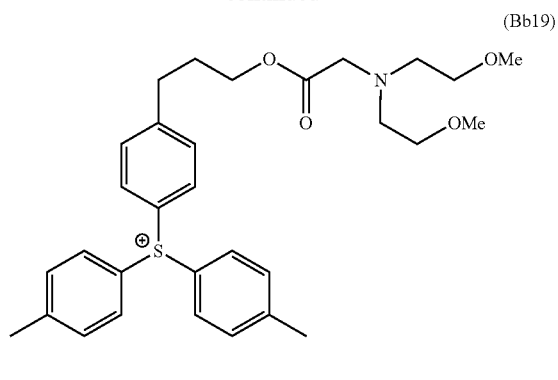
(Bb19)
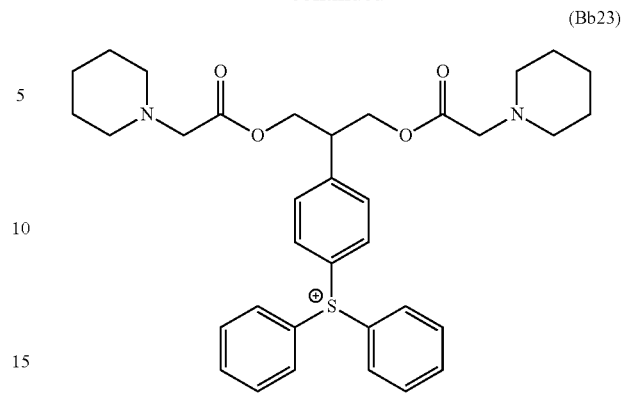
(Bb23)
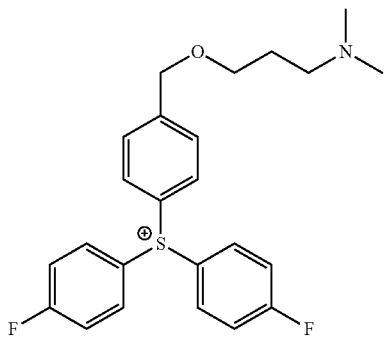
(Bb20)
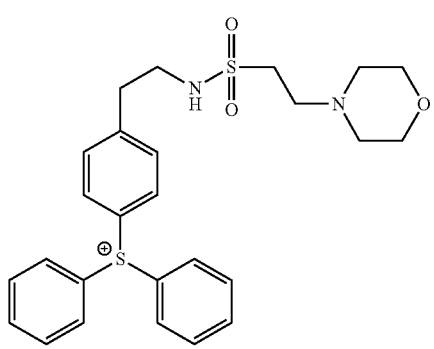
(Bb24)
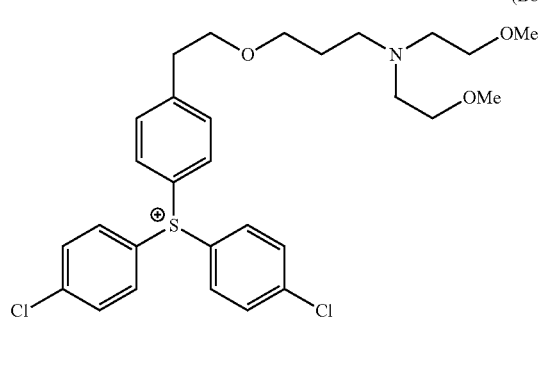
(Bb21)
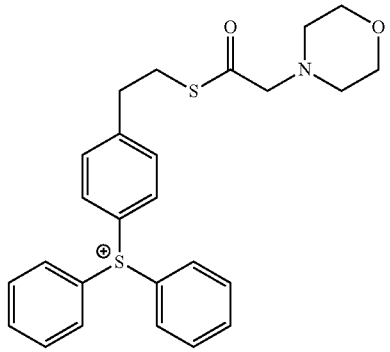
(Bb25)
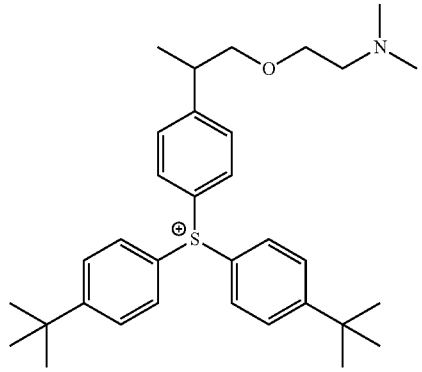
(Bb22)
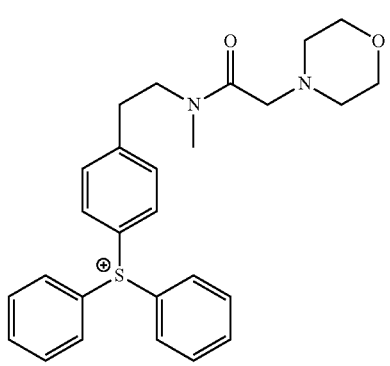
(Bb26)

(Bb27) 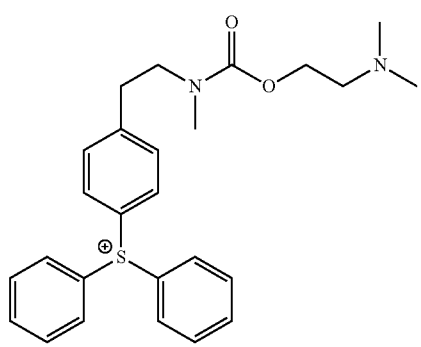
(Bb28) 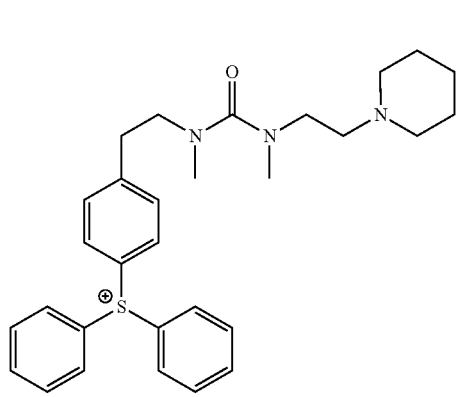
(Bb29) 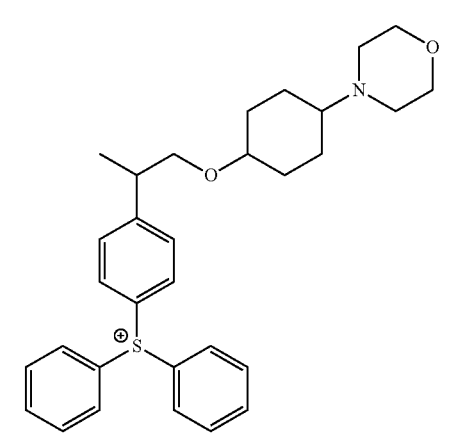
(Bb30) 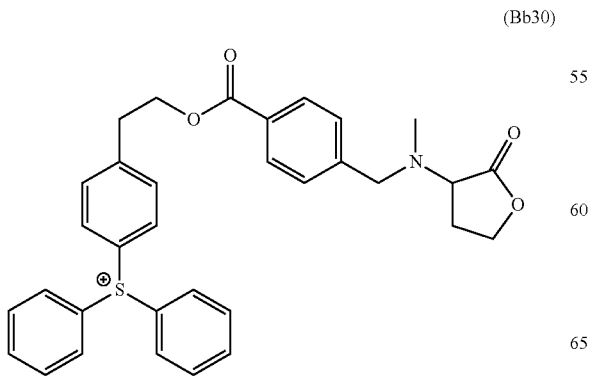
(Bb31) 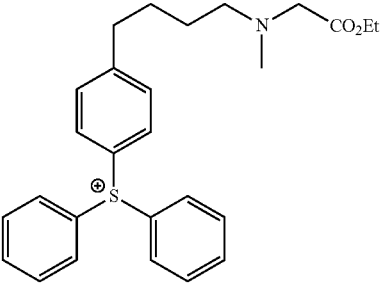
(Bb32) 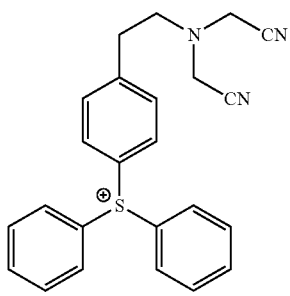
(Bb33) 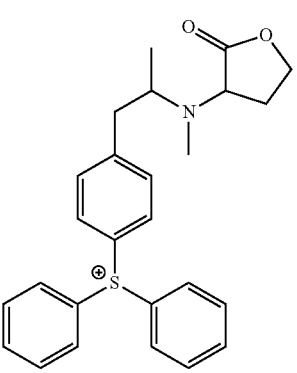
(Bb34) 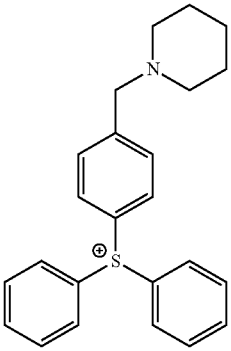

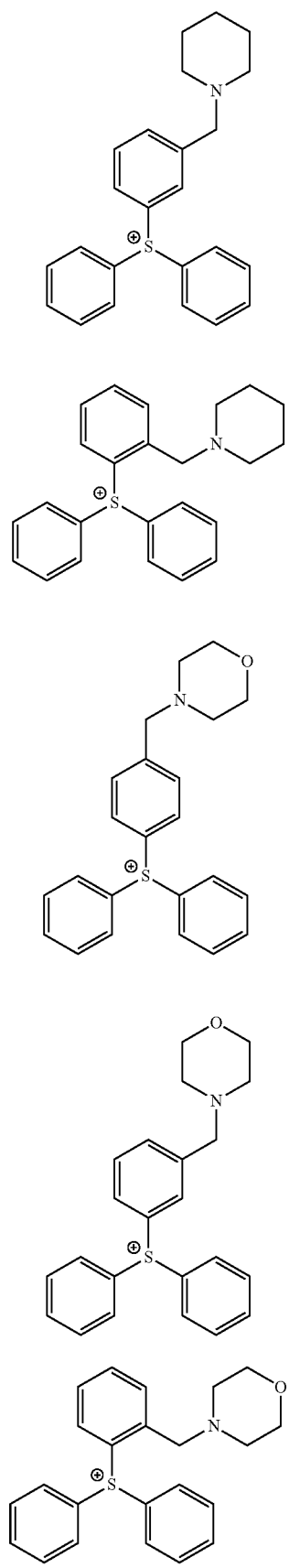
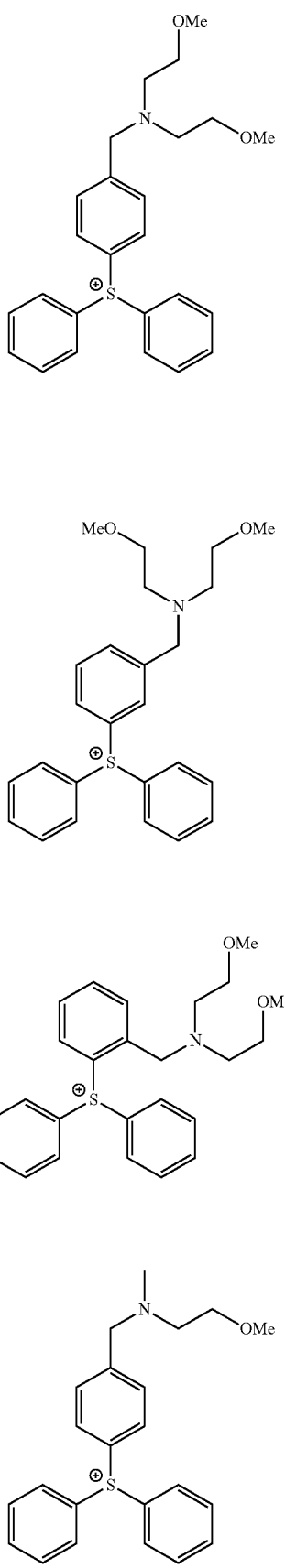

-continued
(Bb44)
(Bb45)
(Bb46)
(Bb47)
(Bb48)
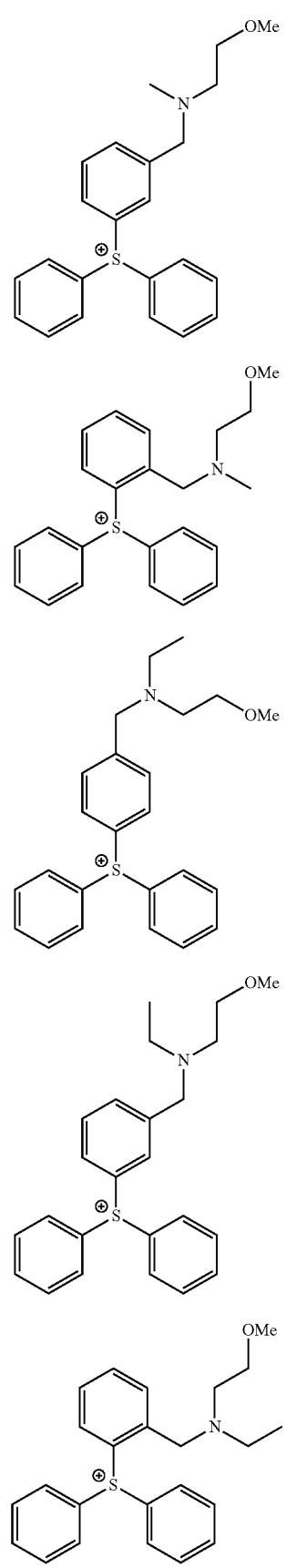
-continued
(Bb49)
(Bb50)
(Bb51)
(Bb52)
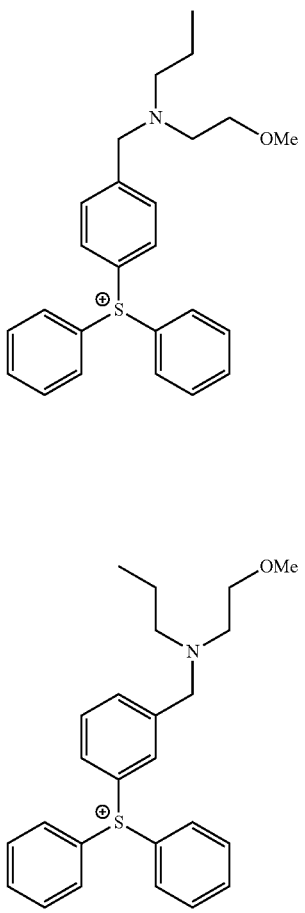

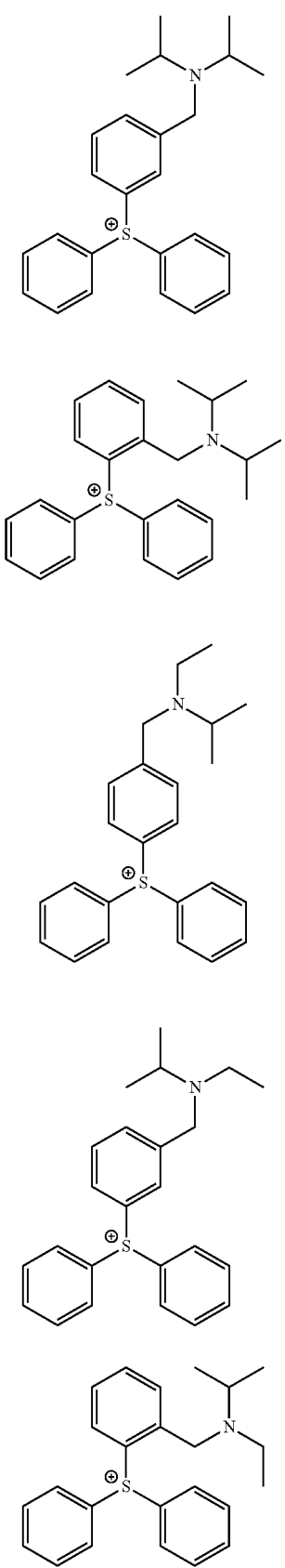
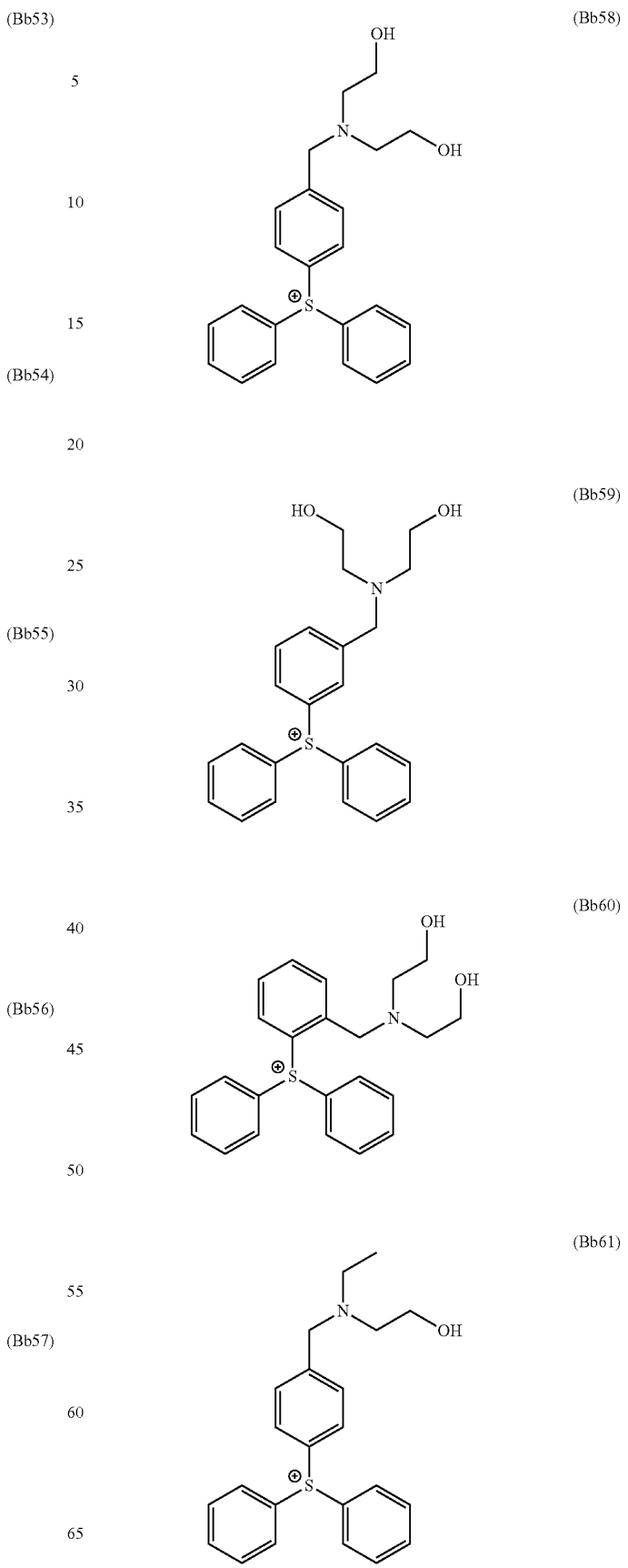

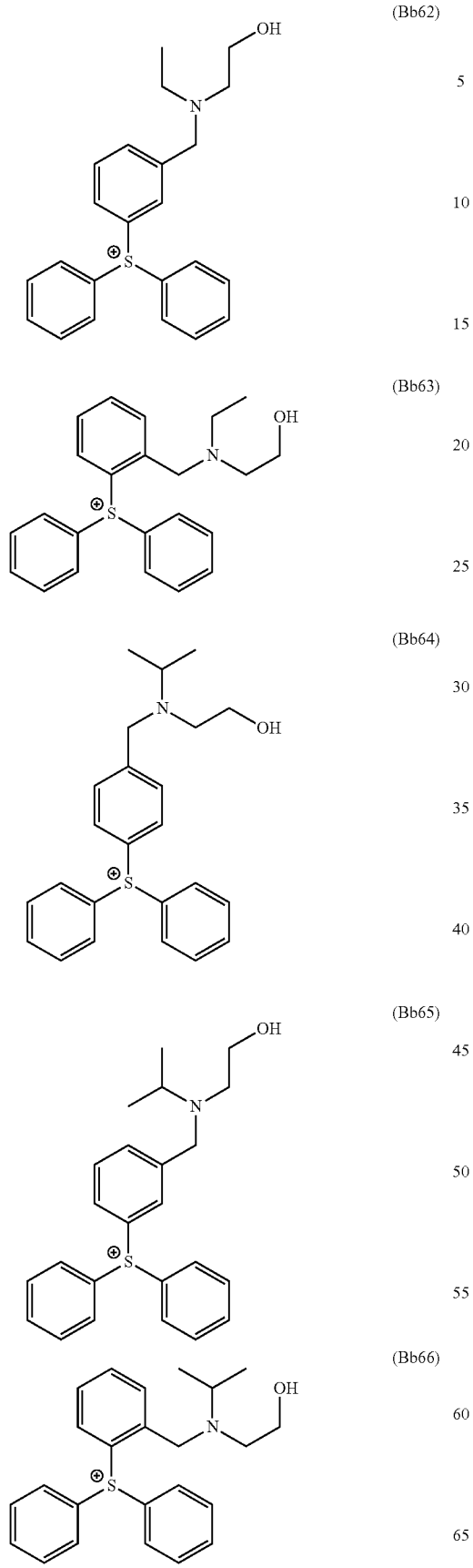
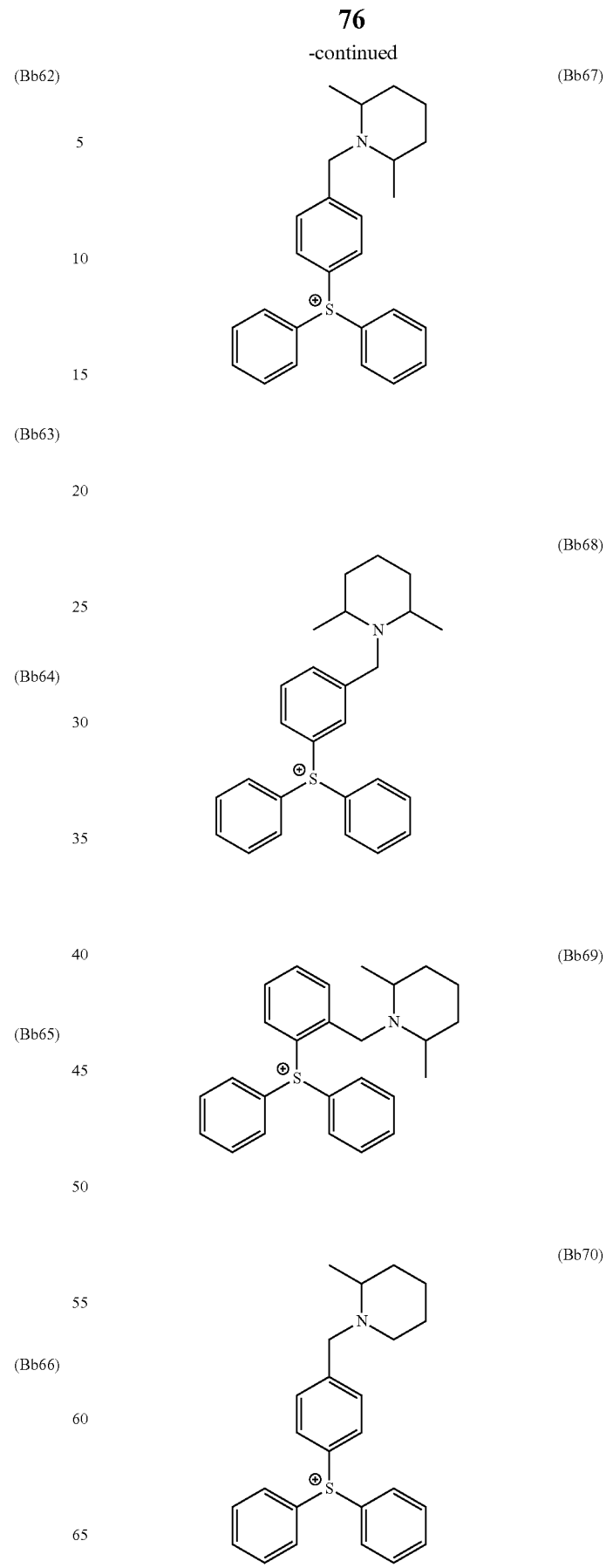

(Bb71) 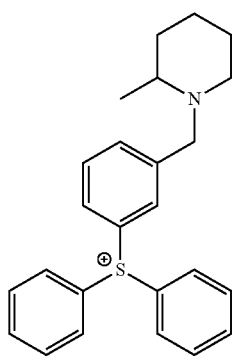
(Bb72) 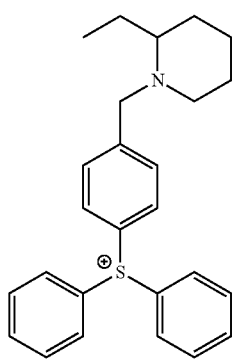
(Bb73) 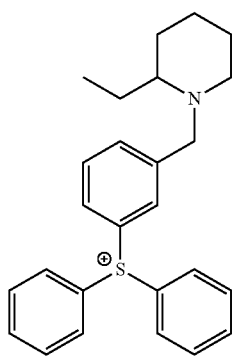
(Bb74) 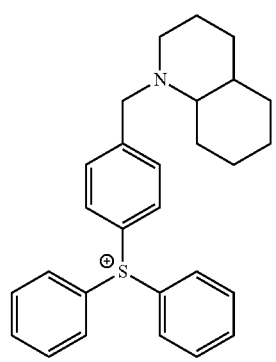
(Bb75) 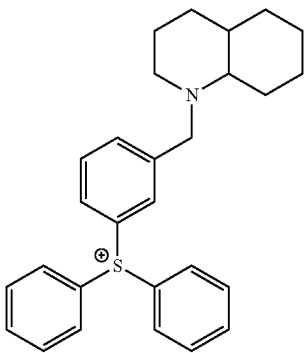
(Bb76) 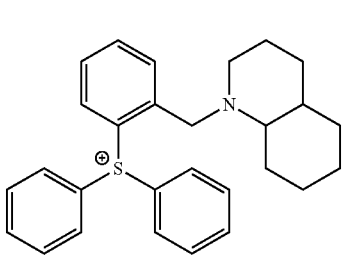
(Bb77) 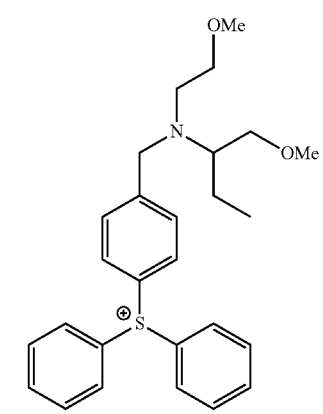
(Bb78) 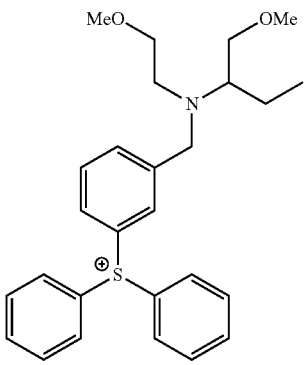

(Bb79) 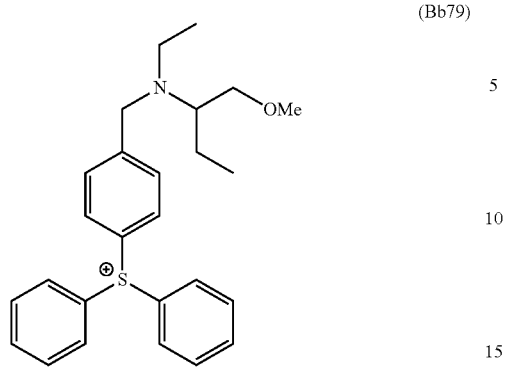
(Bb83) 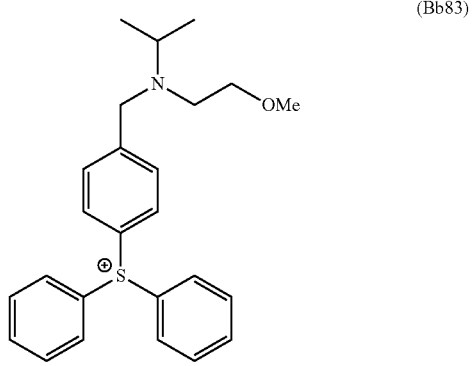
(Bb80) 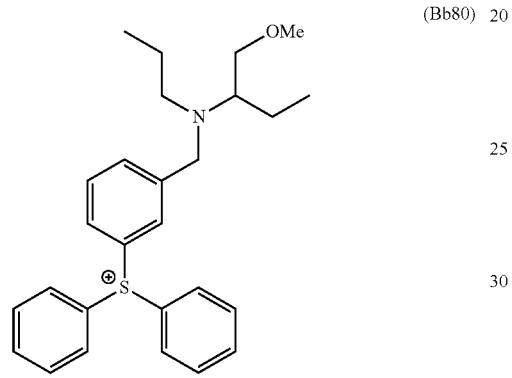
(Bb84) 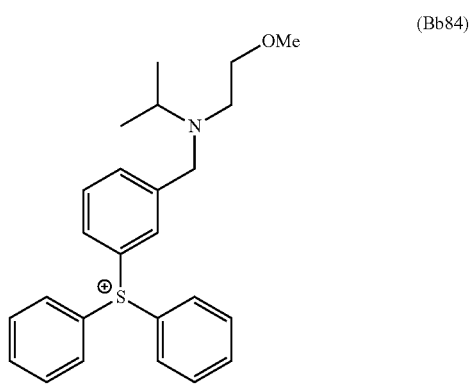
(Bb81) 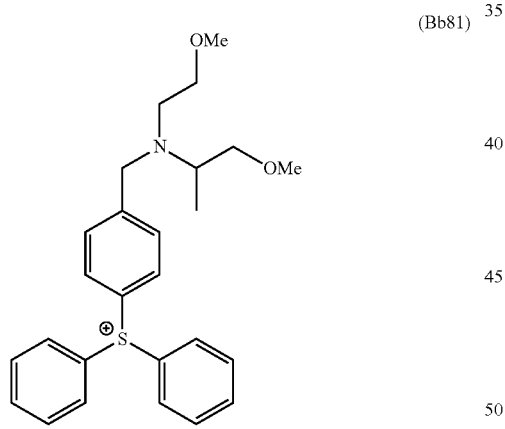
(Bb85) 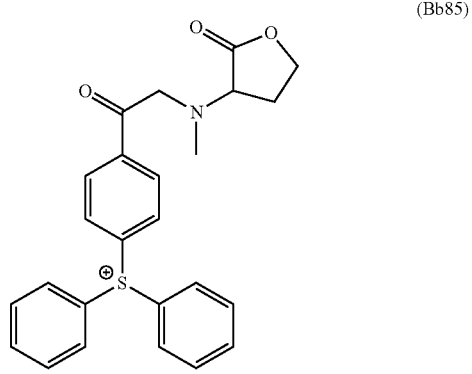
(Bb82) 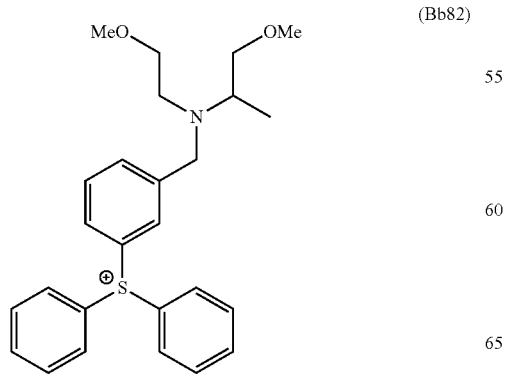
(Bb86) 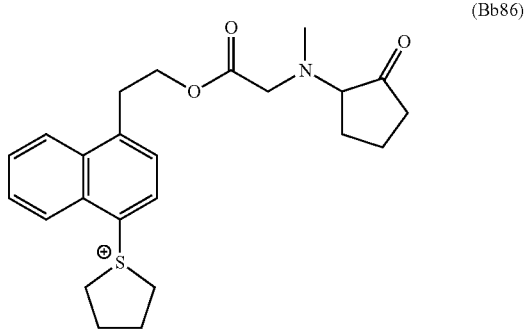

-continued (Bb87) 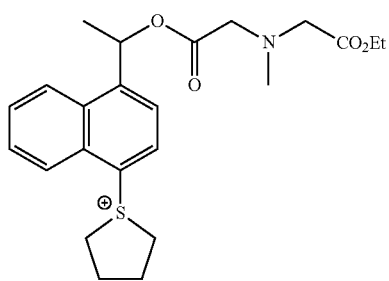

(Bb88) 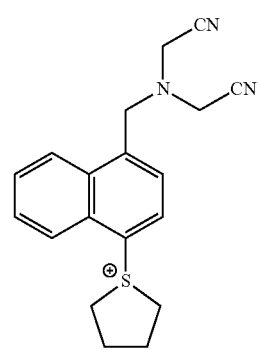

(Bb89) 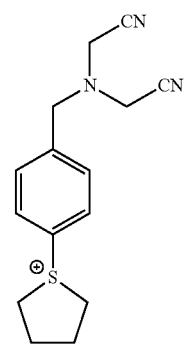

(Bb90) 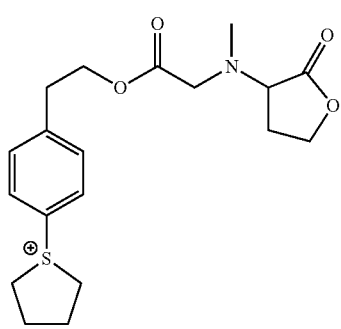

(Bb91) 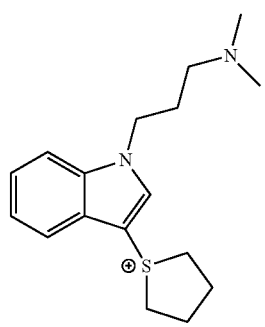

-continued (Bb92) 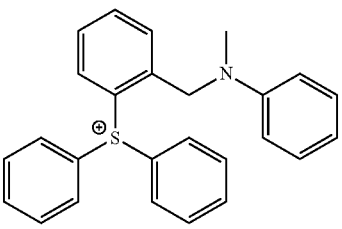

(Bb93) 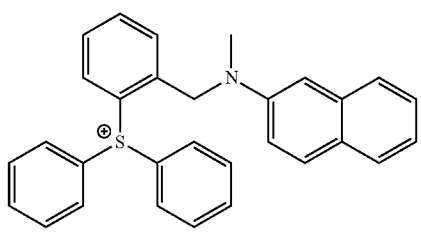

(Bb94) 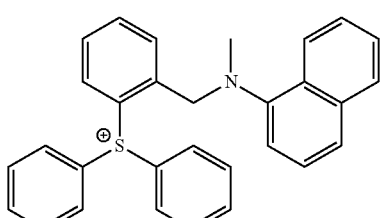

(Bb95) 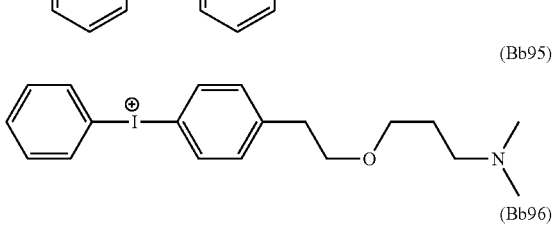

(Bb96) 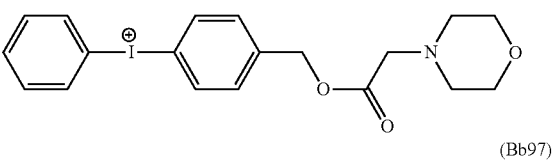

(Bb97) 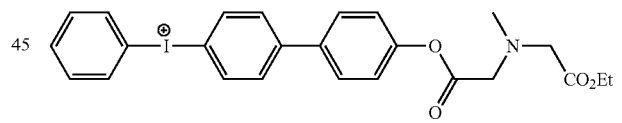

The process for producing the compounds of general formula (1-1) is not particularly limited. For example, the compounds are synthesized by reacting the compounds of general formula (2) below with the compounds of general formula (3) below.

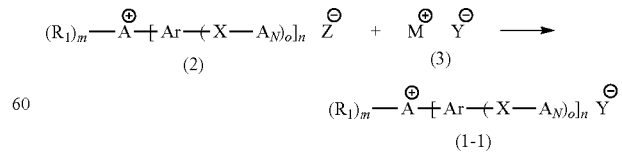

In the formulae, $Z^-$ is, for example, a bromide ion, a chloride ion, an iodide ion, a sulfonate ion, a carboxylate ion, $BF_4^-$, $AsF_6^-$, $SbF_6^-$, $PF_6^-$ or $ClO_4^-$, preferably a bromide ion, a chloride ion, a sulfonate ion or a carboxylate ion.

As the sulfonate ion represented by Z⁻, there can be mentioned, for example, a p-toluenesulfonate ion, a methanesulfonate ion or a trifluoromethanesulfonate ion.

As the carboxylate ion represented by Z⁻, there can be mentioned, for example, a trifluoroacetate ion or an acetate ion.

M⁺ is, for example, an alkali metal ion. As the alkali metal ion, there can be mentioned, for example, a sodium ion, a lithium ion or a potassium ion.

The compounds (2) and (3) may be commercially available products, or may be synthesized.

The process for producing the compounds (2) is not particularly limited. For example, in the use of onium salt compounds of general formula (4) below by way of example, the compounds (2) can be synthesized by reacting the compounds (4) with the basic compounds of general formula (5) in the presence of an appropriate base.

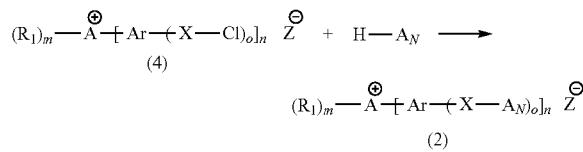

In this reaction, the molar ratio of basic compound (5) to compound (4) is preferably in the range of 1 to 100, more preferably 1 to 10 and most preferably 1 to 5.

As the base for use in the reaction, there can be mentioned, for example, triethylamine, pyridine, sodium hydrogen carbonate, sodium carbonate or potassium carbonate. Of these, triethylamine and potassium carbonate are preferred from the viewpoint of having an appropriate basicity.

This reaction is performed in, for example, an aprotic organic solvent, such as tetrahydrofuran, acetone, methyl ethyl ketone, acetonitrile, pyridine, NMP or methylene chloride. The reaction is preferably performed in acetone, acetonitrile or tetrahydrofuran among these solvents. The ratio of organic solvent used per 100 parts by mass of the sum of organic solvent and water is preferably in the range of 2 to 100 parts by mass, more preferably 5 to 100 parts by mass and most preferably 10 to 95 parts by mass.

The temperature at which the reaction is performed is preferably in the range of −40 to 100° C., more preferably −20 to 80° C. and most preferably 0 to 80° C. The period of time in which the reaction is performed is preferably in the range of 0.1 to 96 hours, more preferably 0.5 to 24 hours.

A particular mode of the process for producing the compounds (2) will be considered using the onium salt compounds of general formula (6) below. In that instance, for example, the compounds (2) can be synthesized by reacting the compounds (6) below with the compounds of general formula (7) in the presence of an appropriate base.

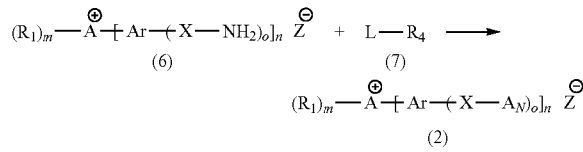

In the formulae, $R_4$ represents an alkyl group or a cycloaliphatic group.

In this reaction, the molar ratio of compound (7) to compound (6) is preferably in the range of 1 to 10, more preferably 1 to 5.

As the base for use in the reaction, there can be mentioned, for example, triethylamine, pyridine, sodium hydrogen carbonate, sodium carbonate, potassium carbonate or sodium hydride. Of these, triethylamine and potassium carbonate are preferred from the viewpoint of having an appropriate basicity.

This reaction is performed in, for example, an aprotic organic solvent, such as tetrahydrofuran, acetone, methyl ethyl ketone, acetonitrile, pyridine, NMP or methylene chloride. The reaction is preferably performed in acetone, acetonitrile or tetrahydrofuran among these solvents. The ratio of organic solvent used per 100 parts by mass of the sum of organic solvent and water is preferably in the range of 2 to 100 parts by mass, more preferably 5 to 100 parts by mass and most preferably 10 to 95 parts by mass.

The temperature at which the reaction is performed is preferably in the range of −40 to 100° C., more preferably −20 to 80° C. and most preferably 0 to 80° C. The period of time in which the reaction is performed is preferably in the range of 0.1 to 96 hours, more preferably 0.5 to 24 hours.

One of the compounds of general formula (1-1) may be used alone, or two or more thereof may be used in combination.

The content of component (B) based on the total solids of the composition is preferably in the range of 0.1 to 20.0 mass %, more preferably 0.5 to 15.0 mass % and further more preferably 1.0 to 10.0 mass %.

The composition of the present invention may contain other components in addition to the above components (A) and (B). The other optional components will be described below.

(C) Acid Generator other than Compounds of General Formula (1-1)

It is preferred for the composition of the present invention to further contain an acid generator other than the compounds of general formula (1-1) (hereinafter also referred to as component (C)).

As the acid generator, use can be made of a member appropriately selected from among a photoinitiator for photocationic polymerization, a photoinitiator for photoradical polymerization, a photo-achromatic agent and photo-discoloring agent for dyes, any of publicly known compounds that generate an acid when exposed to actinic rays or radiation employed in microresists, etc., and mixtures thereof.

As the acid generator, a diazonium salt, a phosphonium salt, a sulfonium salt, an iodonium salt, an imide sulfonate, an oxime sulfonate, diazosulfone, disulfone and o-nitrobenzyl sulfonate can be exemplified.

Further, use can be made of compounds obtained by introducing any of the above groups or compounds that generate an acid when exposed to actinic rays or radiation in a polymer principal chain or side chain, for example, compounds described in U.S. Pat. No. 3,849,137, DE 3914407, JP-A's-63-26653, 55-164824, 62-69263, 63-146038, 63-163452, 62-153853, 63-146029, etc.

Furthermore, use can be made of compounds that generate an acid when exposed to light described in U.S. Pat. No. 3,779,778, EP 126,712, etc.

As preferred compounds among the acid generators, those represented by the following general formulae (ZI), (ZII) and (ZIII) can be exemplified.

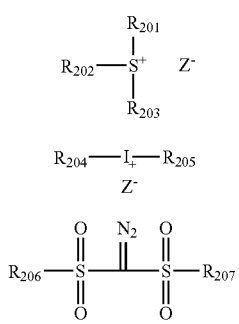

In the above general formula (ZI), each of $R_{201}$, $R_{202}$ and $R_{203}$ independently represents an organic group.

The number of carbon atoms in the organic group represented by $R_{201}$, $R_{202}$ and $R_{203}$ is generally in the range of 1 to 30, preferably 1 to 20.

Two of $R_{201}$ to $R_{203}$ may be bonded to each other to thereby form a ring structure. The ring structure may contain therein an oxygen atom, a sulfur atom, an ester group, an amido group or a carbonyl group. As the group formed by the mutual bonding of two of $R_{201}$ to $R_{203}$, there can be mentioned, for example, an alkylene group, such as a butylene group or a pentylene group.

$Z^-$ represents a nonnucleophilic anion.

$Z^-$ can be, for example, any of those mentioned above in connection with $Y^-$ of general formula (1-1). $Z^-$ and $Y^-$ may be identical to each other, or may be different from each other. Employing $Z^-$ and $Y^-$ identical to each other is preferred from the viewpoint of suppressing any salt exchange reaction between component (B) and component (C).

As the organic groups represented by $R_{201}$, $R_{202}$ and $R_{203}$, there can be mentioned, for example, the corresponding groups of compounds (ZI-1), (ZI-2), (ZI-3) or (ZI-4) to be described hereinafter.

Compounds having two or more of the structures of the general formula (ZI) may be used as the acid generator. For example, use may be made of a compound having a structure in which at least one of the $R_{201}$ to $R_{203}$ of one of the compounds of the general formula (ZI) is bonded to at least one of the $R_{201}$ to $R_{203}$ of another of the compounds of the general formula (ZI).

As preferred (ZI) components, the following compounds (ZI-1) to (ZI-4) can be exemplified.

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group.

As the arylsulfonyl compound, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, nitrogen atom, sulfur atom or the like. As the aryl group having a heterocyclic structure, a pyrrole residue, a furan residue, a thiophene residue, an indole residue, a benzofuran residue, and a benzothiophene residue can be exemplified. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, a methyl group, an ethyl group, a propyl group, an n-butyl group, a sec-butyl group, a t-butyl group, a cyclopropyl group, a cyclobutyl group, and a cyclohexyl group can be exemplified.

The aryl group, alkyl group or cycloalkyl group represented by $R_{201}$ to $R_{203}$ may have one or more substituents. As the substituent, an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxy group, and a phenylthio group can be exemplified. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 6 carbon atoms and an alkoxy group having 1 to 6 carbon atoms. The substituents may be contained in any one of the three $R_{201}$ to $R_{203}$, or alternatively may be contained in all three of $R_{201}$ to $R_{203}$. When $R_{201}$ to $R_{203}$ represent a phenyl group, the substituent preferably lies at the p-position of the phenyl group.

Now, the compounds (ZI-2) will be described.

The compounds (ZI-2) are compounds represented by the formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a 2-oxoalkyl group, an alkoxycarbonylmethyl group, an allyl group, and a vinyl group. More preferred groups include a linear or branched 2-oxoalkyl group and an alkoxycarbonylmethyl group. Especially preferred is a linear or branched 2-oxoalkyl group.

As preferred alkyl groups and cycloalkyl groups represented by $R_{201}$ to $R_{203}$, a linear or branched alkyl group having 1 to 10 carbon atoms (for example, a methyl group, an ethyl group, a propyl group, a butyl group or a pentyl group) and a cycloalkyl group having 3 to 10 carbon atoms (for example, a cyclopentyl group, a cyclohexyl group or a norbornyl group) can be exemplified. As more preferred alkyl groups, a 2-oxoalkyl group and an alkoxycarbonylmethyl group can be exemplified. As more preferred cycloalkyl group, a 2-oxocycloalkyl group can be exemplified.

The 2-oxoalkyl group may be linear or branched. A group having >C=O at the 2-position of the above-described alkyl group can be preferably exemplified.

The 2-oxocycloalkyl group is preferably a group having >C=O at the 2-position of the above-described cycloalkyl group.

As preferred alkoxy groups of the alkoxycarbonylmethyl group, alkoxy groups having 1 to 5 carbon atoms can be exemplified. As such, there can be mentioned, for example, a methoxy group, an ethoxy group, a propoxy group, a butoxy group and a pentoxy group.

The organic groups containing no aromatic ring represented by $R_{201}$ to $R_{203}$ may further have one or more substituents. As the substituents, a halogen atom, an alkoxy group (having, for example, 1 to 5 carbon atoms), a hydroxy group, a cyano group and a nitro group can be exemplified.

The compounds (ZI-3) are those represented by the following general formula (ZI-3) which have a phenacylsulfonium salt structure.

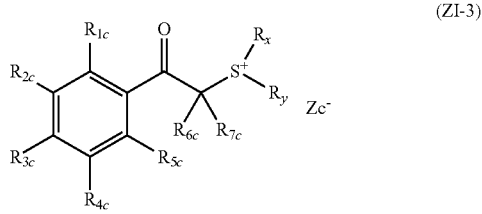

In the formula (ZI-3), each of $R_{1c}$ to $R_{5c}$ independently represents a hydrogen atom, an alkyl group, a cycloalkyl group, an alkoxy group, a halogen atom, or a phenylthio group.

Each of $R_{6c}$ and $R_{7c}$ independently represents a hydrogen atom, an alkyl group, a cycloalkyl group, halogen atom, a cyano group or an aryl group.

Each of $R_x$ and $R_y$ independently represents an alkyl group, a cycloalkyl group, a 2-oxoalkyl group, a 2-oxocycloalkyl group, an alkoxycarbonylalkyl group, an allyl group or a vinyl group.

Any two or more of $R_{1c}$ to $R_{5c}$, and $R_{6c}$ and $R_{7c}$, and $R_x$ and $R_y$ may be bonded with each other to thereby form a ring structure. This ring structure may contain an oxygen atom, a sulfur atom, an ester bond or an amido bond. As the group formed by bonding of any two or more of $R_{1c}$ to $R_{5c}$, and $R_{6c}$ and $R_{7c}$, and $R_x$ and $R_y$, there can be mentioned a butylene group, a pentylene group or the like.

$Zc^-$ represents a nonnucleophilic anion. There can be mentioned the same nonnucleophilic anions as mentioned with respect to the $Z^-$ of the general formula (ZI).

The alkyl group represented by $R_{1c}$ to $R_{7c}$ may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by $R_{1c}$ to $R_{5c}$ may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

Preferably, any one of $R_{1c}$ to $R_{5c}$ is a linear or branched alkyl group, a cycloalkyl group or a linear, branched or cyclic alkoxy group. More preferably, the sum of carbon atoms of $R_{1c}$ to $R_{5c}$ is in the range of 2 to 15. Accordingly, there can be attained an enhancement of solvent solubility and inhibition of particle generation during storage.

Each of the aryl groups represented by $R_{6c}$ and $R_{7c}$ preferably has 5 to 15 carbon atoms. As such, there can be mentioned, for example, a phenyl group or a naphthyl group.

When $R_{6c}$ and $R_{7c}$ are bonded to each other to thereby form a ring, the group formed by the bonding of $R_{6c}$ and $R_{7c}$ is preferably an alkylene group having 2 to 10 carbon atoms. As such, there can be mentioned, for example, an ethylene group, a propylene group, a butylene group, a pentylene group, a hexylene group or the like. Further, the ring formed by the bonding of $R_{6c}$ and $R_7c$ may have a heteroatom, such as an oxygen atom, in the ring.

As the alkyl groups and cycloalkyl groups represented by $R_x$ and $R_y$, there can be mentioned the same alkyl groups and cycloalkyl groups as set forth above with respect to $R_{1c}$ to $R_{7c}$.

As the 2-oxoalkyl group and 2-oxocycloalkyl group, there can be mentioned the alkyl group and cycloalkyl group represented by $R_{1c}$ to $R_{7c}$ having >C=O at the 2-position thereof.

With respect to the alkoxy group of the alkoxycarbonylalkyl group, there can be mentioned the same alkoxy groups as mentioned above with respect to $R_{1c}$ to $R_{5c}$. As the alkyl group thereof, there can be mentioned, for example, an alkyl group having 1 to 12 carbon atoms, preferably a linear alkyl group having 1 to 5 carbon atoms (e.g., a methyl group or an ethyl group).

The allyl groups are not particularly limited. However, preferred use is made of an unsubstituted allyl group or an allyl group substituted with a cycloalkyl group of a single ring or multiple rings.

The vinyl groups are not particularly limited. However, preferred use is made of an unsubstituted vinyl group or a vinyl group substituted with a cycloalkyl group of a single ring or multiple rings.

As the ring structure that may be formed by the mutual bonding of $R_x$ and $R_y$, there can be mentioned a 5-membered or 6-membered ring, especially preferably a 5-membered ring (namely, a tetrahydrothiophene ring), formed by bivalent $R_x$ and $R_y$ (for example, a methylene group, an ethylene group, a propylene group or the like) in cooperation with the sulfur atom of general formula (ZI-3).

Each of $R_x$ and $R_y$ is preferably an alkyl group or cycloalkyl group having preferably 4 or more carbon atoms. The alkyl group or cycloalkyl group has more preferably 6 or more carbon atoms and still more preferably 8 or more carbon atoms.

Specific examples of the cation part in the compound (ZI-3) will be described below.

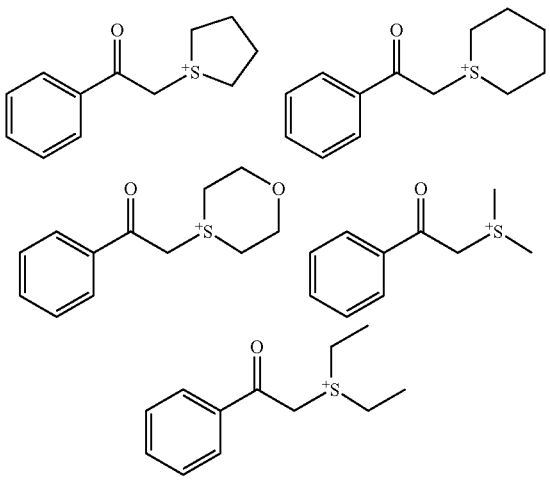

89
-continued
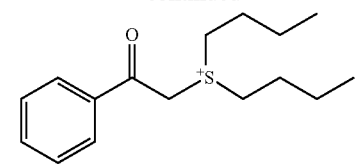
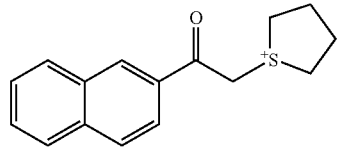
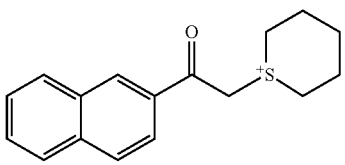
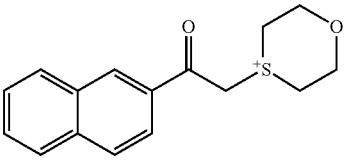
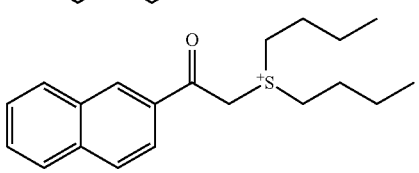
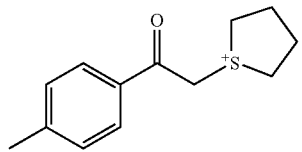
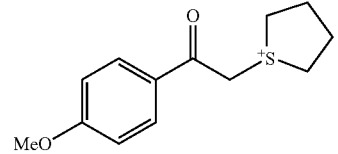
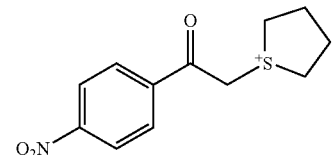
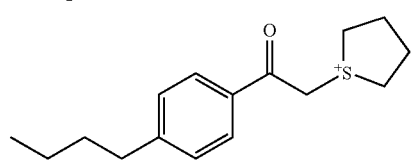
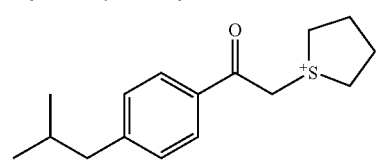
90
-continued
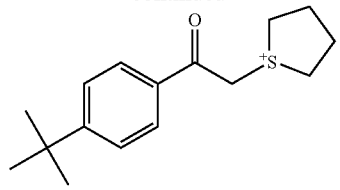
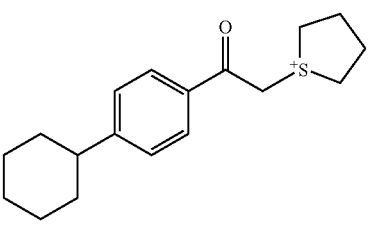
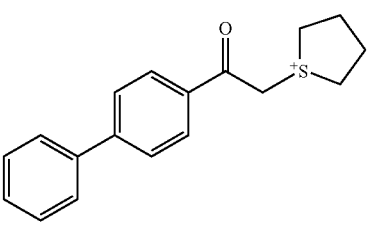
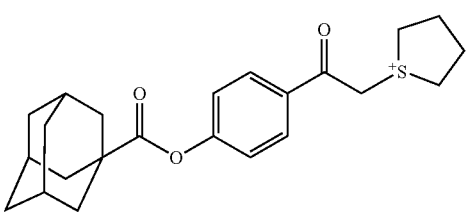
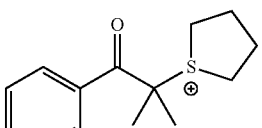
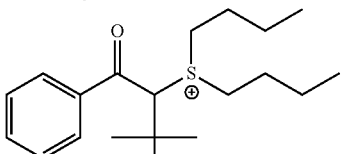
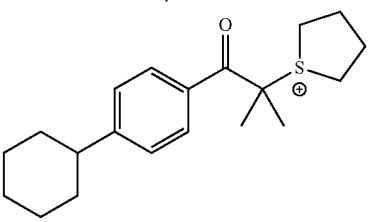
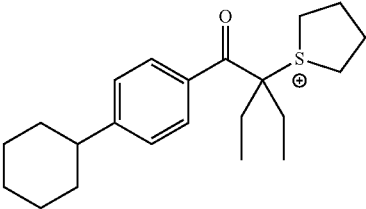

91
-continued
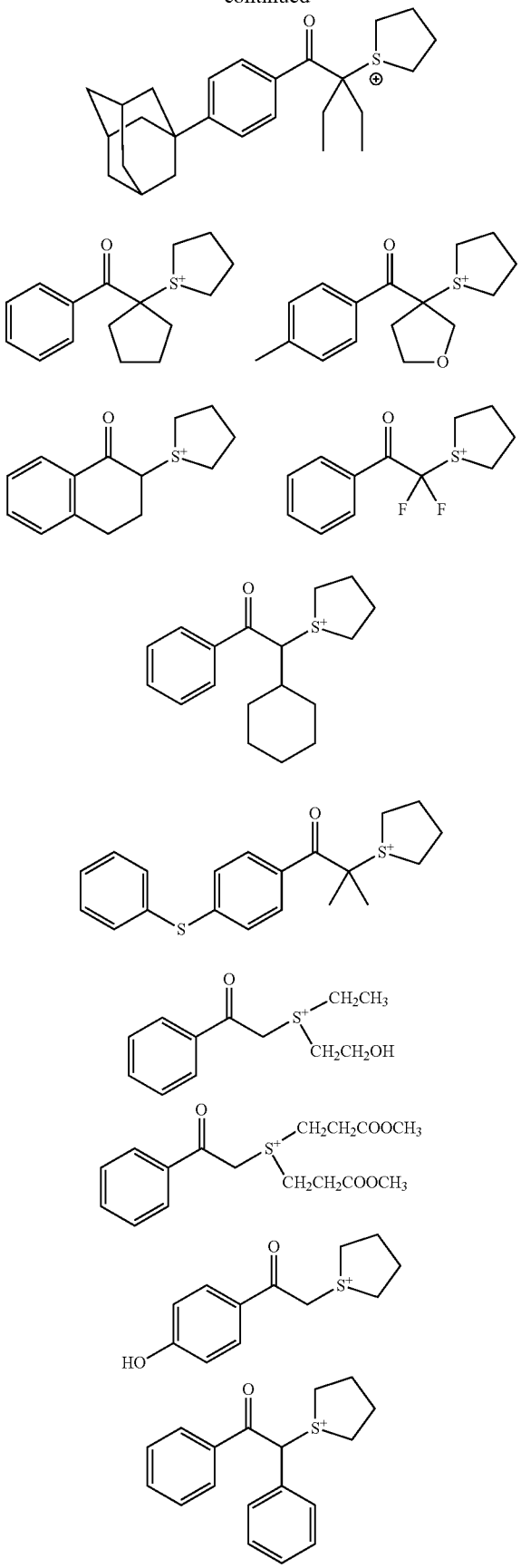
92
-continued
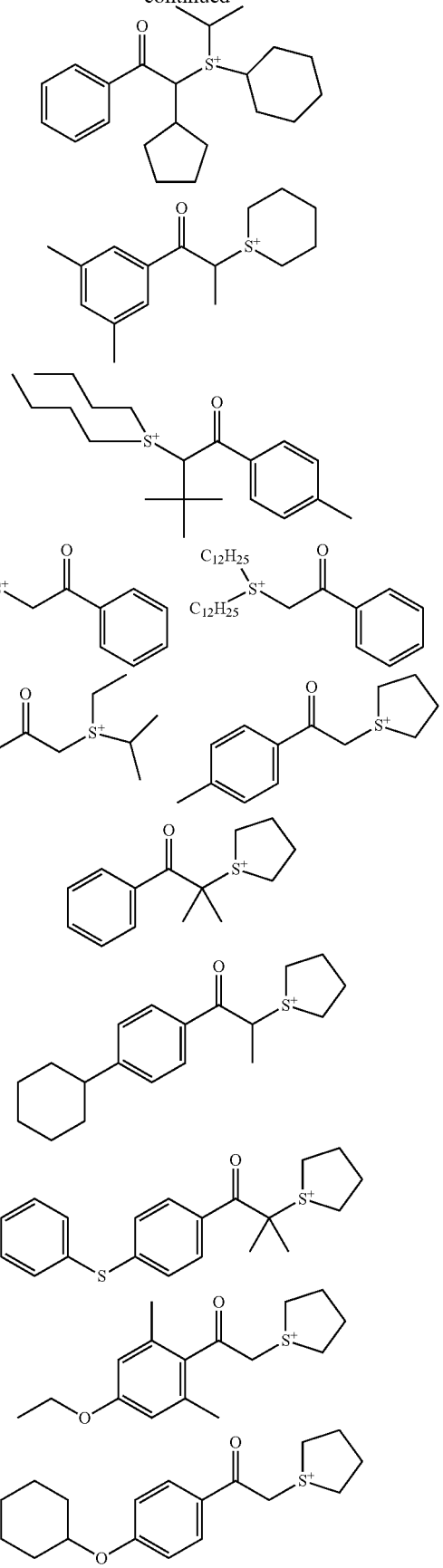

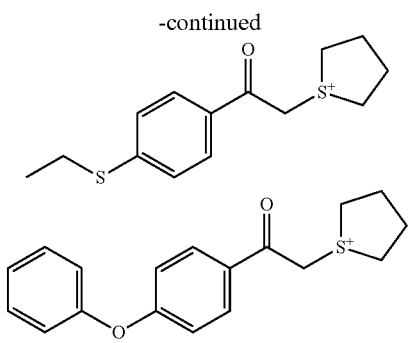

The compounds (ZI-4) are those of general formula (ZI-4) below.

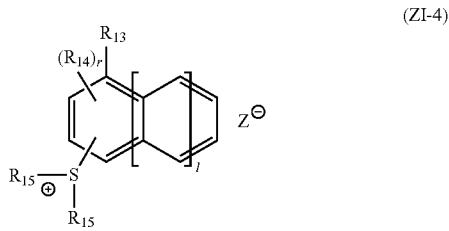

In general formula (ZI-4), $R_{13}$ represents any of a hydrogen atom, a fluorine atom, a hydroxyl group, an alkyl group, a cycloalkyl group, an alkoxy group, an alkoxycarbonyl group and a group with a cycloalkyl skeleton of a single ring or multiple rings. These groups may have one or more substituents.

$R_{14}$, each independently in the instance of $R_{14}$s, represents any of an alkyl group, a cycloalkyl group, an alkoxy group, an alkoxycarbonyl group, an alkylcarbonyl group, an alkylsulfonyl group, a cycloalkylsulfonyl group and a group with a cycloalkyl skeleton of a single ring or multiple rings. These groups may have one or more substituents.

Each of $R_{15}$s independently represents an alkyl group, a cycloalkyl group or a naphthyl group, provided that the two $R_{15}$s may be bonded to each other to thereby form a ring. These groups may have one or more substituents.

In the formula, l is an integer of 0 to 2, and r is an integer of 0 to 8.

$Z^-$ represents a nonnucleophilic anion. As such, there can be mentioned any of the same nonnucleophilic anions as mentioned with respect to the $Z^-$ of the general formula (ZI).

In general formula (ZI-4), the alkyl groups represented by $R_{13}$, $R_{14}$ and $R_{15}$ may be linear or branched and preferably each have 1 to 10 carbon atoms. As such, there can be mentioned a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group and the like. Of these alkyl groups, a methyl group, an ethyl group, an n-butyl group, a t-butyl group and the like are preferred.

As the cycloalkyl groups represented by $R_{13}$, $R_{14}$ and $R_{15}$, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, norbornyl, tricyclodecanyl, tetracyclodecanyl, adamantyl and the like. Cyclopropyl, cyclopentyl, cyclohexyl and cyclooctyl are especially preferred.

The alkoxy groups represented by $R_{13}$ and $R_{14}$ may be linear or branched and preferably each have 1 to 10 carbon atoms. As such, there can be mentioned, for example, a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group and the like. Of these alkoxy groups, a methoxy group, an ethoxy group, an n-propoxy group, an n-butoxy group and the like are preferred.

The alkoxycarbonyl group represented by $R_{13}$ and $R_{14}$ may be linear or branched and preferably has 2 to 11 carbon atoms. As such, there can be mentioned, for example, a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group and the like. Of these alkoxycarbonyl groups, a methoxycarbonyl group, an ethoxycarbonyl group, an n-butoxycarbonyl group and the like are preferred.

As the groups with a cycloalkyl skeleton of a single ring or multiple rings represented by $R_{13}$ and $R_{14}$, there can be mentioned, for example, a cycloalkyloxy group of a single ring or multiple rings and an alkoxy group with a cycloalkyl group of a single ring or multiple rings. These groups may further have one or more substituents.

With respect to each of the cycloalkyloxy groups of a single ring or multiple rings represented by $R_{13}$ and $R_{14}$, the sum of carbon atoms thereof is preferably 7 or greater, more preferably in the range of 7 to 15. Further, having a cycloalkyl skeleton of a single ring is preferred. The cycloalkyloxy group of a single ring of which the sum of carbon atoms is 7 or greater is one composed of a cycloalkyloxy group, such as a cyclopropyloxy group, a cyclobutyloxy group, a cyclopentyloxy group, a cyclohexyloxy group, a cycloheptyloxy group, a cyclooctyloxy group or a cyclododecanyloxy group, optionally having a substituent selected from among an alkyl group such as methyl, ethyl, propyl, butyl, pentyl, hexyl, heptyl, octyl, dodecyl, 2-ethylhexyl, isopropyl, sec-butyl, t-butyl or isoamyl, a hydroxyl group, a halogen atom (fluorine, chlorine, bromine or iodine), a nitro group, a cyano group, an amido group, a sulfonamido group, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group and the like, provided that the sum of carbon atoms thereof, including those of any optional substituent introduced in the cycloalkyl group, is 7 or greater.

As the cycloalkyloxy group of multiple rings of which the sum of carbon atoms is 7 or greater, there can be mentioned a norbornyloxy group, a tricyclodecanyloxy group, a tetracyclodecanyloxy group, an adamantyloxy group or the like.

With respect to each of the alkyloxy groups having a cycloalkyl skeleton of a single ring or multiple rings represented by $R_{13}$ and $R_{14}$, the sum of carbon atoms thereof is preferably 7 or greater, more preferably in the range of 7 to 15. Further, the alkoxy group having a cycloalkyl skeleton of a single ring is preferred. The alkoxy group having a cycloalkyl skeleton of a single ring of which the sum of carbon atoms is 7 or greater is one composed of an alkoxy group, such as methoxy, ethoxy, propoxy, butoxy, pentyloxy, hexyloxy, heptoxy, octyloxy, dodecyloxy, 2-ethylhexyloxy, isopropoxy, sec-butoxy, t-butoxy or isoamyloxy, substituted with the above optionally substituted cycloalkyl group of a single ring, provided that the sum of carbon atoms thereof, including those of the substituents, is 7 or greater. For example, there can be mentioned a cyclohexylmethoxy group, a cyclopentylethoxy group, a cyclohexylethoxy group or the like. A cyclohexylmethoxy group is preferred.

As the alkoxy group having a cycloalkyl skeleton of multiple rings of which the sum of carbon atoms is 7 or greater, there can be mentioned a norbornylmethoxy group, a norbornylethoxy group, a tricyclodecanylmethoxy group, a tricyclodecanylethoxy group, a tetracyclodecanylmethoxy group, a tetracyclodecanylethoxy group, an adamantylmethoxy group, an adamantylethoxy group and the like. Of these, a norbornylmethoxy group, a norbornylethoxy group and the like are preferred.

With respect to the alkyl group of the alkylcarbonyl group represented by $R_{14}$, there can be mentioned the same specific examples as mentioned above with respect to the alkyl groups represented by $R_{13}$ to $R_{15}$.

The alkylsulfonyl and cycloalkylsulfonyl groups represented by $R_{14}$ may be linear, branched or cyclic and preferably each have 1 to 10 carbon atoms. As such, there can be mentioned, for example, a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group and the like. Of these alkylsulfonyl and cycloalkylsulfonyl groups, a methanesulfonyl group, an ethanesulfonyl group, an n-propanesulfonyl group, an n-butanesulfonyl group, a cyclopentanesulfonyl group, a cyclohexanesulfonyl group and the like are preferred.

Each of the groups may have one or more substituents. As such substituents, there can be mentioned, for example, a halogen atom (e.g., a fluorine atom), a hydroxyl group, a carboxyl group, a cyano group, a nitro group, an alkoxy group, an alkoxyalkyl group, an alkoxycarbonyl group, an alkoxycarbonyloxy group or the like.

As the alkoxy group, there can be mentioned, for example, a linear, branched or cyclic alkoxy group having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group or a cyclohexyloxy group.

As the alkoxyalkyl group, there can be mentioned, for example, a linear, branched or cyclic alkoxyalkyl group having 2 to 21 carbon atoms, such as a methoxymethyl group, an ethoxymethyl group, a 1-methoxyethyl group, a 2-methoxyethyl group, a 1-ethoxyethyl group or a 2-ethoxyethyl group.

As the alkoxycarbonyl group, there can be mentioned, for example, a linear, branched or cyclic alkoxycarbonyl group having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group or a cyclohexyloxycarbonyl group.

As the alkoxycarbonyloxy group, there can be mentioned, for example, a linear, branched or cyclic alkoxycarbonyloxy group having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyloxy group or a cyclohexyloxycarbonyloxy group.

The cyclic structure that may be formed by the bonding of the two $R_{15}$s to each other is preferably a 5- or 6-membered ring, especially a 5-membered ring (namely, a tetrahydrothiophene ring) formed by two bivalent $R_{15}$s in cooperation with the sulfur atom of general formula (ZI-4). The cyclic structure may condense with an aryl group or a cycloalkyl group. The bivalent $R_{15}$s may have substituents. As such substituents, there can be mentioned, for example, a hydroxyl group, a carboxyl group, a cyano group, a nitro group, an alkoxy group, an alkoxyalkyl group, an alkoxycarbonyl group, an alkoxycarbonyloxy group and the like as mentioned above. It is especially preferred for the $R_{15}$ of general formula (ZI-4) to be a methyl group, an ethyl group, the above-mentioned bivalent group allowing two $R_{15}$s to be bonded to each other so as to form a tetrahydrothiophene ring structure in cooperation with the sulfur atom of the general formula (ZI-4), or the like.

Each of $R_{13}$ and $R_{14}$ may have one or more substituents. As such substituents, there can be mentioned, for example, a hydroxyl group, an alkoxy group, an alkoxycarbonyl group, a halogen atom (especially, a fluorine atom) or the like.

In the formula, 1 is preferably 0 or 1, more preferably 1, and r is preferably 0 to 2.

Specific examples of the cation part in the compound (ZI-4) will be shown below.

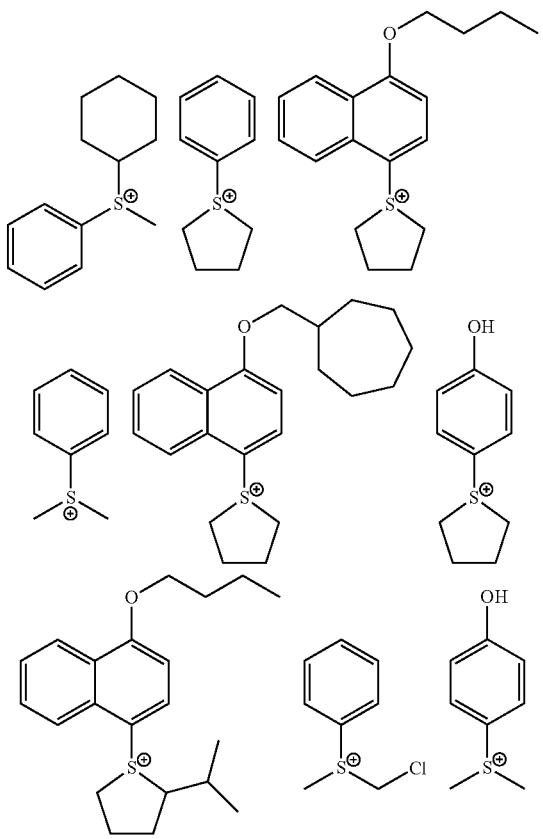

-continued
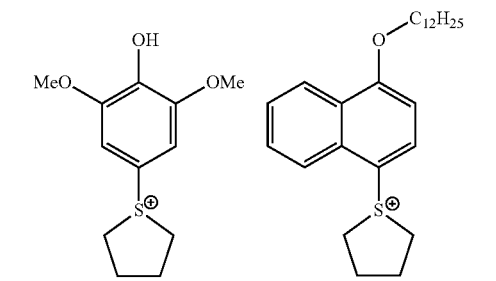
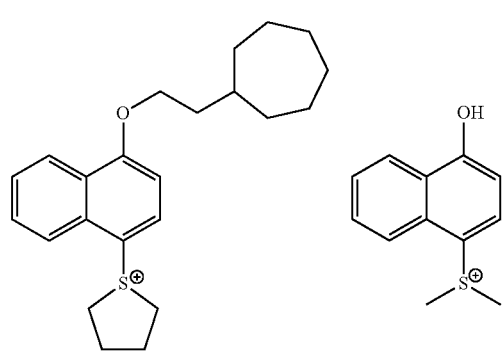
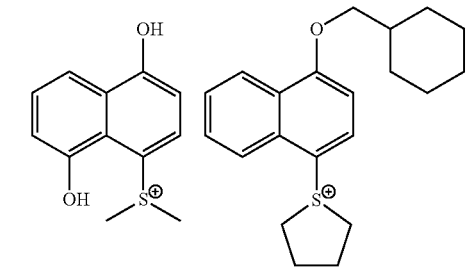
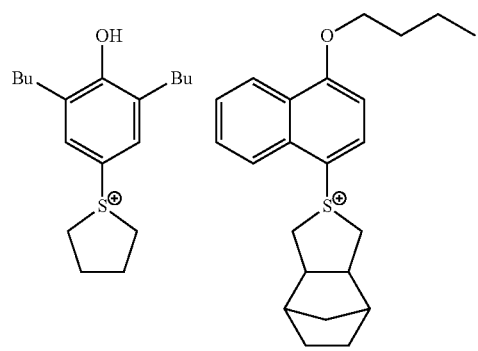
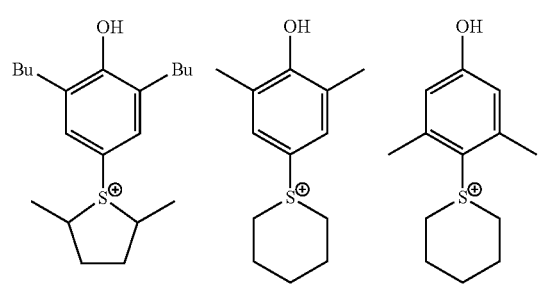
-continued
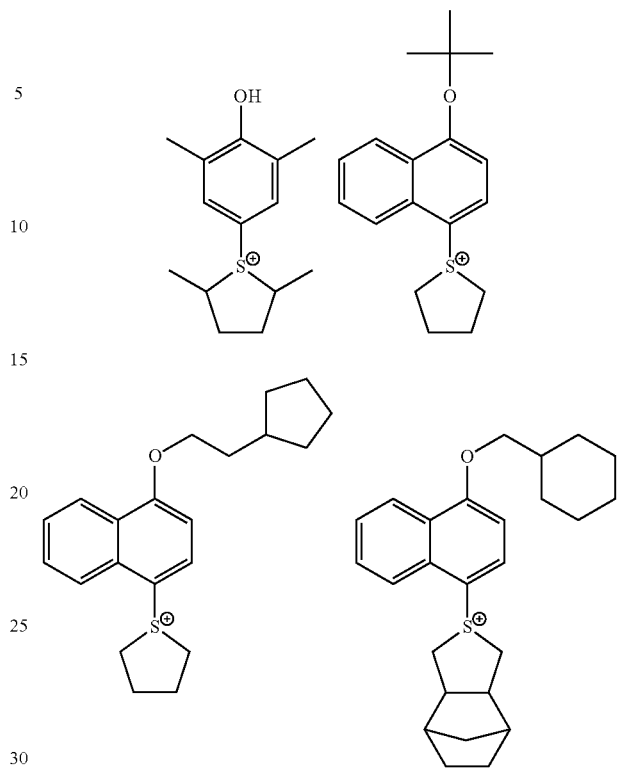
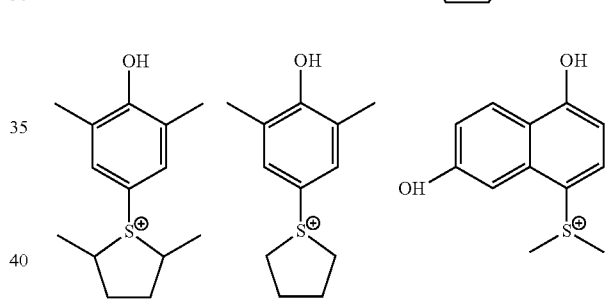
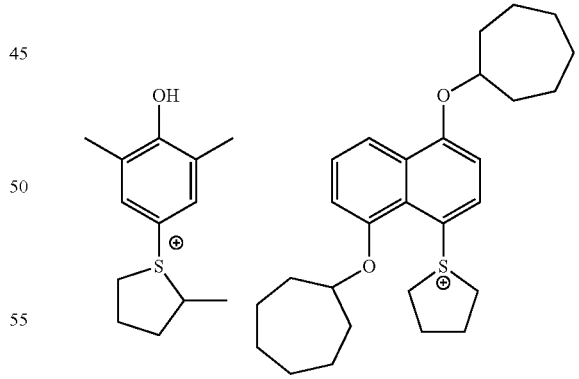
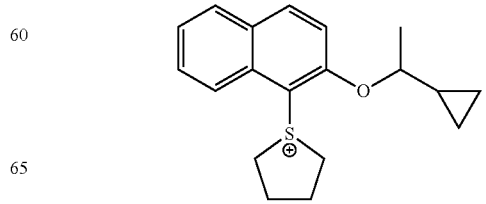

99
-continued
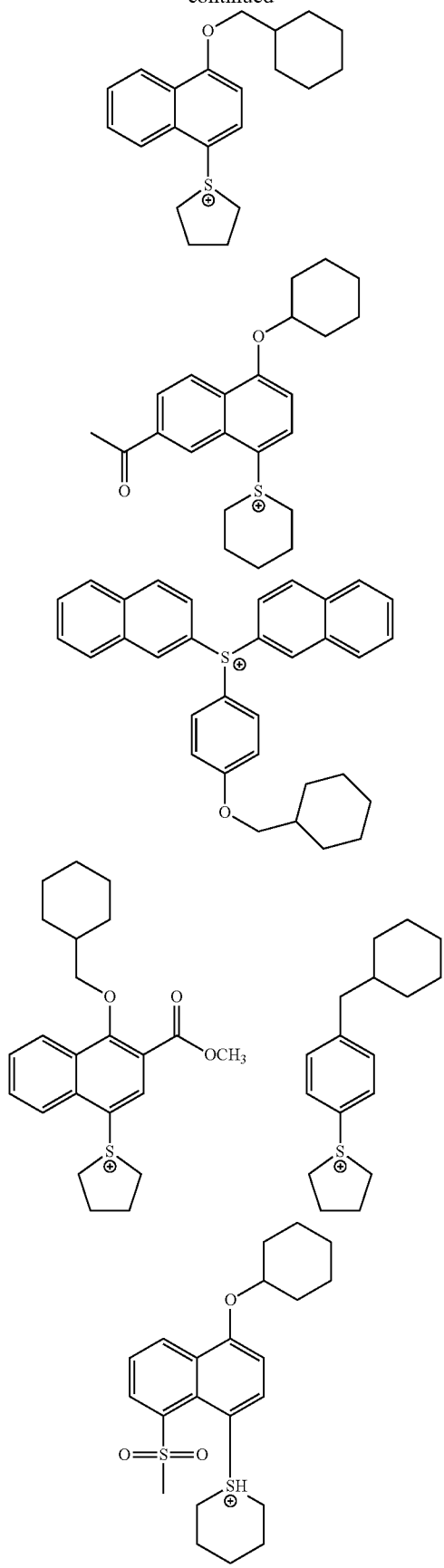
100
-continued
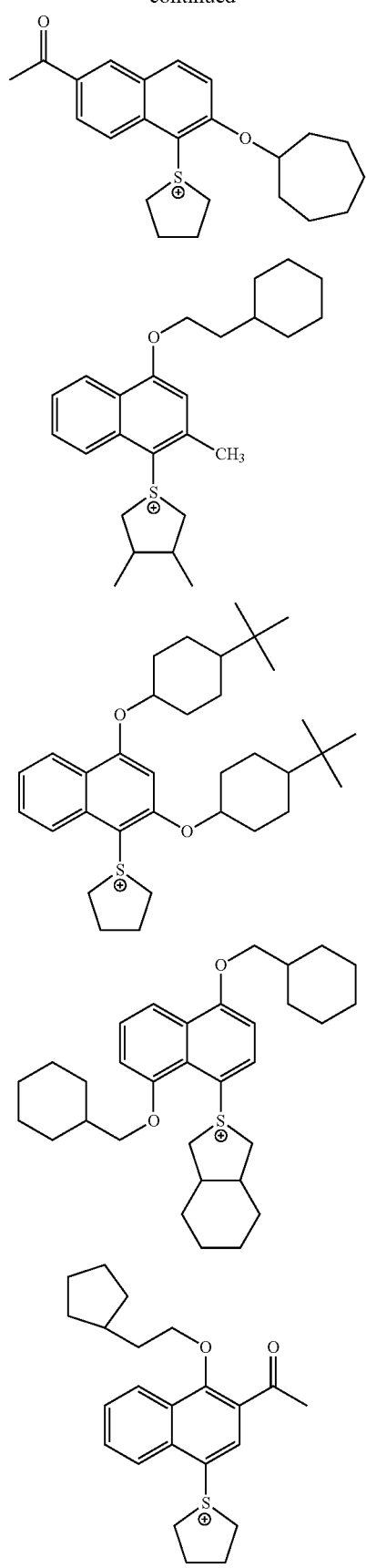

-continued

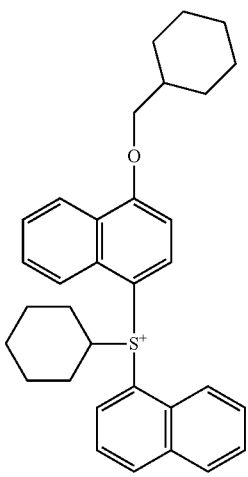

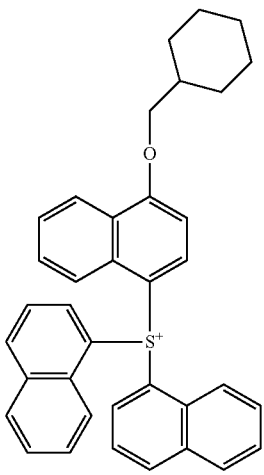

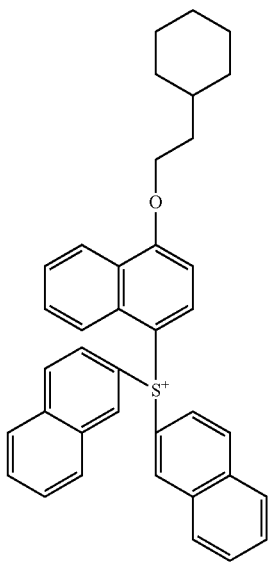

-continued

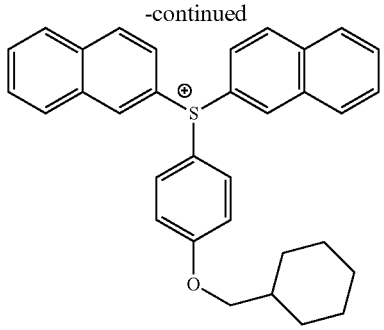

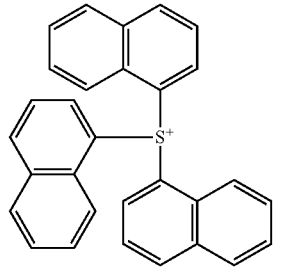

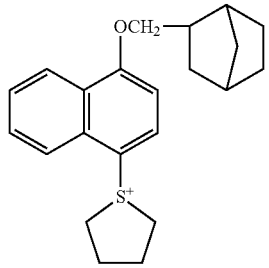

Now the general formulae (ZII) and (ZIII) will be described.

In general formulae (ZII) and (ZIII), each of $R_{204}$ to $R_{207}$ independently represents an aryl group, an alkyl group or a cycloalkyl group.

The aryl group represented by each of $R_{204}$ to $R_{207}$ is preferably a phenyl group or a naphthyl group, more preferably a phenyl group. The aryl group may be one having a heterocyclic structure containing an oxygen atom, nitrogen atom, sulfur atom, etc. As the aryl group having a heterocyclic structure, a pyrrole residue, a furan residue, a thiophene residue, an indole residue, a benzofuran residue, and a benzothiophene residue can be exemplified.

As preferred alkyl groups and cycloalkyl groups represented by $R_{204}$ to $R_{207}$, a linear or branched alkyl group having 1 to 10 carbon atoms and a cycloalkyl group having 3 to 10 carbon atoms can be exemplified. As the alkyl group, for example, a methyl group, an ethyl group, a propyl group, a butyl group and a pentyl group can be exemplified. As the cycloalkyl group, for example, a cyclopentyl group, a cyclohexyl group and a norbornyl group can be exemplified.

The aryl group, alkyl group and cycloalkyl group represented by $R_{204}$ to $R_{207}$ may have one or more substituents. As a possible substituent on the aryl group, alkyl group and cycloalkyl group represented by $R_{204}$ to $R_{207}$, an alkyl group (having, for example, 1 to 15 carbon atoms), a cycloalkyl group (having, for example, 3 to 15 carbon atoms), an aryl group (having, for example, 6 to 15 carbon atoms), an alkoxy group (having, for example, 1 to 15 carbon atoms), a halogen atom, a hydroxy group, and a phenylthio group can be exemplified.

$Z^-$ represents a nonnucleophilic anion. As such, the same nonnucleophilic anions as mentioned with respect to the $Z^-$ in the general formula (ZI) can be exemplified.

As the acid generators, the compounds represented by the following general formulae (ZIV), (ZV) and (ZVI) can further be exemplified.

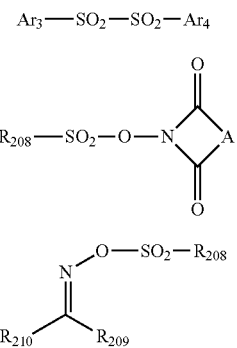

In the general formulae (ZIV) to (ZVI),
each of $Ar_3$ and $Ar_4$ independently represents an aryl group.
Each of $R_{208}$, $R_{209}$ and $R_{210}$ independently represents an alkyl group, a cycloalkyl group or an aryl group.

A represents an alkylene group, an alkenylene group or an arylene group.

Among the acid generators, the compounds represented by the general formulae (ZI) to (ZIII) are more preferred.

The acid generator is preferably a compound capable of generating an acid containing one sulfonic acid group or imido group. More preferably, the acid generator is a compound capable of generating a monovalent perfluoroalkanesulfonic acid, or a compound capable of generating a monovalent aromatic sulfonic acid substituted with a fluorine atom or a group containing a fluorine atom, or a compound capable of generating a monovalent imidic acid substituted with a fluorine atom or a group containing a fluorine atom. Furthermore preferably, the acid generator is a sulfonium salt of fluorinated alkanesulfonic acid, fluorinated benzenesulfonic acid, fluorinated imidic acid or fluorinated methide acid. With respect to useful acid generators, it is especially preferred for the generated acid to be a fluorinated alkanesulfonic acid, fluorinated benzenesulfonic acid or fluorinated imidic acid of −1 or below pKa. When these acid generators are used, the sensitivity can be enhanced.

Especially preferred examples of the acid generators will be shown below.

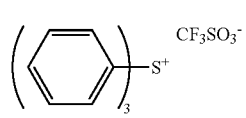 (z1)

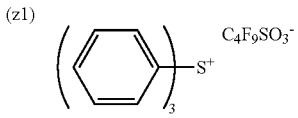 (z2)

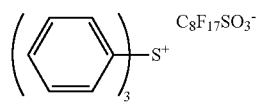 (z3)

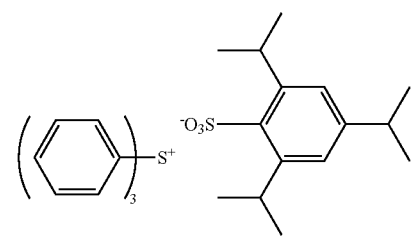 (z4)

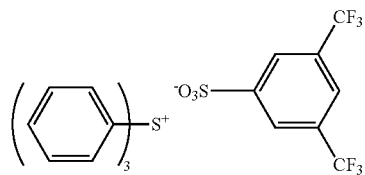 (z5)

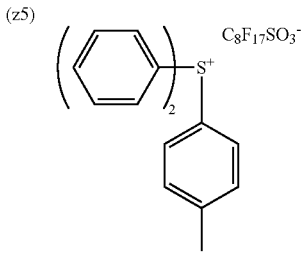 (z6)

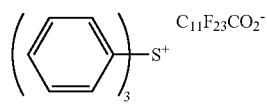 (z7)

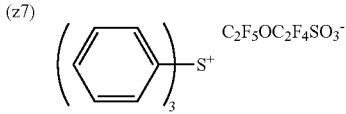 (z8)

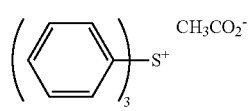 (z9)

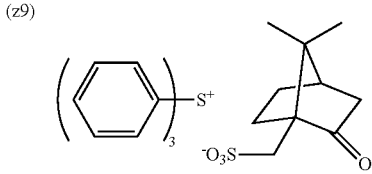 (z10)

-continued
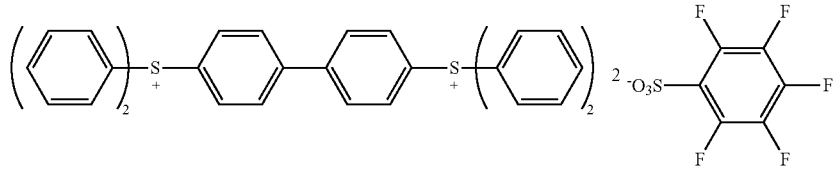
(z11)
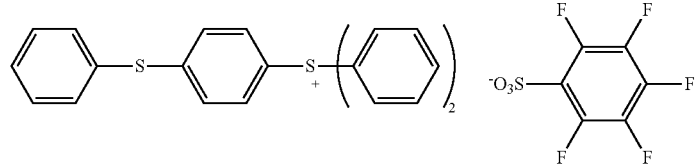
(z12)
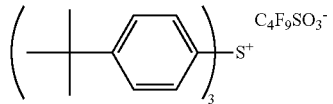
(z13)
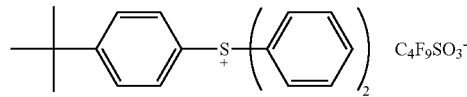
(z14)
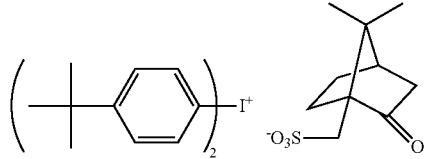
(z15) (z16)
(z17) (z18)
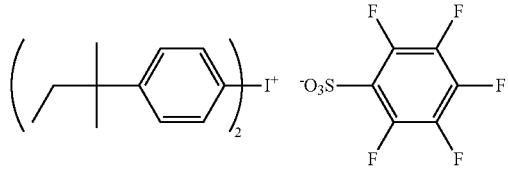
(z19)
(z20)
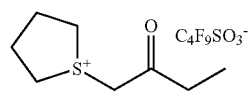
(z21) (z22)
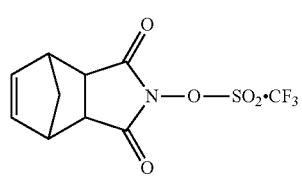
(z23) (z24)
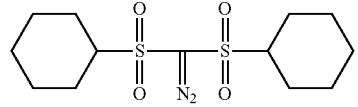
(z25) (z26)
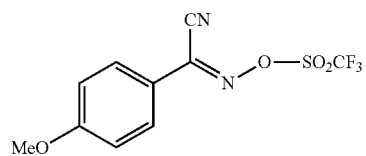
(z27)

-continued
(z28)
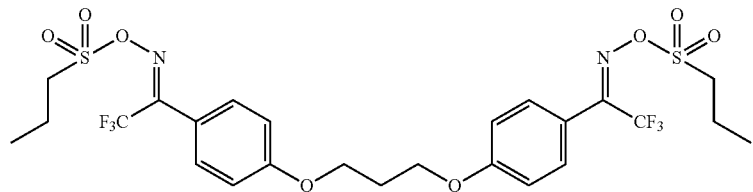
(z29)
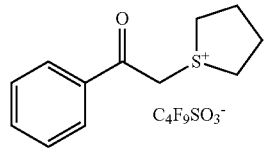
(z30)
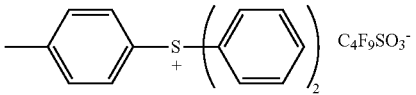
(z31)
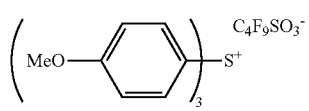
(z32)
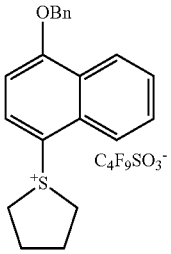
(z33)
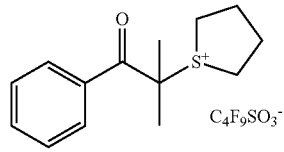
(z34)
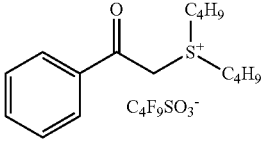
(z35)
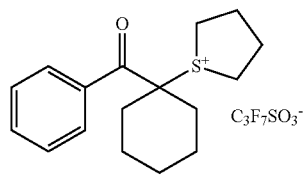
(z36)
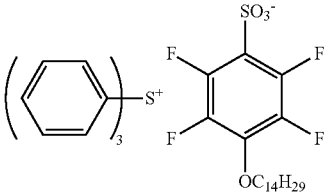
(z37)
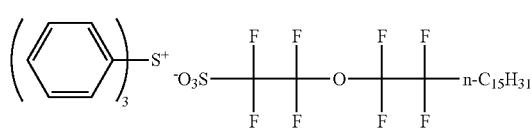
(z38)
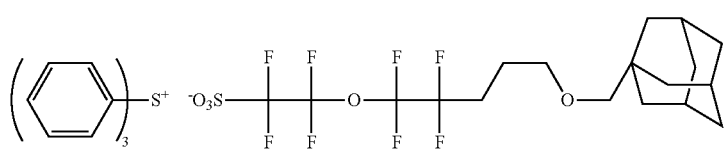
(z39)
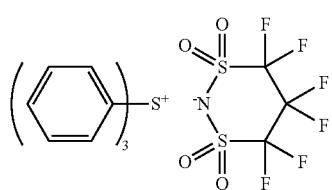
(z40)
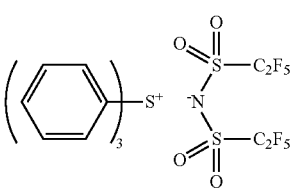

-continued
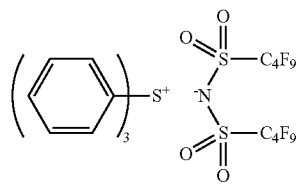 (z41)
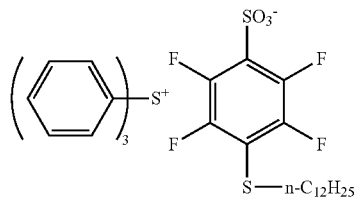 (z42)
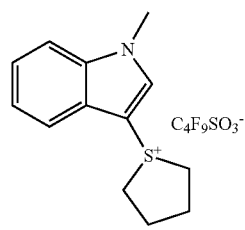 (z43)
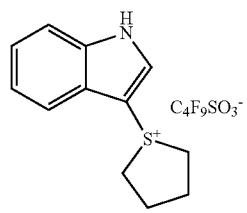 (z44)
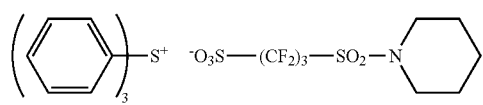 (z45)
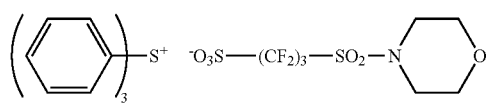 (z46)
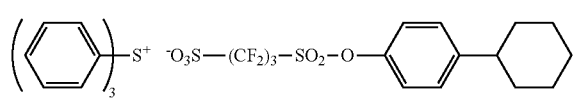 (z47)
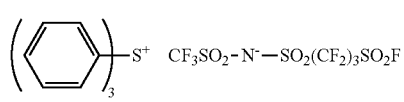 (z48)
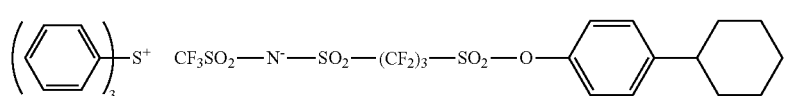 (z49)
 (z50)
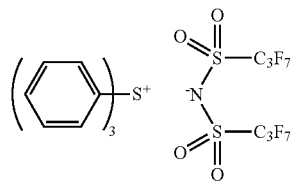 
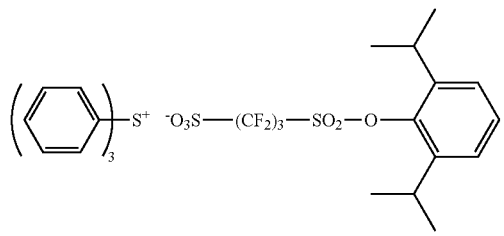 (z51)
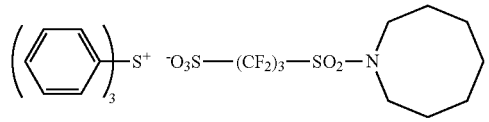 (z52)
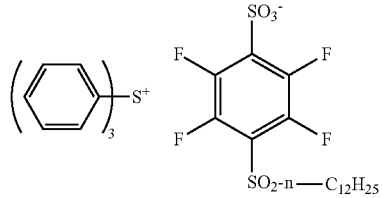 (z53)
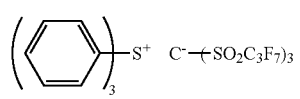 (z54)
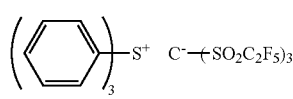 (z55)
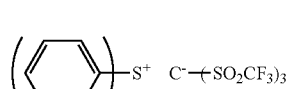 (z56)
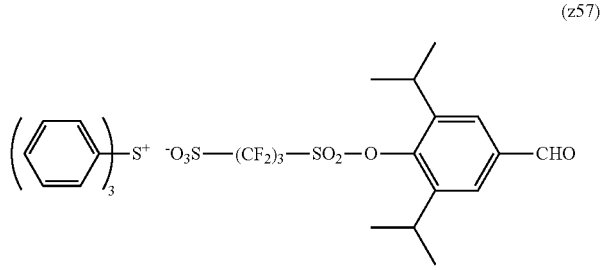 (z57)

-continued
(z58) 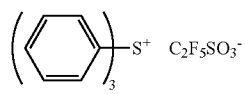 C₂F₅SO₃⁻
(z59) 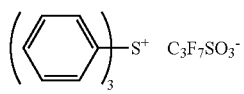 C₃F₇SO₃⁻
(z60) 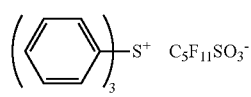 C₅F₁₁SO₃⁻
(z61) 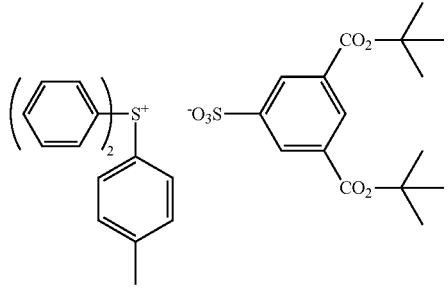
(z62) 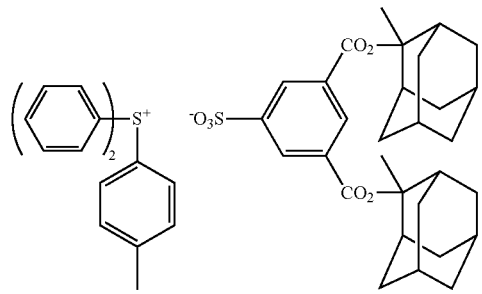
(z63) 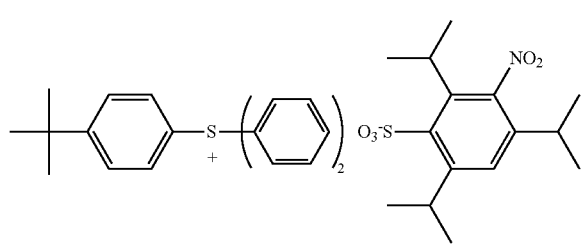
(z64) 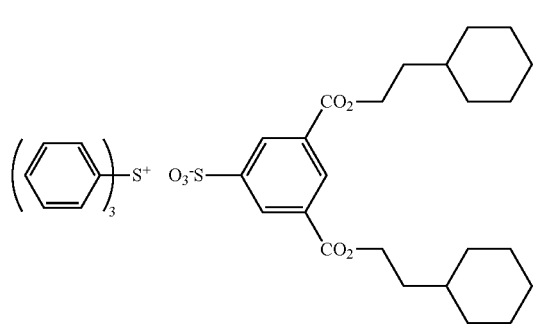
(z65) 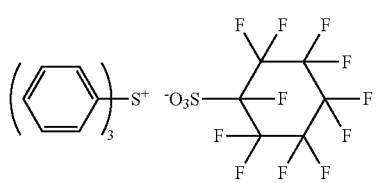
(z66) 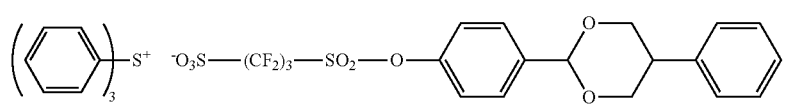
(z67) 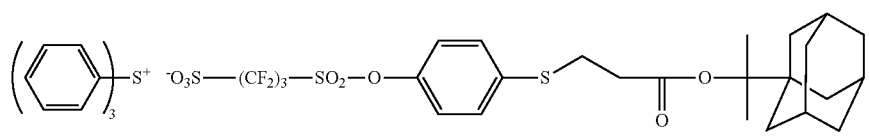
(z68) 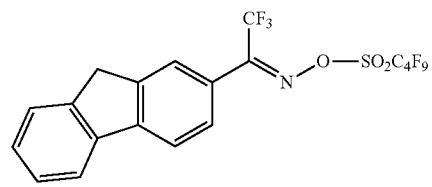
(z69) 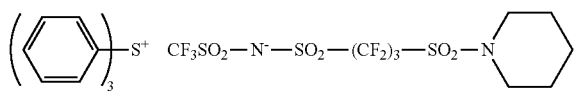

-continued
(z70) 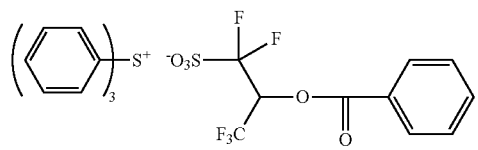
(z71) 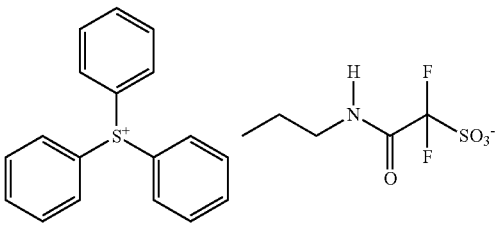
(z72) 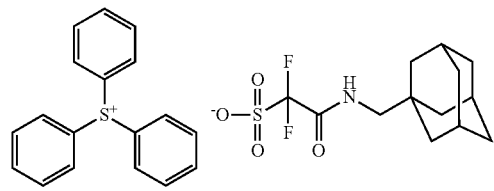
(z73) 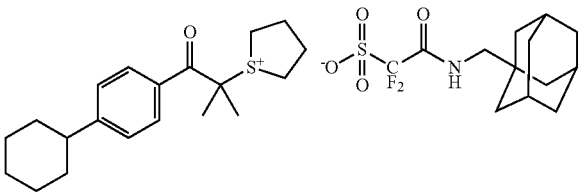
(z74) 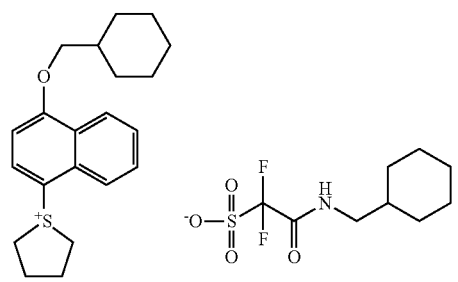
(z75) 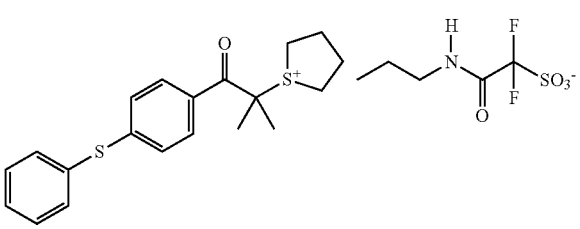
(z76) 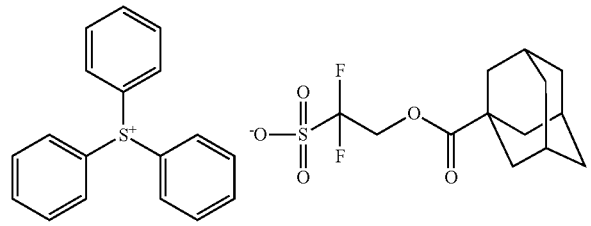
(z77) 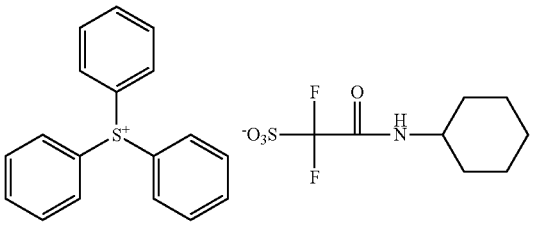
(z78) 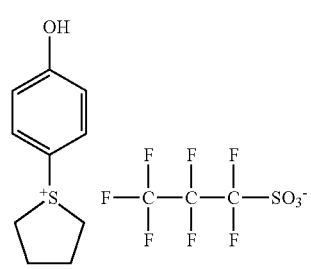
(z79) 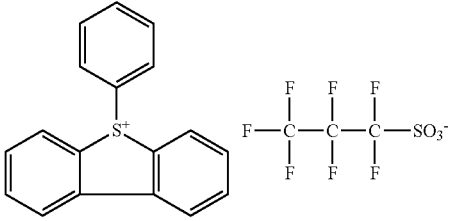
(z80) 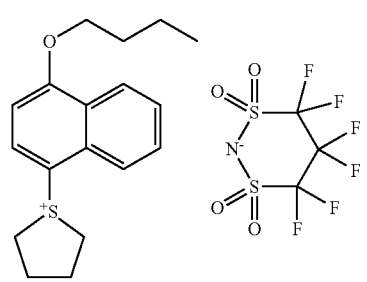
(z81) 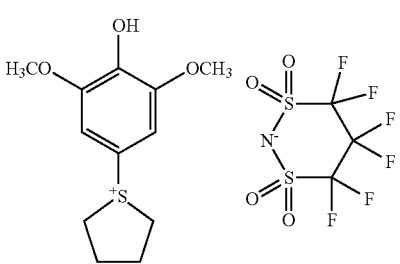

-continued
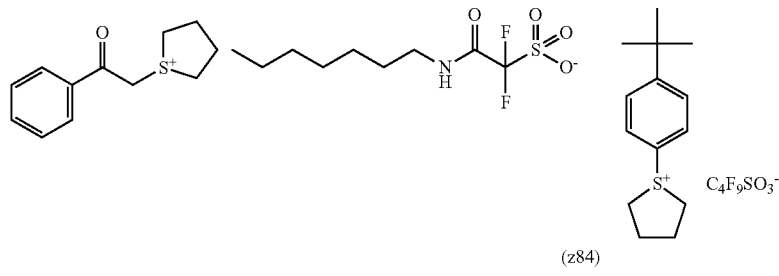
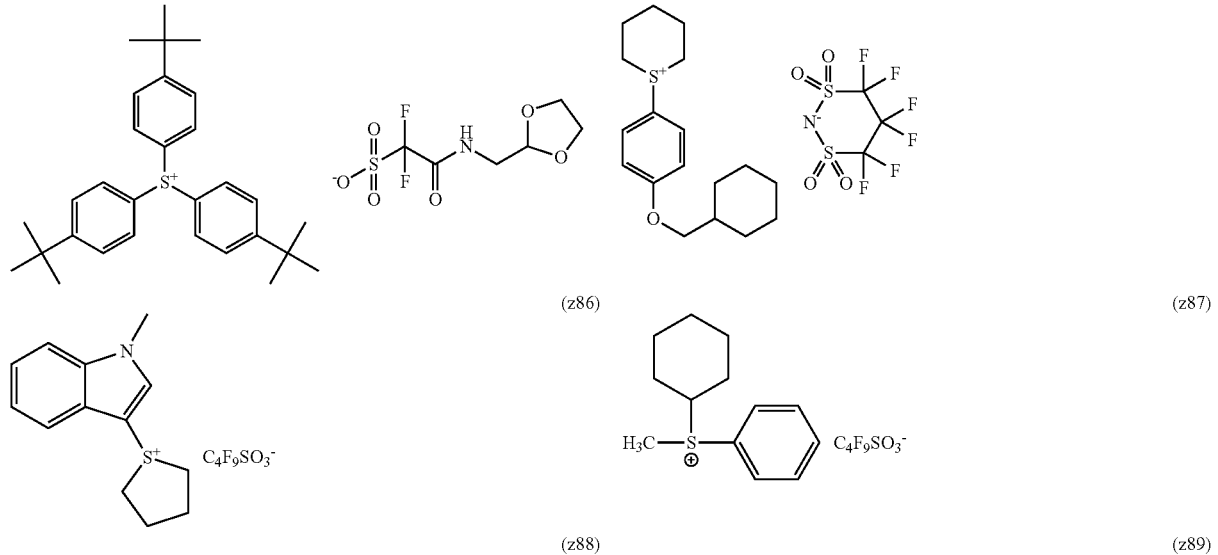
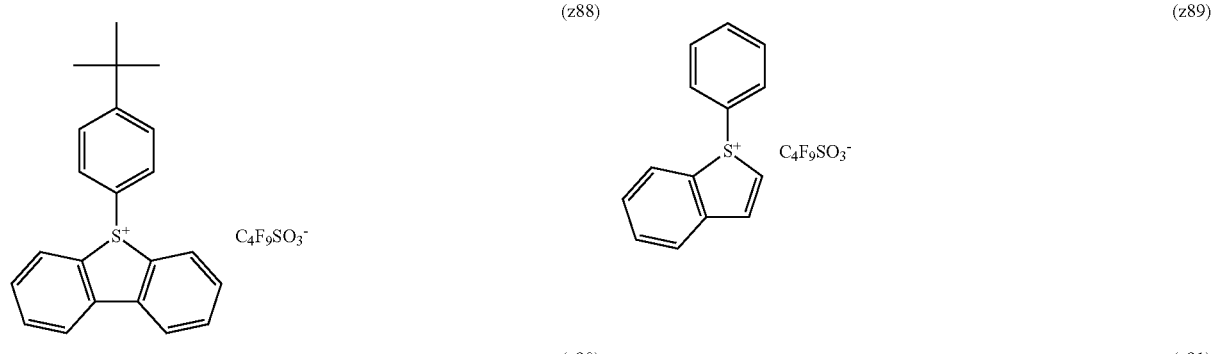
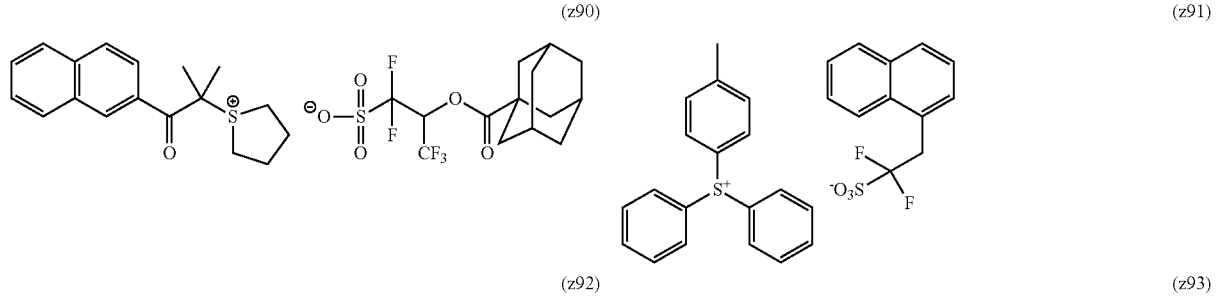
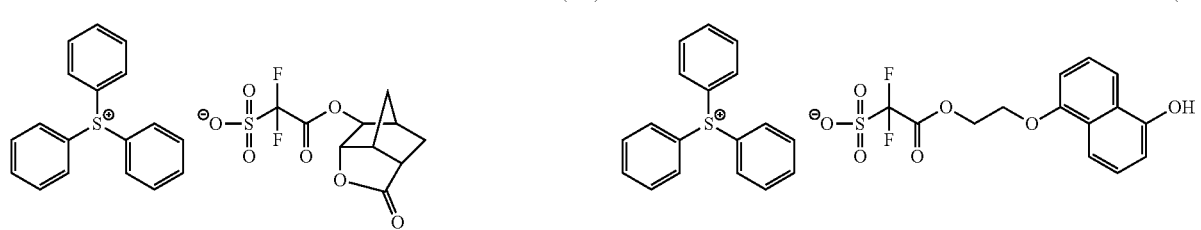

-continued
(z94)
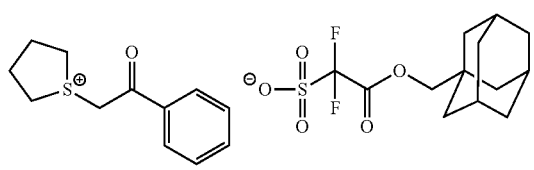
(z95)
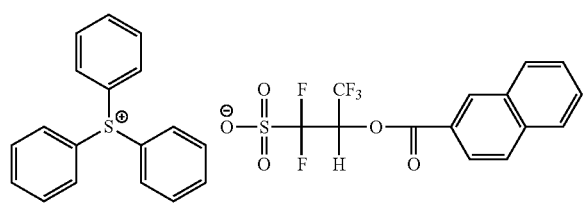
(z96)
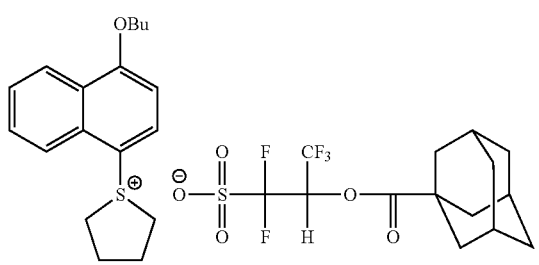
(z97)
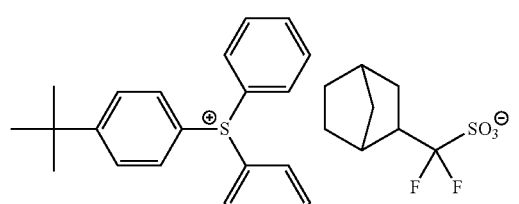
(z98)
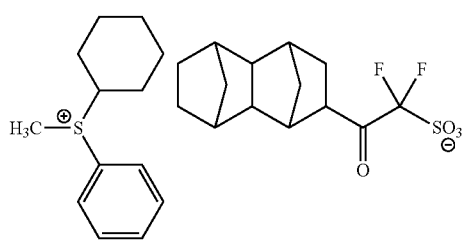
(z99)
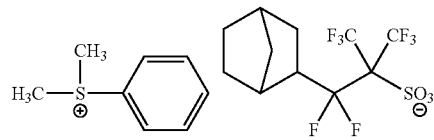
(z100)
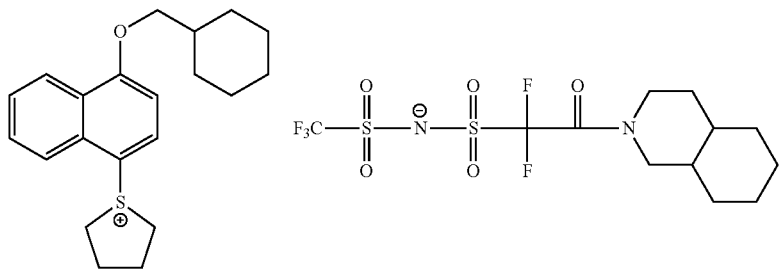
(z101)
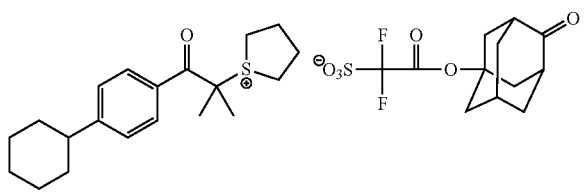
(z102)
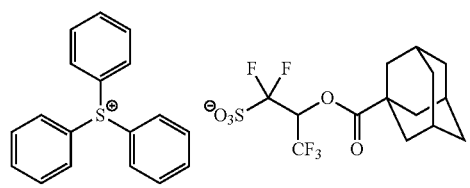
(z103)
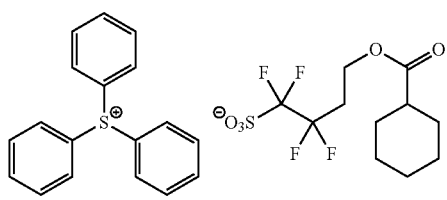
(z104)
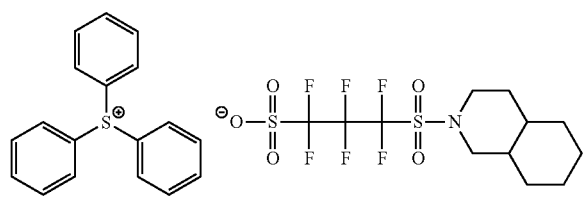

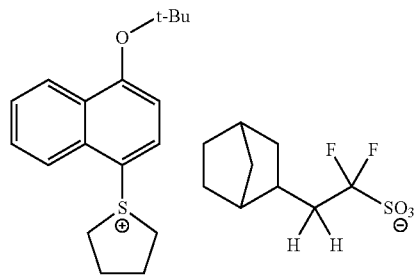
(z105)

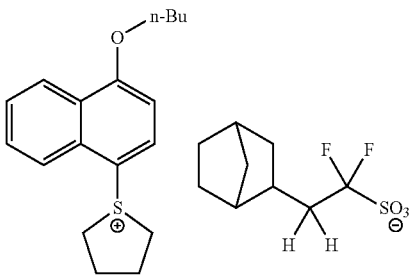
(z106)

One of the acid generators other than the compounds of general formula (1-1) may be used alone, or two or more thereof may be used in combination.

When the composition of the present invention contains the component (C), the content thereof based on the total solids of the composition is preferably in the range of 0.1 to 30 mass %, more preferably 0.5 to 25 mass %, further more preferably 3 to 20 mass % and most preferably 5 to 20 mass %.

When the acid generator is any of those of general formulae (ZI-3) and (ZI-4) above, the content thereof based on the total solids of the composition is preferably in the range of 0.5 to 30 mass %, more preferably 1 to 25 mass %, further more preferably 3 to 20 mass % and most preferably 5 to 20 mass %.

The mass ratio of component (C) to component (B) is preferably in the range of 0.1 to 10, more preferably 0.5 to 5.

(D) Hydrophobic Resin

The composition according to the present invention may further contain a hydrophobic resin (hereinafter also referred to as a "resin (D)"). The hydrophobic resin contains at least either a fluorine atom or a silicon atom.

The fluorine atom and/or silicon atom may be introduced in the principal chain of the hydrophobic resin or a side chain thereof.

When the hydrophobic resin contains a fluorine atom, it is preferred for the resin to comprise, as a partial structure containing a fluorine atom, an alkyl group containing a fluorine atom, a cycloalkyl group containing a fluorine atom or an aryl group containing a fluorine atom.

The alkyl group having a fluorine atom is a linear or branched alkyl group whose at least one hydrogen atom is replaced by a fluorine atom. The alkyl group preferably has 1 to 10 carbon atoms, more preferably 1 to 4 carbon atoms. A further other substituent may be introduced in the alkyl group.

The cycloalkyl group having a fluorine atom is a mono- or polycycloalkyl group whose at least one hydrogen atom is replaced by a fluorine atom. A further other substituent may be introduced in the cycloalkyl group.

As the aryl group containing a fluorine atom, there can be mentioned one having at least one hydrogen atom of an aryl group, such as a phenyl or naphthyl group, substituted with a fluorine atom. Further, other substituents may be contained.

As preferred alkyl groups containing a fluorine atom, cycloalkyl groups containing a fluorine atom and aryl groups containing a fluorine atom, there can be mentioned groups of the following general formulae (F2) to (F4), which however in no way limit the scope of the present invention.

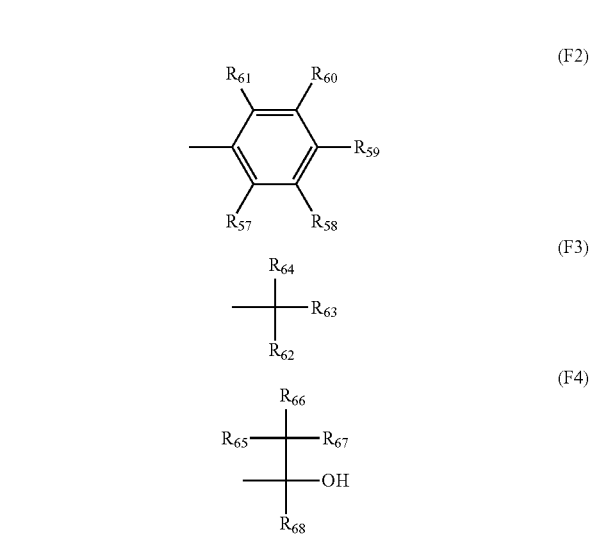

In general formulae (F2) to (F4), each of $R_{57}$ to $R_{68}$ independently represents a hydrogen atom, a fluorine atom or an alkyl group (linear or branched), provided that at least one of each of $R_{57}$-$R_{61}$, at least one of each of $R_{62}$-$R_{64}$ and at least one of each of $R_{65}$-$R_{68}$ represent a fluorine atom or an alkyl group (preferably having 1 to 4 carbon atoms) having at least one hydrogen atom thereof substituted with a fluorine atom.

It is preferred that all of $R_{57}$-$R_{61}$ and $R_{65}$-$R_{67}$ represent fluorine atoms. Each of $R_{62}$, $R_{63}$ and $R_{68}$ preferably represents a fluoroalkyl group (especially having 1 to 4 carbon atoms), more preferably a perfluoroalkyl group having 1 to 4 carbon atoms. When each of $R_{62}$ and $R_{63}$ represents a perfluoroalkyl group, $R_{64}$ preferably represents a hydrogen atom. $R_{62}$ and $R_{63}$ may be bonded with each other to thereby form a ring.

Specific examples of the groups of general formula (F2) include a p-fluorophenyl group, a pentafluorophenyl group, a 3,5-di(trifluoromethyl)phenyl group and the like.

Specific examples of the groups of general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of general formula (F4) include —C(CF$_3$)$_2$OH, —C(C$_2$F$_5$)$_2$OH, —C(CF$_3$)(CF$_3$)OH, —CH(CF$_3$)OH and the like. —C(CF$_3$)$_2$OH is preferred.

The partial structure containing a fluorine atom may be directly bonded to the principal chain, or may be bonded to the principal chain through a group selected from the group consisting of an alkylene group, a phenylene group, an ether group, a thioether group, a carbonyl group, an ester group, an amido group, a urethane group and a ureylene group, or through a group composed of a combination of two or more of these groups.

As preferred repeating units having a fluorine atom, there can be mentioned the repeating units represented by the general formulae below.

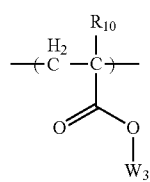
(C-Ia)

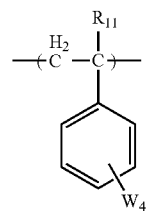
(C-Ib)

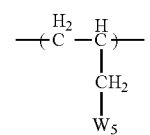
(C-Ic)

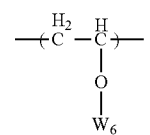
(C-Id)

In the formulae, each of R$_{10}$ and R$_{11}$ independently represents a hydrogen atom, a fluorine atom or an alkyl group. The alkyl group is preferably a linear or branched alkyl group having 1 to 4 carbon atoms. The alkyl group may have a substituent. As a substituted alkyl group, there can be mentioned, in particular, a fluorinated alkyl group.

Each of W$_3$ to W$_6$ independently represents an organic group containing at least one fluorine atom. As such, for example, there can be mentioned the atomic groups of general formulae (F2) to (F4) above.

Further, besides these, the following units may be introduced as the repeating unit containing a fluorine atom.

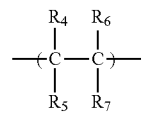
(C-II)

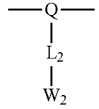
(C-III)

In the formulae, each of R$_4$ to R$_7$ independently represents a hydrogen atom, a fluorine atom or an alkyl group. The alkyl group is preferably a linear or branched alkyl group having 1 to 4 carbon atoms. The alkyl group may have a substituent. As a substituted alkyl group, there can be mentioned, in particular, a fluorinated alkyl group.

At least one of R$_4$ to R$_7$ represents a fluorine atom. R$_4$ and R$_5$, or R$_6$ and R$_7$ may cooperate with each other to thereby form a ring.

W$_2$ represents an organic group containing at least one fluorine atom. As such, for example, there can be mentioned the atomic groups of general formulae (F2) to (F4) above.

L$_2$ represents a single bond or a bivalent connecting group. As the bivalent connecting group, there can be mentioned a substituted or unsubstituted arylene group, a substituted or unsubstituted alkylene group, a substituted or unsubstituted cycloalkylene group, —O—, —SO$_2$—, —CO—, —N(R)— (in the formula, R is a hydrogen atom or an alkyl group), —NHSO$_2$— or a bivalent connecting group consisting of a combination of two or more of these.

Q represents an alicyclic structure. A substituent may be introduced in the alicyclic structure. The alicyclic structure may be monocyclic or polycyclic. The alicyclic structure when being polycyclic may be a bridged one. The alicyclic structure when being monocyclic is preferably a cycloalkyl group having 3 to 8 carbon atoms. As such, there can be mentioned, for example, a cyclopentyl group, a cyclohexyl group, a cyclobutyl group, a cyclooctyl group or the like. As the polycyclic one, there can be mentioned a group with, for example, a bicyclo, tricyclo or tetracyclo structure having 5 or more carbon atoms. A cycloalkyl group having 6 to 20 carbon atoms is preferred. As such, there can be mentioned, for example, an adamantyl group, a norbornyl group, a dicyclopentyl group, a tricyclodecanyl group, a tetracyclododecyl group or the like. The carbon atoms of the cycloalkyl group may be partially replaced with a heteroatom, such as an oxygen atom. It is especially preferred for Q to represent a norbornyl group, a tricyclodecanyl group, a tetracyclododecyl group or the like.

The hydrophobic resin may contain a silicon atom.

It is preferred for the hydrophobic resin to have an alkylsilyl structure (preferably a trialkylsilyl group) or a cyclosiloxane structure as a partial structure having a silicon atom.

As the alkylsilyl structure or cyclosiloxane structure, there can be mentioned, for example, any of the groups of the following general formulae (CS-1) to (CS-3) or the like.

(CS-1)

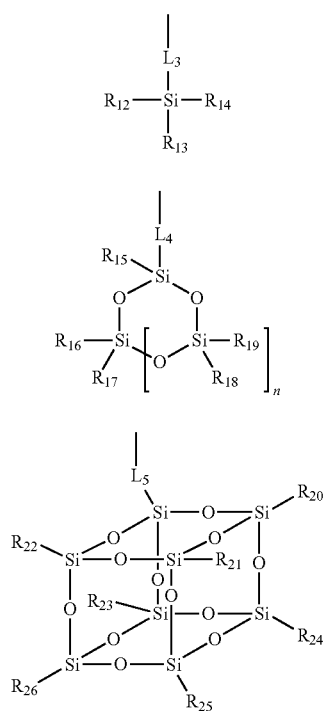

(CS-2)

(CS-3)

In general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one or a combination of two or more groups selected from the group consisting of an alkylene group, a phenylene group, an ether group, a thioether group, a carbonyl group, an ester group, an amido group, a urethane group and a urea group.

In the formulae, n is an integer of 1 to 5. n is preferably an integer of 2 to 4.

It is preferred for the repeating unit containing at least either a fluorine atom or a silicon atom to be a (meth)acrylate repeating unit.

Particular examples of the repeating units each containing at least either a fluorine atom or a silicon atom are shown below, which in no way limit the scope of the present invention.

In the particular examples, $X_1$ represents a hydrogen atom, —$CH_3$, —F or —$CF_3$, and $X_2$ represents —F or —$CF_3$.

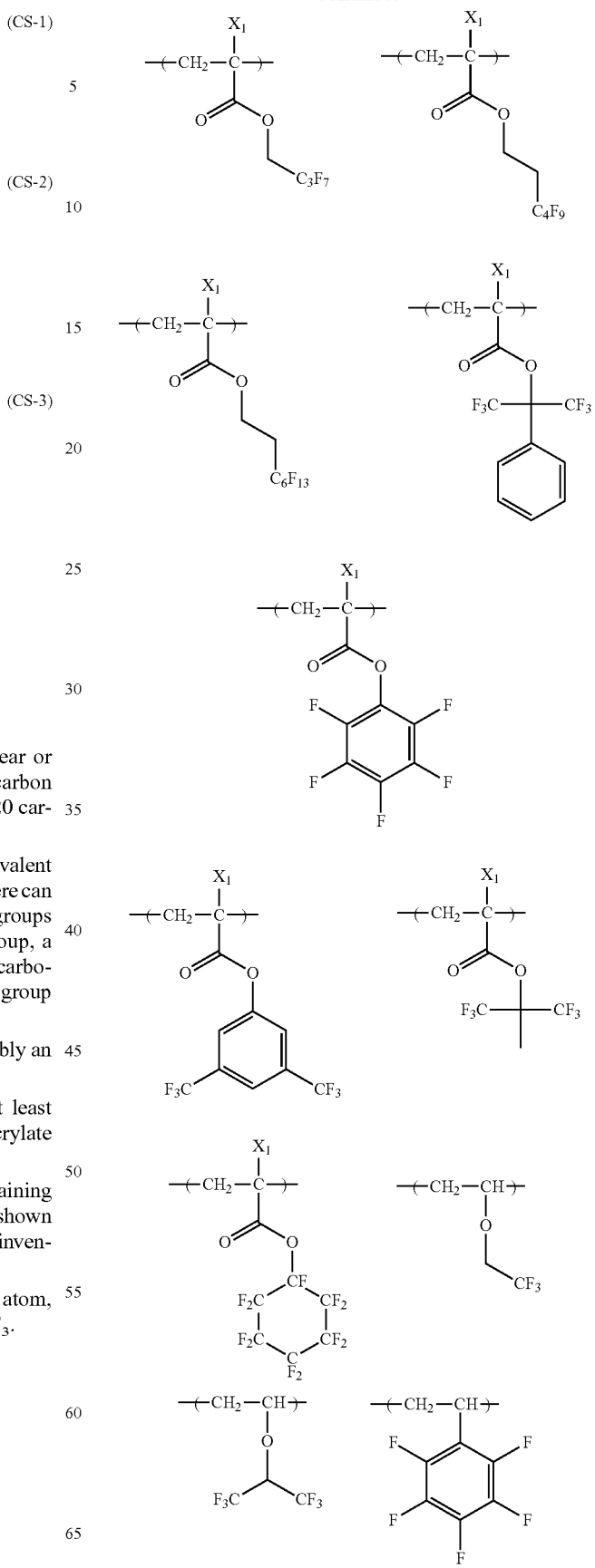

125
-continued
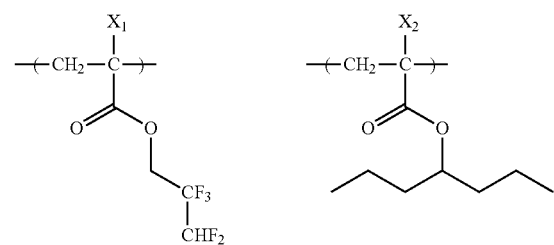
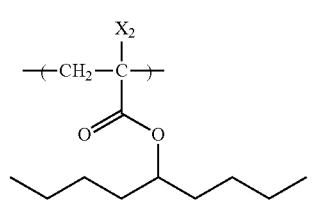
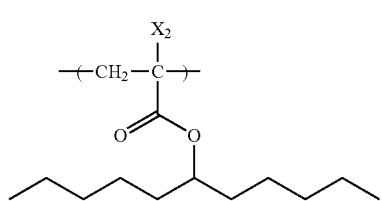
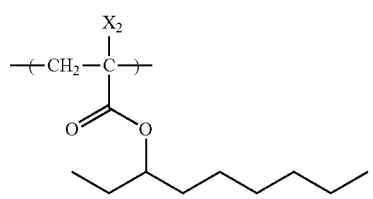
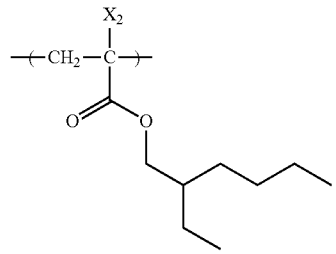
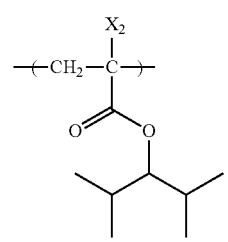
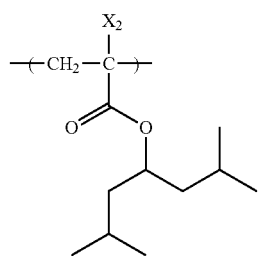
126
-continued
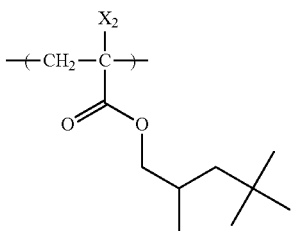
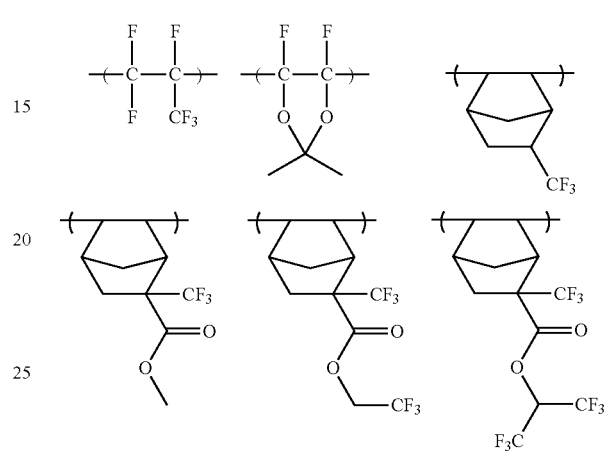
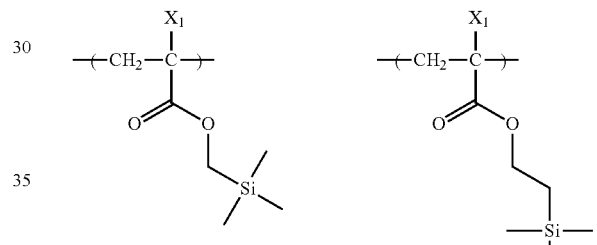
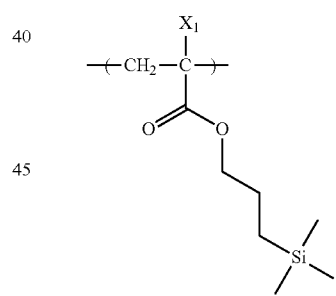
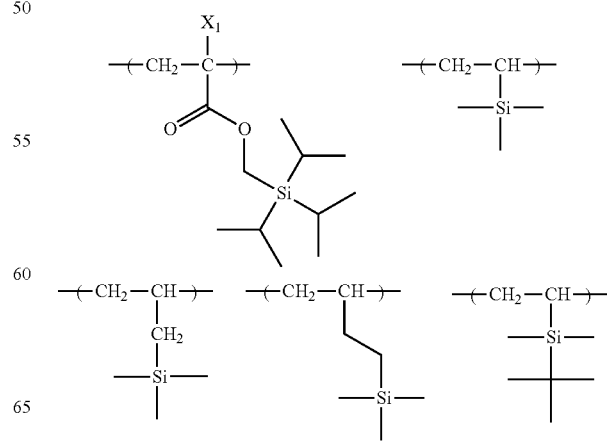

-continued

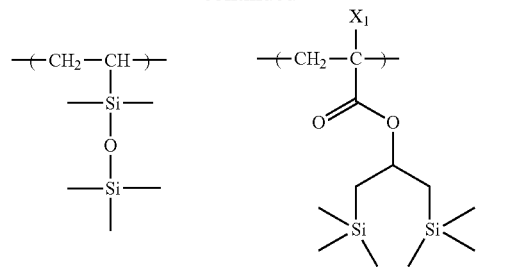
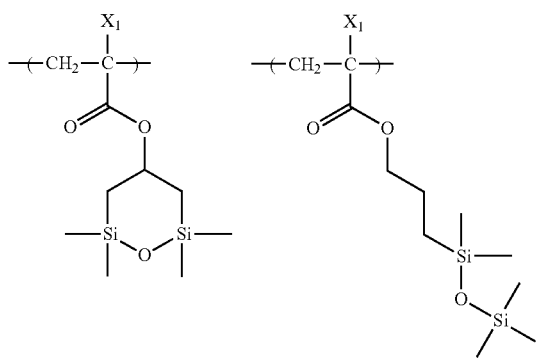
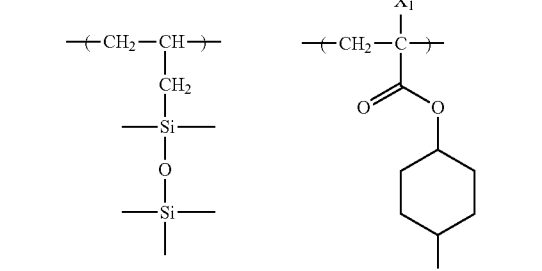
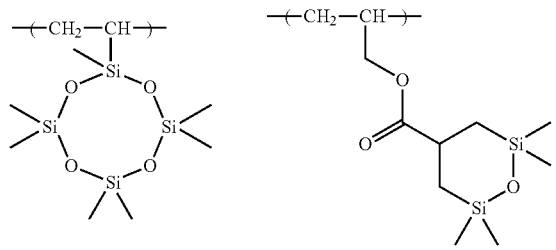
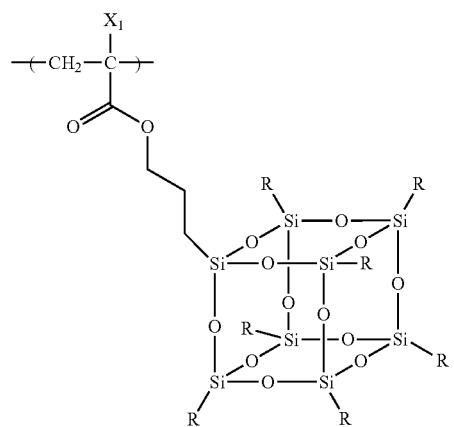

R = CH$_3$, C$_2$H$_5$, C$_3$H$_7$, C$_4$H$_9$

-continued

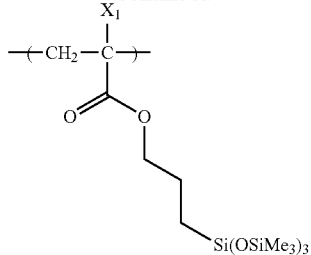

It is preferred for the hydrophobic resin to contain a repeating unit (b) containing at least one group selected from the group consisting of the following groups (x) to (z).

Namely, (x) an alkali-soluble group, (y) a group that when acted on by an alkali developer, is decomposed to thereby increase its solubility in the alkali developer (polarity conversion group), and (z) a group that when acted on by an acid, is decomposed to thereby increase its solubility in an alkali developer.

The following varieties of repeating units (b) can be mentioned.

Namely, the repeating unit (b) may be:

a repeating unit (b') containing at least either a fluorine atom or a silicon atom and at least one group selected from the group consisting of the above groups (x) to (z) simultaneously introduced in one side chain thereof, a repeating unit (b*) containing at least one group selected from the group consisting of the above groups (x) to (z) but containing neither a fluorine atom nor a silicon atom, or a repeating unit (b") in which at least one group selected from the group consisting of the above groups (x) to (z) is introduced in its one side chain while at least either a fluorine atom or a silicon atom is introduced in a side chain other than the above side chain within the same repeating unit.

It is preferred for the hydrophobic resin to contain the repeating unit (b') as the repeating unit (b). Namely, it is preferred for the repeating unit (b) containing at least one group selected from the group consisting of the above groups (x) to (z) to further contain at least either a fluorine atom or a silicon atom.

When the hydrophobic resin contains the repeating unit (b*), it is preferred for the hydrophobic resin to be a copolymer with a repeating unit (repeating unit other than the above-mentioned repeating units (b') and (b")) containing at least either a fluorine atom or a silicon atom. In the repeating unit (b"), it is preferred for the side chain containing at least one group selected from the group consisting of the above groups (x) to (z) and the side chain containing at least either a fluorine atom or a silicon atom to be bonded to the same carbon atom of the principal chain, namely to be in a positional relationship shown in formula (K1) below.

In the formula, B1 represents a partial structure containing at least one group selected from the group consisting of the above groups (x) to (z), and B2 represents a partial structure containing at least either a fluorine atom or a silicon atom.

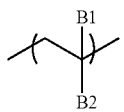

(K1)

The group selected from the group consisting of the above groups (x) to (z) is preferably (x) an alkali-soluble group or (y) a polarity conversion group, more preferably (y) a polarity conversion group.

As the alkali-soluble group (x), there can be mentioned a phenolic hydroxyl group, a carboxylate group, a fluoroalcohol group, a sulfonate group, a sulfonamido group, a sulfonimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali-soluble groups, there can be mentioned a fluoroalcohol group (preferably hexafluoroisopropanol group), a sulfonimido group and a bis(alkylcarbonyl)methylene group.

As the repeating unit (bx) having an alkali soluble group (x), preferred use is made of any of a repeating unit resulting from direct bonding of an alkali soluble group to the principal chain of a resin like a repeating unit of acrylic acid or methacrylic acid, a repeating unit resulting from bonding, via a connecting group, of an alkali soluble group to the principal chain of a resin and a repeating unit resulting from polymerization with the use of a chain transfer agent or polymerization initiator having an alkali soluble group to thereby introduce the same in a polymer chain terminal.

When the repeating unit (bx) is a repeating unit containing at least either a fluorine atom or a silicon atom (namely, when corresponding to the above-mentioned repeating unit (b') or repeating unit (b")), the partial structure containing a fluorine atom contained in the repeating unit (bx) can be the same as set forth above in connection with the repeating unit containing at least either a fluorine atom or a silicon atom. As such, preferably, there can be mentioned any of the groups of general formulae (F2) to (F4) above. Also in that instance, the partial structure containing a silicon atom contained in the repeating unit (bx) can be the same as set forth above in connection with the repeating unit containing at least either a fluorine atom or a silicon atom. As such, preferably, there can be mentioned any of the groups of general formulae (CS-1) to (CS-3) above.

The content ratio of repeating units (bx) having an alkali soluble group (x) is preferably in the range of 1 to 50 mol %, more preferably 3 to 35 mol % and still more preferably 5 to 20 mol % based on all the repeating units of the hydrophobic resin.

Specific examples of the repeating units (bx) having an alkali-soluble group (x) will be shown below.

In the formulae, Rx represents a hydrogen atom, —CH$_3$, —CF$_3$ or —CH$_2$OH, and X$_1$ represents a hydrogen atom, —CH$_3$, —F or —CF$_3$.

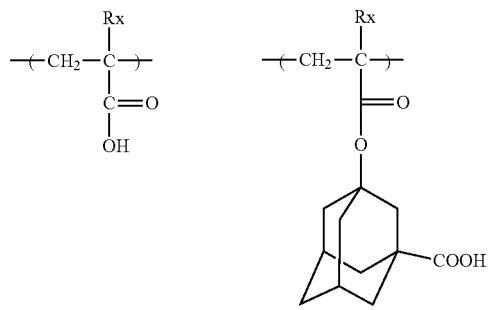

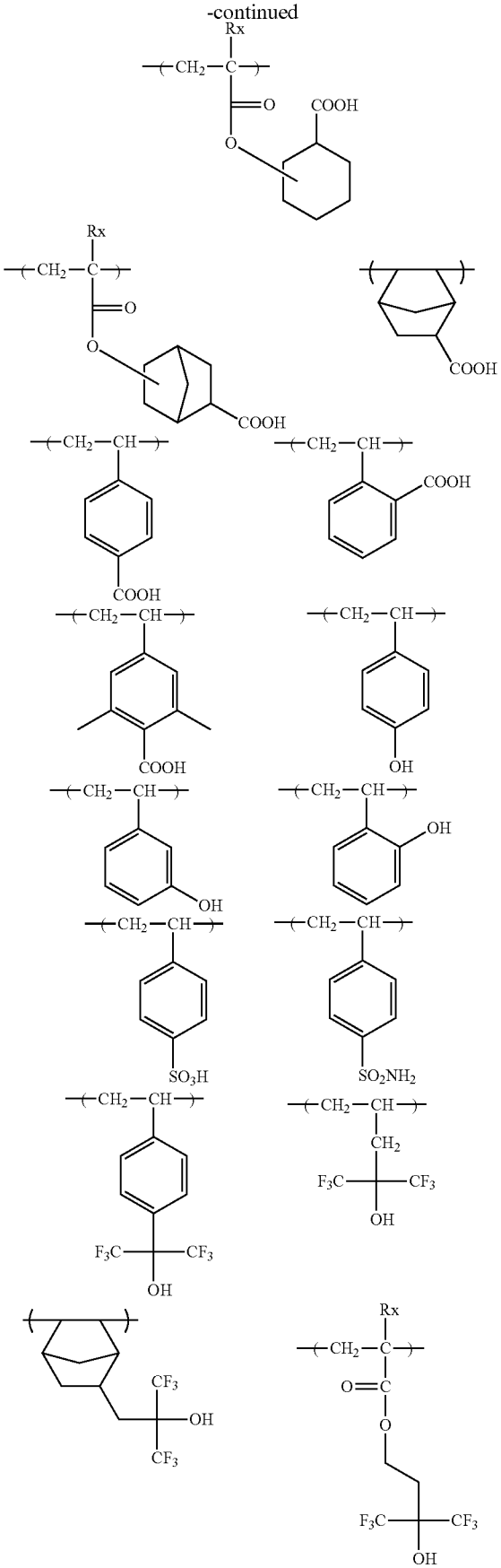

-continued

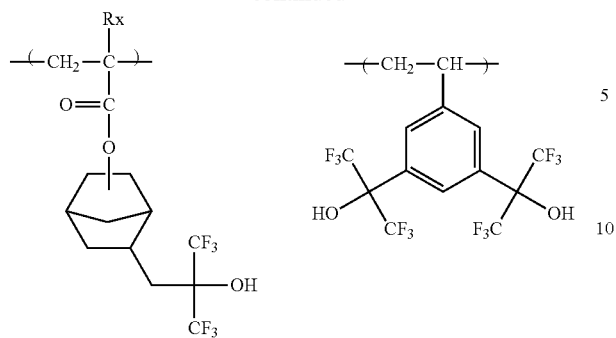
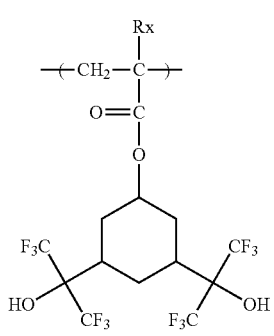
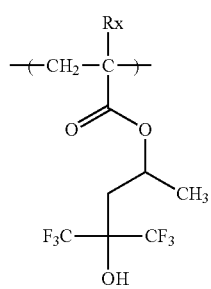
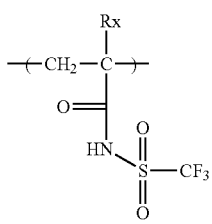
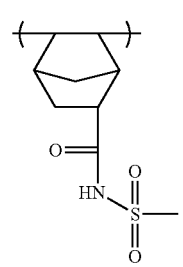

-continued

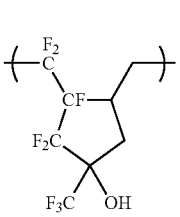
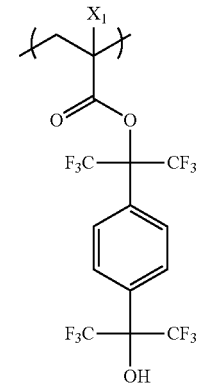
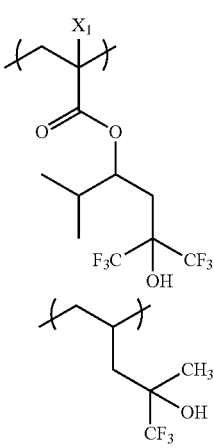
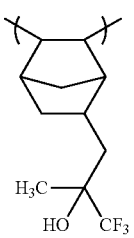
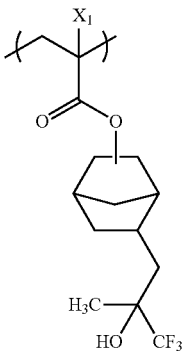

As the polarity conversion group (y), there can be mentioned, for example, a lactone group, a carboxylic ester group (—COO—), an acid anhydride group (—C(O)OC(O)—), an acid imido group (—NHCONH—), a carboxylic thioester group (—COS—), a carbonic ester group (—OC(O)O—), a sulfuric ester group (—OSO$_2$O—), a sulfonic ester group (—SO$_2$O—) or the like. A lactone group is particularly preferred.

The polarity conversion group (y) is contained in, for example, two modes which are both preferred. In one mode, the polarity conversion group (y) is contained in a repeating unit of an acrylic ester or methacrylic ester and introduced in a side chain of a resin. In the other mode, the polarity conversion group is introduced in a terminal of a polymer chain by using a polymerization initiator or chain transfer agent containing the polarity conversion group (y) in the stage of polymerization.

As particular examples of the repeating units (by) each containing a polarity conversion group (y), there can be mentioned the repeating units with a lactone structure of formulae (KA-1-1) to (KA-1-17) to be shown hereinafter.

Further, it is preferred for the repeating unit (by) containing a polarity conversion group (y) to be a repeating unit containing at least either a fluorine atom or a silicon atom (namely, corresponding to the above-mentioned repeating unit (b') or repeating unit (b")). The resin comprising this repeating unit (by) is hydrophobic, and is especially preferred from the viewpoint of the reduction of development defects.

As the repeating unit (by), there can be mentioned, for example, any of the repeating units of formula (K0) below.

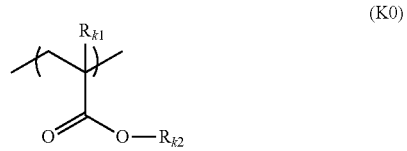

(K0)

In the formula, $R_{k1}$ represents a hydrogen atom, a halogen atom, a hydroxyl group, an alkyl group, a cycloalkyl group, an aryl group or a group containing a polarity conversion group.

$R_{k2}$ represents an alkyl group, a cycloalkyl group, an aryl group or a group containing a polarity conversion group.

Here, at least one of $R_{k1}$ and $R_{k2}$ is a group containing a polarity conversion group.

The polarity conversion group, as mentioned above, refers to a group that is decomposed by the action of an alkali developer to thereby increase its solubility in the alkali developer. It is preferred for the polarity conversion group to be a group represented by X in the partial structures of general formulae (KA-1) and (KB-1) below.

(KA-1)

(KB-1)

In general formulae (KA-1) and (KB-1), X represents a carboxylic ester group (—COO—), an acid anhydride group (—C(O)OC(O)—), an acid imido group (—NHCONH—), a carboxylic thioester group (—COS—), a carbonic ester group (—OC(O)O—), a sulfuric ester group (—OSO$_2$O—) or a sulfonic ester group (—SO$_2$O—).

$Y^1$ and $Y^2$ may be identical to or different from each other, and each thereof represents an electron withdrawing group.

The repeating unit (by) contains a preferred group whose solubility in an alkali developer is increased by containing a group with the partial structure of general formula (KA-1) or (KB-1). When the partial structure has no bonding hand as in the case of the partial structure of general formula (KA-1) or the partial structure of general formula (KB-1) in which $Y^1$ and $Y^2$ are monovalent, the above group with the partial structure refers to a group containing a monovalent or higher-valent group resulting from the deletion of at least one arbitrary hydrogen atom from the partial structure.

The partial structure of general formula (KA-1) or (KB-1) is linked at its arbitrary position to the principal chain of the hydrophobic resin via a substituent.

The partial structure of general formula (KA-1) is a structure in which a ring structure is formed in cooperation with a group represented by X.

In general formula (KA-1) X is preferably a carboxylic ester group (namely, in the case of the formation of a lactone ring structure as KA-1), an acid anhydride group or a carbonic ester group. More preferably, X is a carboxylic ester group.

A substituent may be introduced in the ring structure of general formula (KA-1). For example, when $Z_{ka1}$ is a substituent, nka substituents may be introduced.

$Z_{ka1}$, or each of a plurality of $Z_{ka1}$s independently, represents a halogen atom, an alkyl group, a cycloalkyl group, an ether group, a hydroxyl group, an amido group, an aryl group, a lactone ring group or an electron withdrawing group.

$Z_{ka1}$s may be linked to each other to thereby form a ring. As the ring formed by the mutual linkage of $Z_{ka1}$s, there can be mentioned, for example, a cycloalkyl ring or a heterocycle (for example, a cycloether ring or a lactone ring).

The above nka is an integer of 0 to 10, preferably 0 to 8, more preferably 0 to 5, further more preferably 1 to 4 and most preferably 1 to 3.

The electron withdrawing groups represented by $Z_{ka1}$ are the same as those represented by $Y^1$ and $Y^2$ to be described hereinafter. These electron withdrawing groups may be substituted with other electron withdrawing groups.

$Z_{ka1}$ is preferably an alkyl group, a cycloalkyl group, an ether group, a hydroxyl group or an electron withdrawing group. $Z_{ka1}$ is more preferably an alkyl group, a cycloalkyl group or an electron withdrawing group. It is preferred for the ether group to be one substituted with, for example, an alkyl group or a cycloalkyl group, namely, to be an alkyl ether group or the like. The electron withdrawing group is as mentioned above.

As the halogen atom represented by $Z_{ka1}$, there can be mentioned a fluorine atom, a chlorine atom, a bromine atom, an iodine atom or the like. Among these, a fluorine atom is preferred.

The alkyl group represented by $Z_{ka1}$ may contain a substituent, and may be linear or branched. The linear alkyl group preferably has 1 to 30 carbon atoms, more preferably 1 to 20 carbon atoms. As the linear alkyl group, there can be mentioned, for example, a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, an n-decanyl group or the like. The branched alkyl group preferably has 3 to 30 carbon atoms, more preferably 3 to 20 carbon atoms. As the branched alkyl group, there can be mentioned, for example, an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, a t-decanyl (t-decanoyl) group or the like. It is preferred for the alkyl group represented by $Z_{ka1}$ to be one having 1 to 4 carbon atoms, such as a methyl group, an ethyl group, an n-propyl group, an i-propyl group, an n-butyl group, an i-butyl group or a t-butyl group.

The cycloalkyl group represented by $Z_{ka1}$ may contain a substituent and may be monocyclic or polycyclic. When polycyclic, the cycloalkyl group may be a bridged one. Namely, in that case, the cycloalkyl group may have a bridged structure.

The monocycloalkyl group is preferably a cycloalkyl group having 3 to 8 carbon atoms. As such a cycloalkyl group, there can be mentioned, for example, a cyclopropyl group, a cyclopentyl group, a cyclohexyl group, a cyclobutyl group, a cyclooctyl group or the like. As the polycycloalkyl group, there can be mentioned a group with, for example, a bicyclo, tricyclo or tetracyclo structure having 5 or more carbon atoms. This polycycloalkyl group is preferably a cycloalkyl group having 6 to 20 carbon atoms. As such, there can be mentioned, for example, an adamantyl group, a norbornyl group, an isobornyl group, a camphonyl group, a bicyclopentyl group, an α-pinanyl group, a tricyclodecanyl group, a tetracyclododecyl group, an androstanyl group or the like. As the cycloalkyl groups, there can also be mentioned any of the following structures. The carbon atoms of each of the cycloalkyl groups may be partially replaced with a heteroatom, such as an oxygen atom.

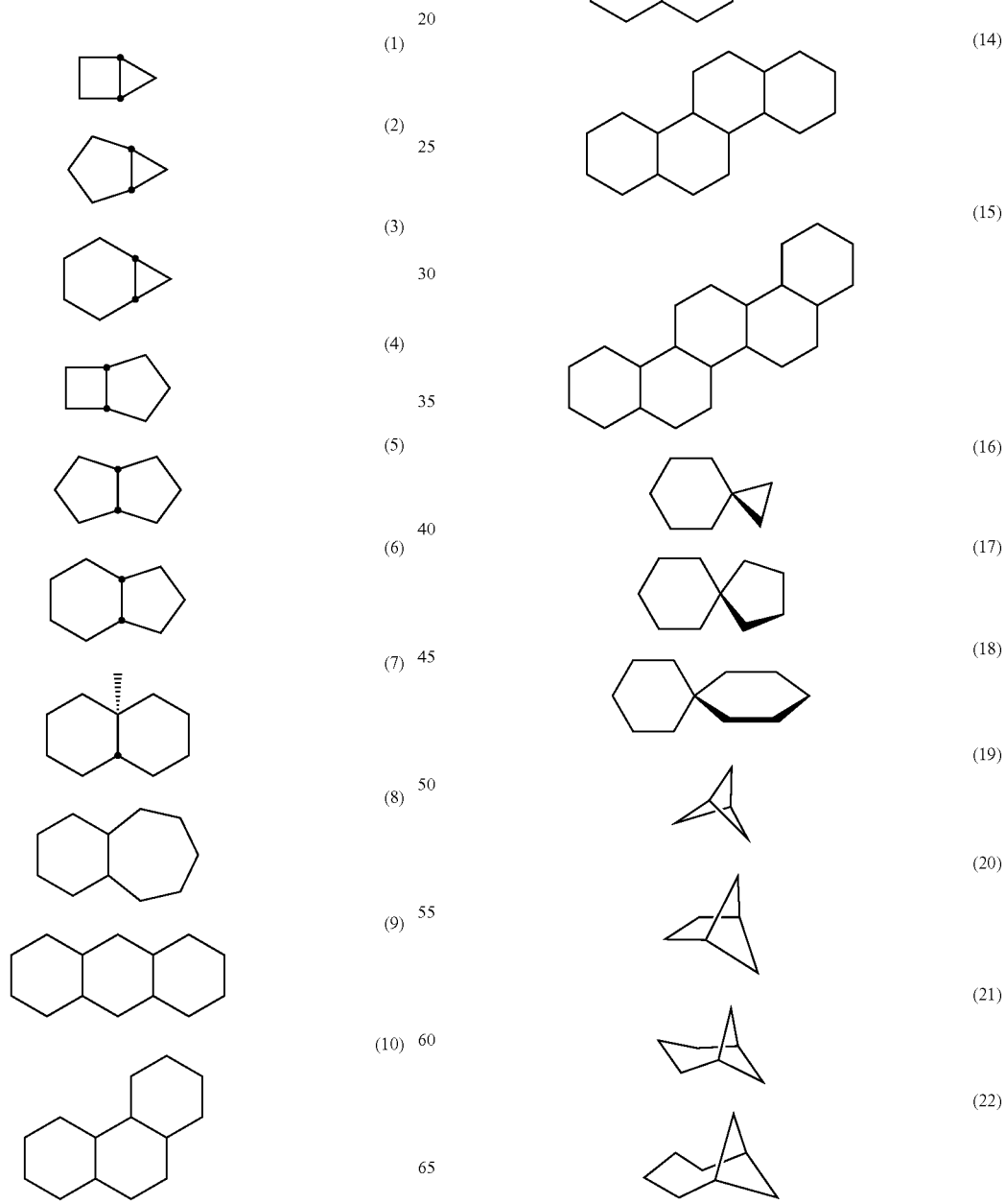

-continued
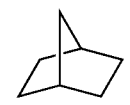 (23)
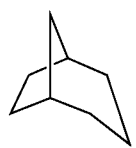 (24)
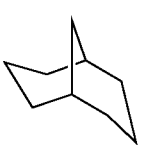 (25)
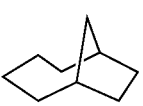 (26)
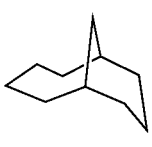 (27)
 (28)
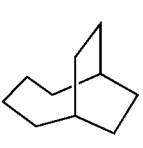 (29)
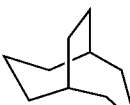 (30)
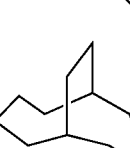 (31)
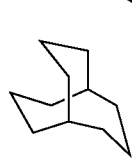 (32)
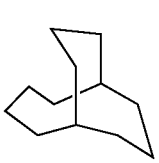 (33)
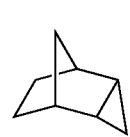 (34)
-continued
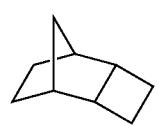 (35)
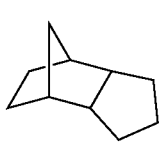 (36)
 (37)
 (38)
 (39)
 (40)
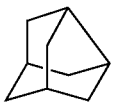 (41)
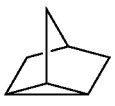 (42)
 (43)
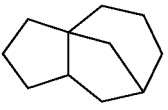 (44)
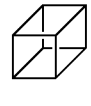 (45)
 (46)
 (47)

(48) 

(49) 

(50) 

As preferred alicyclic moieties among the above, there can be mentioned an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. As more preferred alicyclic moieties, there can be mentioned an adamantyl group, a decalin group, a norbornyl group, a cedrol group, a cyclohexyl group, a cycloheptyl group, a cyclooctyl group, a cyclodecanyl group, a cyclododecanyl group and a tricyclodecanyl group.

As a substituent that can be introduced in these alicyclic structures, there can be mentioned an alkyl group, a halogen atom, a hydroxyl group, an alkoxy group, a carboxyl group or an alkoxycarbonyl group. The alkyl group is preferably a lower alkyl group, such as a methyl group, an ethyl group, a propyl group, an isopropyl group or a butyl group. More preferably, the alkyl group is a methyl group, an ethyl group, a propyl group or an isopropyl group. As preferred alkoxy groups, there can be mentioned those each having 1 to 4 carbon atoms, such as a methoxy group, an ethoxy group, a propoxy group and a butoxy group. As a substituent that may be introduced in these alkyl and alkoxy groups, there can be mentioned a hydroxyl group, a halogen atom, an alkoxy group (preferably having 1 to 4 carbon atoms) or the like.

Further substituents may be introduced in these groups. As further substituents, there can be mentioned a hydroxyl group; a halogen atom (fluorine, chlorine, bromine or iodine); a nitro group; a cyano group; the above alkyl groups; an alkoxy group, such as a methoxy group, an ethoxy group, a hydroxyethoxy group, a propoxy group, a hydroxypropoxy group, an n-butoxy group, an isobutoxy group, a sec-butoxy group or a t-butoxy group; an alkoxycarbonyl group, such as a methoxycarbonyl group or an ethoxycarbonyl group; an aralkyl group, such as a benzyl group, a phenethyl group or a cumyl group; an aralkyloxy group; an acyl group, such as a formyl group, an acetyl group, a butyryl group, a benzoyl group, a cinnamoyl group or a valeryl group; an acyloxy group, such as a butyryloxy group; the above alkenyl groups; an alkenyloxy group, such as a vinyloxy group, a propenyloxy group, an allyloxy group or a butenyloxy group; the above aryl groups; an aryloxy group, such as a phenoxy group; an aryloxycarbonyl group, such as a benzoyloxy group; and the like.

Preferably, X of general formula (KA-1) represents a carboxylic ester group and the partial structure of general formula (KA-1) is a lactone ring. A 5- to 7-membered lactone ring is preferred.

Further, as shown in formulae (KA-1-1) to (KA-1-17) below, the 5- to 7-membered lactone ring as the partial structure of general formula (KA-1) is preferably condensed with another ring structure in such a fashion that a bicyclo structure or a spiro structure is formed.

The peripheral ring structures to which the ring structure of general formula (KA-1) may be bonded can be, for example, those shown in formulae (KA-1-1) to (KA-1-17) below, or those similar to the same.

It is preferred for the structure containing the lactone ring structure of general formula (KA-1) to be the structure of any of formulae (KA-1-1) to (KA-1-17) below. The lactone structure may be directly bonded to the principal chain. As preferred structures, there can be mentioned those of formulae (KA-1-1), (KA-1-4), (KA-1-5), (KA-1-6), (KA-1-13), (KA-1-14) and (KA-1-17).

KA-1-1
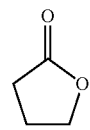

KA-1-2
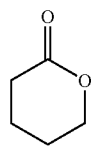

KA-1-3
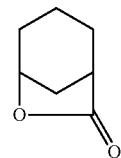

KA-1-4
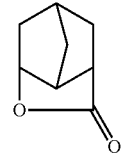

KA-1-5
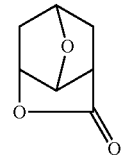

KA-1-6
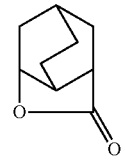

KA-1-7
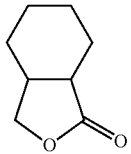

KA-1-8 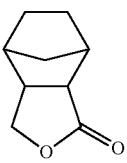

KA-1-9 

KA-1-10 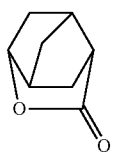

KA-1-11 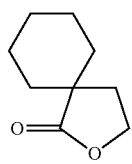

KA-1-12 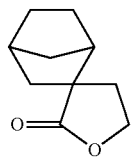

KA-1-13 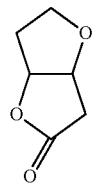

KA-1-14 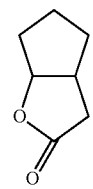

KA-1-15 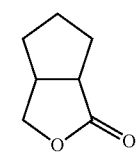

KA-1-16 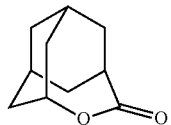

KA-1-17 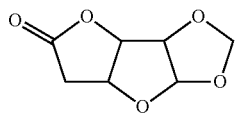

A substituent may or may not be introduced in the above structures containing the lactone ring structure. As preferred substituents, there can be mentioned the same as the substituents $Z_{ka1}$ that may be introduced in the ring structure of general formula (KA-1) above.

In general formula (KB-1), X is preferably a carboxylic ester group (—COO—).

In general formula (KB-1), each of $Y^1$ and $Y^2$ independently represents an electron withdrawing group.

The electron withdrawing group has the partial structure of formula (EW) below. In formula (EW), * represents either a bonding hand directly bonded to the structure of general formula (KA-1) or a bonding hand directly bonded to X of general formula (KB-1).

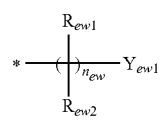

(EW)

In formula (EW), $n_{ew}$ is the number of repetitions of each of the connecting groups of the formula —C($R_{ew1}$)($R_{ew2}$)—, being an integer of 0 or 1. When $n_{ew}$ is 0, a single bond is represented, indicating the direct bonding of $Y_{ew1}$.

$Y_{ew1}$ can be any of a halogen atom, a cyano group, a nitrile group, a nitro group, any of the halo(cyclo)alkyl groups or haloaryl groups of the formula —C($R_{f1}$)($R_{f2}$)—$R_{f3}$ to be described hereinafter, an oxy group, a carbonyl group, a sulfonyl group, a sulfinyl group and a combination thereof. The electron withdrawing groups may have, for example, the following structures. Herein, the "halo(cyclo)alkyl group" refers to an at least partially halogenated alkyl group or cycloalkyl group. The "haloaryl group" refers to an at least partially halogenated aryl group. In the following structural formulae, each of $R_{ew3}$ and $R_{ew4}$ independently represents an arbitrary structure. Regardless of the types of the structures of $R_{ew3}$ and $R_{ew4}$, the partial structures of formula (EW) exhibit electron withdrawing properties, and may be linked to, for example, the principal chain of the resin. Preferably, each of $R_{ew3}$ and $R_{ew4}$ is an alkyl group, a cycloalkyl group or a fluoroalkyl group.

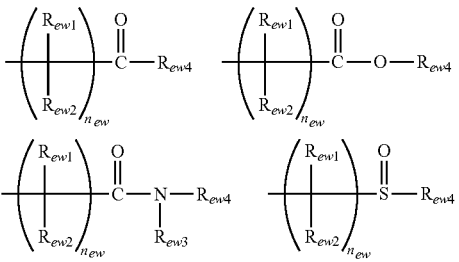

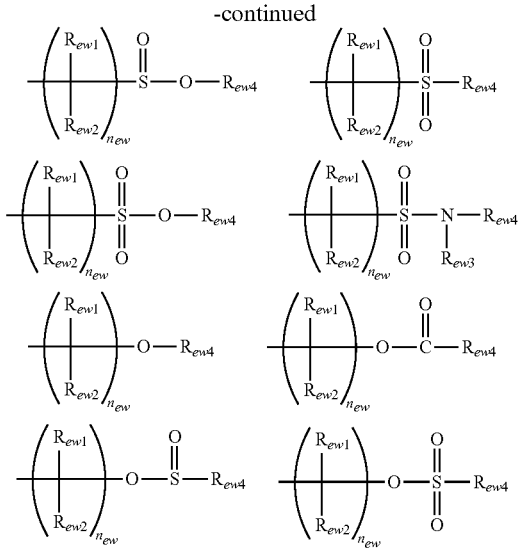

When $Y_{ew1}$ is a bivalent or higher-valent group, the remaining bonding hand or hands form a bond with an arbitrary atom or substituent. At least any of the groups represented by $Y_{ew1}$, $R_{ew1}$ and $R_{ew2}$ may be linked via a further substituent to the principal chain of the hydrophobic resin.

$Y_{ew1}$ is preferably a halogen atom or any of the halo(cyclo)alkyl groups or haloaryl groups of the formula —C($R_{f1}$)($R_{f2}$)—$R_{f3}$.

Each of $R_{ew1}$ and $R_{ew2}$ independently represents an arbitrary substituent, for example, a hydrogen atom, an alkyl group, a cycloalkyl group or an aryl group.

At least two of $R_{ew1}$, $R_{ew2}$ and $Y_{ew1}$ may be linked to each other to thereby form a ring.

In the above formula, $R_{f1}$ represents a halogen atom, a perhaloalkyl group, a perhalocycloalkyl group or a perhaloaryl group. $R_{f1}$ is preferably a fluorine atom, a perfluoroalkyl group or a perfluorocycloalkyl group, more preferably a fluorine atom or a trifluoromethyl group.

Each of $R_{f2}$ and $R_{f3}$ independently represents a hydrogen atom, a halogen atom or an organic group. $R_{f2}$ and $R_{f3}$ may be linked to each other to thereby form a ring. As the organic group, there can be mentioned, for example, an alkyl group, a cycloalkyl group, an alkoxy group or the like. It is preferred for $R_{f2}$ to represent the same groups as $R_{f1}$ or to be linked to $R_{f3}$ to thereby form a ring.

$R_{f1}$ to $R_{f3}$ may be linked to each other to thereby form a ring. As the formed ring, there can be mentioned a (halo)cycloalkyl ring, a (halo)aryl ring or the like.

As the (halo)alkyl groups represented by $R_{f1}$ to $R_{f3}$, there can be mentioned, for example, the alkyl groups mentioned above as being represented by $Z_{ka1}$ and structures resulting from halogenation thereof.

As the (per)halocycloalkyl groups and (per)haloaryl groups represented by $R_{f1}$ to $R_{f3}$ or contained in the ring formed by the mutual linkage of $R_{f2}$ and $R_{f3}$, there can be mentioned, for example, structures resulting from halogenation of the cycloalkyl groups mentioned above as being represented by $Z_{ka1}$, preferably fluorocycloalkyl groups of the formula —$C_{(n)}F_{(2n-2)}$H and perfluoroaryl groups of the formula —$C_{(n)}F_{(n-1)}$. The number of carbon atoms, n, is not particularly limited. Preferably, however, it is in the range of 5 to 13, more preferably 6.

As preferred rings that may be formed by the mutual linkage of at least two of $R_{ew1}$, $R_{ew2}$ and $Y_{ew1}$, there can be mentioned cycloalkyl groups and heterocyclic groups. Preferred heterocyclic groups are lactone ring groups. As the lactone rings, there can be mentioned, for example, the structures of formulae (KA-1-1) to (KA-1-17) above.

The repeating unit (by) may contain two or more of the partial structures of general formula (KA-1), or two or more of the partial structures of general formula (KB-1), or both any one of the partial structures of general formula (KA-1) and any one of the partial structures of general formula (KB-1).

A part or the whole of any of the partial structures of general formula (KA-1) may double as the electron withdrawing group represented by $Y^1$ or $Y^2$ of general formula (KB-1). For example, when X of general formula (KA-1) is a carboxylic ester group, the carboxylic ester group can function as the electron withdrawing group represented by $Y^1$ or $Y^2$ of general formula (KB-1).

When the repeating unit (by) corresponds to the above-mentioned repeating unit (b*) or repeating unit (b″) and contains any of the partial structures of general formula (KA-1), it is preferred for the partial structures of general formula (KA-1) to be a partial structure in which the polarity conversion group is expressed by —COO— appearing in the structures of general formula (KA-1).

The repeating unit (by) can be a repeating unit with the partial structure of general formula (KY-0) below.

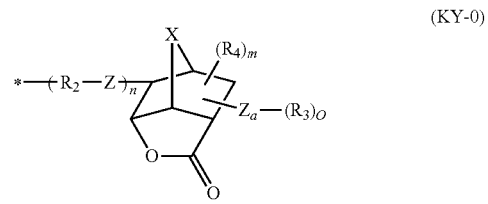

(KY-0)

In general formula (KY-0), $R_2$, when n≥2 each independently, represents an alkylene group or a cycloalkylene group.

$R_3$, when o≥2 each independently, represents a hydrocarbon group whose hydrogen atoms on constituent carbons are partially or entirely replaced with fluorine atoms.

$R_4$, when m≥2 each independently, represents a halogen atom, a cyano group, a hydroxyl group, an amido group, an alkyl group, a cycloalkyl group, an alkoxy group, a phenyl group, an acyl group, an alkoxycarbonyl group or any of the groups of the formula R—C(=O)— or R—C(=O)O— in which R is an alkyl group or a cycloalkyl group. When m≥2, two or more $R_4$s may be bonded to each other to thereby form a ring.

X represents an alkylene group, a cycloalkylene group, an oxygen atom or a sulfur atom.

Each of Z and Za independently represents a single bond, an ether bond, an ester bond, an amido bond, a urethane bond or a urea bond. When a plurality of Zs may be identical to or different from each other.

In the formula, * represents a bonding hand to the principal chain or a side chain of the resin (D); o is an integer of 1 to 7; m is an integer of 0 to 7; and n is an integer of 0 to 5.

The structure —$R_2$—Z— is preferably the structure of formula —$(CH_2)$l-COO— in which l is an integer of 1 to 5.

With respect to the alkylene group and cycloalkylene group represented by $R_2$, the preferred number of carbon atoms and particular examples are as mentioned above in connection with the alkylene group and cycloalkylene group represented by $Z_2$ of general formula (bb).

The number of carbon atoms of the linear, branched or cyclic hydrocarbon group represented by $R_3$ is preferably in the range of 1 to 30, more preferably 1 to 20 when the hydrocarbon group is linear; is preferably in the range of 3 to 30, more preferably 3 to 20 when the hydrocarbon group is branched; and is in the range of 6 to 20 when the hydrocarbon group is cyclic. As particular examples of the $R_3$ groups, there can be mentioned the above particular examples of the alkyl and cycloalkyl groups represented by $Z_{ka1}$.

With respect to the alkyl groups and cycloalkyl groups represented by $R_4$ or R, the preferred number of carbon atoms and particular examples are as mentioned above in connection with the alkyl groups and cycloalkyl groups represented by $Z_{ka1}$.

The acyl group represented by $R_4$ preferably has 1 to 6 carbon atoms. As such, there can be mentioned, for example, a formyl group, an acetyl group, a propionyl group, a butyryl group, an isobutyryl group, a valeryl group, a pivaloyl group or the like.

As the alkyl moiety of the alkoxy group and alkoxycarbonyl group represented by $R_4$, there can be mentioned a linear, branched or cyclic alkyl moiety. With respect to the alkyl moiety, the preferred number of carbon atoms and particular examples are as mentioned above in connection with the alkyl groups and cycloalkyl groups represented by $Z_{ka1}$.

With respect to the alkylene group and cycloalkylene group represented by X, the preferred number of carbon atoms and particular examples are as mentioned above in connection with the alkylene group and cycloalkylene group represented by $R_2$.

Moreover, as particular structures of the repeating units (by), there can be mentioned the repeating units with the following partial structures.

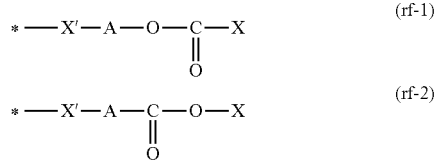

In general formulae (rf-1) and (rf-2),

X' represents an electron withdrawing substituent, preferably a carbonyloxy group, an oxycarbonyl group, an alkylene group substituted with a fluorine atom or a cycloalkylene group substituted with a fluorine atom.

A represents a single bond or a bivalent connecting group of the formula —C(Rx)(Ry)—. In the formula, each of Rx and Ry independently represents a hydrogen atom, a fluorine atom, an alkyl group (preferably having 1 to 6 carbon atoms, optionally substituted with a fluorine atom) or a cycloalkyl group (preferably having 5 to 12 carbon atoms, optionally substituted with a fluorine atom). Each of Rx and Ry is preferably a hydrogen atom, an alkyl group or an alkyl group substituted with a fluorine atom.

X represents an electron withdrawing group. As particular examples thereof, there can be mentioned the electron withdrawing groups set forth above as being represented by $Y^1$ and $Y^2$. X is preferably a fluoroalkyl group, a fluorocycloalkyl group, an aryl group substituted with fluorine or a fluoroalkyl group, an aralkyl group substituted with fluorine or a fluoroalkyl group, a cyano group or a nitro group.

* represents a bonding hand to the principal chain or a side chain of the resin, namely, a bonding hand bonded to the principal chain of the resin through a single bond or a connecting group.

When X' is a carbonyloxy group or an oxycarbonyl group, A is not a single bond.

The receding contact angle with water of the resin composition film after alkali development can be decreased by the polarity conversion effected by the decomposition of the polarity conversion group by the action of an alkali developer. The decrease of the receding contact angle between water and the film after alkali development is preferred from the viewpoint of the inhibition of development defects.

The receding contact angle with water of the resin composition film after alkali development is preferably 50° or less, more preferably 40° or less, further more preferably 35° or less and most preferably 30° or less at 23±3° C. in a humidity of 45±5%.

The receding contact angle refers to a contact angle determined when the contact line at a droplet-substrate interface draws back. It is generally known that the receding contact angle is useful in the simulation of droplet mobility in a dynamic condition. In brief, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

The above receding contact angle of the film after alkali development refers to the contact angle obtained by measuring the following film by the dilation/contraction method to be described in examples. Namely, an organic antireflection film ARC29A (produced by Nissan Chemical Industries, Ltd.) was applied onto a silicon wafer (8-inch caliber) and baked at 205° C. for 60 seconds, thereby forming a 98 nm-thick antireflection film. Each of the compositions of the present invention was applied thereonto and baked at 120° C. for 60 seconds, thereby forming a 120 nm-thick film. The film was developed with an aqueous solution of tetramethylammonium hydroxide (2.38 mass %) for 30 seconds, rinsed with pure water and spin dried. The contact angle of the thus obtained film was measured in accordance with the dilation/contraction method.

The rate of hydrolysis of the hydrophobic resin in an alkali developer is preferably 0.001 nm/sec or greater, more preferably 0.01 nm/sec or greater, further more preferably 0.1 nm/sec or greater and most preferably 1 nm/sec or greater.

Herein, the rate of hydrolysis of the hydrophobic resin in an alkali developer refers to the rate of decrease of the thickness of a resin film formed from only the hydrophobic resin in 23° C. TMAH (aqueous solution of tetramethylammonium hydroxide) (2.38 mass %)

It is preferred for the repeating unit (by) to be a repeating unit containing at least two polarity conversion groups.

When the repeating unit (by) contains at least two polarity conversion groups, it is preferred for the repeating unit to contain a group with any of the partial structures having two polarity conversion groups of general formula (KY-1) below. When the structure of general formula (KY-1) has no bonding hand, a group with a mono- or higher-valent group resulting from the removal of at least any arbitrary one of the hydrogen atoms contained in the structure is referred to.

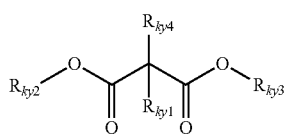
(KY-1)

In general formula (KY-1), each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amido group or an aryl group. Alternatively, both $R_{ky1}$ and $R_{ky4}$ may be bonded to the same atom to thereby form a double bond. For example, both $R_{ky1}$ and $R_{ky4}$ may be bonded to the same oxygen atom to thereby form a part (=O) of a carbonyl group.

Each of $R_{ky2}$ and $R_{ky3}$ independently represents an electron withdrawing group. Alternatively, $R_{ky1}$ and $R_{ky2}$ are linked to each other to thereby form a lactone structure, while $R_{ky3}$ is an electron withdrawing group. The formed lactone structure is preferably any of the above-mentioned structures (KA-1-1) to (KA-1-17). As the electron withdrawing group, there can be mentioned any of the same groups as mentioned above with respect to $Y^1$ and $Y^2$ of general formula (KB-1). This electron withdrawing group is preferably a halogen atom, or any of the halo(cyclo)alkyl groups or haloaryl groups of the formula —$C(R_{f1})(R_{f2})$—$R_{f3}$ above. Preferably, $R_{ky3}$ is a halogen atom, or any of the halo(cyclo)alkyl groups or haloaryl groups of the formula —$C(R_{f1})(R_{f2})$—$R_{f3}$ above, while $R_{ky2}$ is either linked to $R_{ky1}$ to thereby form a lactone ring, or an electron withdrawing group containing no halogen atom.

$R_{ky1}$, $R_{ky2}$ and $R_{ky4}$ may be linked to each other to thereby form a monocyclic or polycyclic structure.

As $R_{ky1}$ and $R_{ky4}$, there can be mentioned, for example, the same groups as set forth above with respect to $Z_{ka1}$ of general formula (KA-1).

The lactone rings formed by the mutual linkage of $R_{ky1}$ and $R_{ky2}$ preferably have the structures of formulae (KA-1-1) to (KA-1-17) above. As the electron withdrawing groups, there can be mentioned those mentioned above as being represented by $Y^1$ and $Y^2$ of general formula (KB-1) above.

It is more preferred for the structure of general formula (KY-1) to be the structure of general formula (KY-2) below. The structure of general formula (KY-2) refers to a group with a mono- or higher-valent group resulting from the removal of at least any arbitrary one of the hydrogen atoms contained in the structure.

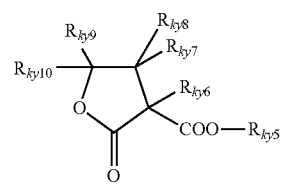
(KY-2)

In formula (KY-2), each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amido group or an aryl group.

At least two of $R_{ky6}$ to $R_{ky10}$ may be linked to each other to thereby form a monocyclic or polycyclic structure.

$R_{ky5}$ represents an electron withdrawing group. As the electron withdrawing group, there can be mentioned any of the same groups as set forth above with respect to $Y^1$ and $Y^2$. This electron withdrawing group is preferably a halogen atom, or any of the halo(cyclo)alkyl groups or haloaryl groups of the formula —$C(R_{f1})(R_{f2})$—$R_{f3}$ above.

As $R_{ky5}$ to $R_{ky10}$, there can be mentioned, for example, the same groups as set forth above with respect to $Z_{ka1}$ of formula (KA-1).

It is more preferred for the structure of formula (KY-2) to be the partial structure of general formula (KY-3) below.

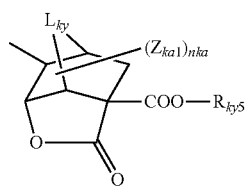
(KY-3)

In formula (KY-3), $Z_{ka1}$ and nka are as defined above in connection with general formula (KA-1). $R_{ky5}$ is as defined above in connection with formula (KY-2).

$L_{ky}$ represents an alkylene group, a cycloalkylene group, an oxygen atom or a sulfur atom. As the alkylene group represented by $L_{ky}$, there can be mentioned a methylene group, an ethylene group or the like. $L_{ky}$ is preferably an oxygen atom or a methylene group, more preferably a methylene group.

The repeating units (b) are not limited as long as they are derived by polymerization, such as addition polymerization, condensation polymerization or addition condensation. Preferred repeating units are those obtained by the addition polymerization of a carbon to carbon double bond. As such repeating units, there can be mentioned, for example, acrylate repeating units (including the family having a substituent at the α- and/or β-position), styrene repeating units (including the family having a substituent at the α- and/or β-position), vinyl ether repeating units, norbornene repeating units, repeating units of maleic acid derivatives (maleic anhydride, its derivatives, maleimide, etc.) and the like. Of these, acrylate repeating units, styrene repeating units, vinyl ether repeating units and norbornene repeating units are preferred. Acrylate repeating units, vinyl ether repeating units and norbornene repeating units are more preferred. Acrylate repeating units are most preferred.

When the repeating unit (by) is a repeating unit containing at least either a fluorine atom or a silicon atom (namely, corresponding to the above repeating unit (b') or (b")), as the partial structure containing a fluorine atom within the repeating unit (by), there can be mentioned any of those set forth in connection with the aforementioned repeating unit containing at least either a fluorine atom or a silicon atom, preferably the groups of general formulae (F2) to (F4) above. As the partial structure containing a silicon atom within the repeating unit (by), there can be mentioned any of those set forth in connection with the aforementioned repeating unit containing at least either a fluorine atom or a silicon atom, preferably the groups of general formulae (CS-1) to (CS-3) above.

Monomers corresponding to the repeating units (by) each containing a group whose solubility is increased in an alkali developer can be synthesized in accordance with any of the processes described in, for example, US 2010/0152400 A, WO 2010/067905 A and WO 2010/067898 A.

The content of repeating unit (by) in the hydrophobic resin, based on all the repeating units of the hydrophobic resin, is preferably in the range of 10 to 100 mol %, more preferably 20 to 99 mol %, further more preferably 30 to 97 mol % and most preferably 40 to 95 mol %.

Particular examples of the repeating units (by) containing a group whose solubility in an alkali developer is increased are shown below, which however in no way limit the scope of the repeating units.

Ra represents a hydrogen atom, a fluorine atom, a methyl group or a trifluoromethyl group.

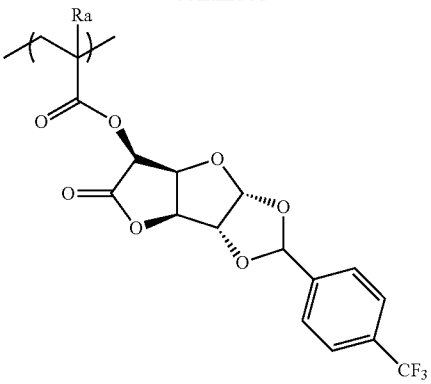

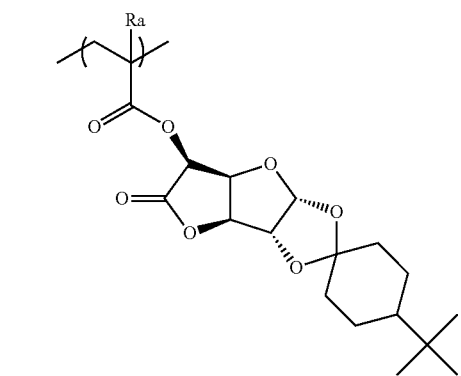

-continued

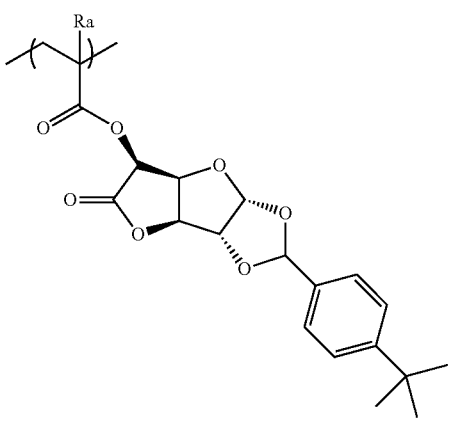

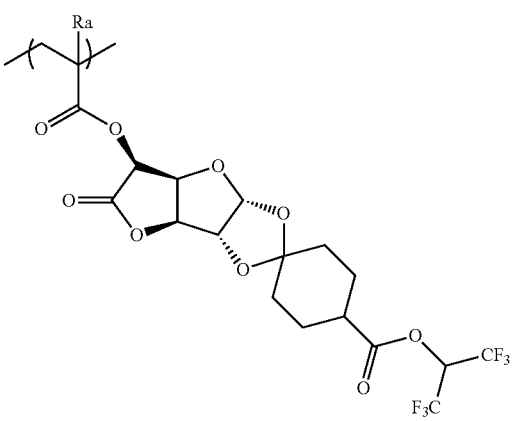

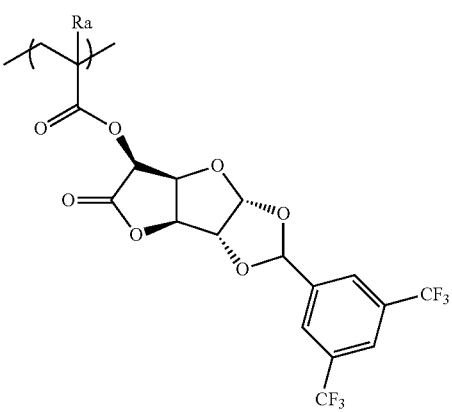

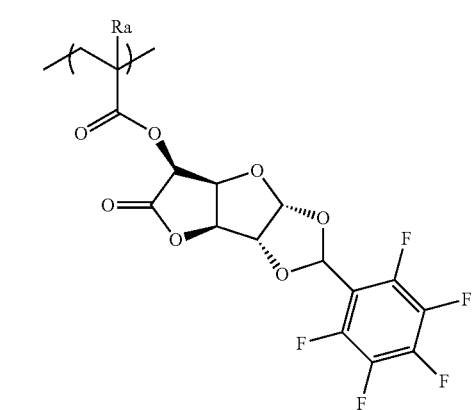

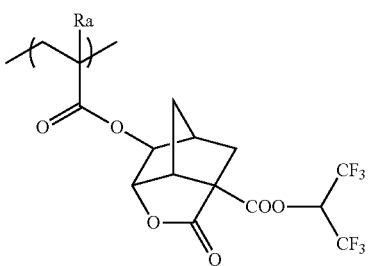

151
-continued
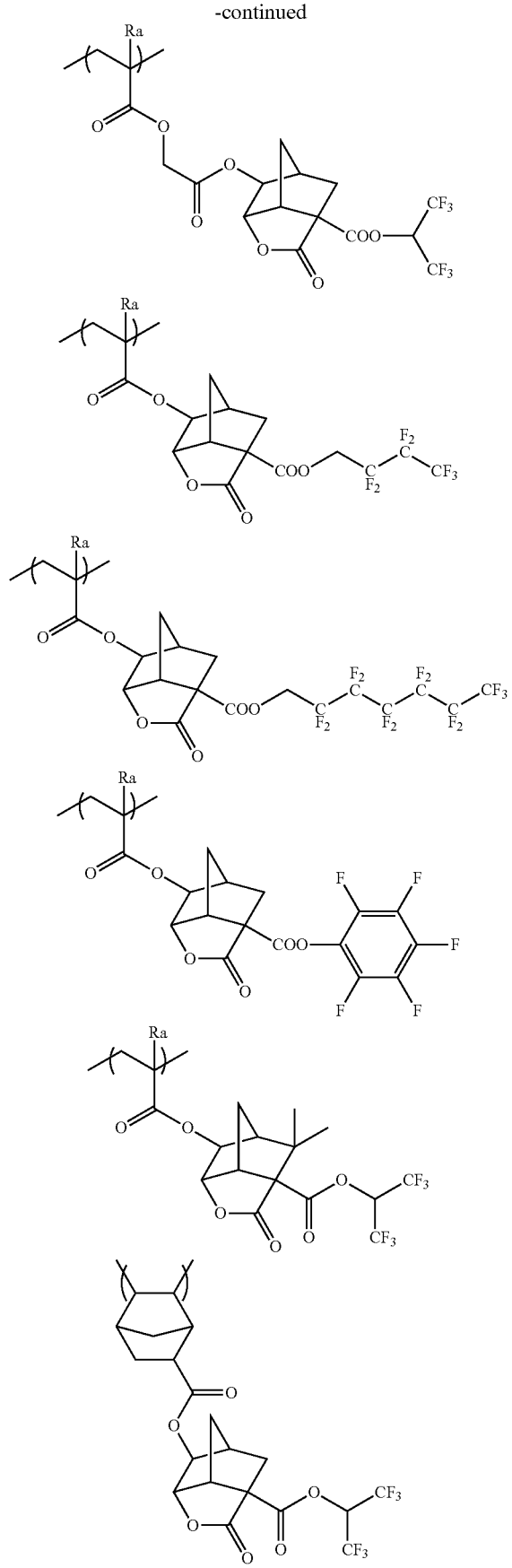
152
-continued
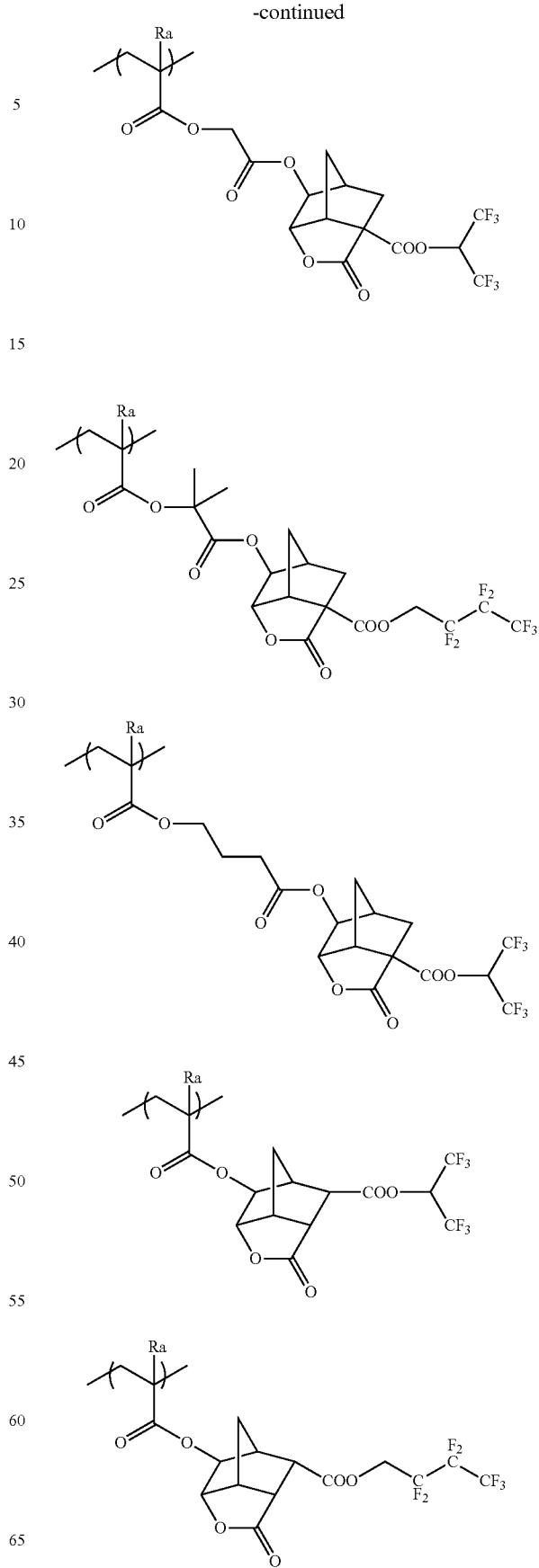

-continued

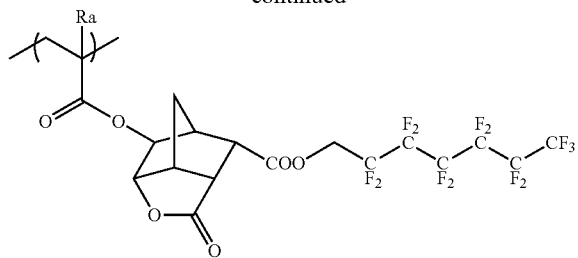
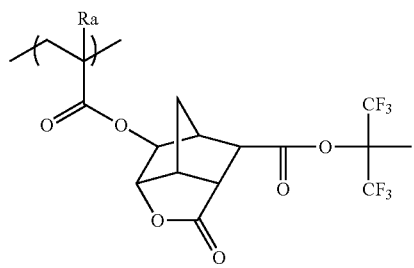
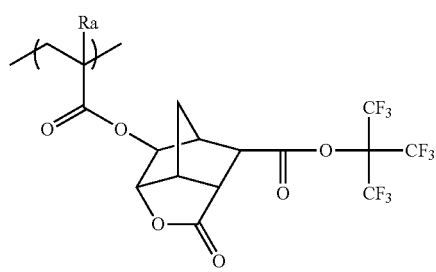
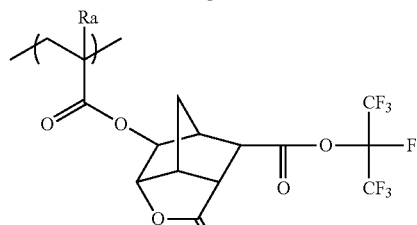
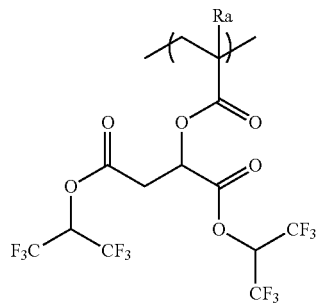
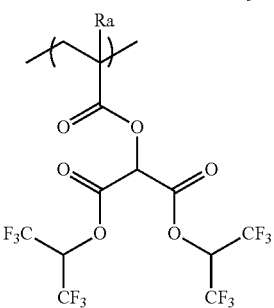

-continued

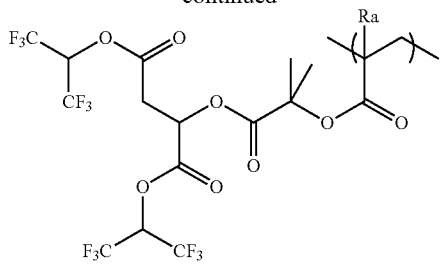
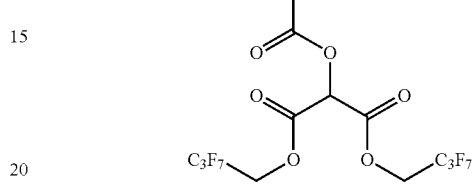
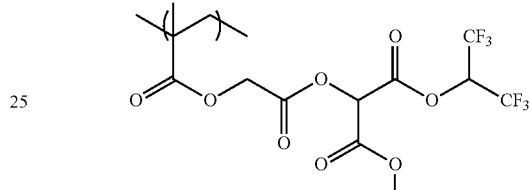
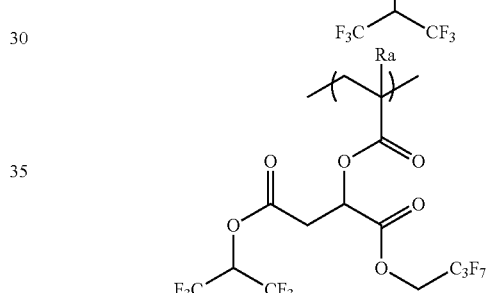

The repeating unit (bz) containing a group that when acted on by an acid, is decomposed (z), contained in the hydrophobic resin can be the same as any of the repeating units each containing an acid-decomposable group set forth above in connection with the resin (A).

When the repeating unit (bz) is a repeating unit containing at least either a fluorine atom or a silicon atom (namely, when corresponding to the above-mentioned repeating unit (b') or repeating unit (b")), the partial structure containing a fluorine atom contained in the repeating unit (bz) can be the same as set forth above in connection with the repeating unit containing at least either a fluorine atom or a silicon atom. As such, preferably, there can be mentioned any of the groups of general formulae (F2) to (F4) above. Also in that instance, the partial structure containing a silicon atom contained in the repeating unit (bz) can be the same as set forth above in connection with the repeating unit containing at least either a fluorine atom or a silicon atom. As such, preferably, there can be mentioned any of the groups of general formulae (CS-1) to (CS-3) above.

The content of repeating unit (bz) containing a group that when acted on by an acid, is decomposed (z) in the hydrophobic resin is preferably in the range of 1 to 80 mol %, more preferably 10 to 80 mol % and further more preferably 20 to 60 mol %, based on all the repeating units of the hydrophobic resin.

The repeating unit (b) containing at least one group selected from the group consisting of the above groups (x) to (z) has been described. The content of repeating unit (b) in the hydrophobic resin is preferably in the range of 1 to 98 mol %, more preferably 3 to 98 mol %, further more preferably 5 to 97 mol % and most preferably 10 to 95 mol %, based on all the repeating units of the hydrophobic resin.

The content of repeating unit (b') in the hydrophobic resin is preferably in the range of 1 to 100 mol %, more preferably 3 to 99 mol %, further more preferably 5 to 97 mol % and most preferably 10 to 95 mol %, based on all the repeating units of the hydrophobic resin.

The content of repeating unit (b*) in the hydrophobic resin is preferably in the range of 1 to 90 mol %, more preferably 3 to 80 mol %, further more preferably 5 to 70 mol % and most preferably 10 to 60 mol %, based on all the repeating units of the hydrophobic resin. The content of repeating unit containing at least either a fluorine atom or a silicon atom used in combination with the repeating unit (b*) is preferably in the range of 10 to 99 mol %, more preferably 20 to 97 mol %, further more preferably 30 to 95 mol % and most preferably 40 to 90 mol %, based on all the repeating units of the hydrophobic resin.

The content of repeating unit (b") in the hydrophobic resin is preferably in the range of 1 to 100 mol %, more preferably 3 to 99 mol %, further more preferably 5 to 97 mol % and most preferably 10 to 95 mol %, based on all the repeating units of the hydrophobic resin.

The hydrophobic resin may further contain any of the repeating units represented by general formula (III) below.

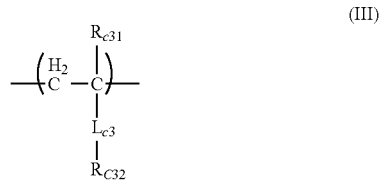

(III)

In formula (III), $R_{c31}$ represents a hydrogen atom, an alkyl group, an alkyl group optionally substituted with one or more fluorine atoms, a cyano group or a group of the formula —$CH_2$—O—$R_{ac2}$ in which $R_{ac2}$ represents a hydrogen atom, an alkyl group or an acyl group. $R_{c31}$ is preferably a hydrogen atom, a methyl group, a hydroxymethyl group, or a trifluoromethyl group, more preferably a hydrogen atom or a methyl group.

$R_{c32}$ represents a group containing an alkyl group, a cycloalkyl group, an alkenyl group, a cycloalkenyl group, or an aryl group. These groups may be substituted with fluorine atom and/or silicon atom.

$L_{c3}$ represents a single bond or a bivalent connecting group.

The alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms such as a phenyl group or a naphthyl group.

These groups may have one or more substituents.

Preferably, $R_{c32}$ represents an unsubstituted alkyl group or an alkyl group substituted with one or more fluorine atoms.

$L_{c3}$ represents a single bond or a bivalent connecting group. As the bivalent connecting group represented by $L_{c3}$, an alkylene group (preferably having 1 to 5 carbon atoms), an oxy group, a phenylene group, or an ester bond (a group represented by —COO—) can be exemplified.

The hydrophobic resin may further contain any of the repeating units represented by general formula (BII-AB) below.

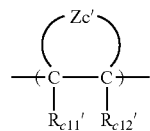

(BII-AB)

In formula (BII-AB), each of $R_{c11'}$ and $R_{c12'}$ independently represents a hydrogen atom, a cyano group, a halogen atom or an alkyl group.

Zc' represents an atomic group required for forming an alicyclic structure in cooperation with two carbon atoms (C—C) to which $R_{c11'}$ and $R_{c12'}$ are respectively bonded.

When any of the groups contained in the repeating unit represented by general formulae (III) or (BII-AB) is substituted with a group containing a fluorine atom or a silicone atom, the repeating unit is also corresponding to the aforementioned repeating unit containing at least either a fluorine atom or a silicon atom.

Specific examples of the repeating unit represented by general formulae (III) or (BII-AB) will be shown below, which however in no way limit the scope of the present invention. In the formulae, Ra represents H, $CH_3$, $CH_2OH$, $CF_3$ or CN. Note that the repeating unit in which Ra represents $CF_3$ also corresponds to the repeating unit containing at least either a fluorine atom or a silicon atom.

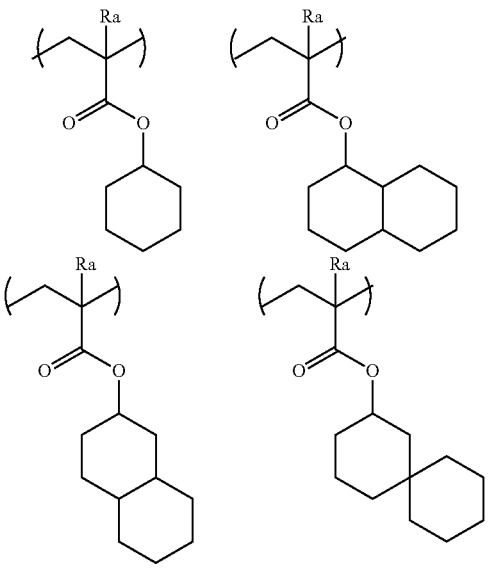

157
-continued
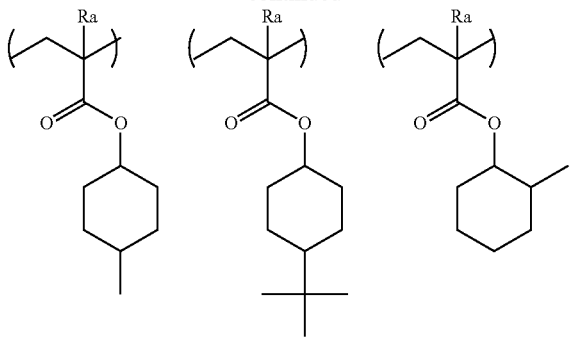
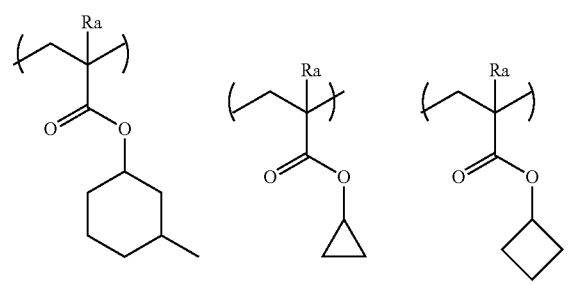
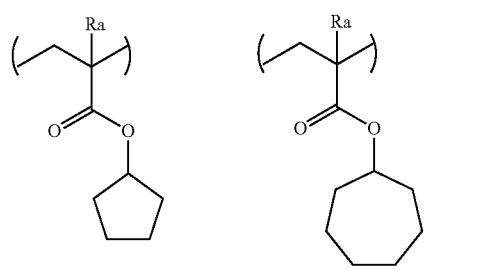
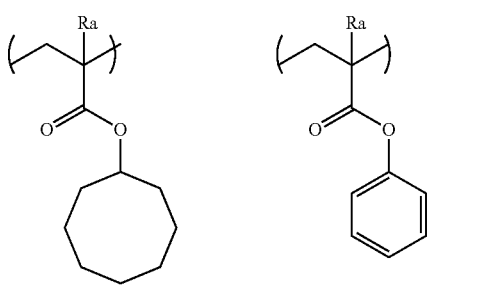
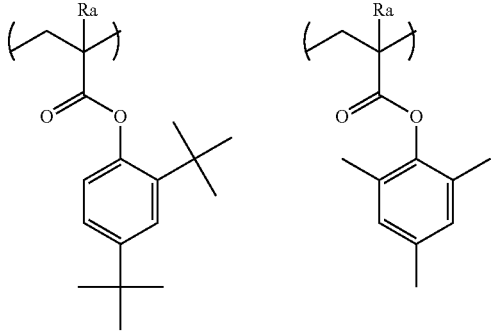
158
-continued
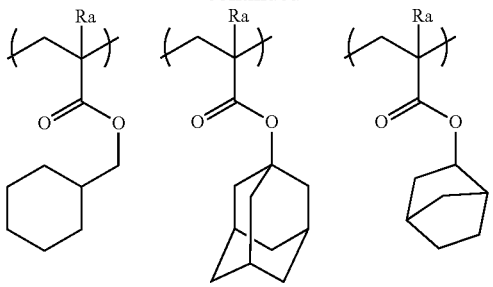
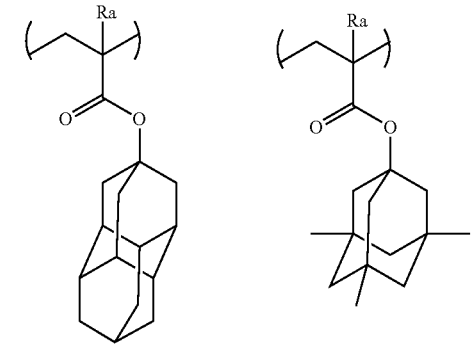
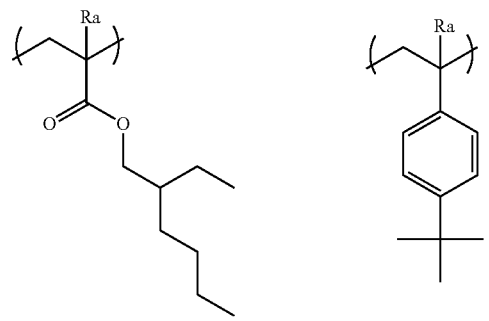
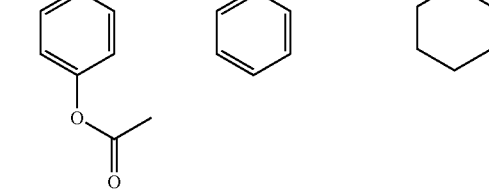
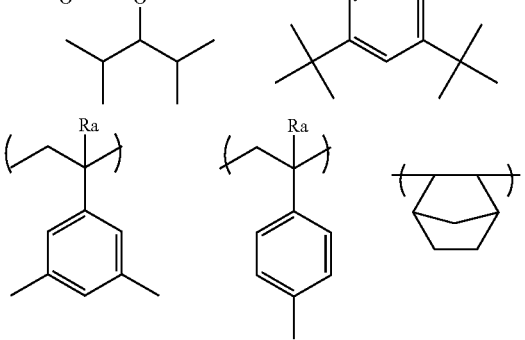

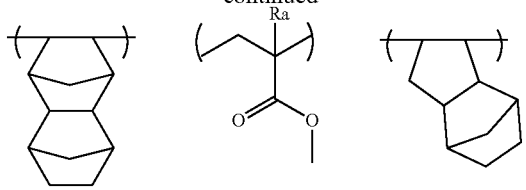

Impurities such as metals in the hydrophobic resin should naturally be of low quantity as in the resin (A). The content of residual monomers and oligomer components is preferably in the range of 0 to 10 mass %, more preferably 0 to 5 mass %, and still more preferably 0 to 1 mass %. Accordingly, there can be obtained a composition being free from in-liquid foreign matters and a change in sensitivity, etc. over time. From the viewpoint of resolving power, pattern profile, side wall of pattern, roughness, etc., the molecular weight distribution (Mw/Mn, also referred to as the degree of dispersal) thereof is preferably in the range of 1 to 3, more preferably 1 to 2, still more preferably 1 to 1.8, and most preferably 1 to 1.5.

A variety of commercially available products can be used as the hydrophobic resin, and also the resin can be synthesized in accordance with conventional methods (for example, by radical polymerization). As general synthesizing methods, a batch polymerization method in which a monomer species and an initiator are dissolved in a solvent and heated to carry out polymerization and a dropping polymerization method in which a solution of monomer species and initiator is dropped into a hot solvent over a period of 1 to 10 hours can be exemplified. Of these, the dropping polymerization method is preferred.

The reaction solvent, polymerization initiator, reaction conditions (temperature, concentration, etc.) and purification method after reaction are the same as described above in connection with the resin (A).

Specific examples of the hydrophobic resins will be shown below. The following Table 1 shows the molar ratio of individual repeating units (corresponding to individual repeating units in order from the left), weight average molecular weight, and degree of dispersal with respect to each of the resins.

(B-1)

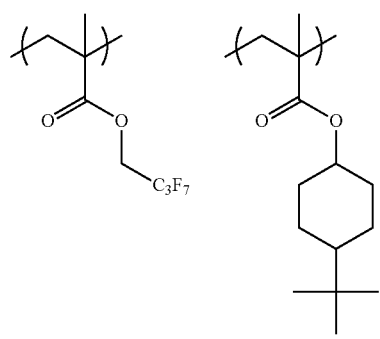

(B-2)

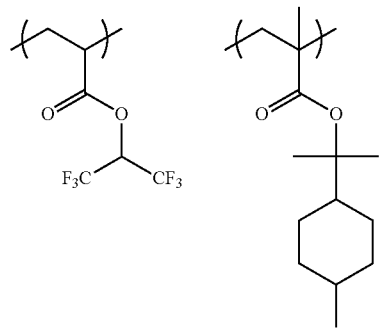

(B-3)

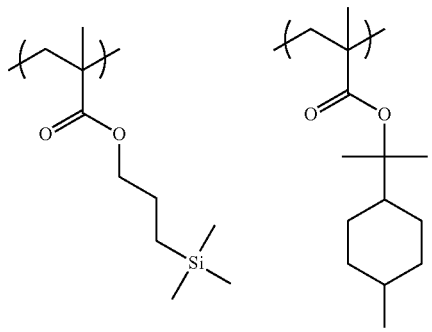

(B-4)

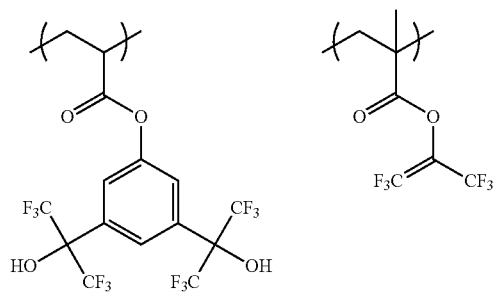

(B-5)

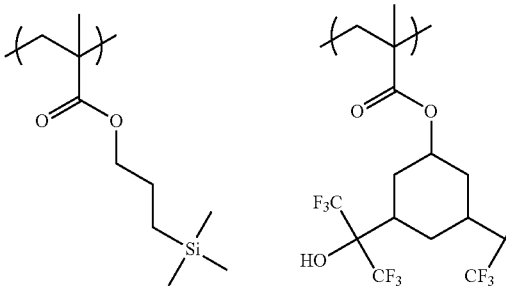

(B-6)

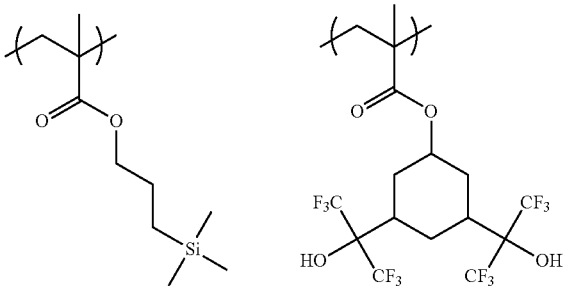

(B-7)

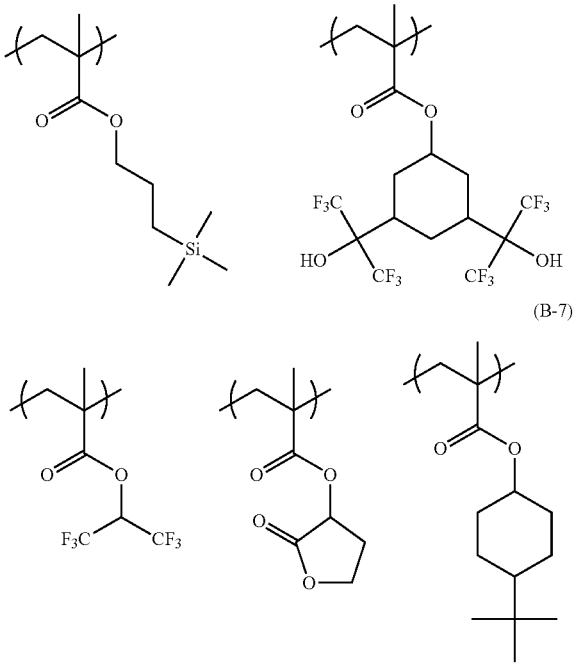

-continued
(B-8)
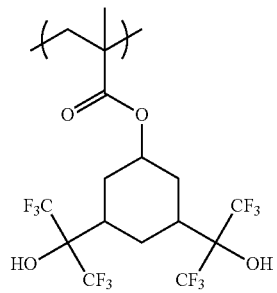 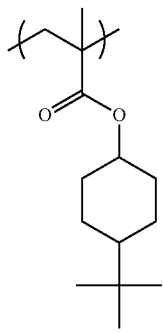
(B-9)
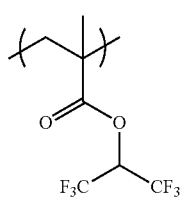 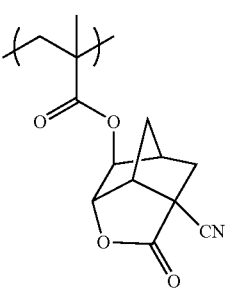
(B-10)
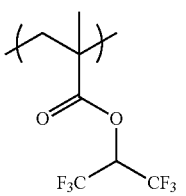 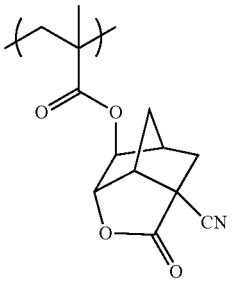
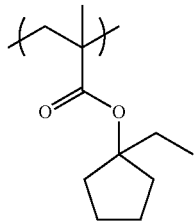
(B-11)
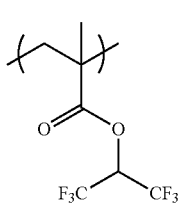 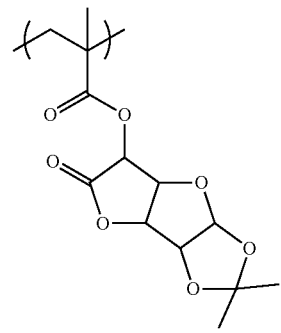
-continued
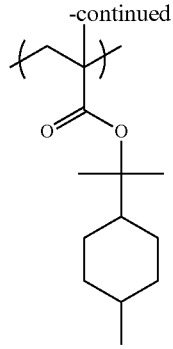
(B-12)
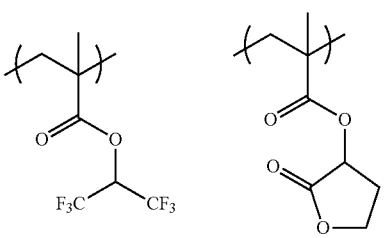
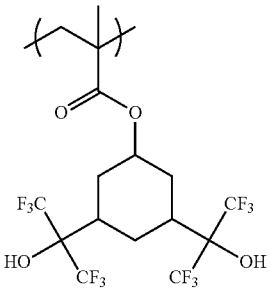
(B-13)
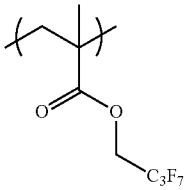
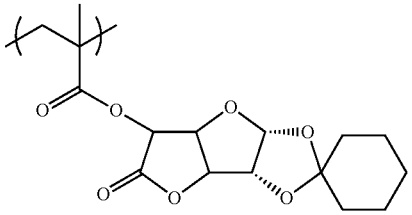
(B-14)
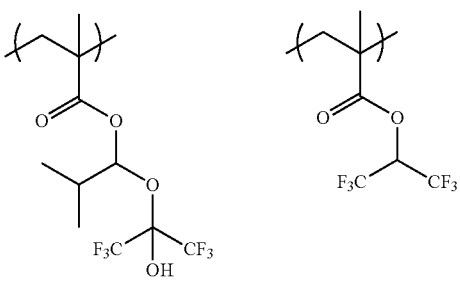

(B-15)
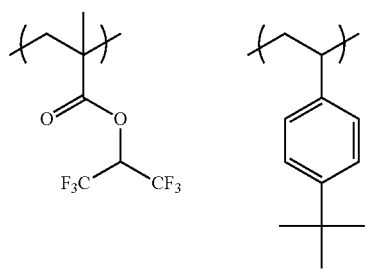
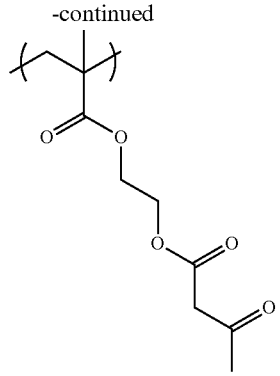
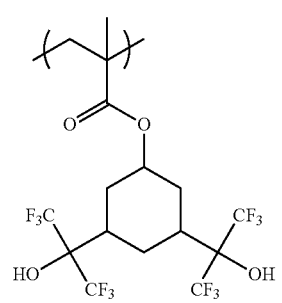
(B-16)
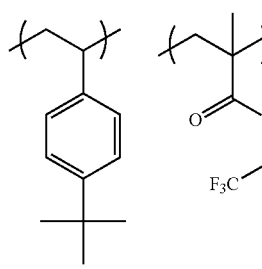 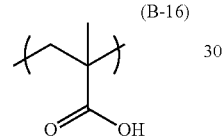
(B-18)
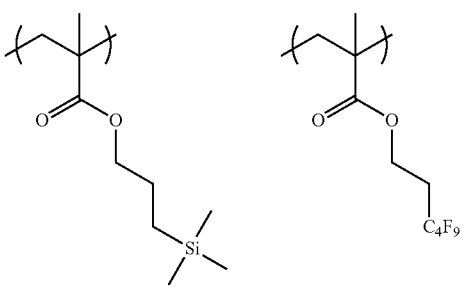
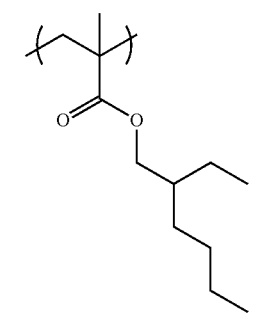
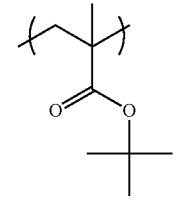
(B-19)
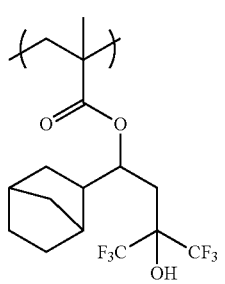
(B-17)
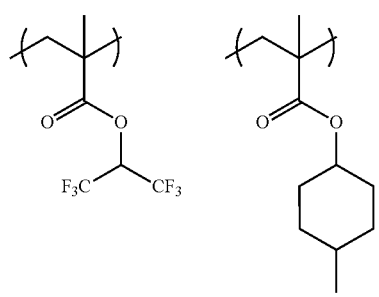
(B-20)
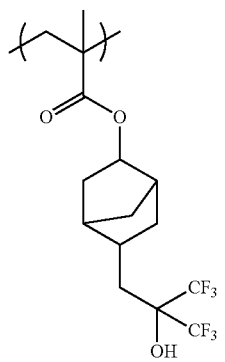

(B-21) 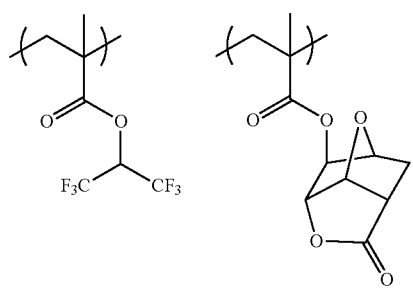 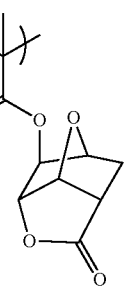
(B-22) 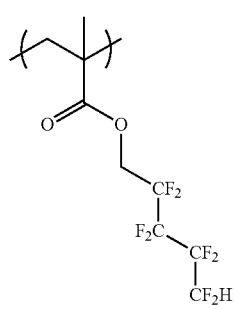 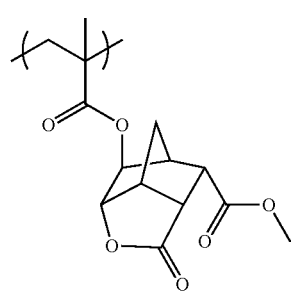
(B-23) 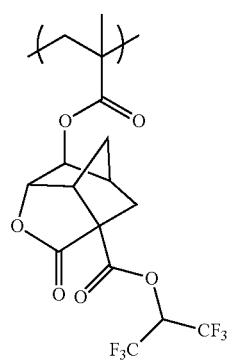
(B-24) 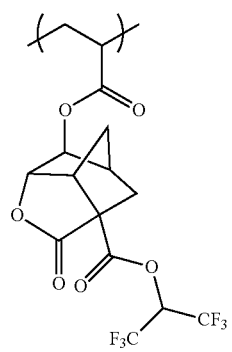
(B-25) 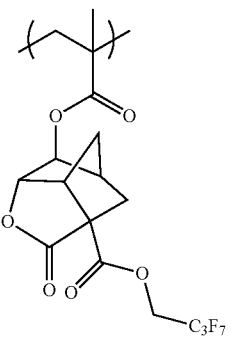
(B-26) 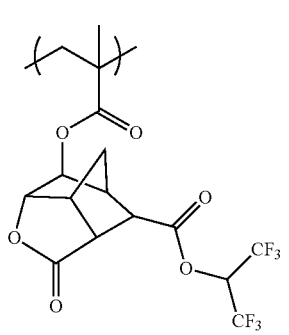
(B-27) 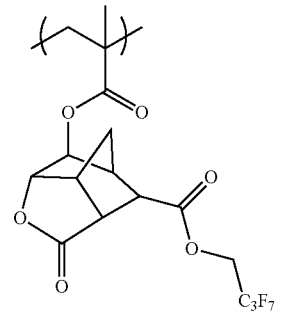
(B-28) 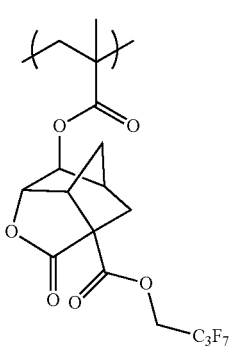 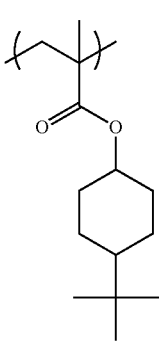

(B-29)
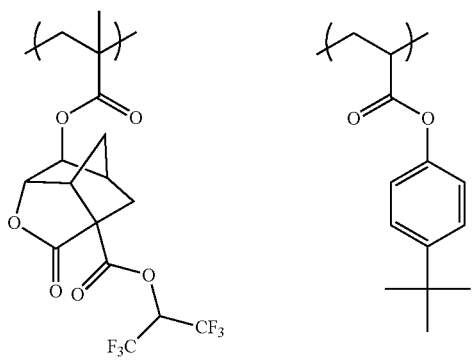
(B-32)
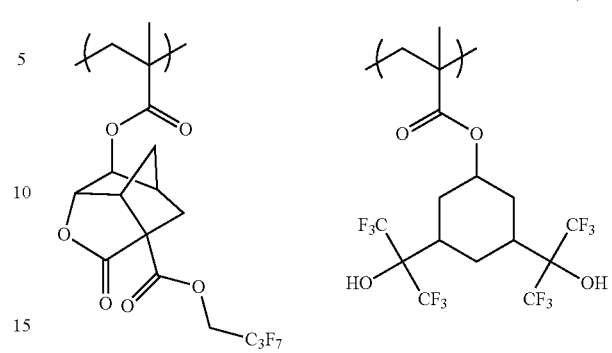
(B-33)
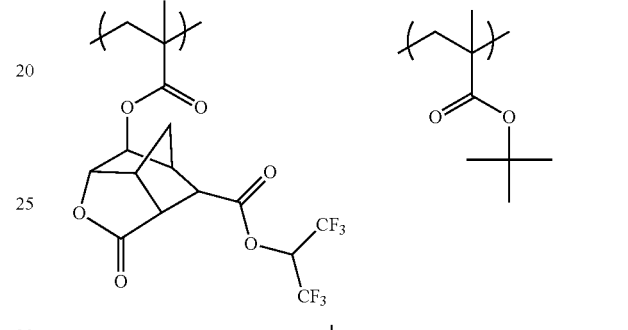
(B-30)
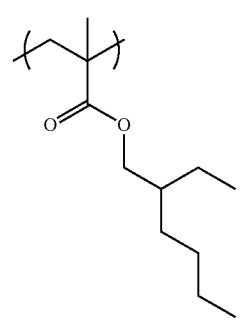
(B-34)
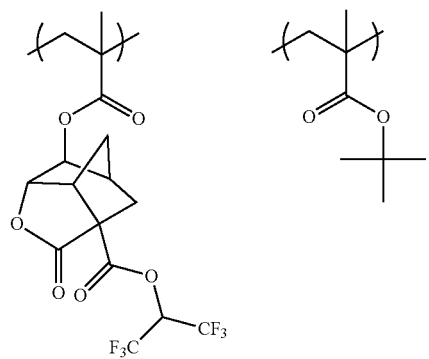
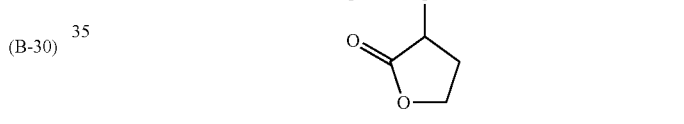
(B-31)
(B-35)
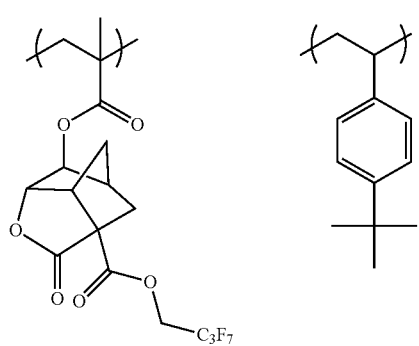
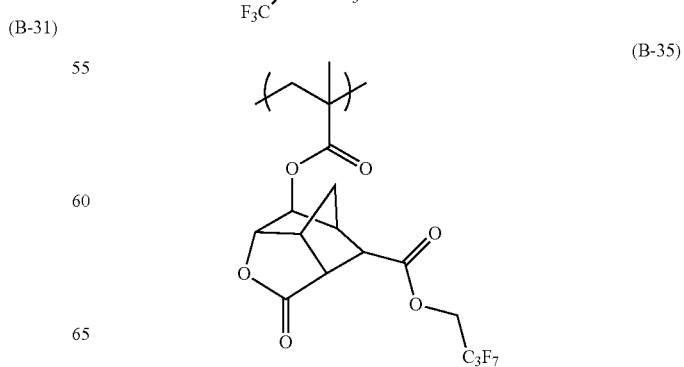

(B-36)
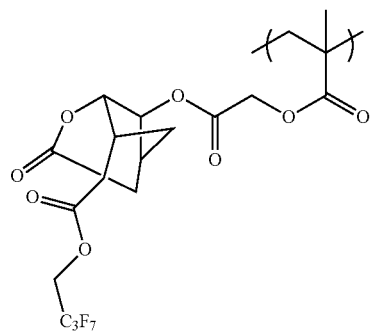
(B-37)
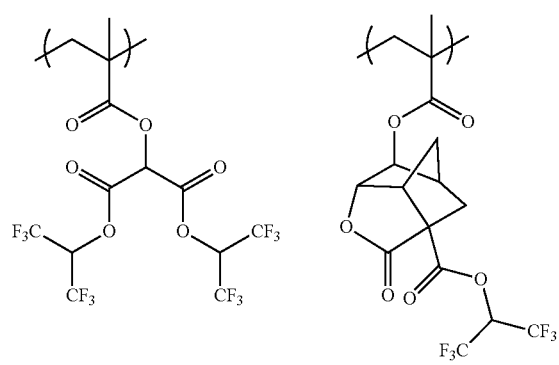
(B-38)
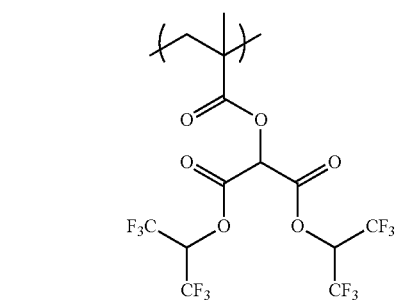
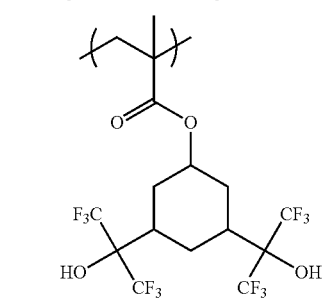
(B-39)
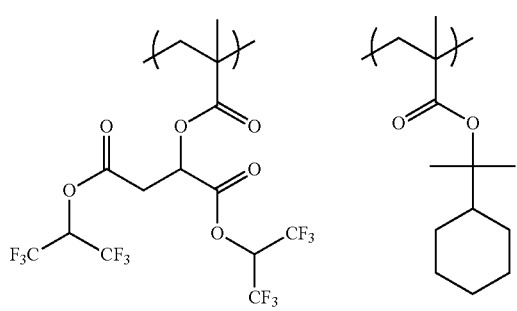
(B-40)
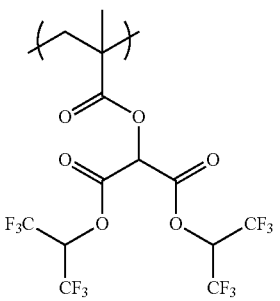
(B-41)
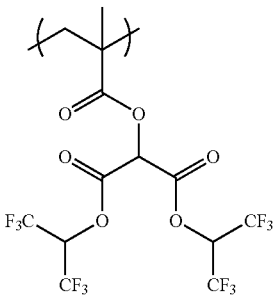
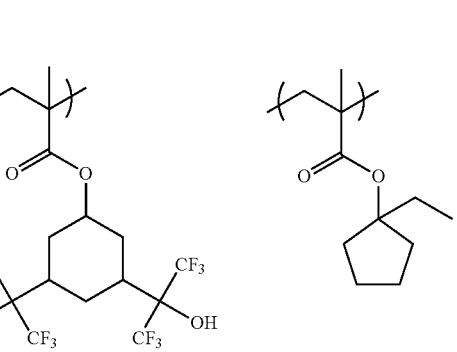
(B-42)
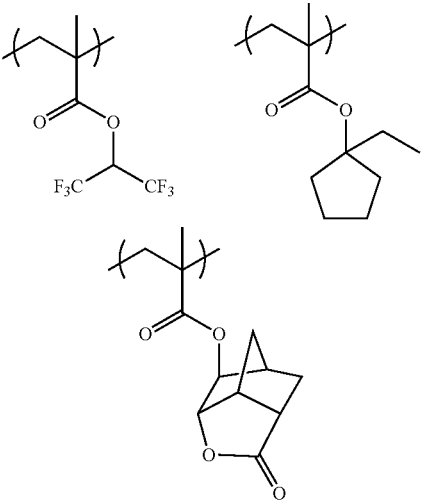

(B-43)
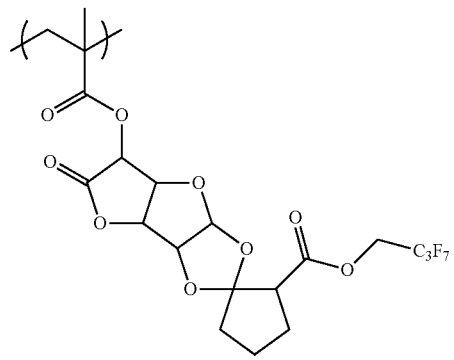
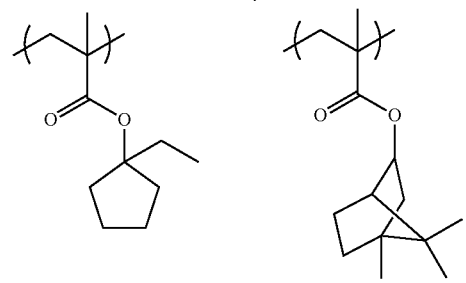
(B-44)
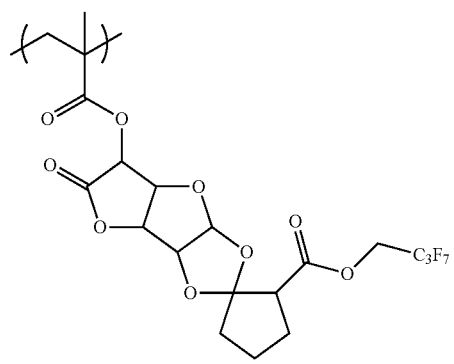
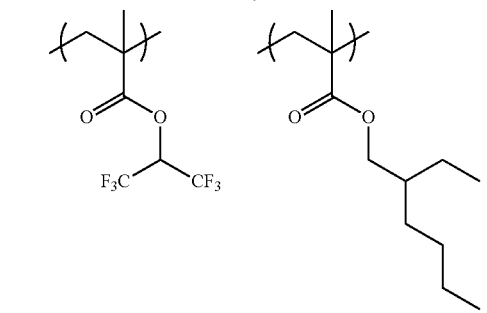
(B-45)
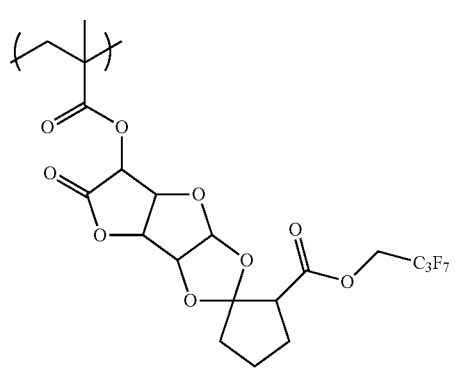
(B-46)
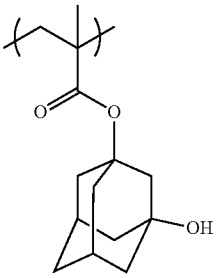
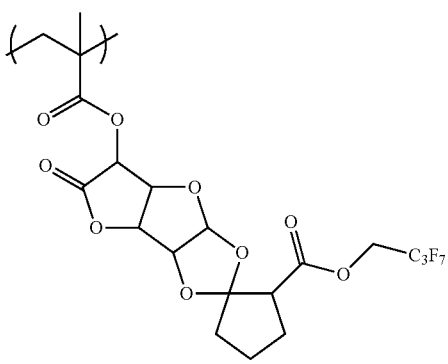
(B-47)
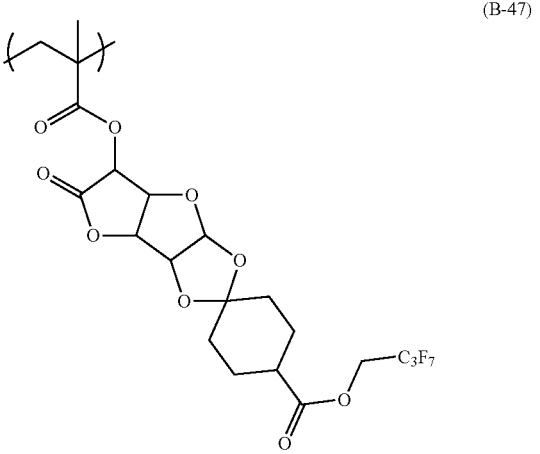
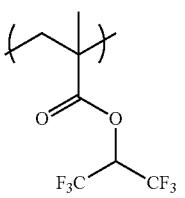

(B-48)
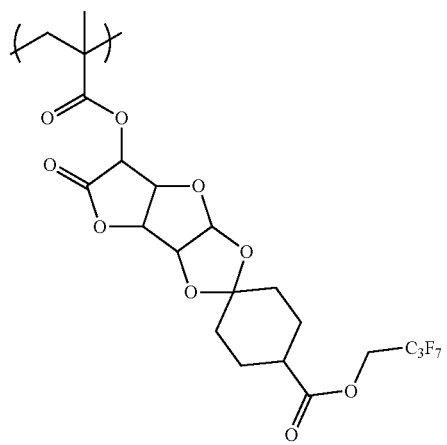
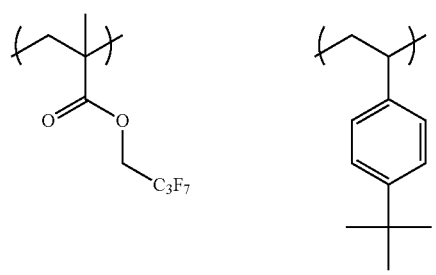
(B-49)
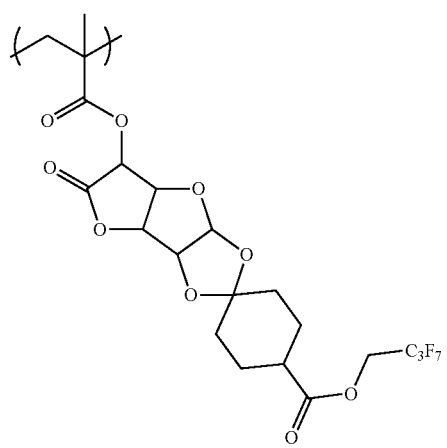
(B-50)
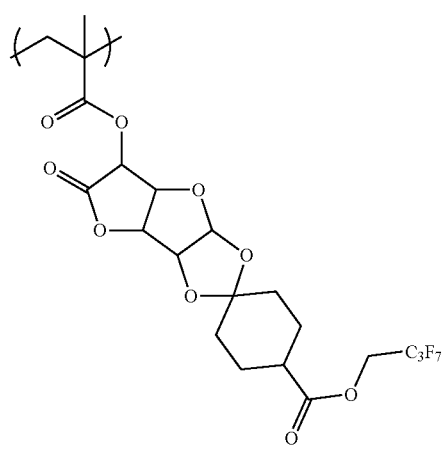
-continued
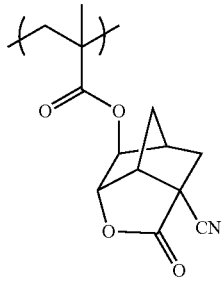
(B-51)
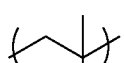
(B-52)
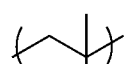

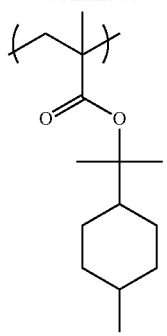
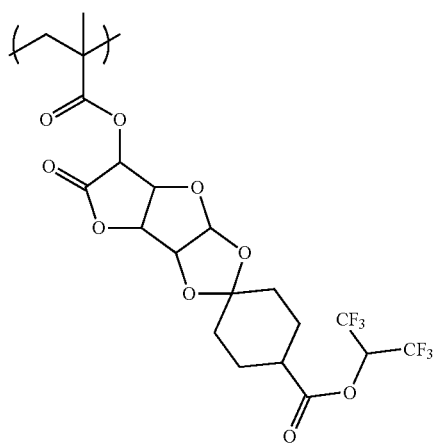
(B-53)
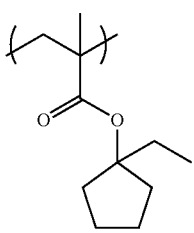
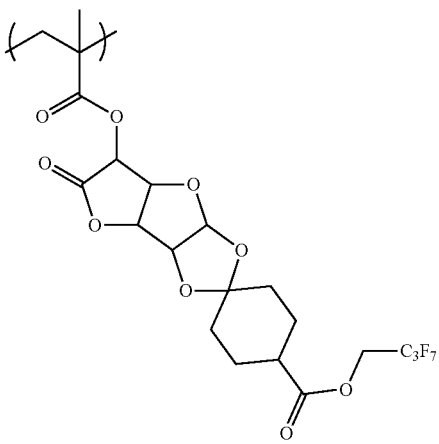
(B-54)
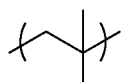
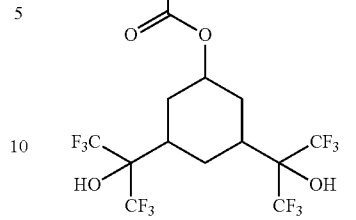
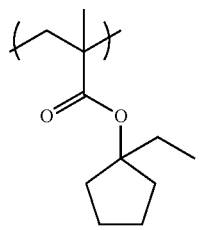
(B-55)
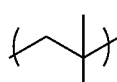
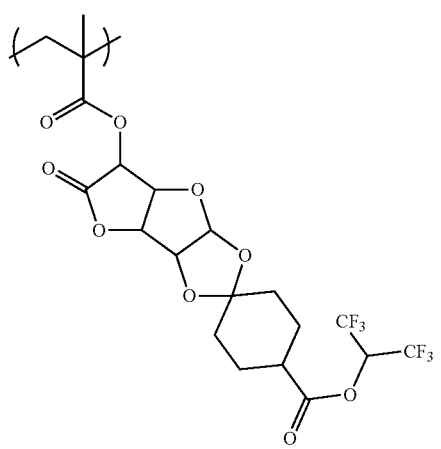
TABLE 1
| Resin | Composition (mol %) | Mw | Mw/Mn |
|---|---|---|---|
| B-1 | 50/50 | 6000 | 1.5 |
| B-2 | 30/70 | 6500 | 1.4 |
| B-3 | 45/55 | 8000 | 1.4 |
| B-4 | 100 | 15000 | 1.7 |
| B-5 | 60/40 | 6000 | 1.4 |
| B-6 | 40/60 | 8000 | 1.4 |
| B-7 | 30/40/30 | 8000 | 1.4 |
| B-8 | 60/40 | 8000 | 1.3 |
| B-9 | 50/50 | 6000 | 1.4 |
| B-10 | 40/40/20 | 7000 | 1.4 |
| B-11 | 40/30/30 | 9000 | 1.6 |
| B-12 | 30/30/40 | 6000 | 1.4 |
| B-13 | 60/40 | 9500 | 1.4 |
| B-14 | 60/40 | 8000 | 1.4 |
| B-15 | 35/35/30 | 7000 | 1.4 |
| B-16 | 50/40/5/5 | 6800 | 1.3 |
| B-17 | 20/30/50 | 8000 | 1.4 |
| B-18 | 25/25/50 | 6000 | 1.4 |
| B-19 | 100 | 9500 | 1.5 |
| B-20 | 100 | 7000 | 1.5 |
| B-21 | 50/50 | 6000 | 1.6 |
| B-22 | 40/60 | 9600 | 1.3 |
| B-23 | 100 | 20000 | 1.7 |
| B-24 | 100 | 25000 | 1.4 |
| B-25 | 100 | 15000 | 1.7 |
| B-26 | 100 | 12000 | 1.8 |
| B-27 | 100 | 18000 | 1.3 |
| B-28 | 70/30 | 15000 | 2.0 |
| B-29 | 80/15/5 | 18000 | 1.8 |
| B-30 | 60/40 | 25000 | 1.8 |
| B-31 | 90/10 | 19000 | 1.6 |
| B-32 | 60/40 | 20000 | 1.8 |
| B-33 | 50/30/20 | 11000 | 1.6 |
| B-34 | 60/40 | 12000 | 1.8 |
| B-35 | 60/40 | 15000 | 1.6 |
| B-36 | 100 | 22000 | 1.8 |

TABLE 1-continued

| Resin | Composition (mol %) | Mw | Mw/Mn |
|---|---|---|---|
| B-37 | 20/80 | 35000 | 1.6 |
| B-38 | 30/70 | 12000 | 1.7 |
| B-39 | 30/70 | 9000 | 1.5 |
| B-40 | 100 | 9000 | 1.5 |
| B-41 | 40/15/45 | 12000 | 1.9 |
| B-42 | 30/30/40 | 13000 | 2.0 |
| B-43 | 40/40/20 | 23000 | 2.1 |
| B-44 | 65/30/5 | 25000 | 1.6 |
| B-45 | 100 | 15000 | 1.7 |
| B-46 | 20/80 | 9000 | 1.7 |
| B-47 | 70/30 | 18000 | 1.5 |
| B-48 | 60/20/20 | 18000 | 1.8 |
| B-49 | 100 | 12000 | 1.4 |
| B-50 | 60/40 | 20000 | 1.6 |
| B-51 | 70/30 | 33000 | 2.0 |
| B-52 | 60/40 | 19000 | 1.8 |
| B-53 | 50/50 | 15000 | 1.5 |
| B-54 | 40/20/40 | 35000 | 1.9 |
| B-55 | 100 | 16000 | 1.4 |

When the hydrophobic resin containing at least either a fluorine atom or a silicon atom is contained, the hydrophobic resin is unevenly distributed in a surface layer portion of the film formed from the composition. When the immersion medium is water, the receding contact angle of the film surface with respect to water is increased so that the immersion-water tracking properties can be enhanced.

The receding contact angle of the film of the composition of the present invention after the bake of the coating but prior to the exposure thereof is preferably in the range of 60° to 90°, more preferably 65° or greater, further more preferably 70° or greater and most preferably 75° or greater at the exposure temperature, generally room temperature 23±3° C. in a humidity of 45±5%.

Although the hydrophobic resin is unevenly localized on any interface, as different from the surfactant, the resin does not necessarily have to have a hydrophilic group in its molecule and does not need to contribute toward uniform mixing of polar/nonpolar substances.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist composition to be capable of tracking the high-speed scanning of the exposure head without leaving droplets.

The hydrophobic resin, due to its hydrophobicity, is likely to cause the blob defect and development residue (scum) after alkali development to deteriorate. When use is made of a hydrophobic resin having three or more polymer chains via at least one branch portion, as compared with a linear-chain resin, the alkali dissolution rate is increased to thereby improve the development residue (scum) and blob defect performance.

When the hydrophobic resin contains fluorine atoms, the content of the fluorine atoms based on the molecular weight of the hydrophobic resin is preferably in the range of 5 to 80 mass %, and more preferably 10 to 80 mass %. The repeating unit containing fluorine atoms preferably exists in the hydrophobic resin in an amount of 10 to 100 mass %, more preferably 30 to 100 mass %.

When the hydrophobic resin contains silicon atoms, the content of the silicon atoms based on the molecular weight of the hydrophobic resin is preferably in the range of 2 to 50 mass %, more preferably 2 to 30 mass %. The repeating unit containing silicon atoms preferably exists in the hydrophobic resin in an amount of 10 to 90 mass %, more preferably 20 to 80 mass %.

The weight average molecular weight of the hydrophobic resin is preferably in the range of 1000 to 100,000, more preferably 2000 to 50,000 and further more preferably 3000 to 30,000. Herein, the weight average molecular weight of the resin refers to the polystyrene-equivalent molecular weight measured by GPC (carrier: tetrahydrofuran (THF)).

One type of hydrophobic resin may be used alone, or two or more types thereof may be used in combination.

The content of hydrophobic resin in the resist composition can be regulated so that the receding contact angle of the actinic-ray- or radiation-sensitive resin film falls within the above-mentioned range. The content of hydrophobic resin based on the total solids of the resist composition is preferably in the range of 0.01 to 20 mass %, more preferably 0.1 to 15 mass %, further more preferably 0.1 to 10 mass % and most preferably 0.5 to 8 mass %.

(E) Solvent

The composition of the present invention may further contain a solvent. As the solvent, an organic solvent such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate and an alkyl pyruvate can be exemplified.

As alkylene glycol monoalkyl ether carboxylates, propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, and ethylene glycol monoethyl ether acetate can be exemplified.

As alkylene glycol monoalkyl ethers, propylene glycol monomethyl ether, propylene glycol monoethyl ether, propylene glycol monopropyl ether, propylene glycol monobutyl ether, ethylene glycol monomethyl ether, and ethylene glycol monoethyl ether can be exemplified.

As alkyl lactates, methyl lactate, ethyl lactate, propyl lactate and butyl lactate can be exemplified.

As alkyl alkoxypropionates, ethyl 3-ethoxypropionate, methyl 3-methoxypropionate, methyl 3-ethoxypropionate, and ethyl 3-methoxypropionate can be exemplified.

As cyclolactones, β-propiolactone, β-butyrolactone, γ-butyrolactone, α-methyl-γ-butyrolactone, β-methyl-γ-butyrolactone, γ-valerolactone, γ-caprolactone, γ-octanoic lactone, and α-hydroxy-γ-butyrolactone can be exemplified.

As optionally cyclized monoketone compounds, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone, and 3-methylcycloheptanone can be exemplified.

As alkylene carbonates, propylene carbonate, vinylene carbonate, ethylene carbonate, and butylene carbonate can be exemplified.

As alkyl alkoxyacetates, acetic acid 2-methoxyethyl ester, acetic acid 2-ethoxyethyl ester, acetic acid 2-(2-ethoxyethoxy)ethyl ester, acetic acid 3-methoxy-3-methylbutyl ester, and acetic acid 1-methoxy-2-propyl ester can be exemplified.

As alkyl pyruvates, methyl pyruvate, ethyl pyruvate and propyl pyruvate can be exemplified.

As a preferably usable solvent, there can be mentioned a solvent having a boiling point of 130° C. or higher measured under ordinary pressure. In particular, there can be mentioned cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, 2-ethoxyethyl acetate, 2-(2-ethoxyethoxy) ethyl acetate or propylene carbonate.

In the present invention, each of these solvents may be used alone, or two or more thereof may be used in combination.

In the present invention, a mixed solvent consisting of a mixture of a solvent having a hydroxyl group in its structure and a solvent having no hydroxyl group may be used as an organic solvent.

The solvent having a hydroxyl group and solvent having no hydroxyl group can appropriately be selected from among the compounds set forth above as examples. The solvent having a hydroxyl group is preferably an alkylene group monoalkyl ether, an alkyl lactate or the like, more preferably propylene glycol monomethyl ether or ethyl lactate. The solvent having no hydroxyl group is preferably an alkylene glycol monoalkyl ether acetate, an alkyl alkoxypropionate, an optionally cyclized monoketone compound, a cyclolactone, an alkyl acetate or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

When employing a mixed solvent consisting of a mixture of a solvent having a hydroxy group in its structure and a solvent having no hydroxy group, the mass ratio between them is preferably in the range of 1/99 to 99/1, more preferably 10/90 to 90/10, and further more preferably 20/80 to 60/40. The mixed solvent containing 50 mass % or more of a solvent having no hydroxy group is especially preferred from the viewpoint of uniform applicability.

It is preferred for the solvent to be a mixed solvent consisting of two or more solvents and to contain propylene glycol monomethyl ether acetate.

(F) Basic Compound other than Compounds of General Formula (1-1)

The composition of the present invention may contain a basic compound (hereinafter also referred to as a "component (F)") other than compounds of general formula (1-1) so as to decrease any performance alteration over time from exposure to heating.

As preferred basic compounds, there can be mentioned the compounds having the structures of the following formulae (A) to (E).

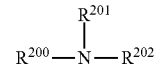
(A)

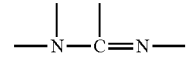
(B)

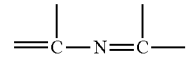
(C)

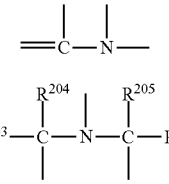
(D)

(E)
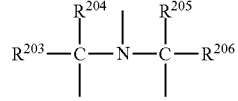

In the general formulae (A) and (E),
$R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded with each other to thereby form a ring. $R^{203}$, $R^{204}$, $R^{205}$ and $R^{206}$ may be identical to or different from each other and each represent an alkyl group having 1 to 20 carbon atoms.

With respect to the above alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

More preferably, in these general formulae (A) and (E) the alkyl group is unsubstituted.

As preferred compounds, there can be mentioned guanidine, aminopyrrolidine, pyrazole, pyrazoline, piperazine, aminomorpholine, aminoalkylmorpholine, piperidine and the like. Further, as preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole, 2-phenylbenzoimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, acetate, adamantane-1-carboxylate, perfluoroalkyl carboxylate and the like. As the compounds with a trialkylamine structure, there can be mentioned tri(n-butyl)amine, tri(n-octyl)amine and the like.

As the aniline compounds, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, N-phenyldiethanolamine, tris(methoxyethoxyethyl) amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

Each of the above amine compound having a phenoxy group, ammonium salt compound having a phenoxy group, amine compound having a sulfonic ester group and ammonium salt compound having a sulfonic ester group preferably has at least one alkyl group bonded to the nitrogen atom thereof. Further preferably, the alkyl group in its chain contains an oxygen atom, thereby forming an oxyalkylene group. The number of oxyalkylene groups in each molecule is one or more, preferably 3 to 9 and more preferably 4 to 6. Oxyalkylene groups having the structure of —$CH_2CH_2O$—, —$CH(CH_3)CH_2O$— or —$CH_2CH_2CH_2O$— are preferred.

As specific examples of the above amine compound having a phenoxy group, ammonium salt compound having a phenoxy group, amine compound having a sulfonic ester group and ammonium salt compound having a sulfonic ester group, there can be mentioned the compounds (C1-1) to (C3-3) shown as examples in Section [0066] of US 2007/0224539 A, which are however nonlimiting.

These basic compounds may be used either individually or in combination.

When the composition of the present invention contains the component (F), the content thereof is typically in the range of 0.001 to 10 mass %, preferably 0.01 to 5 mass % based on the total solids of the composition.

With respect to the ratio of the acid generator to the component (F) used in the composition, preferably, the acid generator/the component (F) (molar ratio)=2.5 to 300. The reason for this is that the molar ratio is preferred to be 2.5 or higher from the viewpoint of sensitivity and resolving power. The molar ratio is preferred to be 300 or below from the viewpoint of the inhibition of any resolving power deterioration due to thickening of resist pattern over time from exposure to heating treatment. The acid generator/the component (F) (molar ratio) is more preferably in the range of 3.5 to 200, still more preferably 3.5 to 150.

(G) Low-molecular Compound Containing a Group Cleaved by the Action of an Acid that upon the Cleavage, Exhibits an Increased Basicity It is preferred for the composition of the present invention to contain a low-molecular compound containing a group cleaved by the action of an acid that upon the cleavage, exhibits an increased basicity (hereinafter also referred to as a "low-molecular compound (G)."

The group that is cleaved when acted on by an acid is not particularly limited. However, an acetal group, a carbonate group, a carbamate group, a tertiary ester group, a tertiary hydroxyl group and a hemiaminal ether group are preferably used. A carbamate group and a hemiaminal ether group are especially preferred.

The molecular weight of the compound (G) is preferably in the range of 100 to 1000, more preferably 100 to 700 and most preferably 100 to 500.

As the compound (G), an amine derivative containing a group that is cleaved when acted on by an acid being connected to a nitrogen atom.

The compound (G) may contain a carbamate group with a protective group, the carbamate group being connected to a nitrogen atom. The protective group contained in the carbamate group can be represented, for example, by the following formula (d-1).

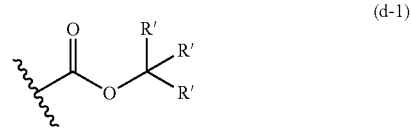

In formula (d-1),

Each of R's independently represents a hydrogen atom, a linear or branched alkyl group, a cycloalkyl group, an aryl group, an aralkyl group, or an alkoxyalkyl group. At least two of R's may be connected to each other to form a ring.

Preferably, R' represents a linear or branched alkyl group, a cycloalkyl group, or an aryl group. More preferably, R' represents a linear or branched alkyl group, or a cycloalkyl group.

The low-molecular compound (G) may have a structure in which any of the above-mentioned basic compounds are combined with the structure represented by general formula (d-1).

The low-molecular compound (G) is especially preferred to be the one represented by general formula (A) below.

Note that, the low-molecular compound (G) may be any of the basic compounds described above as long as it is a low-molecular compound containing a group that is cleaved when acted on by an acid.

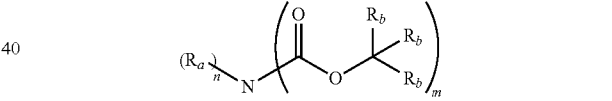

In the general formula (A), Ra represents a hydrogen atom, an alkyl group, a cycloalkyl group, an aryl group, or an aralkyl group. When n=2, two Ra's may be the same or different from each other, and may be connected to each other to form a bivalent heterocyclic hydrocarbon group (preferably having 20 or less carbon atoms) or its derivatives.

Each of Rb's independently represents a hydrogen atom, an alkyl group, a cycloalkyl group, an aryl group, an aralkyl group, or an alkoxyalkyl group, with the proviso that when at least one of Rb's are hydrogen atoms, at least one of the remainder represents a cyclopropyl group, 1-alkoxyalkyl group, or an aryl group.

At least two of Rb's may be connected to each other to form a alicyclic hydrocarbon group, an aromatic hydrocarbon group, a heterocyclic hydrocarbon group, or their derivatives.

In the formula (A), n represents an integer of 0 to 2, m represents an integer of 1 to 3, and n+m=3.

In the formula (A), the alkyl group, the cycloalkyl group, the aryl group, and the aralkyl group represented by Ra and Rb may be substituted with a functional group such as a hydroxyl group, a cyano group, an amino group, a pyrrolidino group, a piperidino group, a morpholino group, and an oxo group; an alkoxy group; or a halogen atom. The same applies to the alkoxyalkyl group represented by Rb.

As the alkyl group, the cycloalkyl group, the aryl group, and the aralkyl group (these groups may be substituted with the above functional group, an alkoxy group, or a halogen atom) represented by Ra and/or Rb, the following groups can be exemplified:

a group derived from a linear or branched alkane such as methane, ethane, propane, butane, pentane, hexane, heptane, octane, nonane, decane, undecane, or dodecane; and the group derived from the alkane and substituted with one or more cycloalkyl groups such as a cyclobutyl group, a cyclopentyl group, or a cyclohexyl group;

a group derived from cycloalkane such as cyclobutane, cyclopentane, cyclohexane, cycloheptane, cyclooctane, norbornane, adamantane, or noradamantane; and the group derived from the cycloalkane and substituted with one or more linear or branched alkyl group such as a methyl group, an ethyl group, a n-propyl group, an i-propyl group, a n-butyl group, a 2-methylpropyl group, a 1-methylpropyl group, or a t-butyl group;

a group derived from aromatic compound such as benzene, naphthalene, or anthracene; and the group derived from the atomatic compound and substituted with one or more linear or branched alkyl group such as a methyl group, an ethyl group, a n-propyl group, an i-propyl group, a n-butyl group, a 2-methylpropyl group, a 1-methylpropyl group, or a t-butyl group;

a group derived from heterocyclic compound such as pyrrolidine, piperidine, morpholine, tetrahydrofuran, tetrahydropyrane, indole, indoline, quinoline, perhydroquinoline, indazole, or benzimidazole; the group derived from heterocyclic compound and substituted with one or more linear or branched alkyl group or a group derived from the aromatic compound;

a group derived from linear or branched alkane and substituted with a group derived from aromatic compound such as a phenyl group, a naphthyl group, or an anthracenyl group;

a group derived from cycloalkane and substituted with a group derived from aromatic compound such as a phenyl group, a naphthyl group, or an anthracenyl group; or each of these groups substituted with a functional group such as a hydroroxyl group, a cyano group, an amino group, a pyrrolidino group, a piperidino group, a morpholino group, or an oxo group.

Further, as the bivalent heterocyclic hydrocarbon group (preferably having 1 to 20 carbon atoms) or its derivative, formed by mutual binding of Ra's, for example, the followings can be exemplified:

a group derived from heterocyclic compound such as pyrrolidine, piperidine, morpholine, 1,4,5,6-tetrahydropyrimidine, 1,2,3,4-tetrahydroquinoline, 1,2,3,6-tetrahydroquinoline, homopiperadine, 4-azabenzimidazole, benztriazole, 5-azabenztriazole, 1H-1,2,3-triazole, 1,4,7-triazacyclononane, tetrazole, 7-azaindole, indazole, benzimidazole, imidazo[1,2-a]pyridine, (1S,4S)-(+)2,5-azabicyclo[2.2.1]heptane, 1,5,7-triazabicyclo[4.4.0]dec-5-en, indole, indoline, 1,2,3,4-tetrahydroquinoxaline, perhydroquinoline, or 1,5,9-triazacyclododecane; or the group derived from heterocyclic compound and substituted with at least one of a group derived from linear or branched alkane, a group derived from cycloalkane, a group derived from aromatic compound, a group derived from heterocyclic compound, or a functional group such as a hydroxyl group, a cyano group, an amino group, a pyrrolidino group, a piperidino group, a morpholino group, or an oxo group.

Particularly preferred examples of the low-molecular compound (G) will be shown below, which however in no way limit the scope of the present invention.

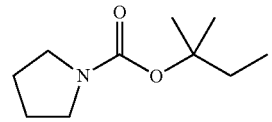 (D-1)

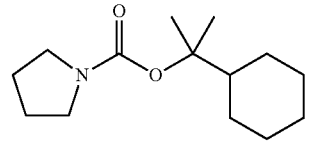 (D-2)

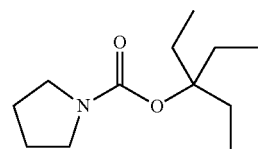 (D-3)

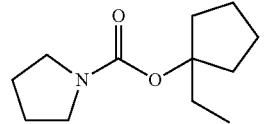 (D-4)

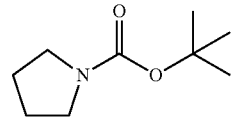 (D-5)

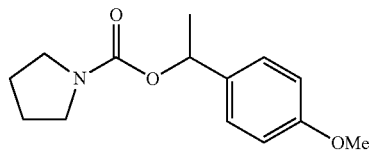 (D-6)

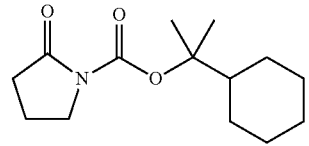 (D-7)

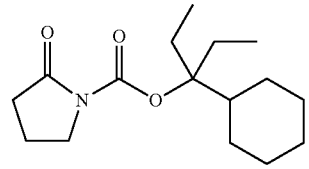 (D-8)

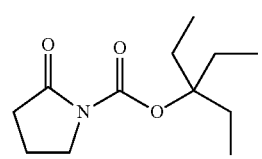 (D-9)

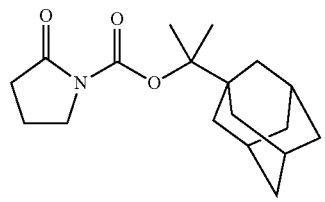 (D-10)

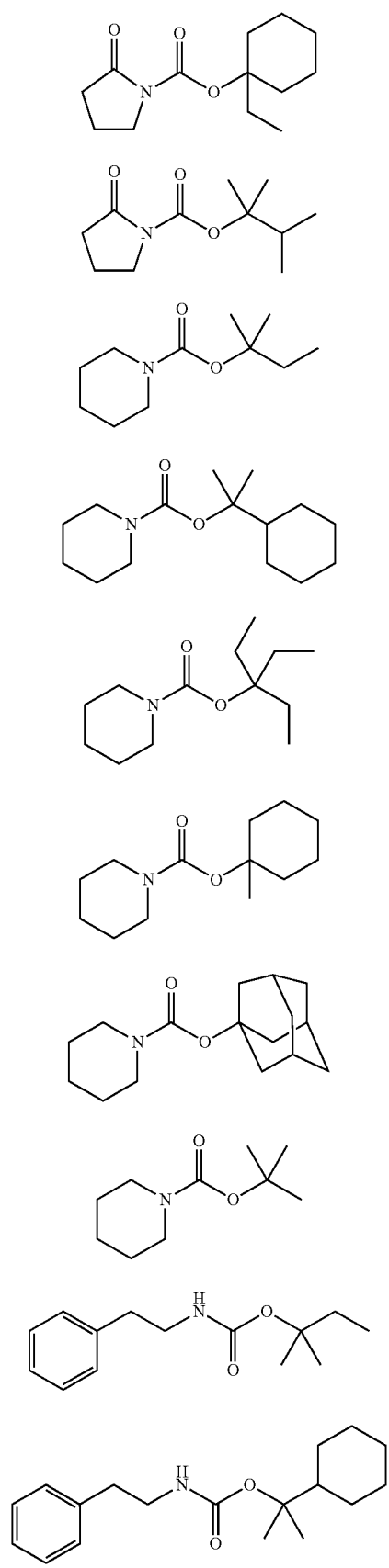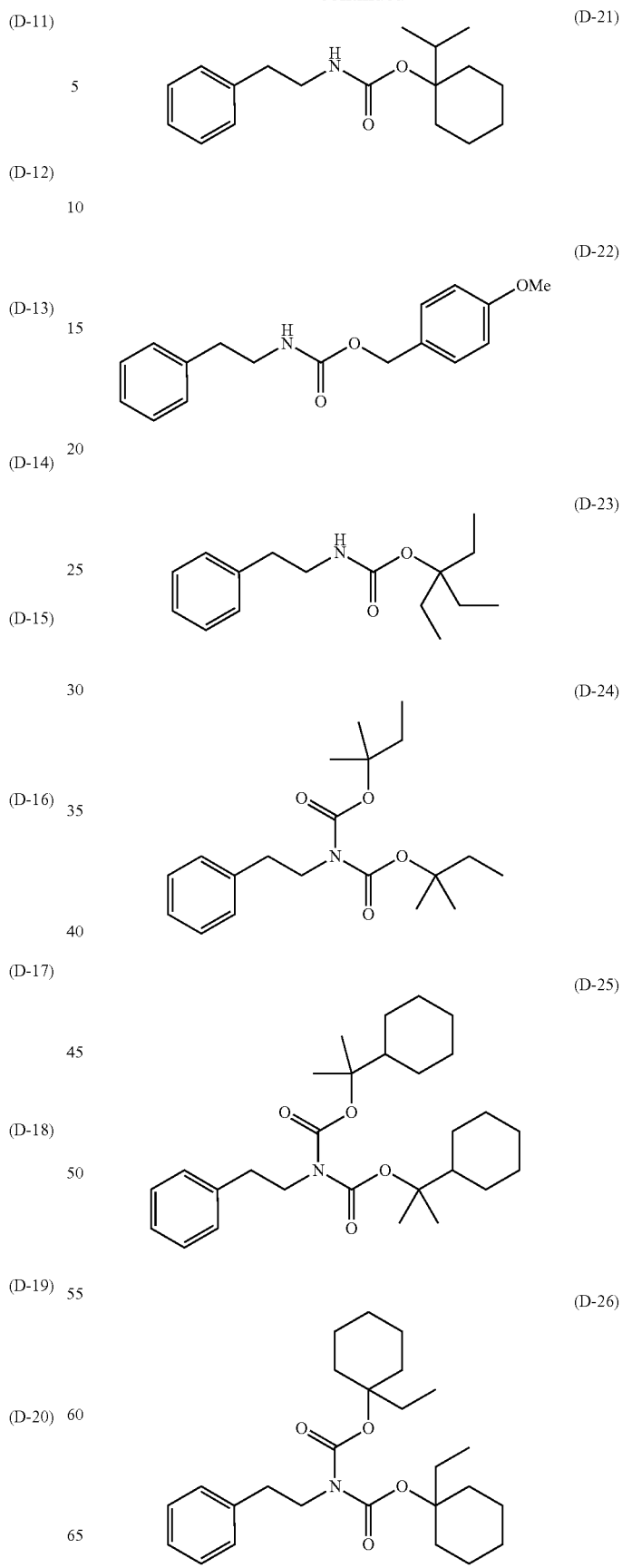

(D-27)
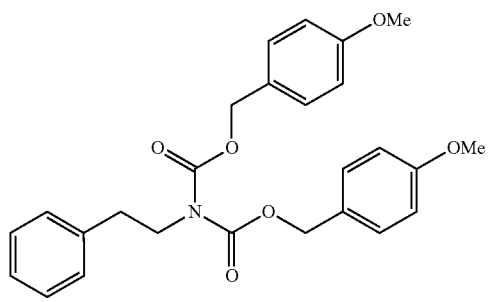
(D-28)
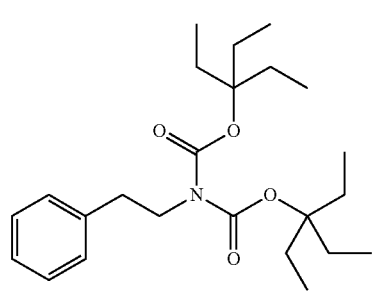
(D-29)
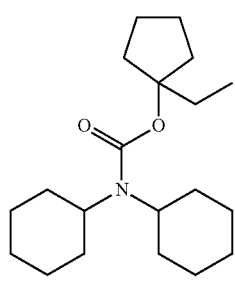
(D-30)
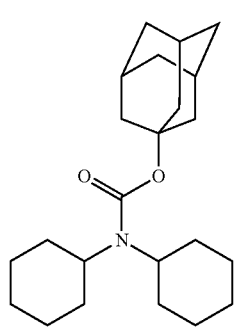
(D-31)
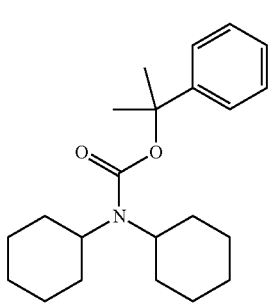
(D-32)
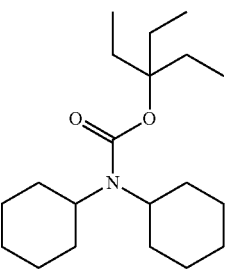
(D-33)
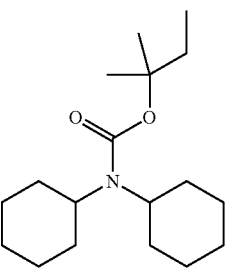
(D-34)
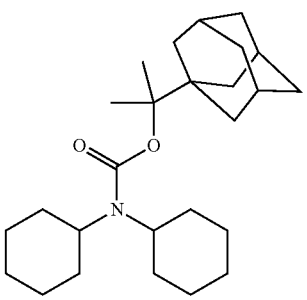
(D-35)
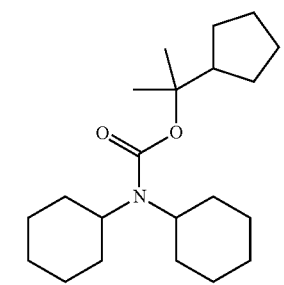
(D-36)
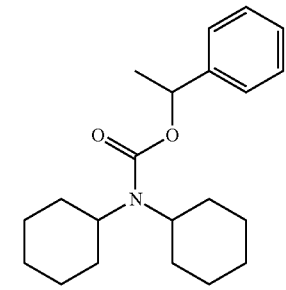
(D-37)
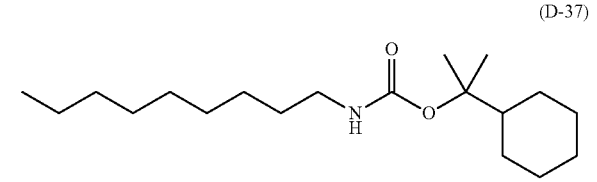

(D-38)
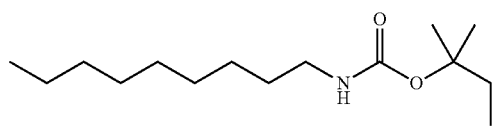
(D-39)
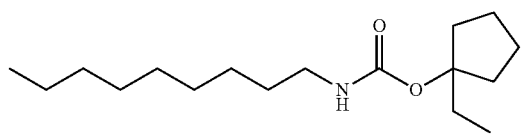
(D-40)
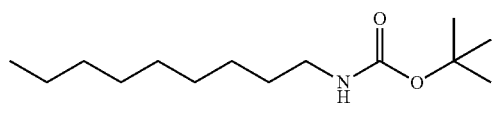
(D-41)
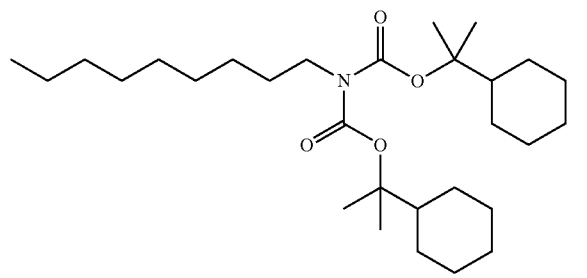
(D-42)
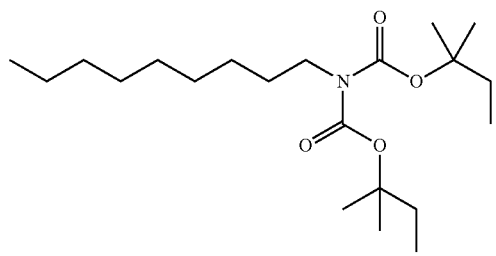
(D-43)
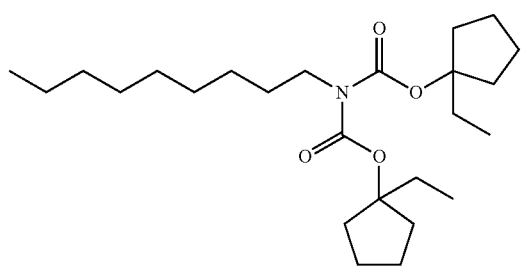
(D-44)
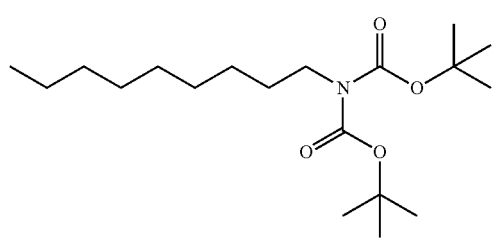
(D-45)
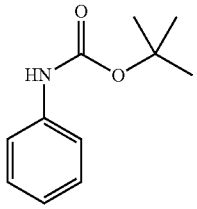
(D-46)
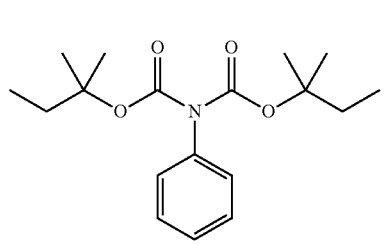
(D-47)
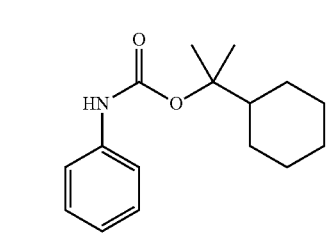
(D-48)
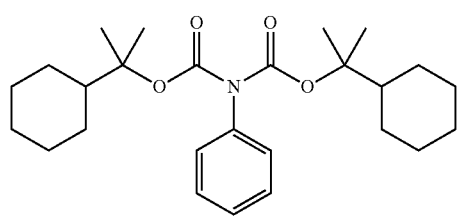
(D-49)
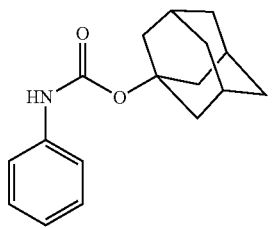
(D-50)
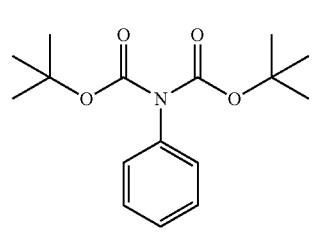
(D-51)
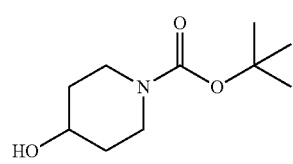

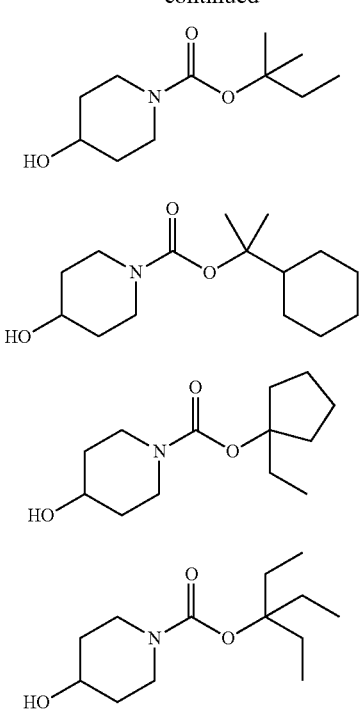

The compounds of general formula (A) can be synthesized by, for example, the method described in JP-A-2009-199021.

In the present invention, one type of low-molecular compound (G) may be used alone, or two or more types thereof may be used in a mixture.

In the present invention, the content of low-molecular compound (G), based on the total solids of the composition mixed with the component (F), is generally in the range of 0.001 to 20 mass %, preferably 0.001 to 10 mass % and more preferably 0.01 to 5 mass %.

With respect to the ratio between acid generator and low-molecular compound (G) used in the composition, it is preferred for the molar ratio of acid generator/[low-molecular compound (G)+component (F)] to be in the range of 2.5 to 300. Namely, the molar ratio is preferred to be 2.5 or higher from the viewpoint of sensitivity and resolution, and the molar ratio is preferred to be 300 or below from the viewpoint of inhibiting the lowering of resolution by thickening of resist pattern over time from exposure to baking treatment. The molar ratio of acid generator/[low-molecular compound (G)+component (F)] is more preferably in the range of 3.5 to 200, further more preferably 3.5 to 150.

(H) Surfactant

The composition of the present invention may further contain a surfactant. When the composition contains a surfactant, the composition preferably contains any one, or two or more members, of fluorinated and/or siliconized surfactants (fluorinated surfactant, siliconized surfactant and surfactant containing both fluorine and silicon atoms).

The composition of the present invention when containing the above surfactant would, in the use of an exposure light source of 250 nm or below, especially 220 nm or below, realize favorable sensitivity and resolving power and produce a resist pattern with less adhesion and development defects.

As fluorinated and/or siliconized surfactants, there can be mentioned, for example, those described in section [0276] of US 2008/0248425 A1. As useful commercially available surfactants, there can be mentioned, for example, fluorinated surfactants/siliconized surfactants, such as Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105 and 106 (produced by Asahi Glass Co., Ltd.), Troy Sol S-366 (produced by Troy Chemical Co., Ltd.), GF-300 and GF-150 (produced by TOA-GOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer having a fluorinated aliphatic group derived from a fluorinated aliphatic compound, produced by a telomerization technique (also called a telomer process) or an oligomerization technique (also called an oligomer process). The fluorinated aliphatic compound can be synthesized by the process described in JP-A-2002-90991.

The polymer containing a fluorinated aliphatic group is preferably a copolymer from a monomer containing a fluorinated aliphatic group and a poly(oxyalkylene)acrylate and/or poly(oxyalkylene)methacrylate, which copolymer may have an irregular distribution or may result from block copolymerization. As the poly(oxyalkylene) group, there can be mentioned a poly(oxyethylene) group, a poly(oxypropylene) group, a poly(oxybutylene) group or the like. Further, use can be made of a unit comprising alkylenes of different chain lengths in a single chain, such as poly(oxyethylene-oxypropylene-oxyethylene block concatenation) or poly(oxyethylene-oxypropylene block concatenation). Moreover, the copolymer from a monomer containing a fluorinated aliphatic group and a poly(oxyalkylene)acrylate (or methacrylate) is not limited to two-monomer copolymers and may be a three-or-more-monomer copolymer obtained by simultaneous copolymerization of two or more different monomers having a fluorinated aliphatic group, two or more different poly(oxyalkylene)acrylates (or methacrylates), etc.

For example, as a commercially available surfactant, there can be mentioned, for example, Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene)acrylate (or methacrylate), a copolymer from an acrylate (or methacrylate) having a $C_3F_7$ group, polyoxyethylene)acrylate (or methacrylate) and poly(oxypropylene)acrylate (or methacrylate), or the like.

In the present invention, surfactants other than the fluorinated and/or siliconized surfactants can also be employed. In particular, there can be mentioned, for example, those described in section [0280] of US 2008/0248425 A1.

These surfactants may be used either individually or in combination.

When the composition of the present invention contains the surfactant, the content thereof based on the total solids of the composition is preferably in the range of 0.1 to 2 mass %, more preferably 0.1 to 1.5 mass %, and most preferably 0.1 to 1 mass %.

(I) Carboxylic Acid Onium Salt

The composition according to the present invention may further contain a carboxylic acid onium salt. Preferred carboxylic acid onium salt is a sulfonium salt and an iodonium salt. A preferred anion moiety thereof is a linear, branched, monocyclic or polycyclic alkylcarboxylate anion having 1 to 30 carbon atoms. A more preferred anion moiety is an anion of carboxylic acid wherein the alkyl group is partially or wholly fluorinated. The alkyl chain may contain an oxygen atom. If so, the transparency to light of wavelength 220 nm or shorter can be ensured, the sensitivity and resolving power can be enhanced, and the iso/dense bias and exposure margin can also be enhanced.

As the fluorinated carboxylic acid anion, any of the anions of fluoroacetic acid, difluoroacetic acid, trifluoroacetic acid, pentafluoropropionic acid, heptafluorobutyric acid, nonafluoropentanoic acid, perfluorododecanoic acid, perfluorotridecanoic acid, perfluorocyclohexanecarboxylic acid, and 2,2-bistrifluoromethylpropionic acid can be exemplified.

The content of the carboxylic acid onium salt based on the total solids of the composition is preferably in the range of 0.1 to 20 mass %, more preferably 0.5 to 10 mass %, and most preferably 1 to 7 mass %.

(J) Dissolution Inhibiting Compound

The composition according to the present invention may further contain a dissolution inhibiting compound. Here the "dissolution inhibiting compound" means compound having 3000 or less molecular weight that is decomposed by the action of an acid to increase the solubility in an alkali developer.

From the viewpoint of preventing lowering of the transmission at the wavelength of 220 nm or shorter, the dissolution inhibiting compound is preferably an alicyclic or aliphatic compound having an acid-decomposable group, such as any of cholic acid derivatives having an acid-decomposable group described in Proceeding of SPIE, 2724, 355 (1996). The acid-decomposable group and alicyclic structure can be the same as described earlier.

When the composition according to the present invention is exposed to a KrF excimer laser or irradiated with electron beams, preferred use is made of one having a structure resulting from substitution of the phenolic hydroxy group of a phenol compound with an acid-decomposable group. The phenol compound preferably contains 1 to 9 phenol skeletons, more preferably 2 to 6 phenol skeletons.

The content of the dissolution inhibiting compound based on the total solids of the composition is preferably in the range of 3 to 50 mass %, and more preferably 5 to 40 mass %.

Specific examples of the dissolution inhibiting compound will be shown below, which however in no way limit the scope of the present invention.

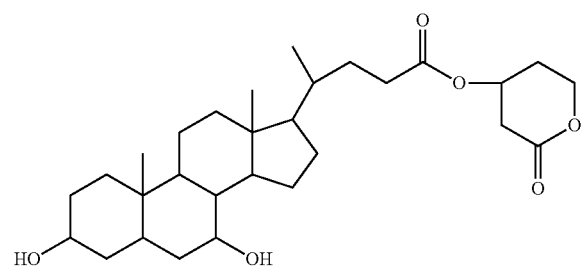

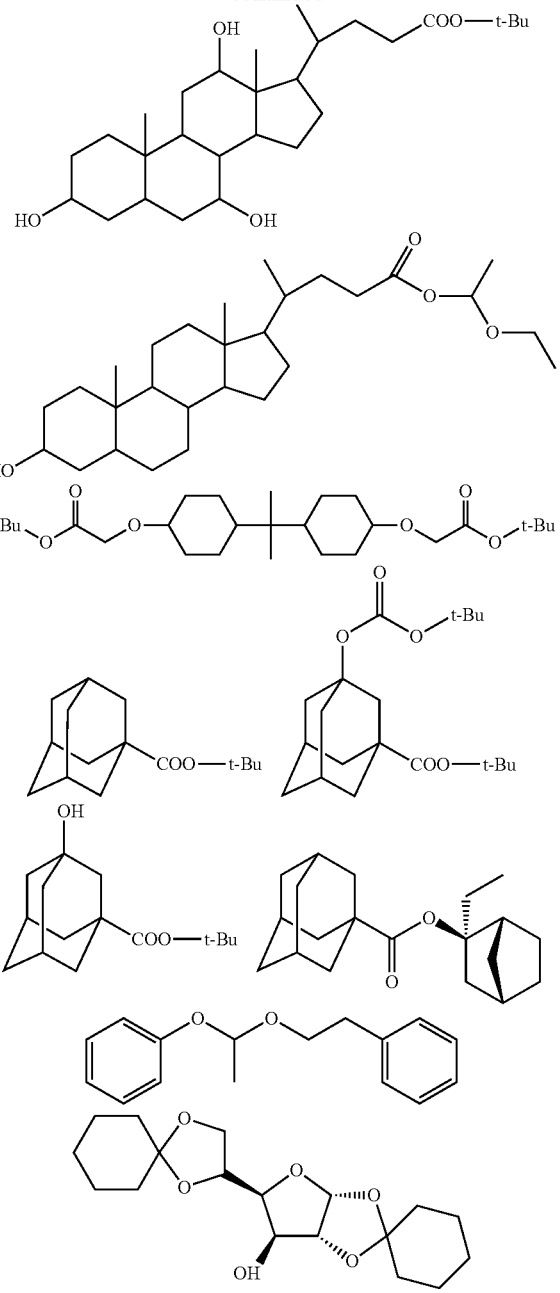

(K) Other Additives

The composition according to the present invention may further contain a dye, a plasticizer, a photosensitizer, a light absorber, and/or a compound capable of increasing the solubility in a developer (for example, a phenolic compound of 1000 or less molecular weight or a carboxylated alicyclic or aliphatic compound), etc.

The above phenolic compound of 1000 or less molecular weight can be easily synthesized by persons of ordinary skill in the art while consulting the processes described in, for example, JP-As 4-122938 and 2-28531, U.S. Pat. No. 4,916, 210, and EP 219294.

As the nonlimiting examples of the carboxylated alicyclic or aliphatic compound, a carboxylic acid derivative of steroid structure such as cholic acid, deoxycholic acid or lithocholic acid, an adamantanecarboxylic acid derivative, adamantanedicarboxylic acid, cyclohexanecarboxylic acid, and cyclohexanedicarboxylic acid can be exemplified.

<Method of Forming Pattern>

From the viewpoint of enhancing the resolving power, it is preferred for the composition of the present invention to be used with a film thickness of 30 to 250 nm. More preferably, the composition is used with a film thickness of 30 to 200 nm. This film thickness can be attained by setting the solid content of the actinic-ray- or radiation-sensitive resin composition within an appropriate range so as to cause the composition to have an appropriate viscosity, thereby improving the applicability and film forming property.

The total solid content of the composition of the present invention is generally in the range of 1 to 10 mass %, preferably 1 to 8.0 mass % and more preferably 1.0 to 7.0 mass %.

The composition of the present invention is used in such a manner that the above components are dissolved in a given organic solvent, preferably the above mixed solvent, and filtered and applied onto a given support in the following manner. Preferably, the filter medium for the filtration is made of a polytetrafluoroethylene, polyethylene or nylon having a pore size of 0.1 μm or less, especially 0.05 μm or less and further especially 0.03 μm or less. In the filtration, use may be made of two or more types of filters connected in series or in parallel. Further, the composition may be filtered two or more times. Still further, before or after the filtration, the composition may be subjected to deaeration, etc.

For example, the actinic-ray- or radiation-sensitive resin composition is applied onto a substrate, such as one for use in the production of precision integrated circuit elements (e.g., silicon/silicon dioxide coating), by appropriate application means, such as a spinner or coater, and dried to thereby form a film.

The obtained film is exposed through a given mask to actinic rays or radiation, preferably baked (heated), developed and rinsed. Thus, a desirable pattern can be obtained.

As the actinic rays or radiation, infrared rays, visible light, ultraviolet rays, far ultraviolet rays, extreme ultraviolet rays (EUV), X-rays, and electron beams can be exemplified. Among them, preferred use is made of far ultraviolet rays with wavelength of preferably 250 nm or less, more preferably 220 nm or less, and still more preferably 1 to 200 nm, such as a KrF excimer laser (248 nm), an ArF excimer laser (193 nm) and an $F_2$ excimer laser (157 nm), EUV (13 nm) and electron beams.

The application of the composition to the substrate can be preceded by the application of an antireflection film.

As the anti-reflection film, use can be made of not only an inorganic film of titanium, titanium oxide, titanium nitride, chromium oxide, carbon, amorphous silicon or the like but also an organic film composed of a light absorber and a polymer material. Also, as the organic anti-reflection film, use can be made of commercially available organic anti-reflection films, such as the DUV30 Series and DUV40 Series produced by Brewer Science Inc. and AR-2, AR-3 and AR-5 produced by Shipley Co., Ltd.

Generally, an aqueous solution of any of quaternary ammonium salts, a typical example thereof being tetramethylammonium hydroxide, is employed as the alkali developer for use in the development operation. However, other aqueous alkali solutions of an inorganic alkali, a primary amine, a secondary amine, a tertiary amine, an alcoholamine, a cycloamine, etc. can also be employed.

An appropriate amount of alcohol and/or surfactant may be added to the alkali developer.

The alkali concentration of the alkali developer is generally in the range of 0.1 to 20 mass %.

The pH value of the alkali developer is generally in the range of 10.0 to 15.0.

Pure water is used as the rinse liquid. An appropriate amount of surfactant may be added to the rinse liquid before use.

The development operation or rinse operation may be followed by the operation for removing any portion of developer or rinse liquid adhering onto the pattern by use of a supercritical fluid.

A liquid immersion exposure may be carried out for the film produced from the composition of the present invention. Namely, the film may be exposed to actinic rays or radiation under the conditions that the space between the film and a lens is filled with a liquid whose refractive index is higher than that of air. If so, an enhanced resolution can be attained.

The liquid for liquid immersion for use in the liquid immersion exposure will now be described.

The liquid for liquid immersion preferably consists of a liquid being transparent in exposure wavelength whose temperature coefficient of refractive index is as low as possible so as to ensure minimization of any distortion of optical image projected on the resist film. Especially in the use of an ArF excimer laser (wavelength; 193 nm) as an exposure light source, however, it is more preferred to use water from not only the above viewpoints but also the viewpoints of easy procurement and easy handling.

For the attainment of further wavelength shortening, use can be made of a medium whose refractive index is 1.5 or higher. This medium may be an aqueous solution or an organic solvent.

In the use of water as a liquid for liquid immersion, a slight proportion of additive (liquid) that would not dissolve the resist film on a wafer and would be negligible with respect to its influence on an optical coat for an under surface of lens element may be added in order to not only decrease the surface tension of water but also increase a surface activating power.

The additive is preferably an aliphatic alcohol with a refractive index approximately equal to that of water, for example, methyl alcohol, ethyl alcohol, isopropyl alcohol or the like. The addition of an alcohol with a refractive index approximately equal to that of water is advantageous in that even when the alcohol component is evaporated from water to thereby cause a change of content concentration, the change of refractive index of the liquid as a whole can be minimized. On the other hand, when a substance being opaque in 193 nm rays or an impurity whose refractive index is greatly different from that of water is mixed therein, the mixing would invite a distortion of optical image projected on the resist film. Accordingly, it is preferred to use distilled water as the liquid immersion water. Furthermore, use may be made of pure water having been filtered through an ion exchange filter or the like.

Desirably, the electrical resistance of the water is 18.3 MΩcm or higher, and the TOC (organic matter concentration) thereof is 20 ppb or below. Prior deaeration of the water is desired.

Raising the refractive index of the liquid for liquid immersion would enable an enhancement of lithography performance. From this viewpoint, an additive suitable for refractive index increase may be added to the water, or heavy water ($D_2O$) may be used in place of water.

EXAMPLES

Embodiments of the present invention will be described in greater detail below by way of examples thereof. However, the scope of the present invention is in no way limited to these examples.

<Acid Generator (1)>
The following compounds (B-1) to (B-57) were synthesized as components (B). Further, the following compounds (B-58) and (B-59) were provided for reference.
(B-1)
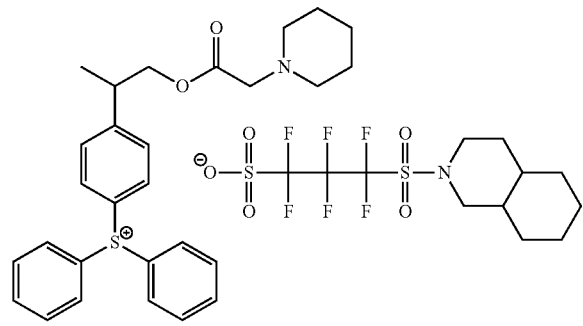
(B-2)
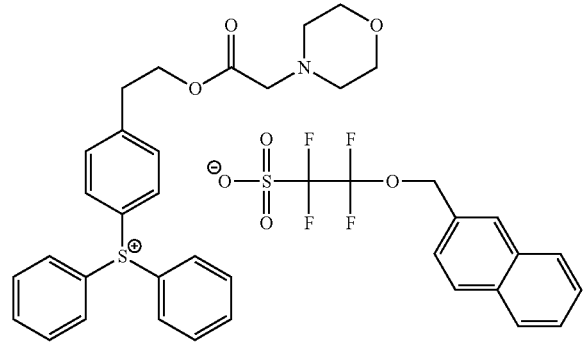
(B-3)
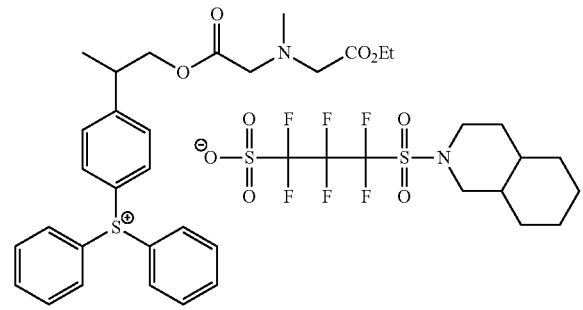
(B-4)
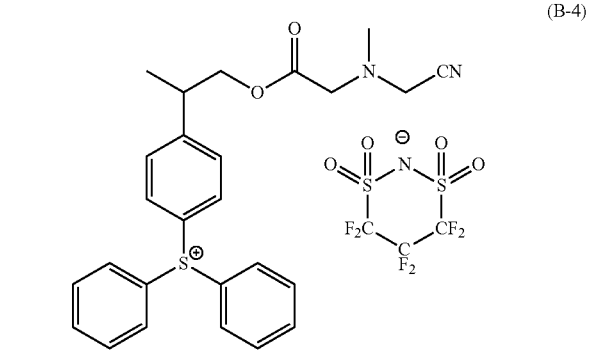
(B-5)
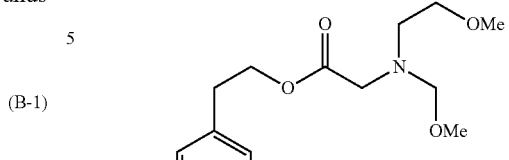
(B-6)
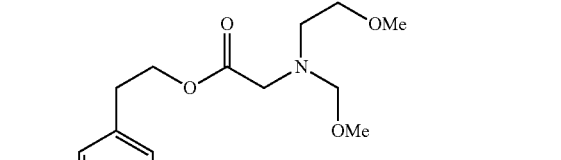
(B-7)
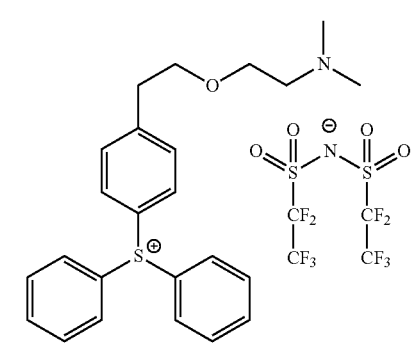
(B-8)
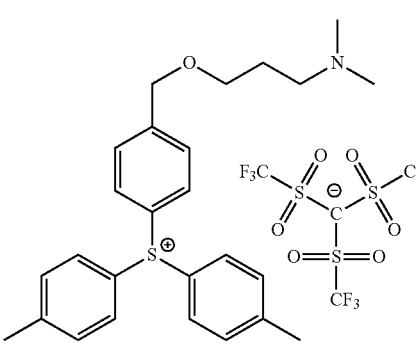

-continued
(B-9)
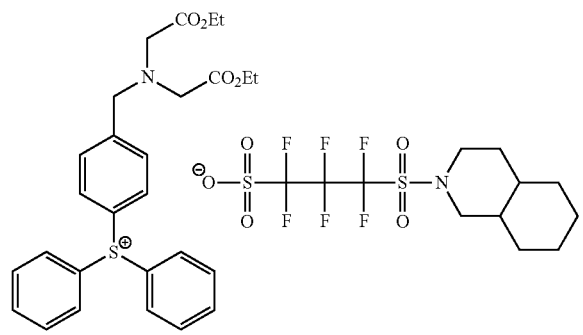
(B-10)
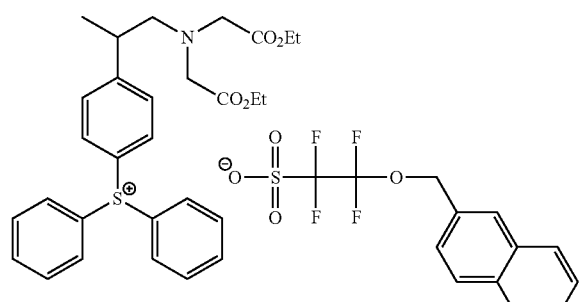
(B-11)
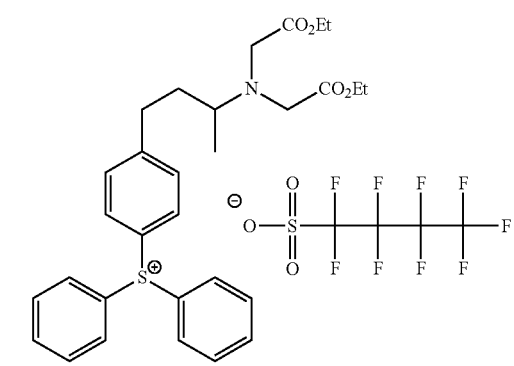
(B-12)
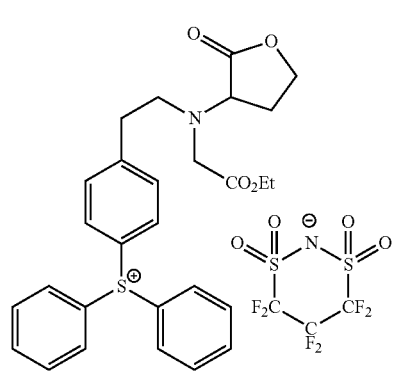
-continued
(B-13)
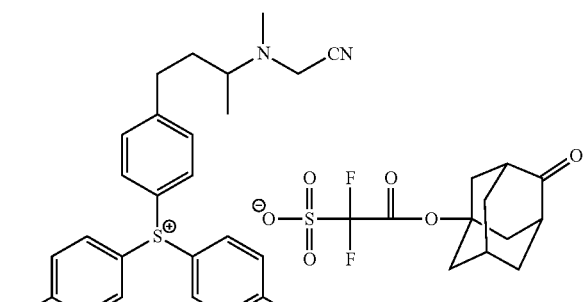
(B-14)
(B-15)
(B-16)
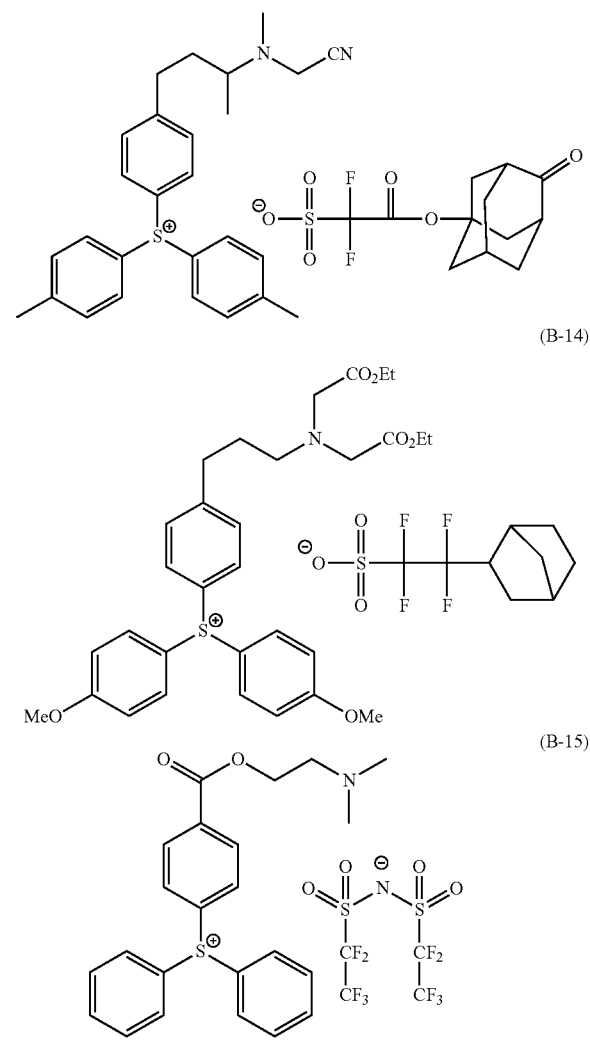
(B-17)
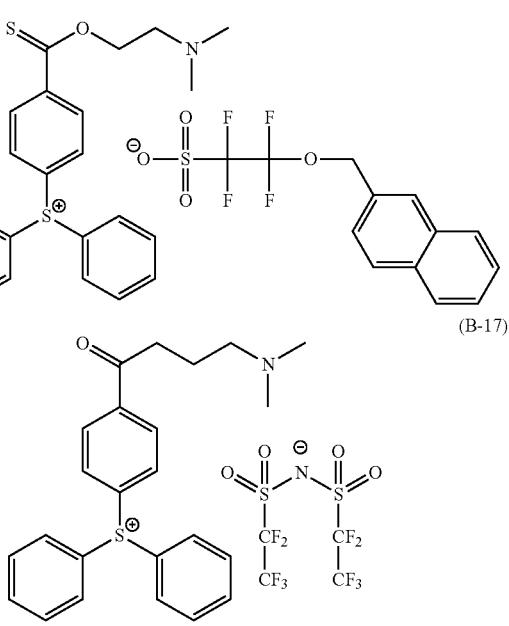

(B-18) 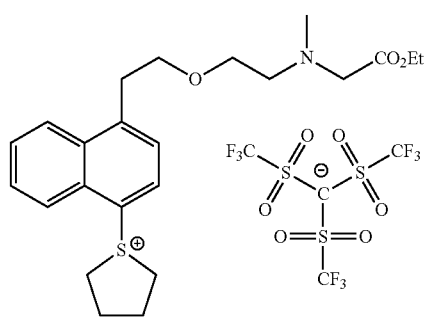
(B-22) 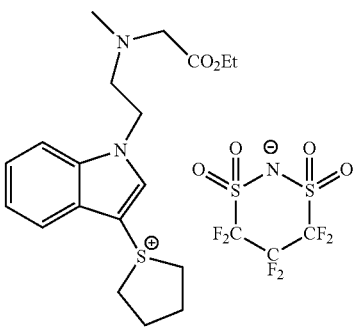
(B-19) 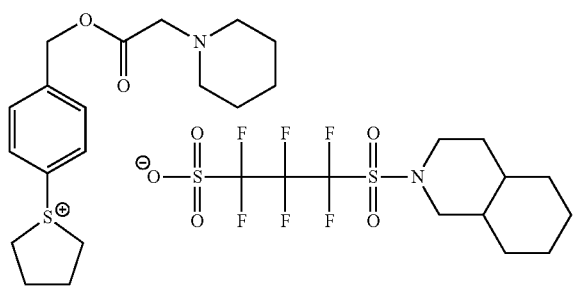
(B-23) 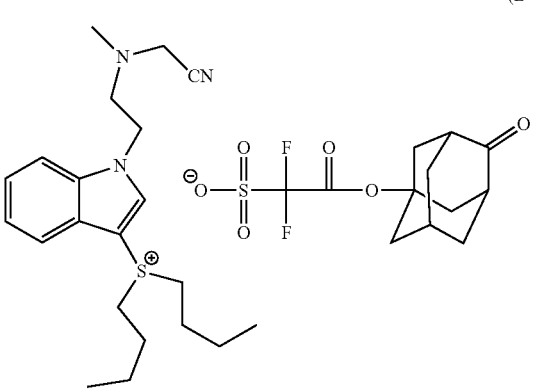
(B-20) 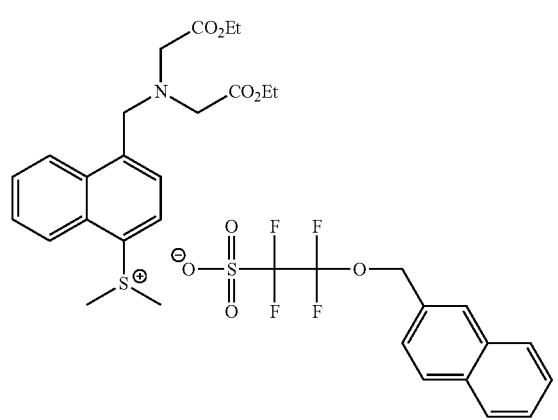
(B-24) 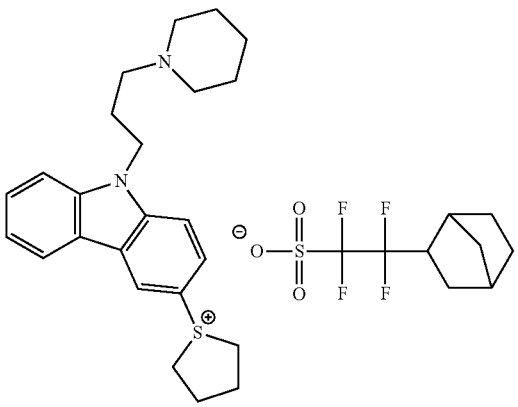
(B-21) 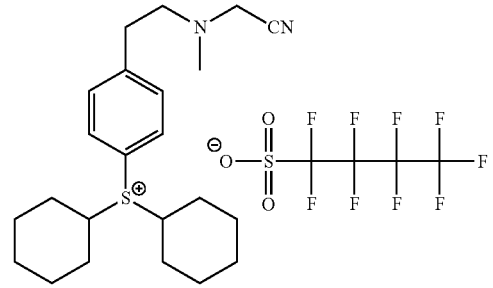
(B-25) 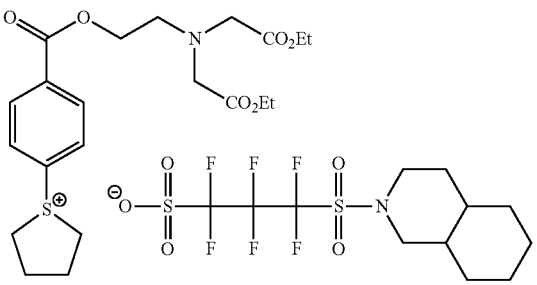

(B-26) 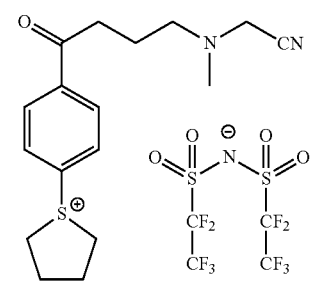
(B-27) 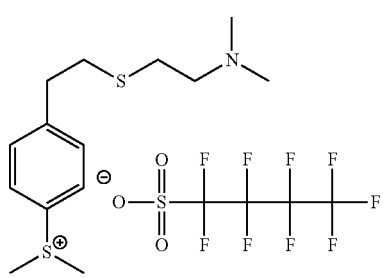
(B-28) 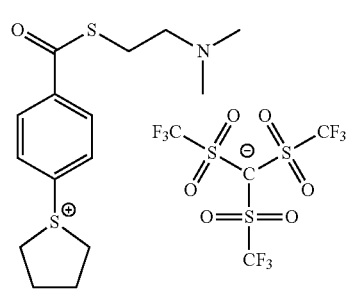
(B-29) 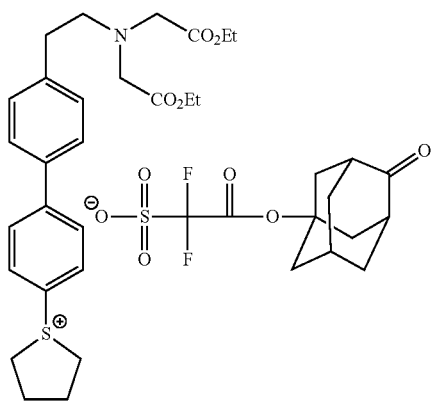
(B-30) 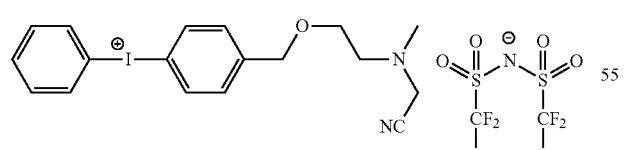
(B-31) 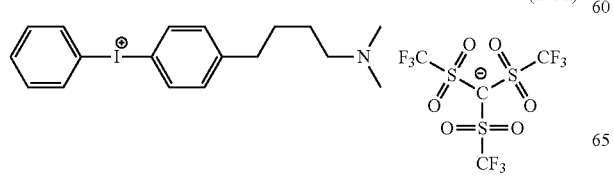
(B-32) 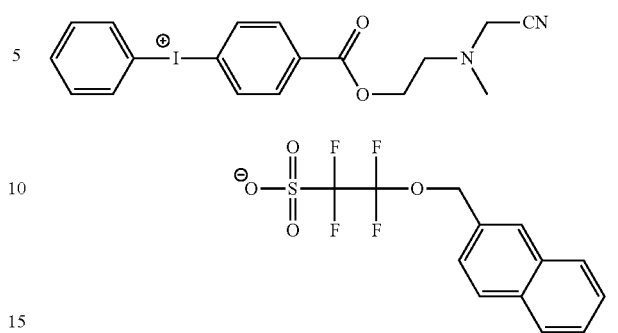
(B-33) 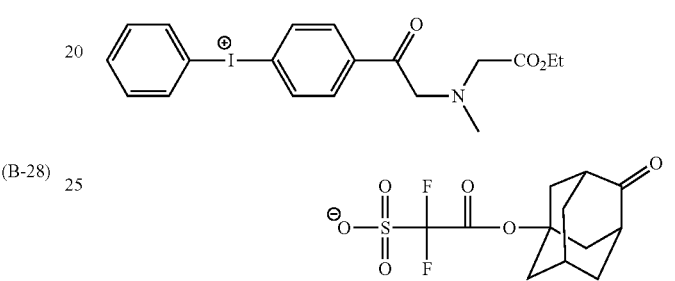
(B-34) 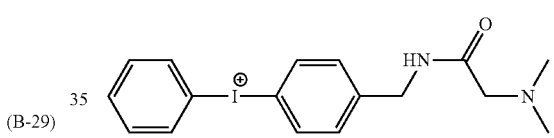
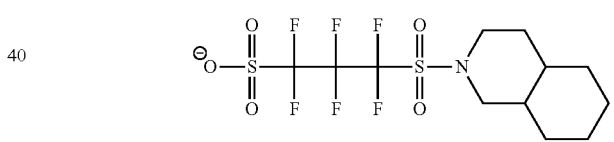
(B-35) 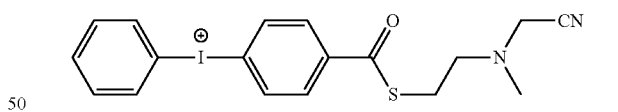
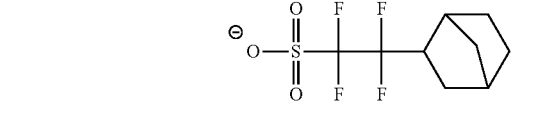
(B-36) 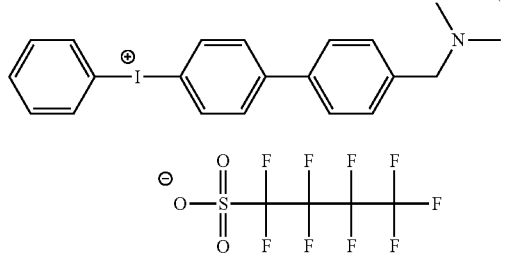

(B-37)
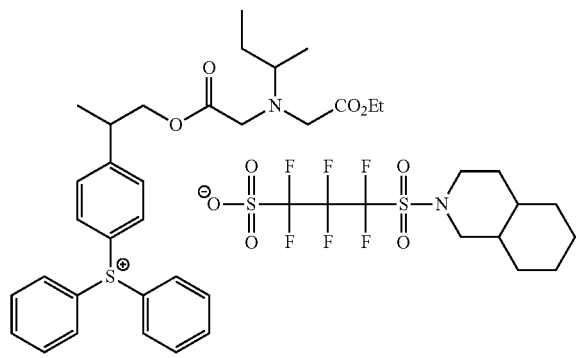
(B-41)
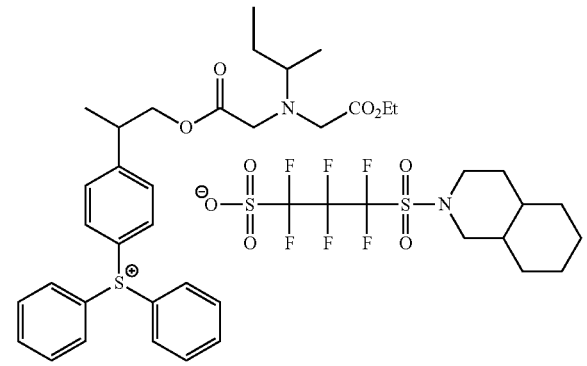
(B-38)
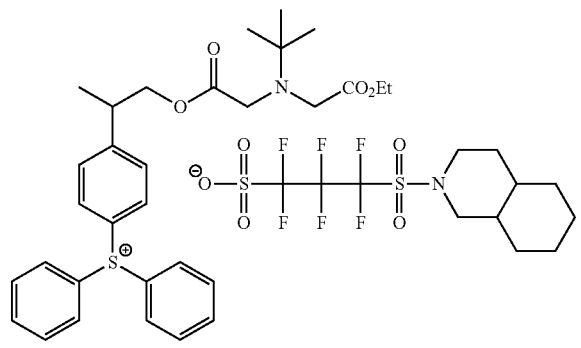
(B-42)
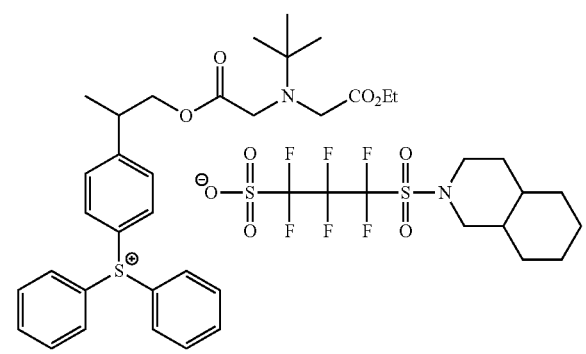
(B-39)
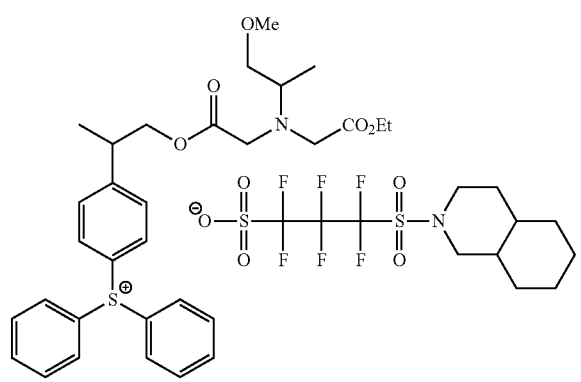
(B-43)
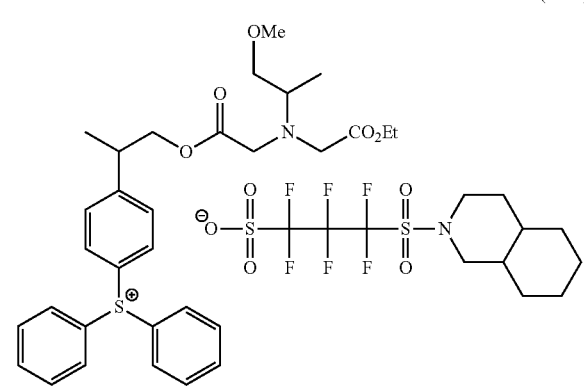
(B-40)
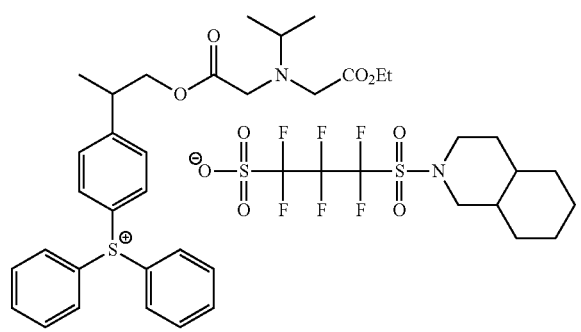
(B-44)
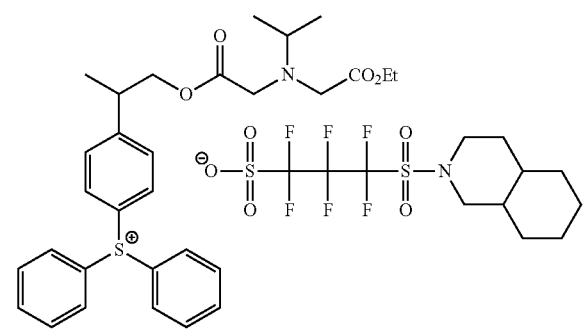

-continued
(B-45)
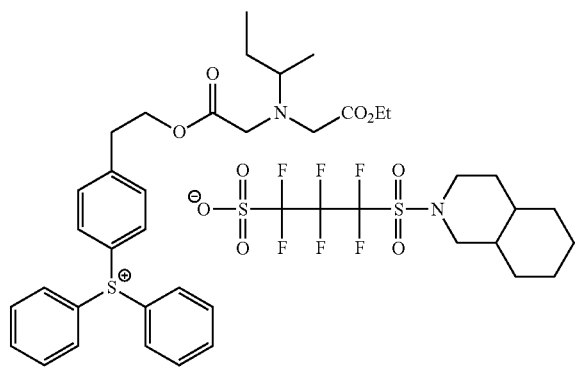
(B-46)
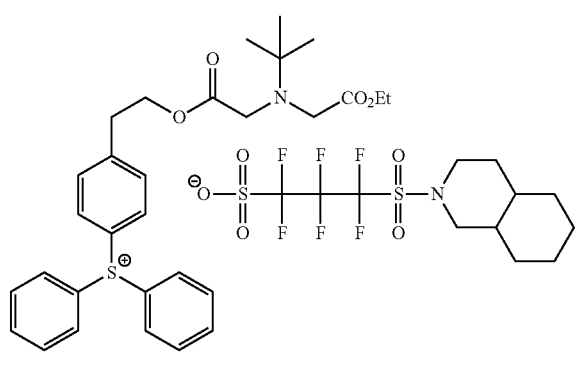
(B-47)
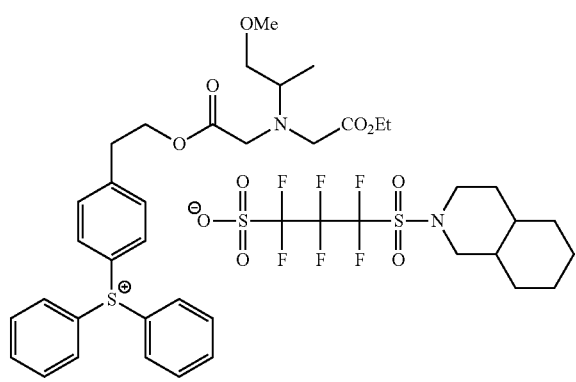
(B-48)
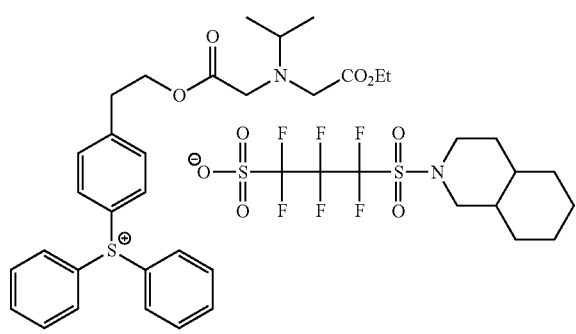
-continued
(B-49)
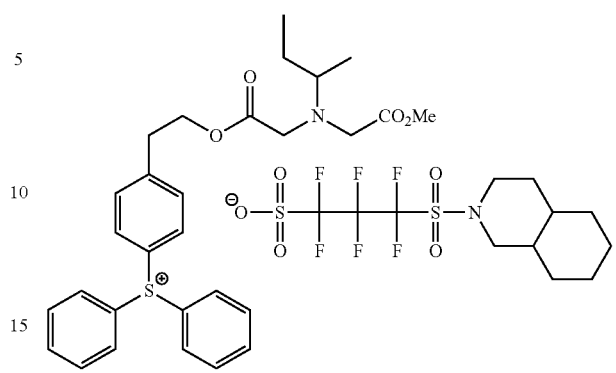
(B-50)
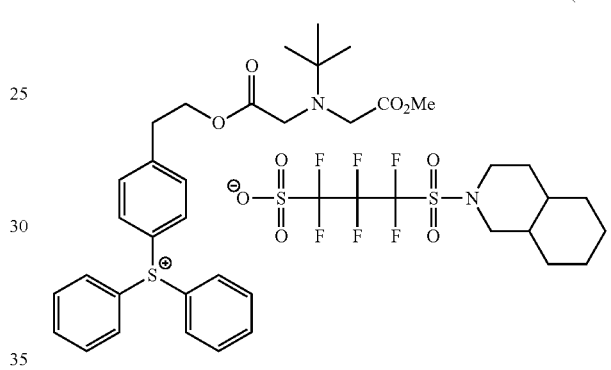
(B-51)
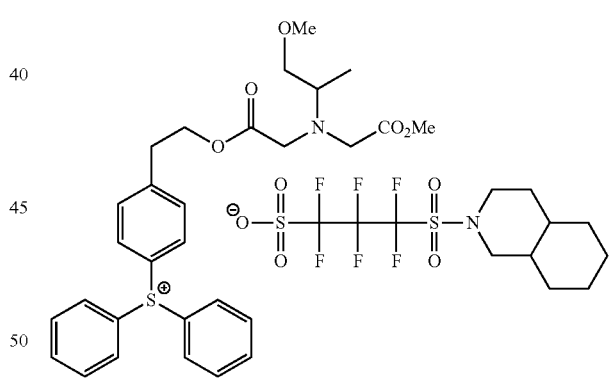
(B-52)
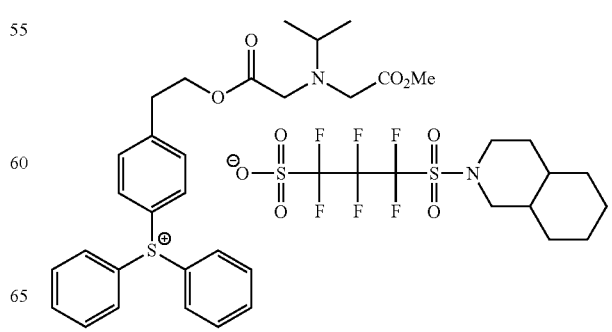

-continued (B-53)
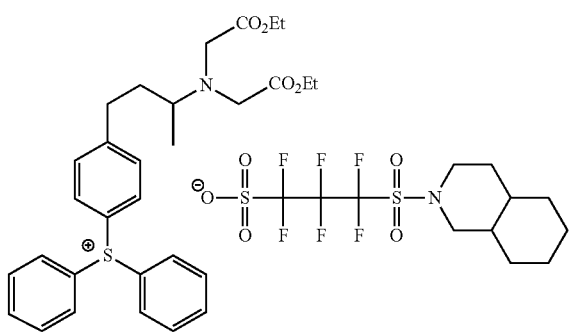

(B-54)
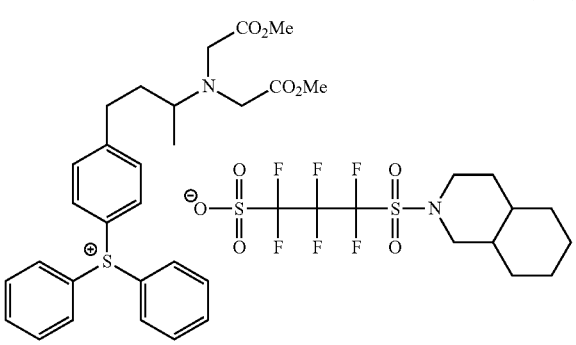

(B-55)
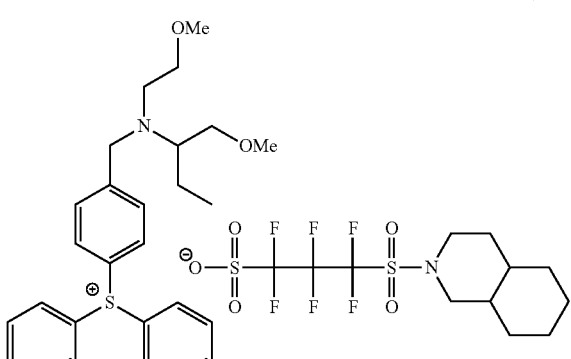

(B-56)
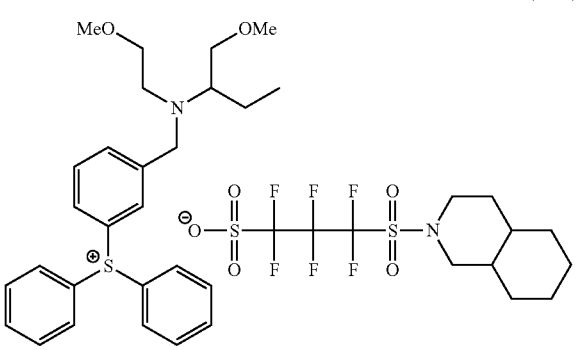

-continued (B-57)
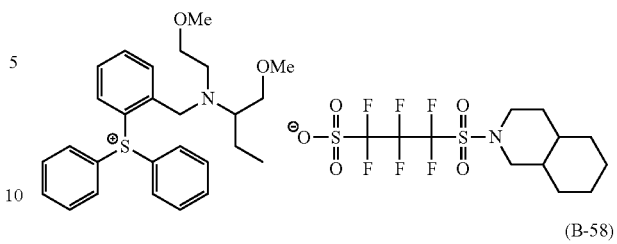

(B-58)
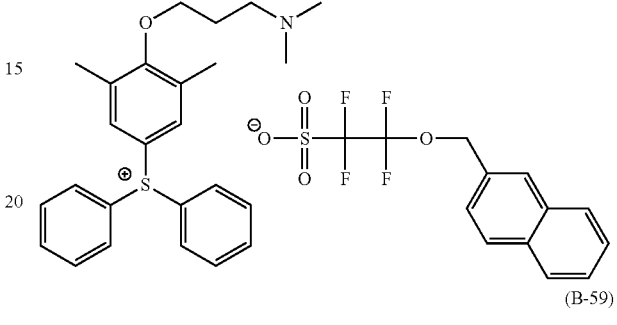

(B-59)
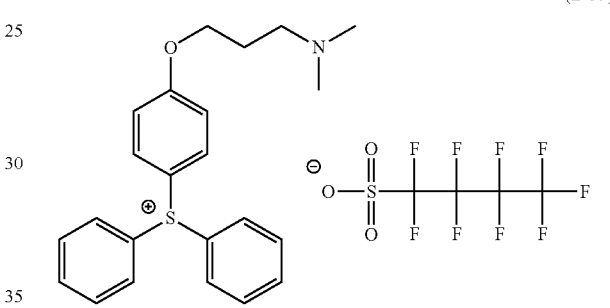

Synthetic Example 1

Synthesis of Compound (B-1)

A sulfonium salt was synthesized by the Friedel-Crafts reaction between 2-phenylpropyl acetate and diphenyl sulfoxide. Thereafter, the salt was hydrolyzed, thereby obtaining compound (B-1-1) shown below.

In a 200 ml three-necked flask, 3.7 g of compound (B-1-1) was dissolved in a mixed solvent consisting of 1.5 g of pyridine and 25 g of THF. While cooling the solution in an ice bath under agitation, 2.1 g of chloroacetyl chloride was dropped thereinto over a period of 30 minutes. After the completion of dropping, the ice bath was removed, and the mixture was warmed to room temperature at which the mixture was agitated for an hour. Thereafter, 100 g of chloroform was added to the mixture, and the resultant organic phase was sequentially washed with water, a saturated aqueous sodium bicarbonate solution and water. The solvent was removed, thereby obtaining brown liquid compound (B-1-2) shown below.

In a 200 ml three-necked flask, obtained compound (B-1-2) was dissolved in 25 g of acetone. While cooling the solution in an ice bath under agitation, 1.7 g of piperidine was dropped thereinto over a period of 30 minutes. After the completion of dropping, the ice bath was removed, and the mixture was warmed to room temperature at which the mixture was agitated for 5 hours. Thereafter, 100 g of chloroform was added to the mixture, and the resultant organic phase was sequentially washed with water, a saturated aqueous sodium bicarbonate solution and water. The solvent was removed, thereby obtaining brown liquid compound (B-1-3) shown below.

Compound (B-1-3) was dissolved in 50 g of water, and 3.6 g of compound (B-1-4) shown below was added to the aqueous solution and agitated for 30 minutes. Thereafter, 100 g of chloroform was added to the mixture, and the resultant organic phase was washed with water, thereby obtaining 3.3 g of brown liquid compound (B-1).

$^1$H-NMR (300 MHz, CDCl$_3$); 7.78-7.62 (m, 12H), 7.55 (d, 2H), 4.22 (m, 2H), 3.95 (d, 1H), 3.76 (d, 1H), 3.23 (m, 1H), 3.13 (s, 2H), 3.04 (t, 1H), 2.65 (t, 1H), 2.40 (m, 4H), 1.82-1.55 (m, 8H), 1.48-1.20 (m, 6H), 1.14-0.84 (m, 3H).

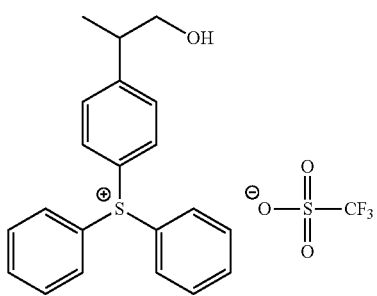

(B-1-1)

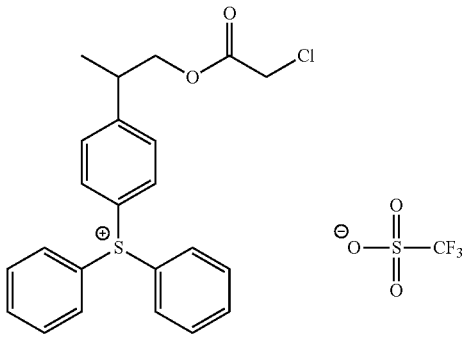

(B-1-2)

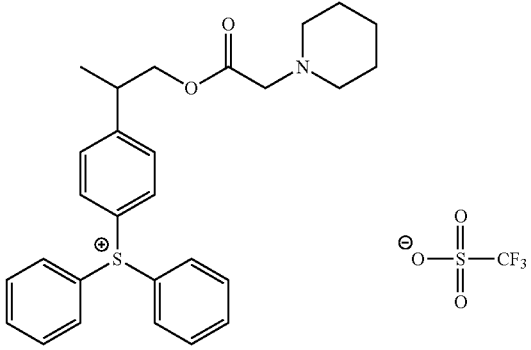

(B-1-3)

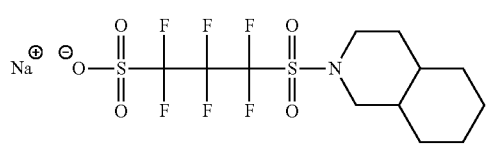

(B-1-4)

Synthetic Example 2

Synthesis of Compound (B-11)

The following compound (B-1-5) was obtained by the Friedel-Crafts reaction between 3-phenyl-1-methylpropylamine and diphenyl sulfoxide.

In a 200 ml three-necked flask, 4.2 g of compound (B-1-5) was dissolved in 40 g of acetonitrile. Then, 3.6 g of potassium carbonate was added to the solution, and while cooling the mixture in an ice bath, 3.2 g of ethyl bromoacetate was dropped thereinto over a period of 30 minutes. Subsequently, the mixture was agitated in the ice bath for 30 minutes. The ice bath was removed, and the mixture was warmed to room temperature at which the mixture was agitated for 5 hours. Thereafter, 100 g of chloroform was added to the mixture, and the resultant organic phase was washed with water. The solvent was removed, thereby obtaining brown liquid compound (B-1-6) shown below.

Compound (B-1-6) was dissolved in 50 g of water, and 2.9 g of potassium nonafluorobutanesulfonate was added to the aqueous solution and agitated for 30 minutes. Thereafter, 100 g of chloroform was added to the mixture, and the resultant organic phase was washed with water. Thus, 2.5 g of brown liquid compound (B-11) was obtained.

$^1$H-NMR (300 MHz, CDCl$_3$): 7.80-7.52 (m, 14H), 4.12 (q, 4H), 3.47 (s, 4H), 3.03-2.72 (m, 3H), 1.78 (m, 1H), 1.63 (m, 1H), 1.26 (t, 6H), 1.05 (d, 3H).

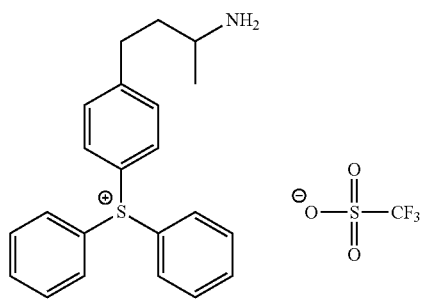

(B-1-5)

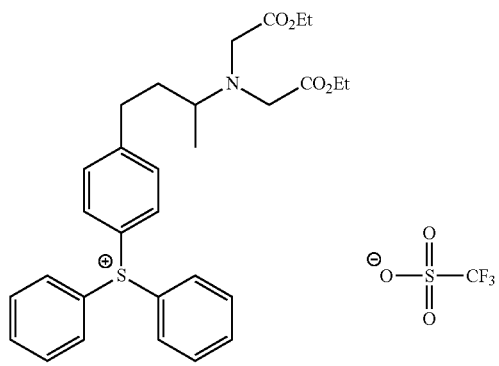

(B-1-6)

Other components (B) were synthesized in the same manner as described above for the compounds (B-1) and (B-11).

<Acid Generator (2)>

The following compounds (C-1) to (C-8) were provided as components (C).

(C-1) 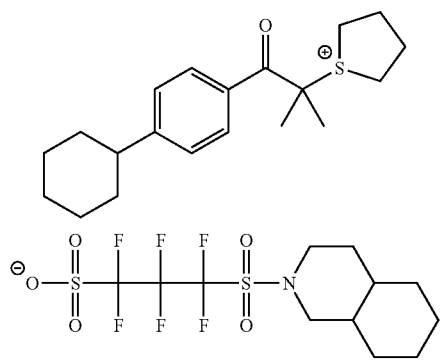
(C-6) 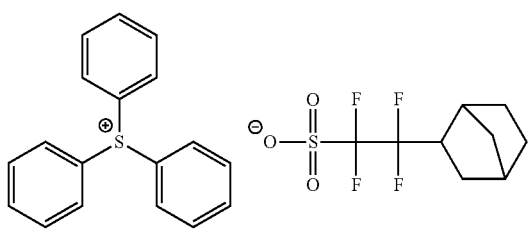
(C-2) 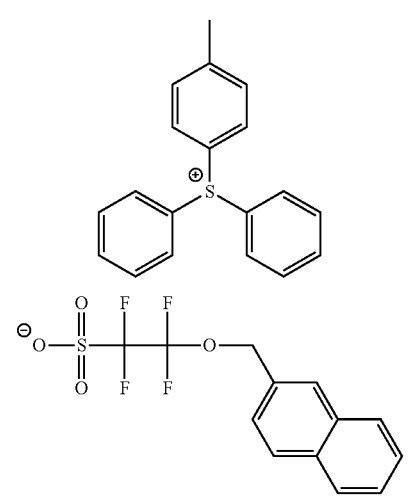
(C-7) 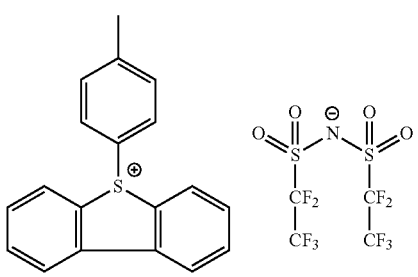
(C-3) 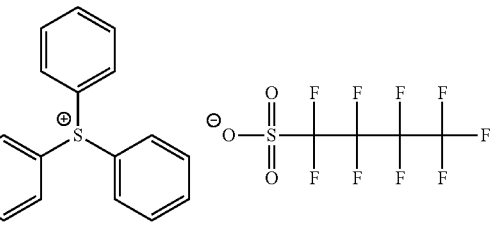
(C-8) 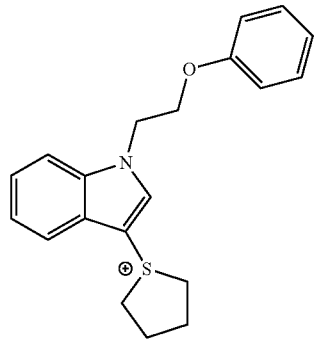
(C-4) 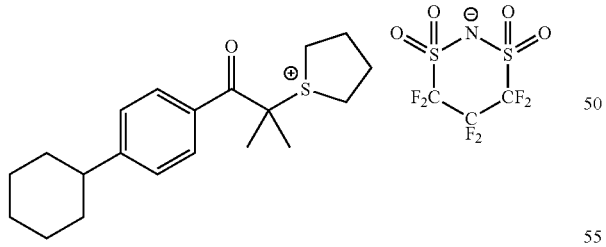
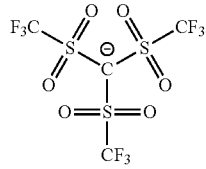
(C-9) 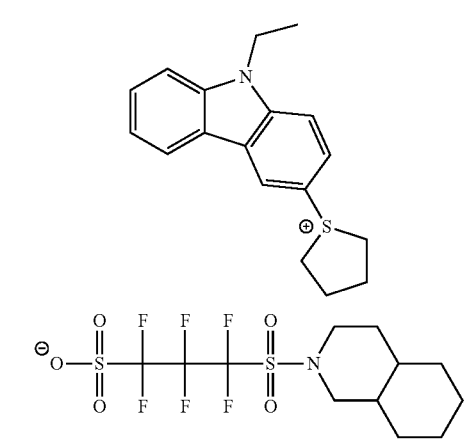
(C-5) 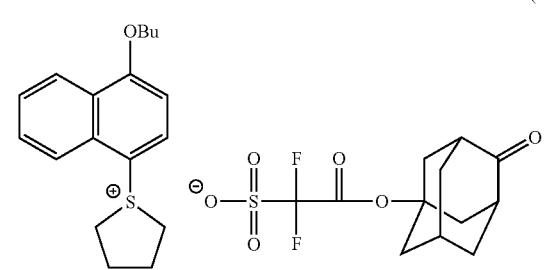

(C-10)
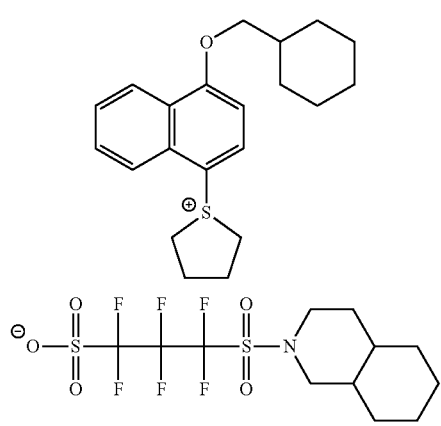
<Resin (A)>
The following resins (A-1) to (A-13) were provided as resins (A).
(A-1)
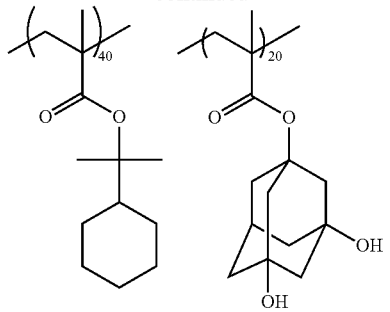
Mw = 7400
Mw/Mn = 1.99
(A-3)
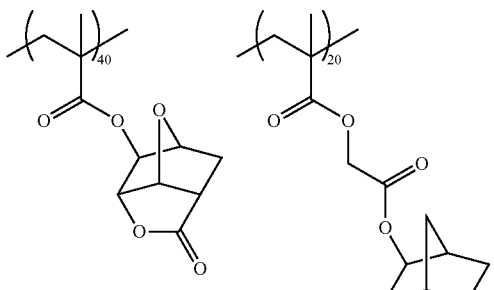
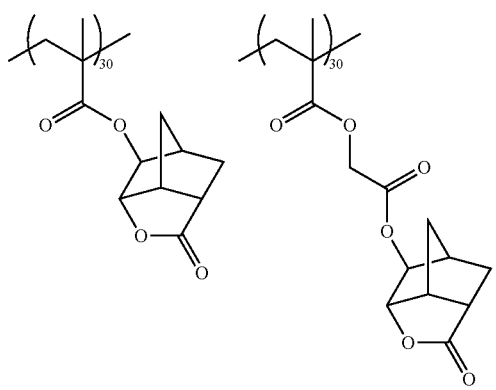
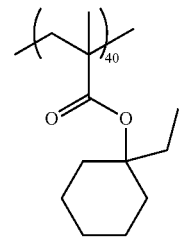
Mw = 8800
Mw/Mn = 1.90
(A-4)
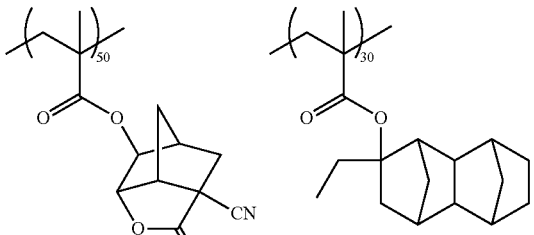
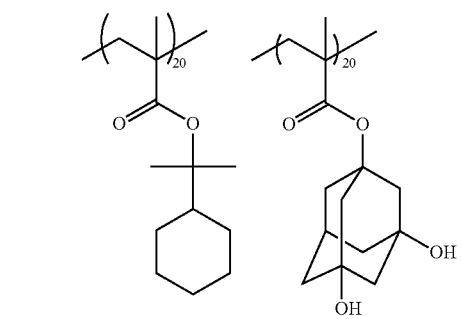
Mw = 12000
Mw/Mn = 1.81
(A-2)
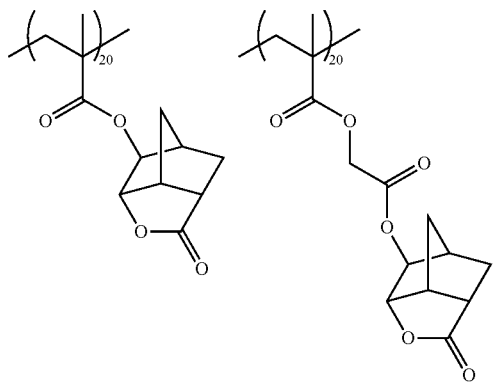
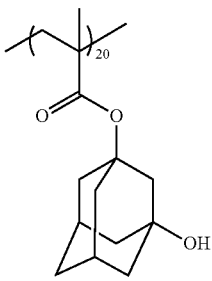
Mw = 8200
Mw/Mn = 1.93

-continued
(A-5)
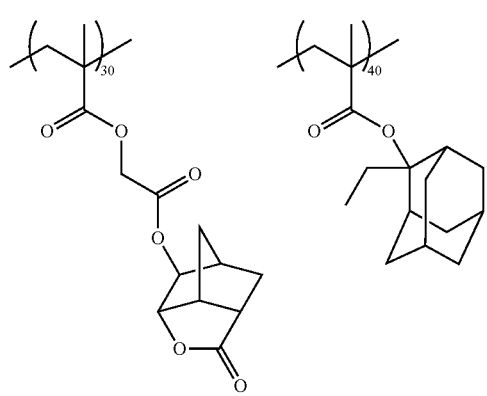
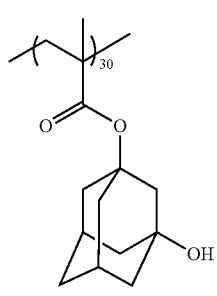
Mw = 7300
Mw/Mn = 1.60
(A-6)
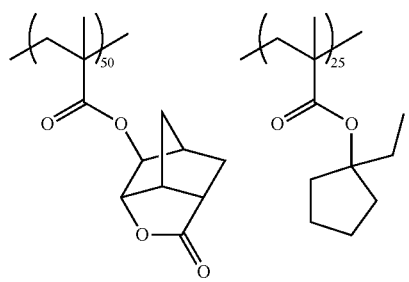
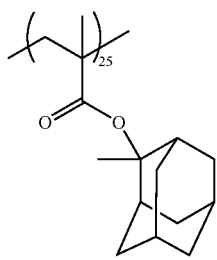
Mw = 9400
Mw/Mn = 1.66
(A-7)
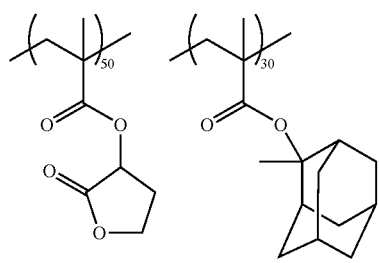
-continued
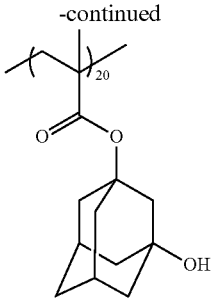
Mw = 9700
Mw/Mn = 2.02
(A-8)
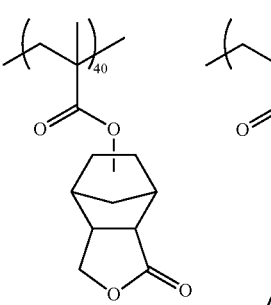
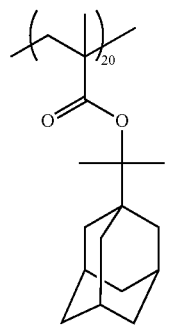
Mw = 10400
Mw/Mn = 1.84
(A-9)
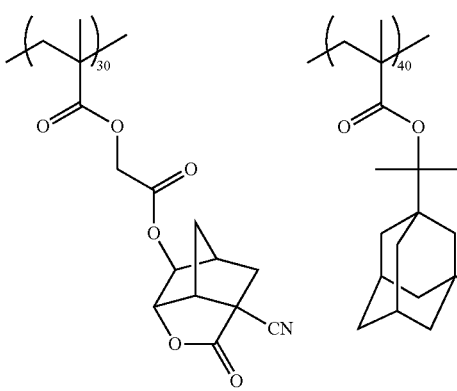

-continued
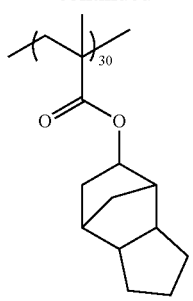
Mw = 9500
Mw/Mn = 1.70
(A-10)
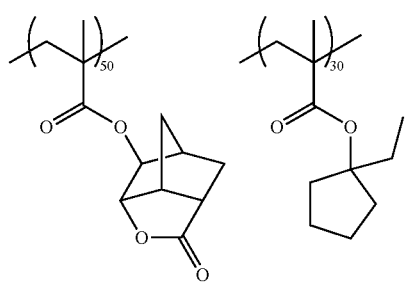
Mw = 9000
Mw/Mn = 1.60
(A-11)
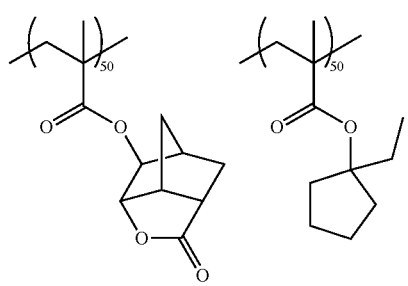
Mw = 8600
Mw/Mn = 1.51
(A-12)
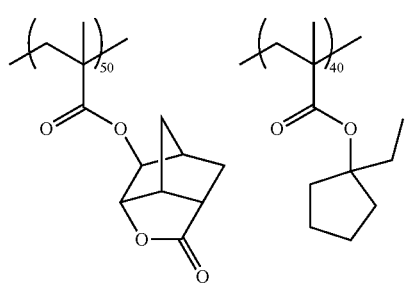
-continued
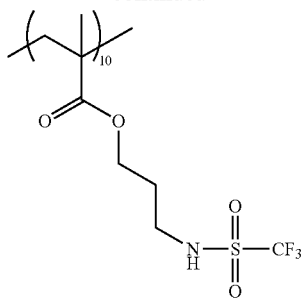
Mw = 8600
Mw/Mn = 1.52
(A-13)
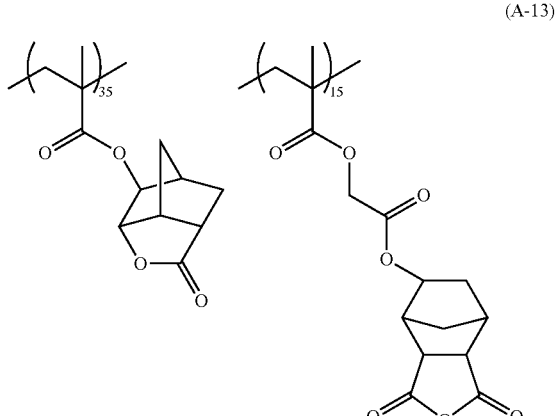
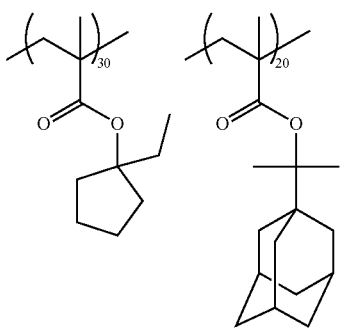
Mw = 9100
Mw/Mn = 1.68
<Hydrophobic Resin>
The following resins (D-1) to (D-9) were provided as hydrophobic resins (D).
(D-1)
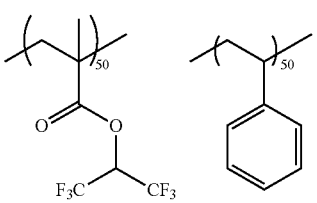
Mw = 8200
Mw/Mn = 1.31

(D-2)
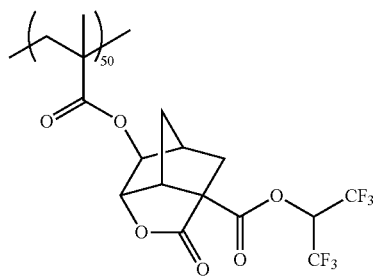
Mw = 9000
Mw/Mn = 1.72
(D-3)
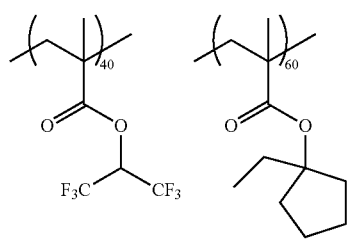
Mw = 7900
Mw/Mn = 1.80
(D-4)
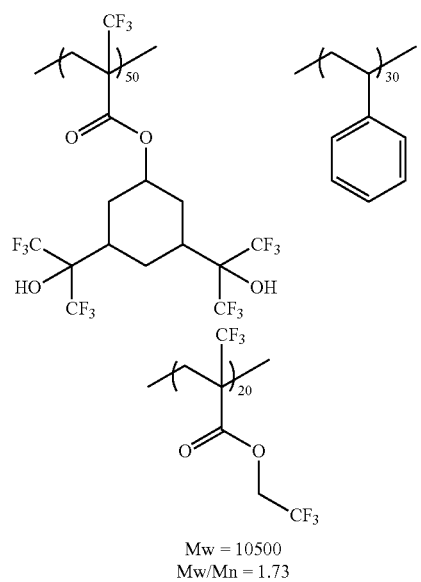
Mw = 10500
Mw/Mn = 1.73
(D-5)
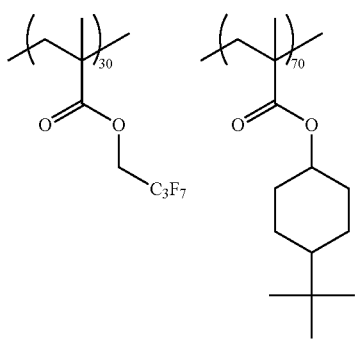
Mw = 8900
Mw/Mn = 1.61
(D-6)
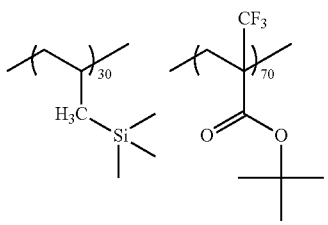
Mw = 7900
Mw/Mn = 1.62
(D-7)
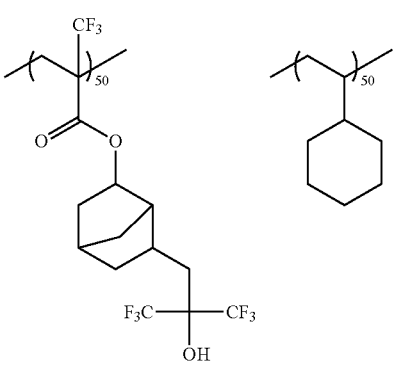
Mw = 9200
Mw/Mn = 1.78
(D-8)
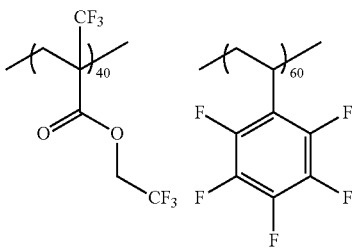
Mw = 11200
Mw/Mn = 1.53
(D-9)
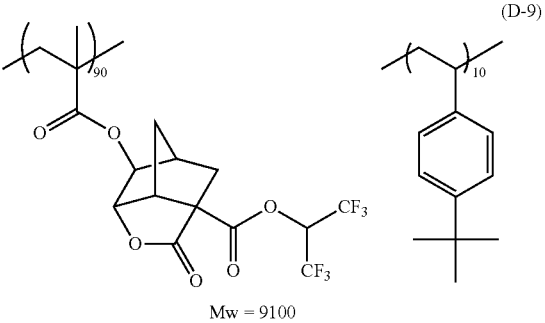
Mw = 9100
Mw/Mn = 1.62
<Basic Compound (F) or Low-molecular Compound (G)>
The following compounds (F-1) to (F-6) were provided as basic compounds (F) or low-molecular compounds (G).

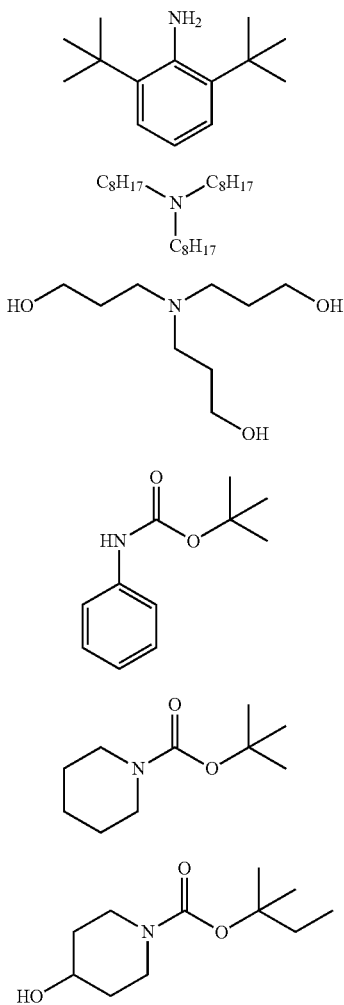

(F-1)
(F-2)
(F-3)
(F-4)
(F-5)
(F-6)

<Solvent>

The following compounds S-1 to S-3 were provided as solvents.

S-1: propylene glycol monomethyl ether acetate,
S-2: propylene glycol monomethyl ether, and
S-3: γ-butyrolactone.

<Surfactant>

The following products W-1 to W-5 were provided as surfactants.

W-1: Megafac F176 (produced by Dainippon Ink & Chemicals, Inc.),
W-2: Megafac R08 (produced by Dainippon Ink & Chemicals, Inc.),
W-3: polysiloxane polymer KP-341 (produced by Shin-Etsu Chemical Co., Ltd.),
W-4: Troy Sol S-366 (produced by Troy Chemical Co., Ltd.), and
W-5: PF6320 (produced by OMNOVA SOLUTIONS, INC.).

<Preparation of Resist Composition>

Components of Table 2 below were dissolved in mixed solvents of the same table, thereby obtaining solutions each of 4.4 mass % solid content. The solutions were each passed through a polyethylene filter of 0.03 μm pore size, thereby obtaining positive resist solutions.

<Exposure Condition (1): ArF Liquid-immersion Evaluation>

An organic antireflection film ARC29SR (produced by Nissan Chemical Industries, Ltd.) was applied onto a silicon wafer and baked at 205° C. for 60 seconds, thereby forming a 78 nm-thick antireflection film. Each of the prepared actinic-ray- or radiation-sensitive resin compositions was applied thereonto and baked at 130° C. for 60 seconds, thereby forming a 110 nm-thick resist film. The resultant wafer was exposed through a 6% half-tone mask of 1:1 line and space pattern of 45 nm line width by means of an ArF excimer laser liquid-immersion scanner (manufactured by ASML, XT1700i, NA 1.35). Pure water was used as an immersion liquid.

Thereafter, the exposed wafer was baked at 90° C. for 60 seconds, developed with an aqueous solution of tetramethylammonium hydroxide (2.38 mass %) for 30 seconds, rinsed with pure water and spin dried, thereby obtaining a resist pattern.

<Exposure Condition (2): ArF Dry Evaluation>

An organic antireflection film ARC29A (produced by Nissan Chemical Industries, Ltd.) was applied onto a silicon wafer and baked at 205° C. for 60 seconds, thereby forming a 78 nm-thick antireflection film. Each of the prepared actinic-ray- or radiation-sensitive resin compositions was applied thereonto and baked at 130° C. for 60 seconds, thereby forming a 120 nm-thick resist film. The resultant wafer was exposed through a 6% half-tone mask of 1:1 line and space pattern of 75 nm line width by means of an ArF excimer laser scanner (manufactured by ASML, PAS5500/1100, NA 0.75). Pure water was used as an immersion liquid.

Thereafter, the exposed wafer was baked at 90° C. for 60 seconds, developed with an aqueous solution of tetramethylammonium hydroxide (2.38 mass %) for 30 seconds, rinsed with pure water and spin dried, thereby obtaining a pattern.

<Evaluation of Resist>

[Sensitivity: Exposure Condition (1)]

The shape of cross section of each of the obtained patterns was observed by means of a scanning electron microscope (model S-9220, manufactured by Hitachi, Ltd.). The sensitivity was defined as the minimum exposure energy at which a 45 nm line (line:space=1:1) could be resolved.

[Sensitivity: Exposure Condition (2)]

The shape of cross section of each of the obtained patterns was observed by means of a scanning electron microscope (model S-9220, manufactured by Hitachi, Ltd.). The sensitivity was defined as the minimum exposure energy at which a 75 nm line (line:space=1:1) could be resolved.

[Exposure Latitude: Exposure Condition (1)]

The optimum exposure amount was defined as the exposure amount in which a line-and-space (1:1) mask pattern of 45 nm line width was reproduced. The exposure amount range in which when the exposure amount was varied, the pattern size allowed 45 nm±10% was measured. The exposure latitude is the quotient of the value of the exposure amount range divided by the optimum exposure amount, the quotient expressed by a percentage. The greater the value of the exposure latitude, the less the change of performance by exposure amount changes and the better the exposure latitude (EL).

[Exposure Latitude: Exposure Condition (2)]

The optimum exposure amount was defined as the exposure amount in which a line-and-space (1:1) mask pattern of 75 nm line width was reproduced. The exposure amount range in which when the exposure amount was varied, the pattern size allowed 75 nm±10% was measured. The exposure latitude is the quotient of the value of the exposure amount range divided by the optimum exposure amount, the quotient expressed by a percentage. The greater the value of the exposure latitude, the less the change of performance by exposure amount changes and the better the exposure latitude (EL).

[LWR: Exposure Condition (1)]

Each line pattern finished into a line width of 45 nm was observed by means of a scanning electron microscope (model 59260 manufactured by Hitachi, Ltd.). In an edge 2 μm region along the longitudinal direction of the line pattern, the distances of actual edges from a reference line on which edges were to be present were measured at 50 points. The standard deviation of measurements was determined, and 3σ was computed therefrom. The smaller the value thereof, the more favorable the performance exhibited.

[LWR: Exposure Condition (2)]

Each line pattern finished into a line width of 75 nm was observed by means of a scanning electron microscope (model 59260 manufactured by Hitachi, Ltd.). In an edge 2 μm region along the longitudinal direction of the line pattern, the distances of actual edges from a reference line on which edges were to be present were measured at 50 points. The standard deviation of measurements was determined, and 3σ was computed therefrom. The smaller the value thereof, the more favorable the performance exhibited.

The thus obtained evaluation results are given in Table 2 below.

TABLE 2

| | Resin (10 g) | Acid generator (B) (g) | Acid generator (C) (g) | Hydrophobic resin (D) (g) | Basic comp. or comp. (G) (g) | Surfactant (0.03 g) | Solvent (mass ratio) | Exposure cond. | Sensitivity (mJ/cm$^2$) | LWR (nm) | EL (%) |
|---|---|---|---|---|---|---|---|---|---|---|---|
| Ex. 1 | A-1 | B-1(0.3) | C-1(0.9) | — | — | W-1 | S-1/S-2(70/30) | (2) | 14.4 | 4.3 | 21.2 |
| Ex. 2 | A-2 | B-2(0.3) | C-2(0.9) | — | — | W-2 | S-2/S-3(60/40) | (2) | 15.0 | 4.6 | 21.0 |
| Ex. 3 | A-3 | B-3(0.3) | C-3(0.9) | — | — | W-3 | S-2/S-3(60/40) | (2) | 14.8 | 4.2 | 21.5 |
| Ex. 4 | A-4 | B-4(0.3) | C-4(1.0) | D-1(1.5) | — | W-4 | S-1/S-2(60/40) | (1) | 16.1 | 4.4 | 20.8 |
| Ex. 5 | A-4 | B-3(0.2)/B-4(0.1) | C-4(0.7) | D-1(3.0) | — | W-2 | S-1/S-2(55/45) | (1) | 15.8 | 4.7 | 20.4 |
| Ex. 6 | A-4 | B-2(0.2)/B-4(0.1) | C-4(1.0) | — | — | W-2 | S-1/S-2(60/40) | (2) | 14.7 | 4.3 | 20.9 |
| Ex. 7 | A-5 | B-5(0.2) | C-5(0.5) | D-2(4.0) | — | W-3 | S-1/S-3(80/20) | (1) | 15.0 | 4.7 | 20.0 |
| Ex. 8 | A-5 | B-5(0.2) | C-2(0.4) | — | — | W-4 | S-1/S-3(70/30) | (2) | 15.5 | 4.7 | 19.9 |
| Ex. 9 | A-5 | B-5(0.6) | C-1(1.0) | — | — | W-3 | S-1/S-3(80/20) | (2) | 15.5 | 4.2 | 20.6 |
| Ex. 10 | A-6 | B-6(0.4) | C-6(0.8) | D-3(1.0) | — | W-4 | S-1/S-3(70/30) | (1) | 14.9 | 4.5 | 20.1 |
| Ex. 11 | A-5(5 g)/A-6(5 g) | B-6(0.3) | C-6(1.0) | — | — | W-1 | S-1/S-2(55/45) | (2) | 14.4 | 4.2 | 20.8 |
| Ex. 12 | A-7(3 g)/A-8(7 g) | B-7(0.3) | C-7(0.9) | — | F-1(0.05) | W-2 | S-1/S-3(75/25) | (2) | 14.9 | 4.5 | 21.6 |
| Ex. 13 | A-8 | B-8(0.3) | C-8(0.9) | — | F-2(0.03) | W-3 | S-1/S-3(75/25) | (2) | 16.0 | 4.1 | 20.1 |
| Ex. 14 | A-1 | B-9(0.2) | C-1(0.9) | — | F-3(0.10) | W-4 | S-1/S-2(60/40) | (2) | 15.7 | 4.3 | 20.7 |
| Ex. 15 | A-2 | B-10(0.3) | C-2(1.2) | — | — | W-2 | S-1/S-2(55/45) | (2) | 15.6 | 4.7 | 21.2 |
| Ex. 16 | A-3 | B-11(0.3) | C-3(0.9) | D-4(3.5) | — | W-3 | S-1/S-2(60/40) | (1) | 16.2 | 4.6 | 21.6 |
| Ex. 17 | A-2(5 g)/A-3(5 g) | B-11(0.2) | C-3(0.8) | — | — | W-4 | S-1/S-3(80/20) | (2) | 16.1 | 4.6 | 21.4 |
| Ex. 18 | A-4 | B-12(0.3) | C-4(0.7) | D-5(3.0) | — | W-1 | S-1/S-3(70/30) | (1) | 15.2 | 4.3 | 20.3 |
| Ex. 19 | A-5 | B-13(0.3) | C-5(0.7) | D-6(5.0) | — | W-2 | S-1/S-2(55/45) | (1) | 15.5 | 4.8 | 21.0 |
| Ex. 20 | A-6 | B-14(0.3) | C-6(0.5) | — | — | W-3 | S-1/S-3(70/30) | (2) | 16.3 | 4.5 | 20.6 |
| Ex. 21 | A-7 | B-15(0.3) | C-7(0.8) | — | — | W-1 | S-1/S-3(70/30) | (2) | 15.0 | 4.4 | 20.1 |
| Ex. 22 | A-6 | B-16(0.3) | C-2(0.5) | — | — | W-2 | S-1/S-2(55/45) | (2) | 15.7 | 4.5 | 20.8 |
| Ex. 23 | A-7 | B-17(0.2) | C-7(0.8) | — | — | W-3 | S-1/S-3(75/25) | (2) | 15.6 | 4.2 | 20.4 |
| Ex. 24 | A-8 | B-18(0.3) | C-8(0.9) | — | — | W-4 | S-1/S-3(75/25) | (2) | 17.3 | 5.1 | 19.0 |
| Ex. 25 | A-1 | B-19(0.7) | C-1(1.2) | — | F-5(0.02) | W-2 | S-1/S-2(60/40) | (2) | 16.9 | 5.3 | 19.5 |
| Ex. 26 | A-2 | B-20(0.3) | C-2(0.7) | D-7(1.5) | F-4(0.02) | W-2 | S-1/S-3(70/30) | (1) | 18.0 | 5.4 | 19.4 |
| Ex. 27 | A-3 | B-21(0.7) | C-3(0.5) | — | — | W-5 | S-1/S-2(55/45) | (2) | 17.5 | 5.2 | 19.3 |
| Ex. 28 | A-4 | B-22(0.1) | C-4(1.1) | D-8(2.0) | F-6(0.01) | W-1 | S-1/S-2(55/45) | (1) | 18.3 | 5.0 | 18.4 |
| Ex. 29 | A-5 | B-23(0.3) | C-5(0.9) | — | — | W-3 | S-1/S-3(75/25) | (2) | 17.5 | 5.0 | 18.2 |
| Ex. 30 | A-5 | B-23(0.1)/B-34(0.3) | C-6(0.9) | — | — | W-4 | S-1/S-2(70/30) | (2) | 18.4 | 4.9 | 18.9 |
| Ex. 31 | A-6 | B-24(0.2) | C-6(0.9) | — | — | W-4 | S-1/S-3(70/30) | (2) | 18.1 | 5.1 | 19.0 |
| Ex. 32 | A-1 | B-25(0.3) | C-1(0.7) | — | — | W-1 | S-1/S-2(55/45) | (2) | 18.0 | 5.1 | 18.4 |
| Ex. 33 | A-2 | B-26(0.2) | C-7(0.7) | — | — | W-2 | S-1/S-3(75/25) | (2) | 17.6 | 5.3 | 17.9 |
| Ex. 34 | A-1 | B-27(0.3) | C-3(0.5) | — | — | W-3 | S-1/S-3(70/30) | (2) | 20.9 | 5.9 | 17.0 |
| Ex. 35 | A-2 | B-28(0.3) | C-8(0.8) | — | — | W-4 | S-1/S-2(55/45) | (2) | 21.1 | 5.7 | 16.9 |
| Ex. 36 | A-3 | B-29(0.3) | C-5(0.5) | — | — | W-2 | S-1/S-3(75/25) | (2) | 24.2 | 6.0 | 15.2 |
| Ex. 37 | A-4 | B-30(0.6) | C-7(0.9) | — | — | W-5 | S-1/S-3(75/25) | (2) | 17.1 | 5.3 | 19.1 |
| Ex. 38 | A-9 | B-31(0.8) | C-8(1.2) | — | — | W-2 | S-1/S-2(60/40) | (2) | 16.4 | 5.3 | 19.9 |
| Ex. 39 | A-1 | B-32(0.4) | C-2(0.9) | — | — | W-5 | S-1/S-2(55/45) | (2) | 17.7 | 5.5 | 18.6 |
| Ex. 40 | A-2 | B-33(0.4) | C-5(0.8) | — | — | W-1 | S-1/S-3(75/25) | (2) | 17.5 | 5.2 | 19.0 |
| Ex. 41 | A-3 | B-34(0.3) | C-1(1.2) | — | — | W-4 | S-1/S-2(70/30) | (2) | 20.0 | 5.9 | 16.9 |
| Ex. 42 | A-8 | B-35(0.6) | C-6(1.1) | — | — | W-2 | S-1/S-2(75/25) | (2) | 19.9 | 5.8 | 17.5 |
| Ex. 43 | A-4 | B-36(0.6) | C-3(0.9) | — | — | W-2 | S-1/S-3(70/30) | (2) | 22.5 | 6.0 | 16.0 |
| Ex. 44 | A-10 | B-37(0.3) | C-9(0.9) | D-9(1.5) | — | W-3 | S-1(100) | (1) | 14.5 | 4.3 | 21.5 |
| Ex. 45 | A-11 | B-38(0.2) | C-10(0.9) | D-1(3.0) | F-6(0.01) | W-4 | S-1(100) | (1) | 14.6 | 4.8 | 21.0 |
| Ex. 46 | A-12 | B-39(0.3) | C-1(0.9) | D-2(3.0) | — | W-3 | S-1/S-2(70/30) | (1) | 14.9 | 4.5 | 20.4 |
| Ex. 47 | A-13 | B-40(0.3) | C-7(0.9) | D-3(3.0) | — | W-4 | S-1/S-2(80/20) | (1) | 14.8 | 4.4 | 20.7 |
| Ex. 48 | A-10 | B-41(0.2) | C-5(0.9) | D-1(3.0) | F-5(0.01) | W-1 | S-1(100) | (1) | 15.0 | 4.7 | 20.4 |
| Ex. 49 | A-10 | B-42(0.3) | C-1(0.9) | D-4(3.0) | — | W-2 | S-1/S-2(70/30) | (1) | 14.8 | 5.0 | 20.6 |
| Ex. 50 | A-11 | B-43(0.3) | C-9(0.9) | D-2(2.0) | — | W-3 | S-1/S-2(70/30) | (1) | 14.5 | 4.1 | 21.0 |
| Ex. 51 | A-12 | B-44(0.3) | C10(0.9) | D-5(3.0) | — | W-3 | S-1/S-3(70/30) | (1) | 15.0 | 4.5 | 20.9 |
| Ex. 52 | A-13 | B-45(0.2) | C-1(0.9) | D-9(3.0) | F-1(0.01) | W-4 | S-1/S-2(55/45) | (1) | 15.3 | 4.4 | 20.9 |

TABLE 2-continued

| | Resin (10 g) | Acid generator (B) (g) | Acid generator (C) (g) | Hydrophobic resin (D) (g) | Basic comp. or comp. (G) (g) | Surfactant (0.03 g) | Solvent (mass ratio) | Exposure cond. | Sensitivity (mJ/cm$^2$) | LWR (nm) | EL (%) |
|---|---|---|---|---|---|---|---|---|---|---|---|
| Ex. 53 | A-10 | B-46(0.4) | C-4(1.1) | D-6(3.0) | — | W-1 | S-1(100) | (1) | 14.4 | 4.4 | 20.1 |
| Ex. 54 | A-1 | B-47(0.3) | C-5(0.9) | D-2(3.0) | — | W-2 | S-1/S-2(70/30) | (1) | 15.1 | 4.7 | 20.3 |
| Ex. 55 | A-12 | B-48(0.3) | C-6(0.9) | D-9(2.5) | — | W-3 | S-1/S-2(70/30) | (1) | 14.4 | 4.5 | 20.7 |
| Ex. 56 | A-10 | B-49(0.3) | C-9(0.9) | D-1(3.0) | — | W-4 | S-1/S-2(55/45) | (1) | 14.2 | 4.1 | 20.8 |
| Ex. 57 | A-11 | B-50(0.2) | C-10(0.7) | D-8(2.0) | — | W-2 | S-1/S-3(70/30) | (1) | 14.9 | 4.3 | 21.2 |
| Ex. 58 | A-2 | B-51(0.2) | C-7(0.7) | D-2(3.0) | — | W-3 | S-1(100) | (1) | 14.8 | 4.3 | 21.4 |
| Ex. 59 | A-3 | B-52(0.2) | C-1(0.9) | D-9(3.0) | — | W-4 | S-1/S-2(70/30) | (1) | 15.2 | 4.7 | 20.4 |
| Ex. 60 | A-10 | B-53(0.3) | C-9(0.9) | D-1(2.0) | — | W-4 | S-1/S-2(70/30) | (1) | 15.3 | 4.2 | 20.6 |
| Ex. 61 | A-11 | B-54(0.3) | C-10(0.9) | D-9(3.0) | — | W-2 | S-1/S-2(70/30) | (1) | 14.8 | 4.6 | 20.5 |
| Ex. 62 | A-12 | B-55(0.3) | C-1(0.9) | D-9(1.5) | — | W-3 | S-1(100) | (1) | 14.6 | 4.8 | 20.5 |
| Ex. 63 | A-13 | B-56(0.3) | C-5(0.9) | D-2(3.0) | — | W-4 | S-1/S-2(70/30) | (1) | 15.0 | 4.6 | 21.0 |
| Ex. 64 | A-10 | B-57(0.3) | C-1(0.9) | D-1(3.0) | — | W-1 | S-1/S-2(70/30) | (1) | 15.7 | 4.7 | 21.4 |
| Comp. ex. 1 | A-2 | B-58(0.3) | C-2(0.9) | — | — | W-2 | S-2/S-3(60/40) | (2) | 28.2 | 6.9 | 14.5 |
| Comp. ex. 2 | A-3 | B-59(0.3) | C-3(0.9) | — | — | W-3 | S-2/S-3(60/40) | (2) | 37.7 | 6.6 | 14.2 |
| Comp. ex. 3 | A-1 | — | C-1(1.2) | — | — | W-1 | S-1/S-2(70/30) | (2) | 45.0 | 7.1 | 12.9 |

As apparent from Table 2, the compositions of Examples excelled the compositions of Comparative Examples in the sensitivity, roughness characteristics and exposure latitude.

The invention claimed is:

1. An actinic-ray- or radiation-sensitive resin composition comprising:
(A) a resin, and
(B) a compound that when exposed to actinic rays or radiation, is decomposed to thereby generate an acid, the compound being any of compounds of general formula (1-1) below,

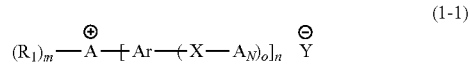

(1-1)

in which A represents a sulfur atom or an iodine atom,
$R_1$, each independently when m=2, represents an alkyl group, an alkenyl group, a cycloaliphatic group, an aromatic hydrocarbon group or a heterocyclic hydrocarbon group, provided that when m=2, two $R_1$s may be bonded to each other to thereby form a ring,
Ar, each independently when n≥2, represents an aromatic ring group,
X, each independently when o≥2 and/or n≥2, represents a connecting group having a carbon atom to which Ar is bonded, $A_N$, each independently when o≥2 and/or n≥2, represents a basic moiety containing a nitrogen-containing heterocyclic group,
n is an integer of 1 to 3 and m is an integer satisfying the relationship m+n=3 when A is a sulfur atom,
n is an integer of 1 or 2 and m is an integer satisfying the relationship m+n=2 when A is an iodine atom,
o is an integer of 1 to 10, and
$Y^-$ represents an anion.

2. The composition according to claim 1, further comprising (C) a compound that when exposed to actinic rays or radiation, is decomposed to thereby generate an acid, the compound being other than the compounds of general formula (1-1) above.

3. The composition according to claim 1, wherein X, or at least one of Xs, is expressed by general formula (1-2) below,

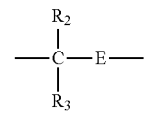

(1-2)

in which
each of $R_2$ and $R_3$ independently represents a hydrogen atom, an alkyl group, an alkenyl group, a cycloaliphatic group, an aromatic hydrocarbon group or a heterocyclic hydrocarbon group, provided that $R_2$ and $R_3$ may be bonded to each other to thereby form a ring, and provided that at least one of $R_2$ and $R_3$ may be bonded to E to thereby form a ring, and
E represents a connecting group or a single bond.

4. The composition according to claim 1, wherein X, or at least one of Xs, is expressed by general formula (1-3) below,

(1-3)

in which
J represents an oxygen atom or a sulfur atom, and
E represents a connecting group or a single bond.

5. The composition according to claim 3, wherein E is an alkylene bond.

6. The composition according to claim 3, wherein E contains at least one bond selected from the group consisting of an ester bond and an ether bond.

7. The composition according to claim 1, wherein A is a sulfur atom.

8. The composition according to claim 1, wherein $R_1$, or each of $R_1$s independently, is an aromatic hydrocarbon group.

9. The composition according to claim 1, wherein $Y^-$ is an organic acid anion.

10. The composition according to claim 1, wherein $Y^-$ is a sulfonate anion, an imidate anion or a methide anion.

11. An actinic-ray- or radiation-sensitive film formed from the composition according to claim 1.

12. The composition according to claim 1, wherein all the atoms adjacent to the nitrogen atom contained in the basic moiety represented by $A_N$ are carbon or hydrogen atoms.

13. The composition according to claim 1, wherein no electron withdrawing functional group is directly bonded to the nitrogen atom contained in the basic moiety represented by $A_N$.

14. A method of forming a pattern, comprising:
   forming the composition according to claim 1 into a film,
   exposing the film to light, and
   developing the exposed film.

15. The method according to claim 14, wherein the exposure is performed through an immersion liquid.

* * * * *